US007179645B2

(12) United States Patent
Humphreys et al.

(10) Patent No.: US 7,179,645 B2
(45) Date of Patent: Feb. 20, 2007

(54) II-KEY/ANTIGENIC EPITOPE HYBRID PEPTIDE VACCINES

(75) Inventors: Robert E. Humphreys, Acton, MA (US); Minzhen Xu, Northborough, MA (US)

(73) Assignee: Antigen Express, Inc., Worcester, MA (US)

( * ) Notice: Subject to any disclaimer, the term of this patent is extended or adjusted under 35 U.S.C. 154(b) by 408 days.

(21) Appl. No.: 10/253,286

(22) Filed: Sep. 24, 2002

(65) Prior Publication Data

US 2004/0058881 A1 Mar. 25, 2004

(51) Int. Cl.

| | |
|---|---|
| ***C12N 15/74*** | (2006.01) |
| ***C07H 21/04*** | (2006.01) |
| *A61K 31/70* | (2006.01) |

(52) U.S. Cl. ................. 435/320.1; 536/23.1; 536/23.4; 514/44

(58) Field of Classification Search ..................... None
See application file for complete search history.

(56) References Cited

U.S. PATENT DOCUMENTS

| | | | |
|---|---|---|---|
| 4,650,764 | A | 3/1987 | Temin et al. |
| 4,708,871 | A | 11/1987 | Geysen |
| 4,797,368 | A | 1/1989 | Carter et al. |
| 5,126,132 | A | 6/1992 | Rosenberg |
| 5,194,392 | A | 3/1993 | Geysen |
| 5,270,170 | A | 12/1993 | Schatz et al. |
| 5,284,935 | A | 2/1994 | Clark et al. |
| 5,399,346 | A | 3/1995 | Anderson et al. |
| 5,539,084 | A | 7/1996 | Geysen |
| 5,556,762 | A | 9/1996 | Pinilla et al. |
| 5,559,028 | A | 9/1996 | Humphreys |
| 5,595,915 | A | 1/1997 | Geysen |
| 5,679,527 | A | 10/1997 | Humphreys |
| 5,693,522 | A | 12/1997 | Chada et al. |
| 5,747,334 | A | 5/1998 | Kay et al. |
| 5,849,586 | A | 12/1998 | Kriegler et al. |
| 5,856,185 | A | 1/1999 | Gruber et al. |
| 5,856,456 | A | 1/1999 | Whitlow et al. |
| 5,874,077 | A | 2/1999 | Kriegler et al. |
| 5,874,214 | A | 2/1999 | Nova et al. |
| 5,910,300 | A | 6/1999 | Tournier et al. |
| 5,919,639 | A | 7/1999 | Humphreys et al. |
| 6,120,769 | A | 9/2000 | Gefter et al. |
| 6,432,409 | B1 | 8/2002 | Humphreys et al. |

OTHER PUBLICATIONS

Bowie et al, Science Mar. 1990; 247:1306-10.*
Makrides et al, Protein Exp Pur. 1999; 17:183-202.*
Eck et al, Phar Basis Ther 1995; 77-101.*
Verma et al, Nat. Sep. 1997; 389:239-242.*
Zink et al, Gene Ther Mol Biol Jan. 2001;6:1-24.*
Robbins et al, Pharmcol Ther 1998;80:35-47.*
Adams et al., Arzneimittelforschung 47: 1069-77 (1997).
Adams et al., Eur. J. Immunol. 25: 1693-702 (1995).
Castilleja et al., Mol. Cell Biochem. 217: 21-33 (2001).
Daibata et al., Mol. Immunol. 31: 255-60 (1994).
Disis et al., J. Clin. Oncol. 20: 2624-32 (2002).
Hess et al., Clin. Immunol. 101: 67-76 (2001).
Humphreys et al., Vaccine 18: 2693-7 (2000).
Kawakami et al., Proc. Natl. Acad. Sci. USA 91: 3515-9 (1994).
Kawakami et al., J. Exp. Med. 180: 347-52 (1994).
Kawakami et al., Proc. Natl. Acad. Sci. USA 91: 6458-6462 (1994).
Knutson et al., J. Clin. Invest. 107: 477-84 (2001).
Kuerer et al., J. Interleron Cytokine Res. 22: 583-92 (2002).
Lustgarten et al., Hum. Immunol. 52: 109-18 (1997).
Moudgil et al., J. Immunol. 163: 4232-7 (1999).
Rammensee et al., Immunogenetics 41: 178-228 (1995).
Texier et al., J. Immunol. 164: 3177-84 (2000).
Xu et al., Arzneimittelforschung 49: 791-9 (1999).
US 5,382,513, 01/1995, Lam et al. (withdrawn)

* cited by examiner

*Primary Examiner*—Q. Janice Li
(74) *Attorney, Agent, or Firm*—Pierce Atwood LLP; Kevin M. Farrell

(57) ABSTRACT

Disclosed is a nucleic acid molecule comprising a first expressible sequence encoding a protein of interest or polypeptide of interest which contains an MHC Class II-presented epitope. In addition, the nucleic acid molecule comprises a second expressible nucleic acid sequence encoding an antigen presentation enhancing hybrid polypeptide. The antigen presentation enhancing hybrid polypeptide includes the following elements: i) an N-terminal element consisting essentially of 4–16 residues of the mammalian Ii-Key peptide LRMKLPKPPKPVSKMR (SEQ ID NO: 1) and non-N-terminal deletion modifications thereof that retain antigen presentation enhancing activity; ii) a C-terminal element comprising an MHC Class II-presented epitope in the form of a polypeptide or peptidomimetic structure which binds to the antigenic peptide binding site of an MHC class II molecule, the MHC Class II-presented epitope being contained in the protein of interest of step a); and iii) an intervening peptidyl structure linking the N-terminal and C-terminal elements of the hybrid, the peptidyl structure having a length of about 20 amino acids or less.

8 Claims, No Drawings

SEQUENCE LISTING

<160> NUMBER OF SEQ ID NOS: 905

<210> SEQ ID NO 1
<211> LENGTH: 16
<212> TYPE: PRT
<213> ORGANISM: Unknown Organism
<220> FEATURE:
<223> OTHER INFORMATION: Description of Unknown Organism: Mammalian
Ii-key peptide

<400> SEQUENCE: 1

Leu Arg Met Lys Leu Pro Lys Pro Pro Lys Pro Val Ser Lys Met Arg
1 5 10 15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
mammalian Ii-key peptide

<400> SEQUENCE: 2

Tyr Arg Met Lys Leu Pro Lys Pro Pro Lys Pro Val Ser Lys Met Arg
1 5 10 15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
Ii-key peptide

<400> SEQUENCE: 3

Leu Arg Met Lys
1

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
Ii-key peptide

<400> SEQUENCE: 4

Leu Arg Met Lys Leu Pro Lys
1 5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
Ii-key peptide

<400> SEQUENCE: 5

Leu Arg Met Lys Leu Pro Lys Ser
1 5

<210> SEQ ID NO 6
<211> LENGTH: 11
<212> TYPE: PRT
<213> ORGANISM: Artificial Sequence -continued

```
<220> FEATURE:
<223> OTHER INFORMATION: Description of Artificial Sequence: Synthetic
      Ii-key peptide

<400> SEQUENCE: 6

Leu Arg Met Lys Leu Pro Lys Ser Ala Lys Pro
  1               5                  10


<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key peptide

<400> SEQUENCE: 7

Leu Arg Met Lys Leu Pro Lys Ser Ala Lys Pro Val Ser Lys
  1               5                  10


<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      Ii-key peptide

<400> SEQUENCE: 8

Leu Arg Met Lys
  1


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      Ii-key peptide
<220> FEATURE:
<221> NAME/KEY: MOD_RES
<222> LOCATION: (5)
<223> OTHER INFORMATION: a-aminovaleric acid

<400> SEQUENCE: 9

Leu Arg Met Lys Xaa
  1               5


<210> SEQ ID NO 10
<211> LENGTH: 626
<212> TYPE: PRT
<213> ORGANISM: Arachis hypogaea

<400> SEQUENCE: 10

Met Arg Gly Arg Val Ser Pro Leu Met Leu Leu Leu Gly Ile Leu Val
  1               5                  10                  15

Leu Ala Ser Val Ser Ala Thr His Ala Lys Ser Ser Pro Tyr Gln Lys
             20                  25                  30

Lys Thr Glu Asn Pro Cys Ala Gln Arg Cys Leu Gln Ser Cys Gln Gln
         35                  40                  45

Glu Pro Asp Asp Leu Lys Gln Lys Ala Cys Glu Ser Arg Cys Thr Lys
     50                  55                  60

Leu Glu Tyr Asp Pro Arg Cys Val Tyr Asp Pro Arg Gly His Thr Gly
 65                  70                  75                  80

Thr Thr Asn Gln Arg Ser Pro Pro Gly Glu Arg Thr Arg Gly Arg Gln
```

-continued

```
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Glu Gly Ser Asn Arg Glu
                485                 490                 495

Val Arg Arg Tyr Thr Ala Arg Leu Lys Glu Gly Asp Val Phe Ile Met
            500                 505                 510
```

-continued

```
Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
        595                 600                 605

Glu Glu Asn Gln Gly Gly Lys Gly Pro Leu Leu Ser Ile Leu Lys Ala
    610                 615                 620

Phe Asn
625


<210> SEQ ID NO 11
<211> LENGTH: 9
<212> TYPE: PRT
<213> ORGANISM: Arachis hypogaea

<400> SEQUENCE: 11

Val Lys Pro Asp Lys Lys Asn Pro Gln
  1               5


<210> SEQ ID NO 12
<211> LENGTH: 9
<212> TYPE: PRT
<213> ORGANISM: Arachis hypogaea

<400> SEQUENCE: 12

Ile Arg Val Leu Gln Arg Phe Asp Gln
  1               5


<210> SEQ ID NO 13
<211> LENGTH: 9
<212> TYPE: PRT
<213> ORGANISM: Arachis hypogaea

<400> SEQUENCE: 13

Leu Gln Gly Phe Ser Arg Asn Thr Leu
  1               5


<210> SEQ ID NO 14
<211> LENGTH: 9
<212> TYPE: PRT
<213> ORGANISM: Arachis hypogaea

<400> SEQUENCE: 14

Met Val Ile Val Val Val Asn Lys Gly
  1               5


<210> SEQ ID NO 15
<211> LENGTH: 9
<212> TYPE: PRT
<213> ORGANISM: Arachis hypogaea

<400> SEQUENCE: 15

Val Val Asn Lys Gly Thr Gly Asn Leu
  1               5
```

<210> SEQ ID NO 16
<211> LENGTH: 9
<212> TYPE: PRT
<213> ORGANISM: Arachis hypogaea

<400> SEQUENCE: 16

Val Arg Arg Tyr Thr Ala Arg Leu Lys
1 5

<210> SEQ ID NO 17
<211> LENGTH: 9
<212> TYPE: PRT
<213> ORGANISM: Arachis hypogaea

<400> SEQUENCE: 17

Leu Gln Asn His Arg Ile Val Gln Ile
1 5

<210> SEQ ID NO 18
<211> LENGTH: 9
<212> TYPE: PRT
<213> ORGANISM: Arachis hypogaea

<400> SEQUENCE: 18

Phe Gln Asn Leu Gln Asn His Arg Ile
1 5

<210> SEQ ID NO 19
<211> LENGTH: 9
<212> TYPE: PRT
<213> ORGANISM: Arachis hypogaea

<400> SEQUENCE: 19

Met Leu Leu Leu Gly Ile Leu Val Leu
1 5

<210> SEQ ID NO 20
<211> LENGTH: 9
<212> TYPE: PRT
<213> ORGANISM: Arachis hypogaea

<400> SEQUENCE: 20

Leu Leu Gly Ile Leu Val Leu Ala Ser
1 5

<210> SEQ ID NO 21
<211> LENGTH: 9
<212> TYPE: PRT
<213> ORGANISM: Arachis hypogaea

<400> SEQUENCE: 21

Met Arg Gly Arg Val Ser Pro Leu Met
1 5

<210> SEQ ID NO 22
<211> LENGTH: 9
<212> TYPE: PRT
<213> ORGANISM: Arachis hypogaea

<400> SEQUENCE: 22

Leu Val Leu Ala Ser Val Ser Ala Thr
1 5

-continued

<210> SEQ ID NO 23
<211> LENGTH: 9
<212> TYPE: PRT
<213> ORGANISM: Arachis hypogaea

<400> SEQUENCE: 23

Leu Asp Met Met Leu Thr Cys Val Glu
1 5

<210> SEQ ID NO 24
<211> LENGTH: 9
<212> TYPE: PRT
<213> ORGANISM: Arachis hypogaea

<400> SEQUENCE: 24

Leu Arg Ile Pro Ser Gly Phe Ile Ser
1 5

<210> SEQ ID NO 25
<211> LENGTH: 9
<212> TYPE: PRT
<213> ORGANISM: Arachis hypogaea

<400> SEQUENCE: 25

Phe Ile Ser Tyr Ile Leu Asn Arg His
1 5

<210> SEQ ID NO 26
<211> LENGTH: 9
<212> TYPE: PRT
<213> ORGANISM: Arachis hypogaea

<400> SEQUENCE: 26

Leu Asn Arg His Asp Asn Gln Asn Leu
1 5

<210> SEQ ID NO 27
<211> LENGTH: 9
<212> TYPE: PRT
<213> ORGANISM: Arachis hypogaea

<400> SEQUENCE: 27

Phe Asn Ala Glu Phe Asn Glu Ile Arg
1 5

<210> SEQ ID NO 28
<211> LENGTH: 9
<212> TYPE: PRT
<213> ORGANISM: Arachis hypogaea

<400> SEQUENCE: 28

Phe Asn Glu Ile Arg Arg Val Leu Leu
1 5

<210> SEQ ID NO 29
<211> LENGTH: 9
<212> TYPE: PRT
<213> ORGANISM: Arachis hypogaea

<400> SEQUENCE: 29

Val Leu Leu Glu Glu Asn Ala Gly Gly
1 5

<210> SEQ ID NO 30
<211> LENGTH: 14

-continued

```
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 30

Leu Arg Met Lys Xaa Ile Arg Val Leu Gln Arg Phe Asp Gln
  1               5                  10


<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 31

Leu Arg Met Lys Xaa Met Arg Gly Arg Val Ser Pro Leu Met
  1               5                  10


<210> SEQ ID NO 32
<211> LENGTH: 28
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 32

Leu Arg Met Lys Xaa Met Arg Gly Arg Val Ser Pro Leu Met Leu Leu
  1               5                  10                  15

Leu Gly Ile Leu Val Leu Ala Ser Val Ser Ala Thr
             20                  25


<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 33

Leu Arg Met Lys Xaa Phe Gln Asn Leu Gln Asn His Arg Ile
  1               5                  10
```

-continued

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 34

Leu Arg Met Lys Xaa Phe Gln Asn Leu Gln Asn His Arg Ile Val Gln
1 5 10 15

Ile

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 35

Leu Arg Met Lys Xaa Leu Asp Met Met Leu Thr Cys Val Glu
1 5 10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 36

Leu Arg Met Lys Xaa Leu Arg Ile Pro Ser Gly Phe Ile Ser
1 5 10

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 37

-continued

```
Leu Arg Met Lys Xaa Leu Arg Ile Pro Ser Gly Phe Ile Ser Tyr Ile
  1               5                  10                  15

Leu Asn Arg His Asp Asn Gln Asn Leu
             20                  25


<210> SEQ ID NO 38
<211> LENGTH: 10
<212> TYPE: PRT
<213> ORGANISM: Arachis hypogaea

<400> SEQUENCE: 38

Asn Asn Phe Gly Lys Leu Phe Glu Val Lys
  1               5                  10


<210> SEQ ID NO 39
<211> LENGTH: 10
<212> TYPE: PRT
<213> ORGANISM: Arachis hypogaea

<400> SEQUENCE: 39

Ser Tyr Leu Gln Glu Phe Ser Arg Asn Thr
  1               5                  10


<210> SEQ ID NO 40
<211> LENGTH: 10
<212> TYPE: PRT
<213> ORGANISM: Arachis hypogaea

<400> SEQUENCE: 40

Arg Arg Tyr Thr Ala Arg Leu Lys Glu Gly
  1               5                  10


<210> SEQ ID NO 41
<211> LENGTH: 10
<212> TYPE: PRT
<213> ORGANISM: Arachis hypogaea

<400> SEQUENCE: 41

Phe Asn Ala Glu Phe Asn Glu Ile Arg Arg
  1               5                  10


<210> SEQ ID NO 42
<211> LENGTH: 10
<212> TYPE: PRT
<213> ORGANISM: Arachis hypogaea

<400> SEQUENCE: 42

Gly Thr Gly Asn Leu Glu Leu Val Ala Val
  1               5                  10


<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 43
```

-continued

```
Leu Arg Met Lys Xaa Asn Asn Phe Gly Lys Leu Phe Glu Val Lys Pro
  1               5                  10                  15

Asp Lys Lys Asn Pro Gln
             20


<210> SEQ ID NO 44
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 44

Leu Arg Met Lys Xaa Leu Gln Gly Phe Ser Arg Asn Thr Leu
  1               5                  10


<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 45

Leu Arg Met Lys Xaa Val Arg Arg Tyr Thr Ala Arg Leu Lys
  1               5                  10


<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 46

Leu Arg Met Lys Xaa Met Val Ile Val Val Val Asn Lys Gly
  1               5                  10


<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
```

-continued

<223> OTHER INFORMATION: C-term amidated

<400> SEQUENCE: 47

```
Leu Arg Met Lys Xaa Val Val Asn Lys Gly Thr Gly Asn Leu
  1               5                  10
```

<210> SEQ ID NO 48
<211> LENGTH: 23
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 48

```
Leu Arg Met Lys Xaa Met Val Ile Val Val Val Asn Lys Gly Thr Gly
  1               5                  10                  15

Asn Leu Glu Leu Val Ala Val
             20
```

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 49

```
Leu Arg Met Lys Xaa Phe Asn Ala Glu Phe Asn Glu Ile Arg
  1               5                  10
```

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 50

```
Leu Arg Met Lys Xaa Phe Asn Glu Ile Arg Arg Val Leu Leu
  1               5                  10
```

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:

-continued

```
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 51

Leu Arg Met Lys Xaa Val Leu Leu Glu Glu Asn Ala Gly Gly
  1               5                  10


<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      Ii-key/Ara h 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 52

Leu Arg Met Lys Xaa Phe Asn Ala Glu Phe Asn Glu Ile Arg Arg Val
  1               5                  10                  15

Leu Leu Glu Glu Asn Ala Gly Gly
             20


<210> SEQ ID NO 53
<211> LENGTH: 156
<212> TYPE: PRT
<213> ORGANISM: Arachis hypogaea

<400> SEQUENCE: 53

Met Ala Lys Leu Thr Ile Leu Val Ala Leu Ala Leu Phe Leu Leu Ala
  1               5                  10                  15

Ala His Ala Ser Ala Arg Gln Gln Trp Glu Leu Gln Gly Asp Arg Arg
             20                  25                  30

Cys Gln Ser Gln Leu Glu Arg Ala Asn Leu Arg Pro Cys Glu Gln His
         35                  40                  45

Leu Met Gln Lys Ile Gln Arg Asp Glu Asp Ser Tyr Glu Arg Asp Pro
     50                  55                  60

Tyr Ser Pro Ser Gln Asp Pro Tyr Ser Pro Ser Pro Tyr Asp Arg Arg
 65                  70                  75                  80

Gly Ala Gly Ser Ser Gln His Gln Glu Arg Cys Cys Asn Glu Leu Asn
                 85                  90                  95

Glu Phe Glu Asn Asn Gln Arg Cys Met Cys Glu Ala Leu Gln Gln Ile
            100                 105                 110

Met Glu Asn Gln Ser Asp Arg Leu Gln Gly Arg Gln Gln Glu Gln Gln
        115                 120                 125

Phe Lys Arg Glu Leu Arg Asn Leu Pro Gln Gln Cys Gly Leu Arg Ala
    130                 135                 140

Pro Gln Arg Cys Asp Leu Asp Val Glu Ser Gly Gly
145                 150                 155


<210> SEQ ID NO 54
<211> LENGTH: 15
<212> TYPE: PRT
<213> ORGANISM: Arachis hypogaea

<400> SEQUENCE: 54
```

```
Arg Gln Gln Trp Glu Leu Gln Gly Asp Arg Arg Cys Gln Ser Gln
  1               5                  10                  15
```

<210> SEQ ID NO 55
<211> LENGTH: 20
<212> TYPE: PRT
<213> ORGANISM: Arachis hypogaea

<400> SEQUENCE: 55

```
Leu Arg Pro Cys Glu Gln His Leu Met Gln Lys Ile Gln Arg Asp Glu
  1               5                  10                  15

Asp Ser Tyr Glu
             20
```

<210> SEQ ID NO 56
<211> LENGTH: 10
<212> TYPE: PRT
<213> ORGANISM: Arachis hypogaea

<400> SEQUENCE: 56

```
His Gln Glu Arg Cys Cys Asn Glu Leu Asn
  1               5                  10
```

<210> SEQ ID NO 57
<211> LENGTH: 10
<212> TYPE: PRT
<213> ORGANISM: Arachis hypogaea

<400> SEQUENCE: 57

```
Gln Arg Cys Met Cys Glu Ala Leu Gln Gln
  1               5                  10
```

<210> SEQ ID NO 58
<211> LENGTH: 10
<212> TYPE: PRT
<213> ORGANISM: Arachis hypogaea

<400> SEQUENCE: 58

```
Pro Gln Gln Cys Gly Leu Arg Ala Pro Gln
  1               5                  10
```

<210> SEQ ID NO 59
<211> LENGTH: 20
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 59

```
Leu Arg Met Lys Xaa Arg Gln Gln Trp Glu Leu Gln Gly Asp Arg Arg
  1               5                  10                  15

Cys Gln Ser Gln
             20
```

<210> SEQ ID NO 60
<211> LENGTH: 25
<212> TYPE: PRT
<213> ORGANISM: Artificial Sequence -continued

```
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 60

Leu Arg Met Lys Xaa Leu Arg Pro Cys Glu Gln His Leu Met Gln Lys
  1               5                  10                  15

Ile Gln Arg Asp Glu Asp Ser Tyr Glu
             20                  25


<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 61

Leu Arg Met Lys Xaa His Gln Glu Arg Cys Cys Asn Glu Leu Asn
  1               5                  10                  15


<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 62

Leu Arg Met Lys Xaa Gln Arg Cys Met Cys Glu Ala Leu Gln Gln
  1               5                  10                  15


<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 63

Leu Arg Met Lys Xaa Pro Gln Gln Cys Gly Leu Arg Ala Pro Gln
  1               5                  10                  15
```

-continued

```
<210> SEQ ID NO 64
<211> LENGTH: 9
<212> TYPE: PRT
<213> ORGANISM: Arachis hypogaea

<400> SEQUENCE: 64

Ile Leu Val Ala Leu Ala Leu Phe Leu
  1               5


<210> SEQ ID NO 65
<211> LENGTH: 9
<212> TYPE: PRT
<213> ORGANISM: Arachis hypogaea

<400> SEQUENCE: 65

Leu Gln Gly Asp Arg Arg Cys Gln Ser
  1               5


<210> SEQ ID NO 66
<211> LENGTH: 9
<212> TYPE: PRT
<213> ORGANISM: Arachis hypogaea

<400> SEQUENCE: 66

Leu Thr Ile Leu Val Ala Leu Ala Leu
  1               5


<210> SEQ ID NO 67
<211> LENGTH: 9
<212> TYPE: PRT
<213> ORGANISM: Arachis hypogaea

<400> SEQUENCE: 67

Leu Met Gln Lys Ile Gln Arg Asp Glu
  1               5


<210> SEQ ID NO 68
<211> LENGTH: 9
<212> TYPE: PRT
<213> ORGANISM: Arachis hypogaea

<400> SEQUENCE: 68

Leu Phe Leu Leu Ala Ala His Ala Ser
  1               5


<210> SEQ ID NO 69
<211> LENGTH: 9
<212> TYPE: PRT
<213> ORGANISM: Arachis hypogaea

<400> SEQUENCE: 69

Leu Val Ala Leu Ala Leu Phe Leu Leu
  1               5


<210> SEQ ID NO 70
<211> LENGTH: 9
<212> TYPE: PRT
<213> ORGANISM: Arachis hypogaea

<400> SEQUENCE: 70

Leu Arg Pro Cys Glu Gln His Leu Met
  1               5


<210> SEQ ID NO 71
<211> LENGTH: 9
```

-continued

```
<212> TYPE: PRT
<213> ORGANISM: Arachis hypogaea

<400> SEQUENCE: 71

Leu Ala Leu Phe Leu Leu Ala Ala His
  1               5


<210> SEQ ID NO 72
<211> LENGTH: 9
<212> TYPE: PRT
<213> ORGANISM: Arachis hypogaea

<400> SEQUENCE: 72

Leu Arg Asn Leu Pro Gln Gln Cys Gly
  1               5


<210> SEQ ID NO 73
<211> LENGTH: 9
<212> TYPE: PRT
<213> ORGANISM: Arachis hypogaea

<400> SEQUENCE: 73

Leu Glu Arg Ala Asn Leu Arg Pro Cys
  1               5


<210> SEQ ID NO 74
<211> LENGTH: 9
<212> TYPE: PRT
<213> ORGANISM: Arachis hypogaea

<400> SEQUENCE: 74

Phe Leu Leu Ala Ala His Ala Ser Ala
  1               5


<210> SEQ ID NO 75
<211> LENGTH: 9
<212> TYPE: PRT
<213> ORGANISM: Arachis hypogaea

<400> SEQUENCE: 75

Tyr Asp Arg Arg Gly Ala Gly Ser Ser
  1               5


<210> SEQ ID NO 76
<211> LENGTH: 9
<212> TYPE: PRT
<213> ORGANISM: Arachis hypogaea

<400> SEQUENCE: 76

Phe Glu Asn Asn Gln Arg Cys Met Cys
  1               5


<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 77
```

-continued

```
Leu Arg Met Lys Xaa Ile Leu Val Ala Leu Ala Leu Phe Leu
  1               5                  10


<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 78

Leu Arg Met Lys Xaa Leu Thr Ile Leu Val Ala Leu Ala Leu
  1               5                  10


<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 79

Leu Arg Met Lys Xaa Leu Val Ala Leu Ala Leu Phe Leu Leu
  1               5                  10


<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 80

Leu Arg Met Lys Xaa Leu Thr Ile Leu Val Ala Leu Ala Leu Phe Leu
  1               5                  10                  15

Leu


<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
```

-continued

<223> OTHER INFORMATION: C-term amidated

<400> SEQUENCE: 81

Leu Arg Met Lys Xaa Leu Arg Asn Leu Pro Gln Gln Cys Gly
1 5 10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 82

Leu Arg Met Lys Xaa Tyr Asp Arg Arg Gly Ala Gly Ser Ser
1 5 10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 83

Leu Arg Met Lys Xaa Phe Glu Asn Asn Gln Arg Cys Met Cys
1 5 10

<210> SEQ ID NO 84
<211> LENGTH: 10
<212> TYPE: PRT
<213> ORGANISM: Arachis hypogaea

<400> SEQUENCE: 84

His Ala Ser Ala Arg Gln Gln Trp Glu Leu
1 5 10

<210> SEQ ID NO 85
<211> LENGTH: 10
<212> TYPE: PRT
<213> ORGANISM: Arachis hypogaea

<400> SEQUENCE: 85

Gln Trp Glu Leu Gln Gly Asp Arg Arg Cys
1 5 10

<210> SEQ ID NO 86
<211> LENGTH: 10
<212> TYPE: PRT
<213> ORGANISM: Arachis hypogaea

<400> SEQUENCE: 86

Asp Arg Arg Cys Gln Ser Gln Leu Glu Arg
1 5 10

-continued

<210> SEQ ID NO 87
<211> LENGTH: 10
<212> TYPE: PRT
<213> ORGANISM: Arachis hypogaea

<400> SEQUENCE: 87

Leu Arg Pro Cys Glu Gln His Leu Met Gln
1 5 10

<210> SEQ ID NO 88
<211> LENGTH: 10
<212> TYPE: PRT
<213> ORGANISM: Arachis hypogaea

<400> SEQUENCE: 88

Lys Ile Gln Arg Asp Glu Asp Ser Tyr Glu
1 5 10

<210> SEQ ID NO 89
<211> LENGTH: 10
<212> TYPE: PRT
<213> ORGANISM: Arachis hypogaea

<400> SEQUENCE: 89

Lys Arg Glu Leu Arg Asn Leu Pro Gln Gln
1 5 10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
hybrid peptide containing predicted MHC Class
II Ara h 2 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 90

Leu Arg Met Lys Xaa Leu Gln Gly Asp Arg Arg Cys Gln Ser
1 5 10

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
hybrid peptide containing predicted MHC Class
II Ara h 2 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 91

Leu Arg Met Lys Xaa Leu Met Gln Lys Ile Gln Arg Asp Glu
1 5 10

<210> SEQ ID NO 92
<211> LENGTH: 14

-continued

<212> TYPE: PRT
<213> ORGANISM: Artificial Sequence
<220> FEATURE:
<223> OTHER INFORMATION: Description of Artificial Sequence: Synthetic hybrid peptide containing predicted MHC Class II Ara h 2 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 92

```
Leu Arg Met Lys Xaa Leu Arg Pro Cys Glu Gln His Leu Met
  1               5                  10
```

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic hybrid peptide containing predicted MHC Class II Ara h 2 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 93

```
Leu Arg Met Lys Xaa Leu Arg Pro Cys Glu Gln His Leu Met Lys Ile
  1               5                  10                  15

Gln Arg Asp Glu
             20
```

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic hybrid peptide containing predicted MHC Class II Ara h 2 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 94

```
Leu Arg Met Lys Xaa Leu Glu Arg Ala Asn Leu Arg Pro Cys Glu Gln
  1               5                  10                  15

His Leu Met Gln
             20
```

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic hybrid peptide containing predicted MHC Class II Ara h 2 epitope
<220> FEATURE:
<221> NAME/KEY: MOD_RES
<222> LOCATION: (5)
<223> OTHER INFORMATION: a-aminovaleric acid -continued
<220> FEATURE:
<223> OTHER INFORMATION: C-term amidated

<400> SEQUENCE: 95

```
Leu Arg Met Lys Xaa Phe Leu Leu Ala Ala His Ala Ser Ala Arg Gln
  1               5                  10                  15

Gln Trp Glu Leu
             20
```

<210> SEQ ID NO 96
<211> LENGTH: 507
<212> TYPE: PRT
<213> ORGANISM: Arachis hypogaea

<400> SEQUENCE: 96

```
Arg Gln Gln Pro Glu Glu Asn Ala Cys Gln Phe Gln Arg Leu Asn Ala
  1               5                  10                  15

Gln Arg Pro Asp Asn Arg Ile Glu Ser Glu Gly Gly Tyr Ile Glu Thr
             20                  25                  30

Trp Asn Pro Asn Asn Gln Glu Phe Glu Cys Ala Gly Val Ala Leu Ser
         35                  40                  45

Arg Leu Val Leu Arg Arg Asn Ala Leu Arg Arg Pro Phe Tyr Ser Asn
     50                  55                  60

Ala Pro Gln Glu Ile Phe Ile Gln Gln Gly Arg Gly Tyr Phe Gly Leu
 65                  70                  75                  80

Ile Phe Pro Gly Cys Pro Arg His Tyr Glu Glu Pro His Thr Gln Gly
                 85                  90                  95

Arg Arg Ser Gln Ser Gln Arg Pro Pro Arg Arg Leu Gln Gly Glu Asp
            100                 105                 110

Gln Ser Gln Gln Gln Arg Asp Ser His Gln Lys Val His Arg Phe Asp
        115                 120                 125

Glu Gly Asp Leu Ile Ala Val Pro Thr Gly Val Ala Phe Trp Leu Tyr
    130                 135                 140

Asn Asp His Asp Thr Asp Val Val Ala Val Ser Leu Thr Asp Thr Asn
145                 150                 155                 160

Asn Asn Asp Asn Gln Leu Asp Gln Phe Pro Arg Arg Phe Asn Leu Ala
                165                 170                 175

Gly Asn Thr Glu Gln Glu Phe Leu Arg Tyr Gln Gln Gln Ser Arg Gln
            180                 185                 190

Ser Arg Arg Arg Ser Leu Pro Tyr Ser Pro Tyr Ser Pro Gln Ser Gln
        195                 200                 205

Pro Arg Gln Glu Glu Arg Glu Phe Ser Pro Arg Gly Gln His Ser Arg
    210                 215                 220

Arg Glu Arg Ala Gly Gln Glu Glu Glu Asn Glu Gly Gly Asn Ile Phe
225                 230                 235                 240

Ser Gly Phe Thr Pro Glu Phe Leu Glu Gln Ala Phe Gln Val Asp Asp
                245                 250                 255

Arg Gln Ile Val Gln Asn Leu Arg Gly Glu Thr Glu Ser Glu Glu Glu
            260                 265                 270

Gly Ala Ile Val Thr Val Arg Gly Gly Leu Arg Ile Leu Ser Pro Asp
        275                 280                 285

Arg Lys Arg Arg Ala Asp Glu Glu Glu Glu Tyr Asp Glu Asp Glu Tyr
    290                 295                 300

Glu Tyr Asp Glu Glu Asp Arg Arg Arg Gly Arg Gly Ser Arg Gly Arg
305                 310                 315                 320
```

-continued

```
Gly Asn Gly Ile Glu Glu Thr Ile Cys Thr Ala Ser Ala Lys Lys Asn
                325                 330                 335

Ile Gly Arg Asn Arg Ser Pro Asp Ile Tyr Asn Pro Gln Ala Gly Ser
            340                 345                 350

Leu Lys Thr Ala Asn Asp Leu Asn Leu Leu Ile Leu Arg Trp Leu Gly
        355                 360                 365

Pro Ser Ala Glu Tyr Gly Asn Leu Tyr Arg Asn Ala Leu Phe Val Ala
    370                 375                 380

His Tyr Asn Thr Asn Ala His Ser Ile Ile Tyr Arg Leu Arg Gly Arg
385                 390                 395                 400

Ala His Val Gln Val Val Asp Ser Asn Gly Asn Arg Val Tyr Asp Glu
                405                 410                 415

Glu Leu Gln Glu Gly His Val Leu Val Val Pro Gln Asn Phe Ala Val
            420                 425                 430

Ala Gly Lys Ser Gln Ser Glu Asn Phe Glu Tyr Val Ala Phe Lys Thr
        435                 440                 445

Asp Ser Arg Pro Ser Ile Ala Asn Leu Ala Gly Glu Asn Ser Val Ile
    450                 455                 460

Asp Asn Leu Pro Glu Glu Val Val Ala Asn Ser Tyr Gly Leu Gln Arg
465                 470                 475                 480

Glu Gln Ala Arg Gln Leu Lys Asn Asn Asn Pro Phe Lys Phe Phe Val
                485                 490                 495

Pro Pro Ser Gln Gln Ser Pro Arg Ala Val Ala
            500                 505


<210> SEQ ID NO 97
<211> LENGTH: 9
<212> TYPE: PRT
<213> ORGANISM: Arachis hypogaea

<400> SEQUENCE: 97

Tyr Arg Leu Arg Gly Arg Ala His Val
  1               5


<210> SEQ ID NO 98
<211> LENGTH: 9
<212> TYPE: PRT
<213> ORGANISM: Arachis hypogaea

<400> SEQUENCE: 98

Ile Ile Tyr Arg Leu Arg Gly Arg Ala
  1               5


<210> SEQ ID NO 99
<211> LENGTH: 9
<212> TYPE: PRT
<213> ORGANISM: Arachis hypogaea

<400> SEQUENCE: 99

Phe Lys Thr Asp Ser Arg Pro Ser Ile
  1               5


<210> SEQ ID NO 100
<211> LENGTH: 9
<212> TYPE: PRT
<213> ORGANISM: Arachis hypogaea

<400> SEQUENCE: 100

Val Arg Gly Gly Leu Arg Ile Leu Ser
  1               5
```

-continued

<210> SEQ ID NO 101
<211> LENGTH: 9
<212> TYPE: PRT
<213> ORGANISM: Arachis hypogaea

<400> SEQUENCE: 101

Ile Val Thr Val Arg Gly Gly Leu Arg
1 5

<210> SEQ ID NO 102
<211> LENGTH: 9
<212> TYPE: PRT
<213> ORGANISM: Arachis hypogaea

<400> SEQUENCE: 102

Leu Arg Ile Leu Ser Pro Asp Arg Lys
1 5

<210> SEQ ID NO 103
<211> LENGTH: 9
<212> TYPE: PRT
<213> ORGANISM: Arachis hypogaea

<400> SEQUENCE: 103

Phe Gln Val Asp Asp Arg Gln Ile Val
1 5

<210> SEQ ID NO 104
<211> LENGTH: 9
<212> TYPE: PRT
<213> ORGANISM: Arachis hypogaea

<400> SEQUENCE: 104

Leu Arg Trp Leu Gly Pro Ser Ala Glu
1 5

<210> SEQ ID NO 105
<211> LENGTH: 9
<212> TYPE: PRT
<213> ORGANISM: Arachis hypogaea

<400> SEQUENCE: 105

Leu Ile Leu Arg Trp Leu Gly Pro Ser
1 5

<210> SEQ ID NO 106
<211> LENGTH: 9
<212> TYPE: PRT
<213> ORGANISM: Arachis hypogaea

<400> SEQUENCE: 106

Phe Asn Leu Ala Gly Asn Thr Glu Gln
1 5

<210> SEQ ID NO 107
<211> LENGTH: 9
<212> TYPE: PRT
<213> ORGANISM: Arachis hypogaea

<400> SEQUENCE: 107

Leu Val Val Pro Gln Asn Phe Ala Val
1 5

-continued

<210> SEQ ID NO 108
<211> LENGTH: 9
<212> TYPE: PRT
<213> ORGANISM: Arachis hypogaea

<400> SEQUENCE: 108

Val Gln Val Val Asp Ser Asn Gly Asn
1 5

<210> SEQ ID NO 109
<211> LENGTH: 9
<212> TYPE: PRT
<213> ORGANISM: Arachis hypogaea

<400> SEQUENCE: 109

Val Val Asp Ser Asn Gly Asn Arg Val
1 5

<210> SEQ ID NO 110
<211> LENGTH: 9
<212> TYPE: PRT
<213> ORGANISM: Arachis hypogaea

<400> SEQUENCE: 110

Phe Val Ala His Tyr Asn Thr Asn Ala
1 5

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 111

Leu Arg Met Lys Xaa Ile Ile Tyr Arg Leu Arg Gly Arg Ala
1 5 10

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 112

Leu Arg Met Lys Xaa Tyr Arg Leu Arg Gly Arg Ala His Val
1 5 10

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic -continued Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 113

Leu Arg Met Lys Xaa Ile Ile Tyr Arg Leu Arg Gly Arg Ala His Val
1 5 10 15

<210> SEQ ID NO 114
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 114

Leu Arg Met Lys Xaa Phe Lys Thr Asp Ser Arg Pro Ser Ile
1 5 10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 115

Leu Arg Met Lys Xaa Leu Ile Leu Arg Trp Leu Gly Pro Ser
1 5 10

<210> SEQ ID NO 116
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 116

Leu Arg Met Lys Xaa Leu Arg Trp Leu Gly Pro Ser Ala Glu
1 5 10

<210> SEQ ID NO 117
<211> LENGTH: 16
<212> TYPE: PRT
<213> ORGANISM: Artificial Sequence
<220> FEATURE:

-continued

<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 117

Leu Arg Met Lys Xaa Leu Ile Leu Arg Trp Leu Gly Pro Ser Ala Glu
  1               5                  10                  15

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 118

Leu Arg Met Lys Xaa Phe Gln Val Asp Asp Arg Gln Ile Val
  1               5                  10

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 119

Leu Arg Met Lys Xaa Phe Asn Leu Ala Gly Asn Thr Glu Gln
  1               5                  10

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 120

Leu Arg Met Lys Xaa Leu Val Val Pro Gln Asn Phe Ala Val
  1               5                  10

<210> SEQ ID NO 121
<211> LENGTH: 14
<212> TYPE: PRT
<213> ORGANISM: Artificial Sequence -continued

```
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 121

Leu Arg Met Lys Xaa Val Gln Val Val Asp Ser Asn Gly Asn
  1               5                  10


<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 122

Leu Arg Met Lys Xaa Val Val Asp Ser Asn Gly Asn Arg Val
  1               5                  10


<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 123

Leu Arg Met Lys Xaa Val Gln Val Val Asp Ser Asn Gly Asn Arg Val
  1               5                  10                  15


<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Ara h 3 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 124

Leu Arg Met Lys Xaa Phe Val Ala His Tyr Asn Thr Asn Ala
  1               5                  10


<210> SEQ ID NO 125
<211> LENGTH: 15
<212> TYPE: PRT
```

-continued

<213> ORGANISM: Arachis hypogaea

<400> SEQUENCE: 125

Val Thr Val Arg Gly Gly Leu Arg Ile Leu Ser Pro Asp Arg Lys
1 5 10 15

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic hybrid peptide containing predicted Class II Ara h 3 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 126

Leu Arg Met Lys Xaa Ile Val Thr Val Arg Gly Gly Leu Arg
1 5 10

<210> SEQ ID NO 127
<211> LENGTH: 14
<212> TYPE: PRT
<213> ORGANISM: Artificial Sequence
<220> FEATURE:
<223> OTHER INFORMATION: Description of Artificial Sequence: Synthetic hybrid peptide containing predicted Class II Ara h 3 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 127

Leu Arg Met Lys Xaa Val Arg Gly Gly Leu Arg Ile Leu Ser
1 5 10

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic hybrid peptide containing predicted Class II Ara h 3 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 128

Leu Arg Met Lys Xaa Ile Val Thr Val Arg Gly Gly Leu Arg Ile Leu
1 5 10 15

Ser Pro Asp Arg Lys
20

<210> SEQ ID NO 129
<211> LENGTH: 21
<212> TYPE: PRT
<213> ORGANISM: Artificial Sequence
<220> FEATURE:

-continued

<223> OTHER INFORMATION: Description of Artificial Sequence: Synthetic
      hybrid peptide containing predicted Class II
      Ara h 3 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 129

Leu Arg Met Lys Xaa Ile Val Thr Val Arg Gly Gly Leu Arg Ile Leu
  1               5                  10                  15

Ser Pro Asp Arg Lys
             20

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      Th1-skewing peptide

<400> SEQUENCE: 130

Ile Ser Gln Ala Val His Ala Ala His Ala Glu Ile Asn Ala Ala Gly
  1               5                  10                  15

Arg

<210> SEQ ID NO 131
<211> LENGTH: 17
<212> TYPE: PRT
<213> ORGANISM: Unknown Organism
<220> FEATURE:
<223> OTHER INFORMATION: Description of Unknown Organism: Wild type
      peptide

<400> SEQUENCE: 131

Ile Ser Gln Ala Val His Ala Ala His Ala Glu Ile Asn Glu Ala Gly
  1               5                  10                  15

Arg

<210> SEQ ID NO 132
<211> LENGTH: 17
<212> TYPE: PRT
<213> ORGANISM: Felis domesticus

<400> SEQUENCE: 132

Leu Phe Leu Thr Gly Thr Pro Asp Glu Tyr Val Glu Gln Val Ala Gln
  1               5                  10                  15

Tyr

<210> SEQ ID NO 133
<211> LENGTH: 16
<212> TYPE: PRT
<213> ORGANISM: Felis domesticus

<400> SEQUENCE: 133

Glu Gln Val Ala Gln Tyr Lys Ala Leu Pro Val Val Leu Glu Asn Ala
  1               5                  10                  15

<210> SEQ ID NO 134
<211> LENGTH: 17
<212> TYPE: PRT
<213> ORGANISM: Felis domesticus -continued

<400> SEQUENCE: 134

Lys Ala Leu Pro Val Val Leu Glu Asn Ala Arg Ile Leu Lys Asn Cys
1 5 10 15

Val

<210> SEQ ID NO 135
<211> LENGTH: 88
<212> TYPE: PRT
<213> ORGANISM: Felis domesticus

<400> SEQUENCE: 135

Met Leu Asp Ala Ala Leu Pro Pro Cys Pro Thr Val Ala Ala Thr Ala
1 5 10 15

Asp Cys Glu Ile Cys Pro Ala Val Lys Arg Asp Val Asp Leu Phe Leu
20 25 30

Thr Gly Thr Pro Asp Glu Tyr Val Glu Gln Val Ala Gln Tyr Lys Ala
35 40 45

Leu Pro Val Val Leu Glu Asn Ala Arg Ile Leu Lys Asn Cys Val Asp
50 55 60

Ala Lys Met Thr Glu Glu Asp Lys Glu Asn Ala Leu Ser Leu Leu Asp
65 70 75 80

Lys Ile Tyr Thr Ser Pro Leu Cys
85

<210> SEQ ID NO 136
<211> LENGTH: 109
<212> TYPE: PRT
<213> ORGANISM: Felis domesticus

<400> SEQUENCE: 136

Met Arg Gly Ala Leu Leu Val Leu Ala Leu Leu Val Thr Gln Ala Leu
1 5 10 15

Gly Val Lys Met Ala Glu Thr Cys Pro Ile Phe Tyr Asp Val Phe Phe
20 25 30

Ala Val Ala Asn Gly Asn Glu Leu Leu Leu Asp Leu Ser Leu Thr Lys
35 40 45

Val Asn Ala Thr Glu Pro Glu Arg Thr Ala Met Lys Lys Ile Gln Asp
50 55 60

Cys Tyr Val Glu Asn Gly Leu Ile Ser Arg Val Leu Asp Gly Leu Val
65 70 75 80

Met Thr Thr Ile Ser Ser Ser Lys Asp Cys Met Gly Glu Ala Val Gln
85 90 95

Asn Thr Val Glu Asp Leu Lys Leu Asn Thr Leu Gly Arg
100 105

<210> SEQ ID NO 137
<211> LENGTH: 9
<212> TYPE: PRT
<213> ORGANISM: Felis domesticus

<400> SEQUENCE: 137

Tyr Lys Ala Leu Pro Val Val Leu Glu
1 5

<210> SEQ ID NO 138
<211> LENGTH: 9
<212> TYPE: PRT
<213> ORGANISM: Felis domesticus -continued

<400> SEQUENCE: 138

Val Val Leu Glu Asn Ala Arg Ile Leu
1 5

<210> SEQ ID NO 139
<211> LENGTH: 9
<212> TYPE: PRT
<213> ORGANISM: Felis domesticus

<400> SEQUENCE: 139

Val Ala Gln Tyr Lys Ala Leu Pro Val
1 5

<210> SEQ ID NO 140
<211> LENGTH: 9
<212> TYPE: PRT
<213> ORGANISM: Felis domesticus

<400> SEQUENCE: 140

Tyr Val Glu Gln Val Ala Gln Tyr Lys
1 5

<210> SEQ ID NO 141
<211> LENGTH: 9
<212> TYPE: PRT
<213> ORGANISM: Felis domesticus

<400> SEQUENCE: 141

Val Lys Arg Asp Val Asp Leu Phe Leu
1 5

<210> SEQ ID NO 142
<211> LENGTH: 9
<212> TYPE: PRT
<213> ORGANISM: Felis domesticus

<400> SEQUENCE: 142

Ile Cys Pro Ala Val Lys Arg Asp Val
1 5

<210> SEQ ID NO 143
<211> LENGTH: 9
<212> TYPE: PRT
<213> ORGANISM: Felis domesticus

<400> SEQUENCE: 143

Leu Ser Leu Leu Asp Lys Ile Tyr Thr
1 5

<210> SEQ ID NO 144
<211> LENGTH: 9
<212> TYPE: PRT
<213> ORGANISM: Felis domesticus

<400> SEQUENCE: 144

Leu Asp Lys Ile Tyr Thr Ser Pro Leu
1 5

<210> SEQ ID NO 145
<211> LENGTH: 9
<212> TYPE: PRT
<213> ORGANISM: Felis domesticus

<400> SEQUENCE: 145

-continued

```
Leu Phe Leu Thr Gly Thr Pro Asp Glu
  1               5


<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 146

Leu Arg Met Lys Xaa Val Ala Gln Tyr Lys Ala Leu Pro Val
  1               5                  10


<210> SEQ ID NO 147
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 147

Leu Arg Met Lys Xaa Tyr Lys Ala Leu Pro Val Val Leu Glu
  1               5                  10


<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 148

Leu Arg Met Lys Xaa Val Val Leu Glu Asn Ala Arg Ile Leu
  1               5                  10


<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated
```

-continued

<400> SEQUENCE: 149

Leu Arg Met Lys Xaa Tyr Val Glu Gln Val Ala Gln Tyr Lys
1 5 10

<210> SEQ ID NO 150
<211> LENGTH: 26
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 150

Leu Arg Met Lys Xaa Tyr Val Glu Gln Val Ala Gln Tyr Lys Ala Leu
1 5 10 15

Pro Val Val Leu Glu Asn Ala Arg Ile Leu
20 25

<210> SEQ ID NO 151
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 151

Leu Arg Met Lys Xaa Ile Cys Pro Ala Val Lys Arg Asp Val
1 5 10

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 152

Leu Arg Met Lys Xaa Val Lys Arg Asp Val Asp Leu Phe Leu
1 5 10

<210> SEQ ID NO 153
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)

-continued

```
<223> OTHER INFORMATION: a-aminovaleric acid
<220> FEATURE:
<223> OTHER INFORMATION: C-term amidated

<400> SEQUENCE: 153

Leu Arg Met Lys Xaa Leu Phe Leu Thr Gly Thr Pro Asp Glu
  1               5                   10


<210> SEQ ID NO 154
<211> LENGTH: 24
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 154

Leu Arg Met Lys Xaa Ile Cys Pro Ala Val Lys Arg Asp Val Asp Leu
  1               5                   10                  15

Phe Leu Thr Gly Thr Pro Asp Glu
             20


<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 155

Leu Arg Met Lys Xaa Leu Ser Leu Leu Asp Lys Ile Tyr Thr
  1               5                   10


<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 156

Leu Arg Met Lys Xaa Leu Asp Lys Ile Tyr Thr Ser Pro Leu
  1               5                   10


<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
```

-continued

Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 157

Leu Arg Met Lys Xaa Leu Ser Leu Leu Asp Lys Ile Tyr Thr Ser Pro
1 5 10 15

Leu

<210> SEQ ID NO 158
<211> LENGTH: 17
<212> TYPE: PRT
<213> ORGANISM: Felis domesticus

<400> SEQUENCE: 158

Glu Ile Cys Pro Ala Val Lys Arg Asp Val Asp Leu Phe Leu Thr Gly
1 5 10 15

Thr

<210> SEQ ID NO 159
<211> LENGTH: 17
<212> TYPE: PRT
<213> ORGANISM: Felis domesticus

<400> SEQUENCE: 159

Leu Phe Leu Thr Gly Thr Pro Asp Glu Tyr Val Glu Gln Val Ala Gln
1 5 10 15

Tyr

<210> SEQ ID NO 160
<211> LENGTH: 16
<212> TYPE: PRT
<213> ORGANISM: Felis domesticus

<400> SEQUENCE: 160

Glu Gln Val Ala Gln Tyr Lys Ala Leu Pro Val Val Leu Glu Asn Ala
1 5 10 15

<210> SEQ ID NO 161
<211> LENGTH: 17
<212> TYPE: PRT
<213> ORGANISM: Felis domesticus

<400> SEQUENCE: 161

Lys Ala Leu Pro Val Val Leu Glu Asn Ala Arg Ile Leu Lys Asn Cys
1 5 10 15

Val

<210> SEQ ID NO 162
<211> LENGTH: 17
<212> TYPE: PRT
<213> ORGANISM: Felis domesticus

<400> SEQUENCE: 162

Arg Ile Leu Lys Asn Cys Val Asp Ala Lys Met Thr Glu Glu Asp Lys
1 5 10 15

Glu

-continued

<210> SEQ ID NO 163
<211> LENGTH: 16
<212> TYPE: PRT
<213> ORGANISM: Felis domesticus

<400> SEQUENCE: 163

Lys Met Thr Glu Glu Asp Lys Glu Asn Ala Leu Ser Leu Leu Asp Lys
1 5 10 15

<210> SEQ ID NO 164
<211> LENGTH: 16
<212> TYPE: PRT
<213> ORGANISM: Felis domesticus

<400> SEQUENCE: 164

Lys Glu Asn Ala Leu Ser Val Leu Asp Lys Ile Tyr Thr Ser Pro Leu
1 5 10 15

<210> SEQ ID NO 165
<211> LENGTH: 22
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 165

Leu Arg Met Lys Xaa Leu Phe Leu Thr Gly Thr Pro Asp Glu Tyr Val
1 5 10 15

Glu Gln Val Ala Gln Tyr
20

<210> SEQ ID NO 166
<211> LENGTH: 21
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 166

Leu Arg Met Lys Xaa Glu Gln Val Ala Gln Tyr Lys Ala Leu Pro Val
1 5 10 15

Val Leu Glu Asn Ala
20

<210> SEQ ID NO 167
<211> LENGTH: 22
<212> TYPE: PRT
<213> ORGANISM: Artificial Sequence
<220> FEATURE:
<223> OTHER INFORMATION: Description of Artificial Sequence: Synthetic Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid -continued
<220> FEATURE:
<223> OTHER INFORMATION: C-term amidated

<400> SEQUENCE: 167

Leu Arg Met Lys Xaa Lys Ala Leu Pro Val Val Leu Glu Asn Ala Arg
1 5 10 15

Ile Leu Lys Asn Cys Val
20

<210> SEQ ID NO 168
<211> LENGTH: 22
<212> TYPE: PRT
<213> ORGANISM: Artificial Sequence
<220> FEATURE:
<223> OTHER INFORMATION: Description of Artificial Sequence: Synthetic
Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 168

Leu Arg Met Lys Xaa Arg Ile Leu Lys Asn Cys Val Asp Ala Lys Met
1 5 10 15

Thr Glu Glu Asp Lys Glu
20

<210> SEQ ID NO 169
<211> LENGTH: 37
<212> TYPE: PRT
<213> ORGANISM: Artificial Sequence
<220> FEATURE:
<223> OTHER INFORMATION: Description of Artificial Sequence: Synthetic
Ii-key/Fel d 1 (chain 1) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 169

Leu Arg Met Lys Xaa Gln Val Ala Gln Tyr Lys Ala Leu Pro Val Val
1 5 10 15

Leu Glu Asn Ala Arg Ile Leu Lys Asn Cys Val Asp Ala Lys Met Thr
20 25 30

Glu Glu Asp Lys Glu
35

<210> SEQ ID NO 170
<211> LENGTH: 9
<212> TYPE: PRT
<213> ORGANISM: Felis domesticus

<400> SEQUENCE: 170

Leu Leu Val Thr Gln Ala Leu Gly Val
1 5

<210> SEQ ID NO 171
<211> LENGTH: 9
<212> TYPE: PRT
<213> ORGANISM: Felis domesticus

<400> SEQUENCE: 171

-continued

```
Leu Leu Leu Asp Leu Ser Leu Thr Lys
  1               5


<210> SEQ ID NO 172
<211> LENGTH: 9
<212> TYPE: PRT
<213> ORGANISM: Felis domesticus

<400> SEQUENCE: 172

Leu Val Met Thr Thr Ile Ser Ser Ser
  1               5


<210> SEQ ID NO 173
<211> LENGTH: 9
<212> TYPE: PRT
<213> ORGANISM: Felis domesticus

<400> SEQUENCE: 173

Val Lys Met Ala Glu Thr Cys Pro Ile
  1               5


<210> SEQ ID NO 174
<211> LENGTH: 9
<212> TYPE: PRT
<213> ORGANISM: Felis domesticus

<400> SEQUENCE: 174

Leu Val Leu Ala Leu Leu Val Thr Gln
  1               5


<210> SEQ ID NO 175
<211> LENGTH: 9
<212> TYPE: PRT
<213> ORGANISM: Felis domesticus

<400> SEQUENCE: 175

Leu Leu Val Leu Ala Leu Leu Val Thr
  1               5


<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 176

Leu Arg Met Lys Xaa Leu Leu Val Thr Gln Ala Leu Gly Val
  1               5                   10


<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
```

-continued

<220> FEATURE:
<223> OTHER INFORMATION: C-term amidated

<400> SEQUENCE: 177

Leu Arg Met Lys Xaa Leu Val Leu Ala Leu Leu Val Thr Gln
1 5 10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 178

Leu Arg Met Lys Xaa Leu Leu Val Leu Ala Leu Leu Val Thr
1 5 10

<210> SEQ ID NO 179
<211> LENGTH: 19
<212> TYPE: PRT
<213> ORGANISM: Artificial Sequence
<220> FEATURE:
<223> OTHER INFORMATION: Description of Artificial Sequence: Synthetic
Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 179

Leu Arg Met Lys Xaa Leu Leu Val Leu Ala Leu Leu Val Thr Gln Ala
1 5 10 15

Leu Gly Val

<210> SEQ ID NO 180
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 180

Leu Arg Met Lys Xaa Val Lys Met Ala Glu Thr Cys Pro Ile
1 5 10

<210> SEQ ID NO 181
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Fel d (chain 2) hybrid peptide
<220> FEATURE:

-continued

<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 181

Leu Arg Met Lys Xaa Leu Leu Leu Asp Leu Ser Leu Thr Lys
1 5 10

<210> SEQ ID NO 182
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Fel d (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 182

Leu Arg Met Lys Xaa Leu Val Met Thr Thr Ile Ser Ser Ser
1 5 10

<210> SEQ ID NO 183
<211> LENGTH: 16
<212> TYPE: PRT
<213> ORGANISM: Felis domesticus

<400> SEQUENCE: 183

Leu Thr Lys Val Asn Ala Thr Glu Pro Glu Arg Thr Ala Met Lys Lys
1 5 10 15

<210> SEQ ID NO 184
<211> LENGTH: 16
<212> TYPE: PRT
<213> ORGANISM: Felis domesticus

<400> SEQUENCE: 184

Thr Ala Met Lys Lys Ile Gln Asp Cys Tyr Val Glu Asn Gly Leu Ile
1 5 10 15

<210> SEQ ID NO 185
<211> LENGTH: 16
<212> TYPE: PRT
<213> ORGANISM: Felis domesticus

<400> SEQUENCE: 185

Cys Tyr Val Glu Asn Gly Leu Ile Ser Arg Val Leu Asp Gly Leu Val
1 5 10 15

<210> SEQ ID NO 186
<211> LENGTH: 16
<212> TYPE: PRT
<213> ORGANISM: Felis domesticus

<400> SEQUENCE: 186

Ile Ser Ser Ser Lys Asp Cys Met Gly Glu Ala Val Gln Asn Thr Val
1 5 10 15

<210> SEQ ID NO 187
<211> LENGTH: 16
<212> TYPE: PRT

-continued

```
<213> ORGANISM: Felis domesticus

<400> SEQUENCE: 187

Ala Val Gln Asn Thr Val Glu Asp Leu Lys Leu Asn Thr Leu Gly Arg
  1               5                  10                  15


<210> SEQ ID NO 188
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 188

Leu Arg Met Lys Xaa Leu Thr Lys Val Asn Ala Thr Glu Pro Glu Arg
  1               5                  10                  15

Thr Ala Met Lys Lys
             20


<210> SEQ ID NO 189
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 189

Leu Arg Met Lys Xaa Thr Ala Met Lys Lys Ile Gln Asp Cys Tyr Val
  1               5                  10                  15

Glu Asn Gly Leu Ile
             20


<210> SEQ ID NO 190
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/Fel d 1 (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 190

Leu Arg Met Lys Xaa Cys Tyr Val Glu Asn Gly Leu Ile Ser Arg Val
  1               5                  10                  15

Leu Asp Gly Leu Val
             20


<210> SEQ ID NO 191
<211> LENGTH: 21
```

-continued

<212> TYPE: PRT
<213> ORGANISM: Artificial Sequence
<220> FEATURE:
<223> OTHER INFORMATION: Description of Artificial Sequence: Synthetic
Ii-key/Fel d 1 (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 191

Leu Arg Met Lys Xaa Ile Ser Ser Ser Lys Asp Cys Met Gly Glu Ala
1 5 10 15

Val Gln Asn Thr Val
20

<210> SEQ ID NO 192
<211> LENGTH: 29
<212> TYPE: PRT
<213> ORGANISM: Artificial Sequence
<220> FEATURE:
<223> OTHER INFORMATION: Description of Artificial Sequence: Synthetic
Ii-key/Fel d 1 (chain 2) hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 192

Leu Arg Met Lys Xaa Thr Ala Met Lys Lys Ile Gln Asp Cys Tyr Val
1 5 10 15

Glu Asn Gly Leu Ile Ser Arg Val Leu Asp Gly Leu Val
20 25

<210> SEQ ID NO 193
<211> LENGTH: 263
<212> TYPE: PRT
<213> ORGANISM: Pheleum pratense

<400> SEQUENCE: 193

Met Ala Ser Ser Ser Ser Val Leu Leu Val Val Val Leu Phe Ala Val
1 5 10 15

Phe Leu Gly Ser Ala Tyr Gly Ile Pro Lys Val Pro Pro Gly Pro Asn
20 25 30

Ile Thr Ala Thr Tyr Gly Asp Lys Trp Leu Asp Ala Lys Ser Thr Trp
35 40 45

Tyr Gly Lys Pro Thr Gly Ala Gly Pro Lys Asp Asn Gly Gly Ala Cys
50 55 60

Gly Tyr Lys Asp Val Asp Lys Pro Pro Phe Ser Gly Met Thr Gly Cys
65 70 75 80

Gly Asn Thr Pro Ile Phe Lys Ser Gly Arg Gly Cys Gly Ser Cys Phe
85 90 95

Glu Ile Lys Cys Thr Lys Pro Glu Ala Cys Ser Gly Glu Pro Val Val
100 105 110

Val His Ile Thr Asp Asp Asn Glu Glu Pro Ile Ala Pro Tyr His Phe
115 120 125

Asp Leu Ser Gly His Ala Phe Gly Ala Met Ala Lys Lys Gly Asp Glu
130 135 140

Gln Lys Leu Arg Ser Ala Gly Glu Leu Glu Leu Gln Phe Arg Arg Val

-continued

```
145                 150                 155                 160

Lys Cys Lys Tyr Pro Glu Gly Thr Lys Val Thr Phe His Val Glu Lys
                165                 170                 175

Gly Ser Asn Pro Asn Tyr Leu Ala Leu Leu Val Lys Tyr Val Asn Gly
            180                 185                 190

Asp Gly Asp Val Val Ala Val Asp Ile Lys Glu Lys Gly Lys Asp Lys
        195                 200                 205

Trp Ile Glu Leu Lys Glu Ser Trp Gly Ala Ile Trp Arg Ile Asp Thr
    210                 215                 220

Pro Asp Lys Leu Thr Gly Pro Phe Thr Val Arg Tyr Thr Thr Glu Gly
225                 230                 235                 240

Gly Thr Lys Thr Glu Ala Glu Asp Val Ile Pro Glu Gly Trp Lys Ala
                245                 250                 255

Asp Thr Ser Tyr Glu Ser Lys
            260


<210> SEQ ID NO 194
<211> LENGTH: 9
<212> TYPE: PRT
<213> ORGANISM: Pheleum pratense

<400> SEQUENCE: 194

Met Ala Ser Ser Ser Ser Val Leu Leu
  1               5


<210> SEQ ID NO 195
<211> LENGTH: 9
<212> TYPE: PRT
<213> ORGANISM: Pheleum pratense

<400> SEQUENCE: 195

Trp Arg Ile Asp Thr Pro Asp Lys Leu
  1               5


<210> SEQ ID NO 196
<211> LENGTH: 9
<212> TYPE: PRT
<213> ORGANISM: Pheleum pratense

<400> SEQUENCE: 196

Val Val Val Leu Phe Ala Val Phe Leu
  1               5


<210> SEQ ID NO 197
<211> LENGTH: 8
<212> TYPE: PRT
<213> ORGANISM: Pheleum pratense

<400> SEQUENCE: 197

Val Val Leu Phe Ala Val Leu Gly
  1               5


<210> SEQ ID NO 198
<211> LENGTH: 9
<212> TYPE: PRT
<213> ORGANISM: Pheleum pratense

<400> SEQUENCE: 198

Val Leu Leu Val Val Val Leu Phe Ala
  1               5
```

-continued

```
<210> SEQ ID NO 199
<211> LENGTH: 9
<212> TYPE: PRT
<213> ORGANISM: Pheleum pratense

<400> SEQUENCE: 199

Phe Glu Ile Lys Cys Thr Lys Pro Glu
  1               5


<210> SEQ ID NO 200
<211> LENGTH: 9
<212> TYPE: PRT
<213> ORGANISM: Pheleum pratense

<400> SEQUENCE: 200

Val Phe Leu Gly Ser Ala Tyr Gly Ile
  1               5


<210> SEQ ID NO 201
<211> LENGTH: 9
<212> TYPE: PRT
<213> ORGANISM: Pheleum pratense

<400> SEQUENCE: 201

Leu Val Lys Tyr Val Asn Gly Asp Gly
  1               5


<210> SEQ ID NO 202
<211> LENGTH: 9
<212> TYPE: PRT
<213> ORGANISM: Pheleum pratense

<400> SEQUENCE: 202

Leu Leu Val Lys Tyr Val Asn Gly Asp
  1               5


<210> SEQ ID NO 203
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 203

Leu Arg Met Lys Xaa Met Ala Ser Ser Ser Ser Val Leu Leu
  1               5                  10


<210> SEQ ID NO 204
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 204
```

-continued

Leu Arg Met Lys Xaa Val Leu Leu Val Val Val Leu Phe Ala
1 5 10

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 205

Leu Arg Met Lys Xaa Val Val Val Leu Phe Ala Val Phe Leu
1 5 10

<210> SEQ ID NO 206
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 206

Leu Arg Met Lys Xaa Val Val Leu Phe Ala Val Phe Leu Gly
1 5 10

<210> SEQ ID NO 207
<211> LENGTH: 24
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 207

Leu Arg Met Lys Xaa Met Ala Ser Ser Ser Ser Val Leu Leu Val Val
1 5 10 15

Val Leu Phe Ala Val Phe Leu Gly
20

<210> SEQ ID NO 208
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid -continued
<220> FEATURE:
<223> OTHER INFORMATION: C-term amidated

<400> SEQUENCE: 208

Leu Arg Met Lys Xaa Trp Arg Ile Asp Thr Pro Asp Lys Leu
1 5 10

<210> SEQ ID NO 209
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 209

Leu Arg Met Lys Xaa Phe Glu Ile Lys Cys Thr Lys Pro Glu
1 5 10

<210> SEQ ID NO 210
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 210

Leu Arg Met Lys Xaa Val Phe Leu Gly Ser Ala Tyr Gly Ile
1 5 10

<210> SEQ ID NO 211
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 211

Leu Arg Met Lys Xaa Leu Leu Val Lys Tyr Val Asn Gly Asp
1 5 10

<210> SEQ ID NO 212
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)

-continued

<223> OTHER INFORMATION: a-aminovaleric acid
<220> FEATURE:
<223> OTHER INFORMATION: C-term amidated

<400> SEQUENCE: 212

Leu Arg Met Lys Xaa Leu Val Lys Tyr Val Asn Gly Asp Gly
1 5 10

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 213

Leu Arg Met Lys Xaa Leu Leu Val Lys Tyr Val Asn Gly Asp Gly
1 5 10 15

<210> SEQ ID NO 214
<211> LENGTH: 12
<212> TYPE: PRT
<213> ORGANISM: Pheleum pratense

<400> SEQUENCE: 214

Phe Glu Ile Lys Cys Thr Lys Pro Glu Ala Cys Ser
1 5 10

<210> SEQ ID NO 215
<211> LENGTH: 12
<212> TYPE: PRT
<213> ORGANISM: Pheleum pratense

<400> SEQUENCE: 215

Ile Ala Pro Tyr His Phe Asp Leu Ser Gly His Ala
1 5 10

<210> SEQ ID NO 216
<211> LENGTH: 17
<212> TYPE: PRT
<213> ORGANISM: Artificial Sequence
<220> FEATURE:
<223> OTHER INFORMATION: Description of Artificial Sequence: Synthetic Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 216

Leu Arg Met Lys Xaa Phe Glu Ile Lys Cys Thr Lys Pro Glu Ala Cys
1 5 10 15

Ser

<210> SEQ ID NO 217
<211> LENGTH: 17
<212> TYPE: PRT
<213> ORGANISM: Artificial Sequence
<220> FEATURE:

-continued

```
<223> OTHER INFORMATION: Description of Artificial Sequence: Synthetic
      Ii-key/Phl p 1 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 217

Leu Arg Met Lys Xaa Ile Ala Pro Tyr His Phe Asp Leu Ser Gly His
  1               5                  10                  15

Ala


<210> SEQ ID NO 218
<211> LENGTH: 30
<212> TYPE: PRT
<213> ORGANISM: Pheleum pratense

<400> SEQUENCE: 218

Ile Pro Lys Val Pro Pro Gly Pro Asn Ile Thr Ala Thr Tyr Gly Asp
  1               5                  10                  15

Lys Trp Leu Asp Ala Lys Ser Thr Trp Tyr Gly Lys Pro Thr
             20                  25                  30


<210> SEQ ID NO 219
<211> LENGTH: 27
<212> TYPE: PRT
<213> ORGANISM: Pheleum pratense

<400> SEQUENCE: 219

Gly Tyr Lys Asp Val Asp Lys Pro Pro Phe Ser Gly Met Thr Gly Cys
  1               5                  10                  15

Gly Asn Thr Pro Ile Phe Lys Ser Gly Arg Gly
             20                  25


<210> SEQ ID NO 220
<211> LENGTH: 31
<212> TYPE: PRT
<213> ORGANISM: Pheleum pratense

<400> SEQUENCE: 220

Glu Pro Val Val Val His Ile Thr Asp Asp Asn Glu Glu Pro Ile Ala
  1               5                  10                  15

Pro Tyr His Phe Asp Leu Ser Gly His Ala Phe Gly Ala Met Ala
             20                  25                  30


<210> SEQ ID NO 221
<211> LENGTH: 27
<212> TYPE: PRT
<213> ORGANISM: Pheleum pratense

<400> SEQUENCE: 221

His Val Glu Lys Gly Ser Asn Pro Asn Tyr Leu Ala Leu Leu Val Lys
  1               5                  10                  15

Tyr Val Asn Gly Asp Gly Asp Val Val Ala Val
             20                  25


<210> SEQ ID NO 222
<211> LENGTH: 29
<212> TYPE: PRT
<213> ORGANISM: Pheleum pratense

<400> SEQUENCE: 222
```

-continued

Arg Tyr Thr Thr Glu Gly Gly Thr Lys Thr Glu Ala Glu Asp Val Ile
1 5 10 15

Pro Glu Gly Trp Lys Ala Asp Thr Ser Tyr Glu Ser Lys
20 25

<210> SEQ ID NO 223
<211> LENGTH: 49
<212> TYPE: PRT
<213> ORGANISM: Artificial Sequence
<220> FEATURE:
<223> OTHER INFORMATION: Description of Artificial Sequence: Synthetic hybrid peptide including an experimentally defined MHC Class II and IgE binding Php 1 epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 223

Leu Arg Met Lys Xaa Phe Glu Ile Lys Cys Thr Lys Pro Glu Ala Cys
1 5 10 15

Ser Gly Glu Pro Val Val Val His Ile Thr Asp Asp Asn Glu Glu Pro
20 25 30

Ile Ala Pro Tyr His Phe Asp Leu Ser Gly His Ala Phe Gly Ala Met
35 40 45

Ala

<210> SEQ ID NO 224
<211> LENGTH: 286
<212> TYPE: PRT
<213> ORGANISM: Pheleum pratense

<400> SEQUENCE: 224

Ala Asp Leu Gly Tyr Gly Pro Ala Thr Pro Ala Ala Pro Ala Ala Gly
1 5 10 15

Tyr Thr Pro Ala Thr Pro Ala Ala Pro Ala Gly Ala Asp Ala Ala Gly
20 25 30

Lys Ala Thr Thr Glu Glu Gln Lys Leu Ile Glu Lys Ile Asn Ala Gly
35 40 45

Phe Lys Ala Ala Leu Ala Gly Ala Gly Val Gln Pro Ala Asp Lys Tyr
50 55 60

Arg Thr Phe Val Ala Thr Phe Gly Pro Ala Ser Asn Lys Ala Phe Ala
65 70 75 80

Glu Gly Leu Ser Gly Glu Pro Lys Gly Ala Ala Glu Ser Ser Ser Lys
85 90 95

Ala Ala Leu Thr Ser Lys Leu Asp Ala Ala Tyr Lys Leu Ala Tyr Lys
100 105 110

Thr Ala Glu Gly Ala Thr Pro Glu Ala Lys Tyr Asp Ala Tyr Val Ala
115 120 125

Thr Leu Ser Glu Ala Leu Arg Ile Ile Ala Gly Thr Leu Glu Val His
130 135 140

Ala Val Lys Pro Ala Ala Glu Glu Val Lys Val Ile Pro Ala Gly Glu
145 150 155 160

Leu Gln Val Ile Glu Lys Val Asp Ala Ala Phe Lys Val Ala Ala Thr
165 170 175

Ala Ala Asn Ala Ala Pro Ala Asn Asp Lys Phe Thr Val Phe Glu Ala
180 185 190

-continued

```
Ala Phe Asn Asp Glu Ile Lys Ala Ser Thr Gly Gly Ala Tyr Glu Ser
        195                 200                 205

Tyr Lys Phe Ile Pro Ala Leu Glu Ala Ala Val Lys Gln Ala Tyr Ala
    210                 215                 220

Ala Thr Val Ala Thr Ala Pro Glu Val Lys Tyr Thr Val Phe Glu Thr
225                 230                 235                 240

Ala Leu Lys Lys Ala Ile Thr Ala Met Ser Glu Ala Gln Lys Ala Ala
                245                 250                 255

Lys Pro Ala Ala Ala Ala Thr Ala Thr Ala Thr Ala Ala Val Gly Ala
            260                 265                 270

Ala Thr Gly Ala Ala Thr Ala Ala Thr Gly Gly Tyr Lys Val
        275                 280                 285


<210> SEQ ID NO 225
<211> LENGTH: 9
<212> TYPE: PRT
<213> ORGANISM: Pheleum pratense

<400> SEQUENCE: 225

Tyr Val Ala Thr Leu Ser Glu Ala Leu
  1               5


<210> SEQ ID NO 226
<211> LENGTH: 9
<212> TYPE: PRT
<213> ORGANISM: Pheleum pratense

<400> SEQUENCE: 226

Val Lys Val Ile Pro Ala Gly Glu Leu
  1               5


<210> SEQ ID NO 227
<211> LENGTH: 9
<212> TYPE: PRT
<213> ORGANISM: Pheleum pratense

<400> SEQUENCE: 227

Leu Arg Ile Ile Ala Gly Thr Leu Glu
  1               5


<210> SEQ ID NO 228
<211> LENGTH: 9
<212> TYPE: PRT
<213> ORGANISM: Pheleum pratense

<400> SEQUENCE: 228

Tyr Lys Phe Ile Pro Ala Leu Glu Ala
  1               5


<210> SEQ ID NO 229
<211> LENGTH: 9
<212> TYPE: PRT
<213> ORGANISM: Pheleum pratense

<400> SEQUENCE: 229

Tyr Glu Ser Tyr Lys Phe Ile Pro Ala
  1               5


<210> SEQ ID NO 230
<211> LENGTH: 9
<212> TYPE: PRT
<213> ORGANISM: Pheleum pratense
```

-continued

<400> SEQUENCE: 230

Phe Lys Val Ala Ala Thr Ala Ala Asn
1 5

<210> SEQ ID NO 231
<211> LENGTH: 9
<212> TYPE: PRT
<213> ORGANISM: Pheleum pratense

<400> SEQUENCE: 231

Tyr Arg Thr Phe Val Ala Thr Phe Gly
1 5

<210> SEQ ID NO 232
<211> LENGTH: 12
<212> TYPE: PRT
<213> ORGANISM: Pheleum pratense

<400> SEQUENCE: 232

Tyr Lys Phe Ile Pro Ala Leu Glu Ala Ala Val Lys
1 5 10

<210> SEQ ID NO 233
<211> LENGTH: 12
<212> TYPE: PRT
<213> ORGANISM: Pheleum pratense

<400> SEQUENCE: 233

Leu Gln Val Ile Glu Lys Val Asp Ala Ala Phe Lys
1 5 10

<210> SEQ ID NO 234
<211> LENGTH: 12
<212> TYPE: PRT
<213> ORGANISM: Pheleum pratense

<400> SEQUENCE: 234

Tyr Lys Cys Ile Pro Ser Leu Glu Ala Ala Val Lys
1 5 10

<210> SEQ ID NO 235
<211> LENGTH: 12
<212> TYPE: PRT
<213> ORGANISM: Pheleum pratense

<400> SEQUENCE: 235

Leu Gln Ile Ile Asp Lys Ile Asp Ala Ala Phe Lys
1 5 10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic hybrid containing Phl p 5 MHC Class II non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 236

-continued

```
Leu Arg Met Lys Xaa Tyr Val Ala Thr Leu Ser Glu Ala Leu
  1               5                  10


<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      hybrid containing Phl p 5 MHC Class II
      non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 237

Leu Arg Met Lys Xaa Val Lys Val Ile Pro Ala Gly Glu Leu
  1               5                  10


<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      hybrid containing Phl p 5 MHC Class II
      non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 238

Leu Arg Met Lys Xaa Leu Arg Ile Ile Ala Gly Thr Leu Glu
  1               5                  10


<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      hybrid containing Phl p 5 MHC Class II
      non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 239

Leu Arg Met Lys Xaa Tyr Arg Thr Phe Val Ala Thr Phe Gly
  1               5                  10


<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      hybrid containing Phl p 5 MHC Class II
      overlapping epitope
<220> FEATURE:
<221> NAME/KEY: MOD_RES
<222> LOCATION: (5)
<223> OTHER INFORMATION: a-aminovaleric acid
```

-continued

<220> FEATURE:
<223> OTHER INFORMATION: C-term amidated

<400> SEQUENCE: 240

Leu Arg Met Lys Xaa Tyr Lys Phe Ile Pro Ala Leu Glu Ala
1 5 10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic hybrid containing Phl p 5 MHC Class II overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 241

Leu Arg Met Lys Xaa Tyr Glu Ser Tyr Lys Phe Ile Pro Ala
1 5 10

<210> SEQ ID NO 242
<211> LENGTH: 17
<212> TYPE: PRT
<213> ORGANISM: Artificial Sequence
<220> FEATURE:
<223> OTHER INFORMATION: Description of Artificial Sequence: Synthetic hybrid containing Phl p 5 MHC Class II overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 242

Leu Arg Met Lys Xaa Tyr Glu Ser Tyr Lys Phe Ile Pro Ala Leu Glu
1 5 10 15

Ala

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic hybrid containing Phl p 5 MHC Class II overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 243

Leu Arg Met Lys Xaa Leu Gln Val Ile Glu Lys Val Asp Ala Ala Phe
1 5 10 15

Lys

<210> SEQ ID NO 244
<211> LENGTH: 14
<212> TYPE: PRT

-continued

```
<213> ORGANISM: Artificial Sequence
<220> FEATURE:
<223> OTHER INFORMATION: Description of Artificial Sequence: Synthetic
      hybrid containing Phl p 5 MHC Class II
      overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 244

Leu Arg Met Lys Xaa Phe Lys Val Ala Ala Thr Ala Ala Asn
  1               5                  10


<210> SEQ ID NO 245
<211> LENGTH: 24
<212> TYPE: PRT
<213> ORGANISM: Artificial Sequence
<220> FEATURE:
<223> OTHER INFORMATION: Description of Artificial Sequence: Synthetic
      hybrid containing Phl p 5 MHC Class II
      overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 245

Leu Arg Met Lys Xaa Leu Gln Val Ile Glu Lys Val Asp Ala Ala Phe
  1               5                  10                  15

Lys Val Ala Ala Thr Ala Ala Asn
             20


<210> SEQ ID NO 246
<211> LENGTH: 162
<212> TYPE: PRT
<213> ORGANISM: Apis mellifera

<400> SEQUENCE: 246

Gly Ser Leu Phe Leu Leu Leu Leu Ser Thr Ser His Gly Trp Gln Ile
  1               5                  10                  15

Arg Asp Arg Ile Gly Asp Asn Glu Leu Glu Glu Arg Ile Ile Tyr Pro
             20                  25                  30

Gly Thr Leu Trp Cys Gly His Gly Asn Lys Ser Ser Gly Pro Asn Glu
         35                  40                  45

Leu Gly Arg Phe Lys His Thr Asp Ala Cys Cys Arg Thr His Asp Met
     50                  55                  60

Cys Pro Asp Val Met Ser Ala Gly Glu Ser Lys His Gly Leu Thr Asn
 65                  70                  75                  80

Thr Ala Ser His Thr Arg Leu Ser Cys Asp Cys Asp Asp Lys Phe Tyr
                 85                  90                  95

Asp Cys Leu Lys Asn Ser Ala Asp Thr Ile Ser Ser Tyr Phe Val Gly
            100                 105                 110

Lys Met Tyr Phe Asn Leu Ile Asp Thr Lys Cys Tyr Lys Leu Glu His
        115                 120                 125

Pro Val Thr Gly Cys Gly Glu Arg Thr Glu Gly Arg Cys Leu His Tyr
    130                 135                 140

Thr Val Asp Lys Ser Lys Pro Lys Val Tyr Gln Trp Phe Asp Leu Arg
145                 150                 155                 160
```

-continued

Lys Tyr

<210> SEQ ID NO 247
<211> LENGTH: 9
<212> TYPE: PRT
<213> ORGANISM: Apis mellifera

<400> SEQUENCE: 247

Trp Gln Ile Arg Asp Arg Ile Gly Asp
1 5

<210> SEQ ID NO 248
<211> LENGTH: 9
<212> TYPE: PRT
<213> ORGANISM: Apis mellifera

<400> SEQUENCE: 248

Phe Leu Leu Leu Leu Ser Thr Ser His
1 5

<210> SEQ ID NO 249
<211> LENGTH: 9
<212> TYPE: PRT
<213> ORGANISM: Apis mellifera

<400> SEQUENCE: 249

Phe Val Gly Lys Met Tyr Phe Asn Leu
1 5

<210> SEQ ID NO 250
<211> LENGTH: 9
<212> TYPE: PRT
<213> ORGANISM: Apis mellifera

<400> SEQUENCE: 250

Leu Ile Asp Thr Lys Cys Tyr Lys Leu
1 5

<210> SEQ ID NO 251
<211> LENGTH: 9
<212> TYPE: PRT
<213> ORGANISM: Apis mellifera

<400> SEQUENCE: 251

Leu Leu Leu Ser Thr Ser His Gly Trp
1 5

<210> SEQ ID NO 252
<211> LENGTH: 9
<212> TYPE: PRT
<213> ORGANISM: Apis mellifera

<400> SEQUENCE: 252

Phe Asn Leu Ile Asp Thr Lys Cys Tyr
1 5

<210> SEQ ID NO 253
<211> LENGTH: 9
<212> TYPE: PRT
<213> ORGANISM: Apis mellifera

<400> SEQUENCE: 253

Leu Leu Leu Leu Ser Thr Ser His Gly
1 5

-continued

<210> SEQ ID NO 254
<211> LENGTH: 9
<212> TYPE: PRT
<213> ORGANISM: Apis mellifera

<400> SEQUENCE: 254

Phe Lys His Thr Asp Ala Cys Cys Arg
1 5

<210> SEQ ID NO 255
<211> LENGTH: 9
<212> TYPE: PRT
<213> ORGANISM: Apis mellifera

<400> SEQUENCE: 255

Tyr Lys Leu Glu His Pro Val Thr Gly
1 5

<210> SEQ ID NO 256
<211> LENGTH: 13
<212> TYPE: PRT
<213> ORGANISM: Apis mellifera

<400> SEQUENCE: 256

Lys Met Tyr Phe Asn Leu Ile Asp Thr Lys Cys Tyr Lys
1 5 10

<210> SEQ ID NO 257
<211> LENGTH: 13
<212> TYPE: PRT
<213> ORGANISM: Apis mellifera

<400> SEQUENCE: 257

Lys Cys Tyr Lys Leu Glu His Pro Val Thr Gly Cys Gly
1 5 10

<210> SEQ ID NO 258
<211> LENGTH: 13
<212> TYPE: PRT
<213> ORGANISM: Apis mellifera

<400> SEQUENCE: 258

Tyr Phe Val Gly Lys Met Tyr Phe Asn Leu Ile Asp Thr
1 5 10

<210> SEQ ID NO 259
<211> LENGTH: 12
<212> TYPE: PRT
<213> ORGANISM: Apis mellifera

<400> SEQUENCE: 259

Cys Leu His Tyr Thr Val Asp Lys Ser Lys Pro Lys
1 5 10

<210> SEQ ID NO 260
<211> LENGTH: 18
<212> TYPE: PRT
<213> ORGANISM: Apis mellifera

<400> SEQUENCE: 260

Glu Ser Lys His Gly Leu Thr Asn Thr Ala Ser His Thr Arg Leu Ser
1 5 10 15

Cys Asp

-continued

```
<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PHL A2 hybrid non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 261

Leu Arg Met Lys Xaa Trp Gln Ile Arg Asp Arg Ile Gly Asp
  1               5                  10


<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PHL A2 hybrid non-overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 262

Leu Arg Met Lys Xaa Phe Lys His Thr Asp Ala Cys Cys Arg
  1               5                  10


<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 263

Leu Arg Met Lys Xaa Phe Leu Leu Leu Leu Ser Thr Ser His
  1               5                  10


<210> SEQ ID NO 264
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 264

Leu Arg Met Lys Xaa Leu Leu Leu Leu Ser Thr Ser His Gly
  1               5                  10
```

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 265

Leu Arg Met Lys Xaa Leu Leu Leu Ser Thr Ser His Gly Trp
1 5 10

<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 266

Leu Arg Met Lys Xaa Phe Leu Leu Leu Leu Ser Thr Ser His Gly Trp
1 5 10 15

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 267

Leu Arg Met Lys Xaa Phe Val Gly Lys Met Tyr Phe Asn Leu
1 5 10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 268

Leu Arg Met Lys Xaa Phe Asn Leu Ile Asp Thr Lys Cys Tyr

-continued 1 5 10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 269

Leu Arg Met Lys Xaa Leu Ile Asp Thr Lys Cys Tyr Lys Leu
1 5 10

<210> SEQ ID NO 270
<211> LENGTH: 22
<212> TYPE: PRT
<213> ORGANISM: Artificial Sequence
<220> FEATURE:
<223> OTHER INFORMATION: Description of Artificial Sequence: Synthetic
Ii-key/PHL A2 hybrid overlapping epitope
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 270

Leu Arg Met Lys Xaa Phe Val Gly Lys Met Tyr Phe Asn Leu Ile Asp
1 5 10 15

Thr Lys Cys Tyr Lys Leu
20

<210> SEQ ID NO 271
<211> LENGTH: 204
<212> TYPE: PRT
<213> ORGANISM: Blattella germanica

<400> SEQUENCE: 271

Met Ala Pro Ser Tyr Lys Leu Thr Tyr Cys Pro Val Lys Ala Leu Gly
1 5 10 15

Glu Pro Ile Arg Phe Leu Leu Ser Tyr Gly Glu Lys Asp Phe Glu Asp
20 25 30

Tyr Arg Phe Gln Glu Gly Asp Trp Pro Asn Leu Lys Pro Ser Met Pro
35 40 45

Phe Gly Lys Thr Pro Val Leu Glu Ile Asp Gly Lys Gln Thr His Gln
50 55 60

Ser Val Ala Ile Ser Arg Tyr Leu Gly Lys Gln Phe Gly Leu Ser Gly
65 70 75 80

Lys Asp Asp Trp Glu Asn Leu Glu Ile Asp Met Ile Val Asp Thr Ile
85 90 95

Ser Asp Phe Arg Ala Ala Ile Ala Asn Tyr His Tyr Asp Ala Asp Glu
100 105 110

Asn Ser Lys Gln Lys Lys Trp Asp Pro Leu Lys Lys Glu Thr Ile Pro
115 120 125

Tyr Tyr Thr Lys Lys Phe Asp Glu Val Val Lys Ala Asn Gly Gly Tyr
130 135 140

-continued

```
Leu Ala Ala Gly Lys Leu Thr Trp Ala Asp Phe Tyr Phe Val Ala Ile
145                 150                 155                 160

Leu Asp Tyr Leu Asn His Met Ala Lys Glu Asp Leu Val Ala Asn Gln
                165                 170                 175

Pro Asn Leu Lys Ala Leu Arg Glu Lys Val Leu Gly Leu Pro Ala Ile
            180                 185                 190

Lys Ala Trp Val Ala Lys Arg Pro Pro Thr Asp Leu
        195                 200


<210> SEQ ID NO 272
<211> LENGTH: 9
<212> TYPE: PRT
<213> ORGANISM: Blattella germanica

<400> SEQUENCE: 272

Phe Gly Lys Thr Pro Val Leu Glu Ile
  1               5


<210> SEQ ID NO 273
<211> LENGTH: 9
<212> TYPE: PRT
<213> ORGANISM: Blattella germanica

<400> SEQUENCE: 273

Trp Val Ala Lys Arg Pro Pro Thr Asp
  1               5


<210> SEQ ID NO 274
<211> LENGTH: 9
<212> TYPE: PRT
<213> ORGANISM: Blattella germanica

<400> SEQUENCE: 274

Met Ile Val Asp Thr Ile Ser Asp Phe
  1               5


<210> SEQ ID NO 275
<211> LENGTH: 9
<212> TYPE: PRT
<213> ORGANISM: Blattella germanica

<400> SEQUENCE: 275

Phe Tyr Phe Val Ala Ile Leu Asp Tyr
  1               5


<210> SEQ ID NO 276
<211> LENGTH: 9
<212> TYPE: PRT
<213> ORGANISM: Blattella germanica

<400> SEQUENCE: 276

Ile Arg Phe Leu Leu Ser Tyr Gly Glu
  1               5


<210> SEQ ID NO 277
<211> LENGTH: 9
<212> TYPE: PRT
<213> ORGANISM: Blattella germanica

<400> SEQUENCE: 277

Leu Glu Ile Asp Gly Lys Gln Thr His
  1               5
```

-continued

<210> SEQ ID NO 278
<211> LENGTH: 9
<212> TYPE: PRT
<213> ORGANISM: Blattella germanica

<400> SEQUENCE: 278

Phe Arg Ala Ala Ile Ala Asn Tyr His
1 5

<210> SEQ ID NO 279
<211> LENGTH: 20
<212> TYPE: PRT
<213> ORGANISM: Blattella germanica

<400> SEQUENCE: 279

Ile Val Asp Thr Ile Ser Asp Phe Arg Ala Ala Ile Ala Asn Tyr His
1 5 10 15

Tyr Asp Ala Asp
20

<210> SEQ ID NO 280
<211> LENGTH: 20
<212> TYPE: PRT
<213> ORGANISM: Blattella germanica

<400> SEQUENCE: 280

Asp Tyr Leu Asn His Met Ala Lys Glu Asp Leu Val Ala Asn Gln Pro
1 5 10 15

Asn Leu Lys Ala
20

<210> SEQ ID NO 281
<211> LENGTH: 9
<212> TYPE: PRT
<213> ORGANISM: Homo sapiens

<400> SEQUENCE: 281

Ile Pro Gln Gln His Thr Gln Val Leu
1 5

<210> SEQ ID NO 282
<211> LENGTH: 702
<212> TYPE: PRT
<213> ORGANISM: Homo sapiens

<400> SEQUENCE: 282

Met Glu Ser Pro Ser Ala Pro Pro His Arg Trp Cys Ile Pro Trp Gln
1 5 10 15

Arg Leu Leu Leu Thr Ala Ser Leu Leu Thr Phe Trp Asn Pro Pro Thr
20 25 30

Thr Ala Lys Leu Thr Ile Glu Ser Thr Pro Phe Asn Val Ala Glu Gly
35 40 45

Lys Glu Val Leu Leu Leu Val His Asn Leu Pro Gln His Leu Phe Gly
50 55 60

Tyr Ser Trp Tyr Lys Gly Glu Arg Val Asp Gly Asn Arg Gln Ile Ile
65 70 75 80

Gly Tyr Val Ile Gly Thr Gln Gln Ala Thr Pro Gly Pro Ala Tyr Ser
85 90 95

Gly Arg Glu Ile Ile Tyr Pro Asn Ala Ser Leu Leu Ile Gln Asn Ile
100 105 110

-continued

```
Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285

Ile Thr Val Asn Asn Ser Gly Ser Tyr Thr Cys Gln Ala His Asn Ser
    290                 295                 300

Asp Thr Gly Leu Asn Arg Thr Thr Val Thr Thr Ile Thr Val Tyr Ala
305                 310                 315                 320

Glu Pro Pro Lys Pro Phe Ile Thr Ser Asn Asn Ser Asn Pro Val Glu
                325                 330                 335

Asp Glu Asp Ala Val Ala Leu Thr Cys Glu Pro Glu Ile Gln Asn Thr
            340                 345                 350

Thr Tyr Leu Trp Trp Val Asn Asn Gln Ser Leu Pro Val Ser Pro Arg
        355                 360                 365

Leu Gln Leu Ser Asn Asp Asn Arg Thr Leu Thr Leu Leu Ser Val Thr
    370                 375                 380

Arg Asn Asp Val Gly Pro Tyr Glu Cys Gly Ile Gln Asn Glu Leu Ser
385                 390                 395                 400

Val Asp His Ser Asp Pro Val Ile Leu Asn Val Leu Tyr Gly Pro Asp
                405                 410                 415

Asp Pro Thr Ile Ser Pro Ser Tyr Thr Tyr Tyr Arg Pro Gly Val Asn
            420                 425                 430

Leu Ser Leu Ser Cys His Ala Ala Ser Asn Pro Pro Ala Gln Tyr Ser
        435                 440                 445

Trp Leu Ile Asp Gly Asn Ile Gln Gln His Thr Gln Glu Leu Phe Ile
    450                 455                 460

Ser Asn Ile Thr Glu Lys Asn Ser Gly Leu Tyr Thr Cys Gln Ala Asn
465                 470                 475                 480

Asn Ser Ala Ser Gly His Ser Arg Thr Thr Val Lys Thr Ile Thr Val
                485                 490                 495

Ser Ala Glu Leu Pro Lys Pro Ser Ile Ser Ser Asn Asn Ser Lys Pro
            500                 505                 510

Val Glu Asp Lys Asp Ala Val Ala Phe Thr Cys Glu Pro Glu Ala Gln
        515                 520                 525

Asn Thr Thr Tyr Leu Trp Trp Val Asn Gly Gln Ser Leu Pro Val Ser
```

-continued

```
    530                 535                 540

Pro Arg Leu Gln Leu Ser Asn Gly Asn Arg Thr Leu Thr Leu Phe Asn
545                 550                 555                 560

Val Thr Arg Asn Asp Ala Arg Ala Tyr Val Cys Gly Ile Gln Asn Ser
                565                 570                 575

Val Ser Ala Asn Arg Ser Asp Pro Val Thr Leu Asp Val Leu Tyr Gly
            580                 585                 590

Pro Asp Thr Pro Ile Ile Ser Pro Pro Asp Ser Ser Tyr Leu Ser Gly
        595                 600                 605

Ala Asn Leu Asn Leu Ser Cys His Ser Ala Ser Asn Pro Ser Pro Gln
    610                 615                 620

Tyr Ser Trp Arg Ile Asn Gly Ile Pro Gln Gln His Thr Gln Val Leu
625                 630                 635                 640

Phe Ile Ala Lys Ile Thr Pro Asn Asn Asn Gly Thr Tyr Ala Cys Phe
                645                 650                 655

Val Ser Asn Leu Ala Thr Gly Arg Asn Asn Ser Ile Val Lys Ser Ile
            660                 665                 670

Thr Val Ser Ala Ser Gly Thr Ser Pro Gly Leu Ser Ala Gly Ala Thr
        675                 680                 685

Val Gly Ile Met Ile Gly Val Leu Val Gly Val Ala Leu Ile
    690                 695                 700
```

<210> SEQ ID NO 283
<211> LENGTH: 9
<212> TYPE: PRT
<213> ORGANISM: Homo sapiens

<400> SEQUENCE: 283

```
Tyr Arg Pro Gly Val Asn Leu Ser Leu
  1               5
```

<210> SEQ ID NO 284
<211> LENGTH: 9
<212> TYPE: PRT
<213> ORGANISM: Homo sapiens

<400> SEQUENCE: 284

```
Trp Val Asn Gly Gln Ser Leu Pro Val
  1               5
```

<210> SEQ ID NO 285
<211> LENGTH: 9
<212> TYPE: PRT
<213> ORGANISM: Homo sapiens

<400> SEQUENCE: 285

```
Trp Val Asn Asn Gln Ser Leu Pro Val
  1               5
```

<210> SEQ ID NO 286
<211> LENGTH: 9
<212> TYPE: PRT
<213> ORGANISM: Homo sapiens

<400> SEQUENCE: 286

```
Trp Arg Ile Asn Gly Ile Pro Gln Gln
  1               5
```

<210> SEQ ID NO 287
<211> LENGTH: 9

<212> TYPE: PRT
<213> ORGANISM: Homo sapiens

<400> SEQUENCE: 287

Tyr Arg Ser Gly Glu Asn Leu Asn Leu
1 5

<210> SEQ ID NO 288
<211> LENGTH: 9
<212> TYPE: PRT
<213> ORGANISM: Homo sapiens

<400> SEQUENCE: 288

Leu Leu Leu Val His Asn Leu Pro Gln
1 5

<210> SEQ ID NO 289
<211> LENGTH: 9
<212> TYPE: PRT
<213> ORGANISM: Homo sapiens

<400> SEQUENCE: 289

Trp Leu Ile Asp Gly Asn Ile Gln Gln
1 5

<210> SEQ ID NO 290
<211> LENGTH: 9
<212> TYPE: PRT
<213> ORGANISM: Homo sapiens

<400> SEQUENCE: 290

Tyr Gly Pro Asp Thr Pro Ile Ile Ser
1 5

<210> SEQ ID NO 291
<211> LENGTH: 9
<212> TYPE: PRT
<213> ORGANISM: Homo sapiens

<400> SEQUENCE: 291

Phe Tyr Thr Leu His Val Ile Lys Ser
1 5

<210> SEQ ID NO 292
<211> LENGTH: 9
<212> TYPE: PRT
<213> ORGANISM: Homo sapiens

<400> SEQUENCE: 292

Ile Ile Gly Tyr Val Ile Gly Thr Gln
1 5

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CEA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 293

```
Leu Arg Met Lys Xaa Trp Val Asn Asn Gln Ser Leu Pro Val
  1               5                  10


<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/CEA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 294

Leu Arg Met Lys Xaa Tyr Arg Pro Gly Val Asn Leu Ser Leu
  1               5                  10


<210> SEQ ID NO 295
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/CEA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 295

Leu Arg Met Lys Xaa Trp Arg Ile Asn Gly Ile Pro Gln Gln
  1               5                  10


<210> SEQ ID NO 296
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/CEA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 296

Leu Arg Met Lys Xaa Tyr Arg Ser Gly Glu Asn Leu Asn Leu
  1               5                  10


<210> SEQ ID NO 297
<211> LENGTH: 9
<212> TYPE: PRT
<213> ORGANISM: Homo sapiens

<400> SEQUENCE: 297

His Leu Phe Gly Tyr Ser Trp Tyr Lys
  1               5


<210> SEQ ID NO 298
<211> LENGTH: 9
<212> TYPE: PRT
```

-continued

<213> ORGANISM: Homo sapiens

<400> SEQUENCE: 298

Thr Tyr Tyr Arg Pro Gly Val Asn Leu
1 5

<210> SEQ ID NO 299
<211> LENGTH: 9
<212> TYPE: PRT
<213> ORGANISM: Homo sapiens

<400> SEQUENCE: 299

Thr Tyr Ala Cys Phe Val Ser Asn Leu
1 5

<210> SEQ ID NO 300
<211> LENGTH: 9
<212> TYPE: PRT
<213> ORGANISM: Homo sapiens

<400> SEQUENCE: 300

Ile Met Ile Gly Val Leu Val Gly Val
1 5

<210> SEQ ID NO 301
<211> LENGTH: 9
<212> TYPE: PRT
<213> ORGANISM: Homo sapiens

<400> SEQUENCE: 301

Tyr Leu Ser Gly Ala Asn Leu Asn Leu
1 5

<210> SEQ ID NO 302
<211> LENGTH: 9
<212> TYPE: PRT
<213> ORGANISM: Homo sapiens

<400> SEQUENCE: 302

Ile Met Ile Gly Val Leu Val Gly Val
1 5

<210> SEQ ID NO 303
<211> LENGTH: 9
<212> TYPE: PRT
<213> ORGANISM: Homo sapiens

<400> SEQUENCE: 303

Leu Met Thr Phe Trp Asn Pro Pro Val
1 5

<210> SEQ ID NO 304
<211> LENGTH: 9
<212> TYPE: PRT
<213> ORGANISM: Homo sapiens

<400> SEQUENCE: 304

Tyr Leu Ser Gly Ala Asn Leu Asn Leu
1 5

<210> SEQ ID NO 305
<211> LENGTH: 10
<212> TYPE: PRT
<213> ORGANISM: Homo sapiens -continued

<400> SEQUENCE: 305

Gln Tyr Ser Trp Phe Val Asn Gly Thr Phe
1 5 10

<210> SEQ ID NO 306
<211> LENGTH: 9
<212> TYPE: PRT
<213> ORGANISM: Homo sapiens

<400> SEQUENCE: 306

Thr Tyr Ala Cys Phe Val Ser Asn Leu
1 5

<210> SEQ ID NO 307
<211> LENGTH: 8
<212> TYPE: PRT
<213> ORGANISM: Homo sapiens

<400> SEQUENCE: 307

His Leu Phe Tyr Ser Trp Tyr Lys
1 5

<210> SEQ ID NO 308
<211> LENGTH: 9
<212> TYPE: PRT
<213> ORGANISM: Homo sapiens

<400> SEQUENCE: 308

Leu Leu Thr Phe Trp Asn Pro Pro Val
1 5

<210> SEQ ID NO 309
<211> LENGTH: 9
<212> TYPE: PRT
<213> ORGANISM: Homo sapiens

<400> SEQUENCE: 309

Leu Leu Thr Phe Trp Asn Pro Pro Thr
1 5

<210> SEQ ID NO 310
<211> LENGTH: 23
<212> TYPE: PRT
<213> ORGANISM: Artificial Sequence
<220> FEATURE:
<223> OTHER INFORMATION: Description of Artificial Sequence: Synthetic Ii-key/MHC Class II/MHC Class I CEA hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 310

Leu Arg Met Lys Xaa Trp Val Asn Asn Gln Ser Leu Pro Val Ile Met
1 5 10 15

Ile Gly Val Leu Val Gly Val
20

<210> SEQ ID NO 311
<211> LENGTH: 16
<212> TYPE: PRT
<213> ORGANISM: Artificial Sequence
<220> FEATURE:

-continued

<223> OTHER INFORMATION: Description of Artificial Sequence: Synthetic
      Ii-key/MHC Class II/MHC Class I CEA hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 311

Leu Arg Met Lys Xaa Thr Tyr Tyr Arg Pro Gly Val Asn Leu Ser Leu
  1               5                  10                  15

<210> SEQ ID NO 312
<211> LENGTH: 24
<212> TYPE: PRT
<213> ORGANISM: Artificial Sequence
<220> FEATURE:
<223> OTHER INFORMATION: Description of Artificial Sequence: Synthetic
      Ii-key/MHC Class II/MHC Class I CEA hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 312

Leu Arg Met Lys Xaa Tyr Arg Ser Gly Glu Asn Leu Asn Leu Gln Tyr
  1               5                  10                  15

Ser Trp Phe Val Asn Gly Thr Phe
             20

<210> SEQ ID NO 313
<211> LENGTH: 22
<212> TYPE: PRT
<213> ORGANISM: Artificial Sequence
<220> FEATURE:
<223> OTHER INFORMATION: Description of Artificial Sequence: Synthetic
      Ii-key/MHC Class II/MHC Class I CEA hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 313

Leu Arg Met Lys Xaa Leu Leu Leu Val His Asn Leu Pro Gln His Leu
  1               5                  10                  15

Phe Tyr Ser Trp Tyr Lys
             20

<210> SEQ ID NO 314
<211> LENGTH: 1890
<212> TYPE: PRT
<213> ORGANISM: Homo sapiens

<400> SEQUENCE: 314

Arg Val Asp Pro Ile Gly Pro Gly Leu Asp Arg Glu Arg Leu Tyr Trp
  1               5                  10                  15

Glu Leu Ser Gln Leu Thr Asn Ser Ile Thr Glu Leu Gly Pro Tyr Thr
             20                  25                  30

Leu Asp Arg Asp Ser Leu Tyr Val Asn Gly Phe Asn Pro Trp Ser Ser
         35                  40                  45

-continued

```
Val Pro Thr Thr Ser Thr Pro Gly Thr Ser Thr Val His Leu Ala Thr
     50                  55                  60

Ser Gly Thr Pro Ser Ser Leu Pro Gly His Thr Ala Pro Val Pro Leu
 65                  70                  75                  80

Leu Ile Pro Phe Thr Leu Asn Phe Thr Ile Thr Asn Leu His Tyr Glu
                 85                  90                  95

Glu Asn Met Gln His Pro Gly Ser Arg Lys Phe Asn Thr Thr Glu Arg
            100                 105                 110

Val Leu Gln Gly Leu Leu Lys Pro Leu Phe Lys Ser Thr Ser Val Gly
        115                 120                 125

Pro Leu Tyr Ser Gly Cys Arg Leu Thr Leu Leu Arg Pro Glu Lys His
    130                 135                 140

Gly Ala Ala Thr Gly Val Asp Ala Ile Cys Thr Leu Arg Leu Asp Pro
145                 150                 155                 160

Thr Gly Pro Gly Leu Asp Arg Glu Arg Leu Tyr Trp Glu Leu Ser Gln
                165                 170                 175

Leu Thr Asn Ser Val Thr Glu Leu Gly Pro Tyr Thr Leu Asp Arg Asp
            180                 185                 190

Ser Leu Tyr Val Asn Gly Phe Thr His Arg Ser Ser Val Pro Thr Thr
        195                 200                 205

Ser Ile Pro Gly Thr Ser Ala Val His Leu Glu Thr Ser Gly Thr Pro
    210                 215                 220

Ala Ser Leu Pro Gly His Thr Ala Pro Gly Pro Leu Leu Val Pro Phe
225                 230                 235                 240

Thr Leu Asn Phe Thr Ile Thr Asn Leu Gln Tyr Glu Glu Asp Met Arg
                245                 250                 255

His Pro Gly Ser Arg Lys Phe Asn Thr Thr Glu Arg Val Leu Gln Gly
            260                 265                 270

Leu Leu Lys Pro Leu Phe Lys Ser Thr Ser Val Gly Pro Leu Tyr Ser
        275                 280                 285

Gly Cys Arg Leu Thr Leu Leu Arg Pro Glu Lys Arg Gly Ala Ala Thr
    290                 295                 300

Gly Val Asp Thr Ile Cys Thr His Arg Leu Asp Pro Leu Asn Pro Gly
305                 310                 315                 320

Leu Asp Arg Glu Gln Leu Tyr Trp Glu Leu Ser Lys Leu Thr Arg Gly
                325                 330                 335

Ile Ile Glu Leu Gly Pro Tyr Leu Leu Asp Arg Gly Ser Leu Tyr Val
            340                 345                 350

Asn Gly Phe Thr His Arg Asn Phe Val Pro Ile Thr Ser Thr Pro Gly
        355                 360                 365

Thr Ser Thr Val His Leu Gly Thr Ser Glu Thr Pro Ser Ser Leu Pro
    370                 375                 380

Arg Pro Ile Val Pro Gly Pro Leu Leu Val Pro Phe Thr Leu Asn Phe
385                 390                 395                 400

Thr Ile Thr Asn Leu Gln Tyr Glu Glu Ala Met Arg His Pro Gly Ser
                405                 410                 415

Arg Lys Phe Asn Thr Thr Glu Arg Val Leu Gln Gly Leu Leu Arg Pro
            420                 425                 430

Leu Phe Lys Asn Thr Ser Ile Gly Pro Leu Tyr Ser Ser Cys Arg Leu
        435                 440                 445

Thr Leu Leu Arg Pro Glu Lys Asp Lys Ala Ala Thr Arg Val Asp Ala
    450                 455                 460
```

-continued

```
Ile Cys Thr His His Pro Asp Pro Gln Ser Pro Gly Leu Asn Arg Glu
465                 470                 475                 480

Gln Leu Tyr Trp Glu Leu Ser Gln Leu Thr His Gly Ile Thr Glu Leu
                485                 490                 495

Gly Pro Tyr Thr Leu Asp Arg Asp Ser Leu Tyr Val Asp Gly Phe Thr
            500                 505                 510

His Trp Ser Pro Ile Pro Thr Thr Ser Thr Pro Gly Thr Ser Ile Val
        515                 520                 525

Asn Leu Gly Thr Ser Gly Ile Pro Pro Ser Leu Pro Glu Thr Thr Ala
    530                 535                 540

Thr Gly Pro Leu Leu Val Pro Phe Thr Leu Asn Phe Thr Ile Thr Asn
545                 550                 555                 560

Leu Gln Tyr Glu Glu Asn Met Gly His Pro Gly Ser Arg Lys Phe Asn
                565                 570                 575

Ile Thr Glu Ser Val Leu Gln Gly Leu Leu Lys Pro Leu Phe Lys Ser
            580                 585                 590

Thr Ser Val Gly Pro Leu Tyr Ser Gly Cys Arg Leu Thr Leu Leu Arg
        595                 600                 605

Pro Glu Lys Asp Gly Val Ala Thr Arg Val Asp Ala Ile Cys Thr His
    610                 615                 620

Arg Pro Asp Pro Lys Ile Pro Gly Leu Asp Arg Gln Gln Leu Tyr Trp
625                 630                 635                 640

Glu Leu Ser Gln Leu Thr His Ser Ile Thr Glu Leu Gly Pro Tyr Thr
                645                 650                 655

Leu Asp Arg Asp Ser Leu Tyr Val Asn Gly Phe Thr Gln Arg Ser Ser
            660                 665                 670

Val Pro Thr Thr Ser Thr Pro Gly Thr Phe Thr Val Gln Pro Glu Thr
        675                 680                 685

Ser Glu Thr Pro Ser Ser Leu Pro Gly Pro Thr Ala Thr Gly Pro Val
    690                 695                 700

Leu Leu Pro Phe Thr Leu Asn Phe Thr Ile Ile Asn Leu Gln Tyr Glu
705                 710                 715                 720

Glu Asp Met His Arg Pro Gly Ser Arg Lys Phe Asn Thr Thr Glu Arg
                725                 730                 735

Val Leu Gln Gly Leu Leu Met Pro Leu Phe Lys Asn Thr Ser Val Ser
            740                 745                 750

Ser Leu Tyr Ser Gly Cys Arg Leu Thr Leu Leu Arg Pro Glu Lys Asp
        755                 760                 765

Gly Ala Ala Thr Arg Val Asp Ala Val Cys Thr His Arg Pro Asp Pro
    770                 775                 780

Lys Ser Pro Gly Leu Asp Arg Glu Arg Leu Tyr Trp Lys Leu Ser Gln
785                 790                 795                 800

Leu Thr His Gly Ile Thr Glu Leu Gly Pro Tyr Thr Leu Asp Arg His
                805                 810                 815

Ser Leu Tyr Val Asn Gly Phe Thr His Gln Ser Ser Met Thr Thr Thr
            820                 825                 830

Arg Thr Pro Asp Thr Ser Thr Met His Leu Ala Thr Ser Arg Thr Pro
        835                 840                 845

Ala Ser Leu Ser Gly Pro Thr Thr Ala Ser Pro Leu Leu Val Leu Phe
    850                 855                 860

Thr Ile Asn Phe Thr Ile Thr Asn Leu Arg Tyr Glu Glu Asn Met His
865                 870                 875                 880

His Pro Gly Ser Arg Lys Phe Asn Thr Thr Glu Arg Val Leu Gln Gly
```

-continued

```
                885                 890                 895

Leu Leu Arg Pro Val Phe Lys Asn Thr Ser Val Gly Pro Leu Tyr Ser
            900                 905                 910

Gly Cys Arg Leu Thr Leu Leu Arg Pro Lys Lys Asp Gly Ala Ala Thr
        915                 920                 925

Lys Val Asp Ala Ile Cys Thr Tyr Arg Pro Asp Pro Lys Ser Pro Gly
    930                 935                 940

Leu Asp Arg Glu Gln Leu Tyr Trp Glu Leu Ser Gln Leu Thr His Ser
945                 950                 955                 960

Ile Thr Glu Leu Gly Pro Tyr Thr Leu Asp Arg Asp Ser Leu Tyr Val
                965                 970                 975

Asn Gly Phe Thr Gln Arg Ser Ser Val Pro Thr Thr Ser Ile Pro Gly
            980                 985                 990

Thr Pro Thr Val Asp Leu Gly Thr Ser Gly Thr Pro Val Ser Lys Pro
        995                1000                1005

Gly Pro Ser Ala Ala Ser Pro Leu Leu Val Leu Phe Thr Leu Asn Phe
   1010                1015                1020

Thr Ile Thr Asn Leu Arg Tyr Glu Glu Asn Met Gln His Pro Gly Ser
1025                1030                1035                1040

Arg Lys Phe Asn Thr Thr Glu Arg Val Leu Gln Gly Leu Leu Arg Ser
               1045                1050                1055

Leu Phe Lys Ser Thr Ser Val Gly Pro Leu Tyr Ser Gly Cys Arg Leu
           1060                1065                1070

Thr Leu Leu Arg Pro Glu Lys Asp Gly Thr Ala Thr Gly Val Asp Ala
       1075                1080                1085

Ile Cys Thr His His Pro Asp Pro Lys Ser Pro Arg Leu Asp Arg Glu
   1090                1095                1100

Gln Leu Tyr Trp Glu Leu Ser Gln Leu Thr His Asn Ile Thr Glu Leu
1105                1110                1115                1120

Gly Pro Tyr Ala Leu Asp Asn Asp Ser Leu Phe Val Asn Gly Phe Thr
               1125                1130                1135

His Arg Ser Ser Val Ser Thr Thr Ser Thr Pro Gly Thr Pro Thr Val
           1140                1145                1150

Tyr Leu Gly Ala Ser Lys Thr Pro Ala Ser Ile Phe Gly Pro Ser Ala
       1155                1160                1165

Ala Ser His Leu Leu Ile Leu Phe Thr Leu Asn Phe Thr Ile Thr Asn
   1170                1175                1180

Leu Arg Tyr Glu Glu Asn Met Trp Pro Gly Ser Arg Lys Phe Asn Thr
1185                1190                1195                1200

Thr Glu Arg Val Leu Gln Gly Leu Leu Arg Pro Leu Phe Lys Asn Thr
               1205                1210                1215

Ser Val Gly Pro Leu Tyr Ser Gly Cys Arg Leu Thr Leu Leu Arg Pro
           1220                1225                1230

Glu Lys Asp Gly Glu Ala Thr Gly Val Asp Ala Ile Cys Thr His Arg
       1235                1240                1245

Pro Asp Pro Thr Gly Pro Gly Leu Asp Arg Glu Gln Leu Tyr Leu Glu
   1250                1255                1260

Leu Ser Gln Leu Thr His Ser Ile Thr Glu Leu Gly Pro Tyr Thr Leu
1265                1270                1275                1280

Asp Arg Asp Ser Leu Tyr Val Asn Gly Phe Thr His Arg Ser Ser Val
               1285                1290                1295

Pro Thr Thr Ser Thr Gly Val Val Ser Glu Glu Pro Phe Thr Leu Asn
           1300                1305                1310
```

-continued

```
Phe Thr Ile Asn Asn Leu Arg Tyr Met Ala Asp Met Gly Gln Pro Gly
        1315                1320                1325

Ser Leu Lys Phe Asn Ile Thr Asp Asn Val Met Gln His Leu Leu Ser
    1330                1335                1340

Pro Leu Phe Gln Arg Ser Ser Leu Gly Ala Arg Tyr Thr Gly Cys Arg
1345                1350                1355                1360

Val Ile Ala Leu Arg Ser Val Lys Asn Gly Ala Glu Thr Arg Val Asp
                1365                1370                1375

Leu Leu Cys Thr Tyr Leu Gln Pro Leu Ser Gly Pro Gly Leu Pro Ile
            1380                1385                1390

Lys Gln Val Phe His Glu Leu Ser Gln Gln Thr His Gly Ile Thr Arg
        1395                1400                1405

Leu Gly Pro Tyr Ser Leu Asp Lys Asp Ser Leu Tyr Leu Asn Gly Tyr
    1410                1415                1420

Asn Glu Pro Gly Pro Asp Glu Pro Pro Thr Thr Pro Lys Pro Ala Thr
1425                1430                1435                1440

Thr Phe Leu Pro Pro Leu Ser Glu Ala Thr Thr Ala Met Gly Tyr His
                1445                1450                1455

Leu Lys Thr Leu Thr Leu Asn Phe Thr Ile Ser Asn Leu Gln Tyr Ser
            1460                1465                1470

Pro Asp Met Gly Lys Gly Ser Ala Thr Phe Asn Ser Thr Glu Gly Val
        1475                1480                1485

Leu Gln His Leu Leu Arg Pro Leu Phe Gln Lys Ser Ser Met Gly Pro
    1490                1495                1500

Phe Tyr Leu Gly Cys Gln Leu Ile Ser Leu Arg Pro Glu Lys Asp Gly
1505                1510                1515                1520

Ala Ala Thr Gly Val Asp Thr Thr Cys Thr Tyr His Pro Asp Pro Val
                1525                1530                1535

Gly Pro Gly Leu Asp Ile Gln Gln Leu Tyr Trp Glu Leu Ser Gln Leu
            1540                1545                1550

Thr His Gly Val Thr Gln Leu Gly Phe Tyr Val Leu Asp Arg Asp Ser
        1555                1560                1565

Leu Phe Ile Asn Gly Tyr Ala Pro Gln Asn Leu Ser Ile Arg Gly Glu
    1570                1575                1580

Tyr Gln Ile Asn Phe His Ile Val Asn Trp Asn Leu Ser Asn Pro Asp
1585                1590                1595                1600

Pro Thr Ser Ser Glu Tyr Ile Thr Leu Leu Arg Asp Ile Gln Asp Lys
                1605                1610                1615

Val Thr Thr Leu Tyr Lys Gly Ser Gln Leu His Asp Thr Phe Arg Phe
            1620                1625                1630

Cys Leu Val Thr Asn Leu Thr Met Asp Ser Val Leu Val Thr Val Lys
        1635                1640                1645

Ala Leu Phe Ser Ser Asn Leu Asp Pro Ser Leu Val Glu Gln Val Phe
    1650                1655                1660

Leu Asp Lys Thr Leu Asn Ala Ser Phe His Trp Leu Gly Ser Thr Tyr
1665                1670                1675                1680

Gln Leu Val Asp Ile His Val Thr Glu Met Glu Ser Ser Val Tyr Gln
                1685                1690                1695

Pro Thr Ser Ser Ser Ser Thr Gln His Phe Tyr Pro Asn Phe Thr Ile
            1700                1705                1710

Thr Asn Leu Pro Tyr Ser Gln Asp Lys Ala Gln Pro Gly Thr Thr Asn
        1715                1720                1725
```

-continued

```
Tyr Gln Arg Asn Lys Arg Asn Ile Glu Asp Ala Leu Asn Gln Leu Phe
   1730                1735                1740

Arg Asn Ser Ser Ile Lys Ser Tyr Phe Ser Asp Cys Gln Val Ser Thr
1745                1750                1755                1760

Phe Arg Ser Val Pro Asn Arg His His Thr Gly Val Asp Ser Leu Cys
               1765                1770                1775

Asn Phe Ser Pro Leu Ala Arg Arg Val Asp Arg Val Ala Ile Tyr Glu
           1780                1785                1790

Glu Phe Leu Arg Met Thr Arg Asn Gly Thr Gln Leu Gln Asn Phe Thr
       1795                1800                1805

Leu Asp Arg Ser Ser Val Leu Val Asp Gly Tyr Ser Pro Asn Arg Asn
   1810                1815                1820

Glu Pro Leu Thr Gly Asn Ser Asp Leu Pro Phe Trp Ala Val Ile Leu
1825                1830                1835                1840

Ile Gly Leu Ala Gly Leu Leu Gly Leu Ile Thr Cys Leu Ile Cys Gly
               1845                1850                1855

Val Leu Val Thr Thr Arg Arg Arg Lys Lys Glu Gly Glu Tyr Asn Val
           1860                1865                1870

Gln Gln Gln Cys Pro Gly Tyr Tyr Gln Ser His Leu Asp Leu Glu Asp
       1875                1880                1885

Leu Gln
   1890


<210> SEQ ID NO 315
<211> LENGTH: 9
<212> TYPE: PRT
<213> ORGANISM: Homo sapiens

<400> SEQUENCE: 315

Phe Arg Phe Cys Leu Val Thr Asn Leu
  1               5


<210> SEQ ID NO 316
<211> LENGTH: 9
<212> TYPE: PRT
<213> ORGANISM: Homo sapiens

<400> SEQUENCE: 316

Val Leu Phe Thr Leu Asn Phe Thr Ile
  1               5


<210> SEQ ID NO 317
<211> LENGTH: 9
<212> TYPE: PRT
<213> ORGANISM: Homo sapiens

<400> SEQUENCE: 317

Ile Leu Phe Thr Leu Asn Phe Thr Ile
  1               5


<210> SEQ ID NO 318
<211> LENGTH: 9
<212> TYPE: PRT
<213> ORGANISM: Homo sapiens

<400> SEQUENCE: 318

Leu Arg Leu Asp Pro Thr Gly Pro Gly
  1               5


<210> SEQ ID NO 319
```

-continued

<211> LENGTH: 9
<212> TYPE: PRT
<213> ORGANISM: Homo sapiens

<400> SEQUENCE: 319

Leu Val Leu Phe Thr Leu Asn Phe Thr
1 5

<210> SEQ ID NO 320
<211> LENGTH: 9
<212> TYPE: PRT
<213> ORGANISM: Homo sapiens

<400> SEQUENCE: 320

Leu Val Leu Phe Thr Ile Asn Phe Thr
1 5

<210> SEQ ID NO 321
<211> LENGTH: 9
<212> TYPE: PRT
<213> ORGANISM: Homo sapiens

<400> SEQUENCE: 321

Ile Val Asn Leu Gly Thr Ser Gly Ile
1 5

<210> SEQ ID NO 322
<211> LENGTH: 9
<212> TYPE: PRT
<213> ORGANISM: Homo sapiens

<400> SEQUENCE: 322

Leu Arg Tyr Met Ala Asp Met Gly Gln
1 5

<210> SEQ ID NO 323
<211> LENGTH: 9
<212> TYPE: PRT
<213> ORGANISM: Homo sapiens

<400> SEQUENCE: 323

Leu Arg Tyr Glu Glu Asn Met Gln His
1 5

<210> SEQ ID NO 324
<211> LENGTH: 9
<212> TYPE: PRT
<213> ORGANISM: Homo sapiens

<400> SEQUENCE: 324

Leu Arg Tyr Glu Glu Asn Met His His
1 5

<210> SEQ ID NO 325
<211> LENGTH: 9
<212> TYPE: PRT
<213> ORGANISM: Homo sapiens

<400> SEQUENCE: 325

Val Phe Leu Asp Lys Thr Leu Asn Ala
1 5

<210> SEQ ID NO 326
<211> LENGTH: 9
<212> TYPE: PRT

-continued

<213> ORGANISM: Homo sapiens

<400> SEQUENCE: 326

Leu Leu Ile Leu Phe Thr Leu Asn Phe
1 5

<210> SEQ ID NO 327
<211> LENGTH: 9
<212> TYPE: PRT
<213> ORGANISM: Homo sapiens

<400> SEQUENCE: 327

Tyr Arg Pro Asp Pro Lys Ser Pro Gly
1 5

<210> SEQ ID NO 328
<211> LENGTH: 9
<212> TYPE: PRT
<213> ORGANISM: Homo sapiens

<400> SEQUENCE: 328

Leu Val Pro Phe Thr Leu Asn Phe Thr
1 5

<210> SEQ ID NO 329
<211> LENGTH: 9
<212> TYPE: PRT
<213> ORGANISM: Homo sapiens

<400> SEQUENCE: 329

Leu Arg Pro Leu Phe Lys Asn Thr Ser
1 5

<210> SEQ ID NO 330
<211> LENGTH: 9
<212> TYPE: PRT
<213> ORGANISM: Homo sapiens

<400> SEQUENCE: 330

Leu Arg Tyr Glu Glu Asn Met Trp Pro
1 5

<210> SEQ ID NO 331
<211> LENGTH: 9
<212> TYPE: PRT
<213> ORGANISM: Homo sapiens

<400> SEQUENCE: 331

Leu Val Thr Asn Leu Thr Met Asp Ser
1 5

<210> SEQ ID NO 332
<211> LENGTH: 9
<212> TYPE: PRT
<213> ORGANISM: Homo sapiens

<400> SEQUENCE: 332

Phe Val Pro Ile Thr Ser Thr Pro Gly
1 5

<210> SEQ ID NO 333
<211> LENGTH: 9
<212> TYPE: PRT
<213> ORGANISM: Homo sapiens -continued

<400> SEQUENCE: 333

Leu Arg Pro Leu Phe Lys Asn Thr Ser
1 5

<210> SEQ ID NO 334
<211> LENGTH: 9
<212> TYPE: PRT
<213> ORGANISM: Homo sapiens

<400> SEQUENCE: 334

Leu Arg Pro Val Phe Lys Asn Thr Ser
1 5

<210> SEQ ID NO 335
<211> LENGTH: 9
<212> TYPE: PRT
<213> ORGANISM: Homo sapiens

<400> SEQUENCE: 335

Tyr His Pro Asp Pro Val Gly Pro Gly
1 5

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 336

Leu Arg Met Lys Xaa Val Leu Phe Thr Leu Asn Phe Thr Ile
1 5 10

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 337

Leu Arg Met Lys Xaa Ile Leu Phe Thr Leu Asn Phe Thr Ile
1 5 10

<210> SEQ ID NO 338
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 338

Leu Arg Met Lys Xaa Leu Val Leu Phe Thr Ile Asn Phe Thr
1 5 10

<210> SEQ ID NO 339
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 339

Leu Arg Met Lys Xaa Leu Arg Tyr Glu Glu Asn Met Gln His
1 5 10

<210> SEQ ID NO 340
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 340

Leu Arg Met Lys Xaa Leu Arg Tyr Glu Glu Asn Met His His
1 5 10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 conserved tandem-repeat hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 341

Leu Arg Met Lys Xaa Leu Arg Tyr Glu Glu Asn Met Trp Pro
1 5 10

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/CA125 overlapping MHC II hybrid peptide
<220> FEATURE:
<221> NAME/KEY: MOD_RES
<222> LOCATION: (5)

-continued

<223> OTHER INFORMATION: a-aminovaleric acid
<220> FEATURE:
<223> OTHER INFORMATION: C-term amidated

<400> SEQUENCE: 342

Leu Arg Met Lys Xaa Phe Arg Phe Cys Leu Val Thr Asn Leu
1 5 10

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/CA125 overlapping MHC II hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 343

Leu Arg Met Lys Xaa Leu Val Thr Asn Leu Thr Met Asp Ser
1 5 10

<210> SEQ ID NO 344
<211> LENGTH: 18
<212> TYPE: PRT
<213> ORGANISM: Artificial Sequence
<220> FEATURE:
<223> OTHER INFORMATION: Description of Artificial Sequence: Synthetic Ii-key/CA125 overlapping MHC II hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 344

Leu Arg Met Lys Xaa Phe Arg Phe Cys Leu Val Thr Asn Leu Thr Met
1 5 10 15

Asp Ser

<210> SEQ ID NO 345
<211> LENGTH: 9
<212> TYPE: PRT
<213> ORGANISM: Homo sapiens

<400> SEQUENCE: 345

Trp Leu Gly Ser Thr Tyr Gln Leu Val
1 5

<210> SEQ ID NO 346
<211> LENGTH: 9
<212> TYPE: PRT
<213> ORGANISM: Homo sapiens

<400> SEQUENCE: 346

Val Leu Phe Thr Leu Asn Phe Thr Ile
1 5

<210> SEQ ID NO 347
<211> LENGTH: 9
<212> TYPE: PRT
<213> ORGANISM: Homo sapiens -continued

<400> SEQUENCE: 347

Ile Leu Phe Thr Leu Asn Phe Thr Ile
1 5

<210> SEQ ID NO 348
<211> LENGTH: 9
<212> TYPE: PRT
<213> ORGANISM: Homo sapiens

<400> SEQUENCE: 348

Val Leu Phe Thr Ile Asn Phe Thr Ile
1 5

<210> SEQ ID NO 349
<211> LENGTH: 9
<212> TYPE: PRT
<213> ORGANISM: Homo sapiens

<400> SEQUENCE: 349

Leu Leu Asp Arg Gly Ser Leu Tyr Val
1 5

<210> SEQ ID NO 350
<211> LENGTH: 9
<212> TYPE: PRT
<213> ORGANISM: Homo sapiens

<400> SEQUENCE: 350

Tyr Leu Gly Cys Gln Leu Ile Ser Leu
1 5

<210> SEQ ID NO 351
<211> LENGTH: 9
<212> TYPE: PRT
<213> ORGANISM: Homo sapiens

<400> SEQUENCE: 351

Thr Leu Asn Ala Ser Phe His Trp Leu
1 5

<210> SEQ ID NO 352
<211> LENGTH: 9
<212> TYPE: PRT
<213> ORGANISM: Homo sapiens

<400> SEQUENCE: 352

Gly Val Thr Gln Leu Gly Phe Tyr Val
1 5

<210> SEQ ID NO 353
<211> LENGTH: 9
<212> TYPE: PRT
<213> ORGANISM: Homo sapiens

<400> SEQUENCE: 353

Gly Leu Leu Gly Leu Ile Thr Cys Leu
1 5

<210> SEQ ID NO 354
<211> LENGTH: 9
<212> TYPE: PRT
<213> ORGANISM: Homo sapiens

<400> SEQUENCE: 354

-continued

```
Lys Leu Thr Arg Gly Ile Ile Glu Leu
  1               5


<210> SEQ ID NO 355
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/MHC II epitope/MHC I epitope hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 355

Leu Arg Met Lys Xaa Phe Arg Phe Cys Leu Val Thr Asn Leu
  1               5                  10


<210> SEQ ID NO 356
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/MHC II epitope/MHC I epitope hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 356

Leu Arg Met Lys Xaa Leu Val Pro Phe Thr Leu Asn Phe Thr Ile
  1               5                  10                  15


<210> SEQ ID NO 357
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 357

His His His His His His
  1               5


<210> SEQ ID NO 358
<211> LENGTH: 261
<212> TYPE: PRT
<213> ORGANISM: Homo sapiens

<400> SEQUENCE: 358

Met Trp Val Pro Val Val Phe Leu Thr Leu Ser Val Thr Trp Ile Gly
  1               5                  10                  15

Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
         35                  40                  45

Val Cys Gly Gly Val Leu Val His Pro Gln Trp Val Leu Thr Ala Ala
     50                  55                  60
```

-continued

```
His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260


<210> SEQ ID NO 359
<211> LENGTH: 9
<212> TYPE: PRT
<213> ORGANISM: Homo sapiens

<400> SEQUENCE: 359

Trp Val Leu Thr Ala Ala His Cys Ile
  1               5


<210> SEQ ID NO 360
<211> LENGTH: 9
<212> TYPE: PRT
<213> ORGANISM: Homo sapiens

<400> SEQUENCE: 360

Trp Val Pro Val Val Phe Leu Thr Leu
  1               5


<210> SEQ ID NO 361
<211> LENGTH: 9
<212> TYPE: PRT
<213> ORGANISM: Homo sapiens

<400> SEQUENCE: 361

Leu Arg Leu Ser Glu Pro Ala Glu Leu
  1               5


<210> SEQ ID NO 362
<211> LENGTH: 9
<212> TYPE: PRT
<213> ORGANISM: Homo sapiens

<400> SEQUENCE: 362
```

-continued

Ile Arg Asn Lys Ser Val Ile Leu Leu
1 5

<210> SEQ ID NO 363
<211> LENGTH: 9
<212> TYPE: PRT
<213> ORGANISM: Homo sapiens

<400> SEQUENCE: 363

Leu Leu Gly Arg His Ser Leu Phe His
1 5

<210> SEQ ID NO 364
<211> LENGTH: 9
<212> TYPE: PRT
<213> ORGANISM: Homo sapiens

<400> SEQUENCE: 364

Val Ile Leu Leu Gly Arg His Ser Leu
1 5

<210> SEQ ID NO 365
<211> LENGTH: 9
<212> TYPE: PRT
<213> ORGANISM: Homo sapiens

<400> SEQUENCE: 365

Leu Gln Gly Ile Thr Ser Trp Gly Ser
1 5

<210> SEQ ID NO 366
<211> LENGTH: 16
<212> TYPE: PRT
<213> ORGANISM: Homo sapiens

<400> SEQUENCE: 366

Glu Arg Pro Ser Leu Tyr Thr Lys Val Val His Tyr Arg Lys Trp Ile
1 5 10 15

<210> SEQ ID NO 367
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PSA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 367

Leu Arg Met Lys Xaa Trp Val Pro Val Val Phe Leu Thr Leu
1 5 10

<210> SEQ ID NO 368
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PSA non-overlapping hybrid peptide
<220> FEATURE:
<221> NAME/KEY: MOD_RES
<222> LOCATION: (5)

-continued

```
<223> OTHER INFORMATION: a-aminovaleric acid
<220> FEATURE:
<223> OTHER INFORMATION: C-term amidated

<400> SEQUENCE: 368

Leu Arg Met Lys Xaa Leu Arg Leu Ser Glu Pro Ala Glu Leu
  1               5                  10


<210> SEQ ID NO 369
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PSA non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 369

Leu Arg Met Lys Xaa Leu Gln Gly Ile Thr Ser Trp Gly Ser
  1               5                  10


<210> SEQ ID NO 370
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PSA overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 370

Leu Arg Met Lys Xaa Trp Val Leu Thr Ala Ala His Cys Ile
  1               5                  10


<210> SEQ ID NO 371
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PSA overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 371

Leu Arg Met Lys Xaa Ile Arg Asn Lys Ser Val Ile Leu Leu
  1               5                  10


<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PSA overlapping hybrid peptide
<220> FEATURE:
<221> NAME/KEY: MOD_RES
```

-continued

<222> LOCATION: (5)
<223> OTHER INFORMATION: a-aminovaleric acid
<220> FEATURE:
<223> OTHER INFORMATION: C-term amidated

<400> SEQUENCE: 372

Leu Arg Met Lys Xaa Val Ile Leu Leu Gly Arg His Ser Leu
1 5 10

<210> SEQ ID NO 373
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/PSA overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 373

Leu Arg Met Lys Xaa Leu Leu Gly Arg His Ser Leu Phe His
1 5 10

<210> SEQ ID NO 374
<211> LENGTH: 29
<212> TYPE: PRT
<213> ORGANISM: Artificial Sequence
<220> FEATURE:
<223> OTHER INFORMATION: Description of Artificial Sequence: Synthetic
Ii-key/PSA overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 374

Leu Arg Met Lys Xaa Trp Val Leu Thr Ala Ala His Cys Ile Arg Asn
1 5 10 15

Lys Ser Val Ile Leu Leu Gly Arg His Ser Leu Phe His
20 25

<210> SEQ ID NO 375
<211> LENGTH: 8
<212> TYPE: PRT
<213> ORGANISM: Homo sapiens

<400> SEQUENCE: 375

Gly Arg Ala Val Cys Gly Val Leu
1 5

<210> SEQ ID NO 376
<211> LENGTH: 9
<212> TYPE: PRT
<213> ORGANISM: Homo sapiens

<400> SEQUENCE: 376

Ile Arg Asn Lys Ser Val Ile Leu Leu
1 5

<210> SEQ ID NO 377
<211> LENGTH: 9
<212> TYPE: PRT

-continued

<213> ORGANISM: Homo sapiens

<400> SEQUENCE: 377

Leu Arg Leu Ser Glu Pro Ala Glu Leu
1 5

<210> SEQ ID NO 378
<211> LENGTH: 9
<212> TYPE: PRT
<213> ORGANISM: Homo sapiens

<400> SEQUENCE: 378

Ala Pro Leu Ile Leu Ser Arg Ile Val
1 5

<210> SEQ ID NO 379
<211> LENGTH: 9
<212> TYPE: PRT
<213> ORGANISM: Homo sapiens

<400> SEQUENCE: 379

Phe Leu Thr Leu Ser Val Thr Trp Ile
1 5

<210> SEQ ID NO 380
<211> LENGTH: 9
<212> TYPE: PRT
<213> ORGANISM: Homo sapiens

<400> SEQUENCE: 380

Tyr Arg Lys Trp Ile Lys Asp Thr Ile
1 5

<210> SEQ ID NO 381
<211> LENGTH: 10
<212> TYPE: PRT
<213> ORGANISM: Homo sapiens

<400> SEQUENCE: 381

His Pro Gln Lys Val Thr Lys Phe Met Leu
1 5 10

<210> SEQ ID NO 382
<211> LENGTH: 19
<212> TYPE: PRT
<213> ORGANISM: Artificial Sequence
<220> FEATURE:
<223> OTHER INFORMATION: Description of Artificial Sequence: Synthetic Ii-key/PSA MHC II-presented epitope/PSA MHC I-presented overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 382

Leu Arg Met Lys Xaa Trp Val Pro Val Val Phe Leu Thr Leu Ser Val
1 5 10 15

Thr Trp Ile

<210> SEQ ID NO 383
<211> LENGTH: 14
<212> TYPE: PRT
<213> ORGANISM: Artificial Sequence -continued

```
<220> FEATURE:
<223> OTHER INFORMATION: Description of Artificial Sequence: Synthetic
      Ii-key/PSA MHC II-presented epitope/PSA MHC I-
      presented overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 383

Leu Arg Met Lys Xaa Ile Arg Asn Lys Ser Val Ile Leu Leu
  1               5                  10


<210> SEQ ID NO 384
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/PSA MHC II-presented epitope/PSA MHC I-
      presented overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 384

Leu Arg Met Lys Xaa Leu Arg Leu Ser Glu Pro Ala Glu Leu
  1               5                  10


<210> SEQ ID NO 385
<211> LENGTH: 660
<212> TYPE: PRT
<213> ORGANISM: Homo sapiens

<400> SEQUENCE: 385

Met Asp Leu Val Leu Lys Arg Cys Leu Leu His Leu Ala Val Ile Gly
  1               5                  10                  15

Ala Leu Leu Ala Val Gly Ala Thr Lys Val Pro Arg Asn Gln Asp Trp
             20                  25                  30

Leu Gly Val Ser Arg Gln Leu Arg Thr Lys Ala Trp Asn Arg Gln Leu
         35                  40                  45

Tyr Pro Glu Trp Thr Glu Ala Gln Arg Leu Asp Cys Trp Arg Gly Gly
     50                  55                  60

Gln Val Ser Leu Lys Val Ser Asn Asp Gly Pro Thr Leu Ile Gly Ala
 65                  70                  75                  80

Asn Ala Ser Phe Ser Ile Ala Leu Asn Phe Pro Gly Ser Gln Lys Val
                 85                  90                  95

Leu Pro Asp Gly Val Ile Trp Val Asn Asn Thr Ile Ile Asn Gly Ser
            100                 105                 110

Gln Val Trp Gly Gly Gln Pro Val Tyr Pro Gln Glu Thr Asp Asp Ala
        115                 120                 125

Cys Ile Phe Pro Asp Gly Gly Pro Cys Pro Ser Gly Ser Trp Ser Gln
    130                 135                 140

Lys Arg Ser Phe Val Tyr Val Trp Lys Thr Trp Gly Gln Tyr Trp Gln
145                 150                 155                 160

Val Leu Gly Gly Pro Val Ser Gly Leu Ser Ile Gly Thr Gly Arg Ala
                165                 170                 175

Met Leu Gly Thr His Thr Met Glu Val Thr Val Tyr His Arg Arg Gly
```

-continued

```
            180                 185                 190

Ser Arg Ser Tyr Val Pro Leu Ala His Ser Ser Ser Ala Phe Thr Ile
        195                 200                 205

Thr Asp Gln Val Pro Phe Ser Val Ser Val Ser Gln Leu Arg Ala Leu
    210                 215                 220

Asp Gly Gly Asn Lys His Phe Leu Arg Asn Gln Pro Leu Thr Phe Ala
225                 230                 235                 240

Leu Gln Leu His Asp Pro Ser Gly Tyr Leu Ala Glu Ala Asp Leu Ser
                245                 250                 255

Tyr Thr Trp Asp Phe Gly Asp Ser Ser Gly Thr Leu Ile Ser Arg Ala
            260                 265                 270

Leu Val Val Thr His Thr Tyr Leu Glu Pro Gly Pro Val Thr Ala Gln
        275                 280                 285

Val Val Leu Gln Ala Ala Ile Pro Leu Thr Ser Cys Gly Ser Ser Pro
    290                 295                 300

Val Pro Gly Thr Thr Asp Gly His Arg Pro Thr Ala Glu Ala Pro Asn
305                 310                 315                 320

Thr Thr Ala Gly Gln Val Pro Thr Thr Glu Val Val Gly Thr Thr Pro
                325                 330                 335

Gly Gln Ala Pro Thr Ala Glu Pro Ser Gly Thr Thr Ser Val Gln Val
            340                 345                 350

Pro Thr Thr Glu Val Ile Ser Thr Ala Pro Val Gln Met Pro Thr Ala
        355                 360                 365

Glu Ser Thr Gly Met Thr Pro Glu Lys Val Pro Val Ser Glu Val Met
    370                 375                 380

Gly Thr Thr Leu Ala Glu Met Ser Thr Pro Glu Ala Thr Gly Met Thr
385                 390                 395                 400

Pro Ala Glu Val Ser Ile Val Val Leu Ser Gly Thr Thr Ala Ala Gln
                405                 410                 415

Val Thr Thr Thr Glu Trp Val Glu Thr Thr Ala Arg Glu Leu Pro Ile
            420                 425                 430

Pro Glu Pro Glu Gly Pro Asp Ala Ser Ser Ile Met Ser Thr Glu Ser
        435                 440                 445

Ile Thr Gly Ser Leu Gly Pro Leu Leu Asp Gly Thr Ala Thr Leu Arg
    450                 455                 460

Leu Val Lys Arg Gln Val Pro Leu Asp Cys Val Leu Tyr Arg Tyr Gly
465                 470                 475                 480

Ser Phe Ser Val Thr Leu Asp Ile Val Gln Gly Ile Glu Ser Ala Glu
                485                 490                 495

Ile Leu Gln Ala Val Pro Ser Gly Glu Gly Asp Ala Phe Glu Leu Thr
            500                 505                 510

Val Ser Cys Gln Gly Gly Leu Pro Lys Glu Ala Cys Met Glu Ile Ser
        515                 520                 525

Ser Pro Gly Cys Gln Pro Pro Ala Gln Arg Leu Cys Gln Pro Val Leu
    530                 535                 540

Pro Ser Pro Ala Cys Gln Leu Val Leu His Gln Ile Leu Lys Gly Gly
545                 550                 555                 560

Ser Gly Thr Tyr Cys Leu Asn Val Ser Leu Ala Asp Thr Asn Ser Leu
                565                 570                 575

Ala Val Val Ser Thr Gln Leu Ile Met Pro Gly Gln Glu Ala Gly Leu
            580                 585                 590

Gly Gln Val Pro Leu Ile Val Gly Ile Leu Leu Val Leu Met Ala Val
        595                 600                 605
```

-continued

```
Val Leu Ala Ser Leu Ile Tyr Arg Arg Arg Leu Met Lys Gln Asp Phe
    610                 615                 620

Ser Val Pro Gln Leu Pro His Ser Ser Ser His Trp Leu Arg Leu Pro
625                 630                 635                 640

Arg Ile Phe Cys Ser Cys Pro Ile Gly Glu Asn Ser Pro Leu Leu Ser
                645                 650                 655

Gly Gln Gln Val
            660
```

<210> SEQ ID NO 386
<211> LENGTH: 9
<212> TYPE: PRT
<213> ORGANISM: Homo sapiens

<400> SEQUENCE: 386

```
Val Tyr Val Trp Lys Thr Trp Gly Gln
  1               5
```

<210> SEQ ID NO 387
<211> LENGTH: 8
<212> TYPE: PRT
<213> ORGANISM: Homo sapiens

<400> SEQUENCE: 387

```
Trp Val Glu Thr Thr Arg Glu Leu
  1               5
```

<210> SEQ ID NO 388
<211> LENGTH: 9
<212> TYPE: PRT
<213> ORGANISM: Homo sapiens

<400> SEQUENCE: 388

```
Leu Tyr Arg Tyr Gly Ser Phe Ser Val
  1               5
```

<210> SEQ ID NO 389
<211> LENGTH: 9
<212> TYPE: PRT
<213> ORGANISM: Homo sapiens

<400> SEQUENCE: 389

```
Val Val Leu Gln Ala Ala Ile Pro Leu
  1               5
```

<210> SEQ ID NO 390
<211> LENGTH: 9
<212> TYPE: PRT
<213> ORGANISM: Homo sapiens

<400> SEQUENCE: 390

```
Leu Val Leu His Gln Ile Leu Lys Gly
  1               5
```

<210> SEQ ID NO 391
<211> LENGTH: 9
<212> TYPE: PRT
<213> ORGANISM: Homo sapiens

<400> SEQUENCE: 391

```
Val Pro Leu Ile Val Gly Ile Leu Leu
  1               5
```

-continued

<210> SEQ ID NO 392
<211> LENGTH: 9
<212> TYPE: PRT
<213> ORGANISM: Homo sapiens

<400> SEQUENCE: 392

Val Gly Ile Leu Leu Val Leu Met Ala
1 5

<210> SEQ ID NO 393
<211> LENGTH: 9
<212> TYPE: PRT
<213> ORGANISM: Homo sapiens

<400> SEQUENCE: 393

Val Leu Met Ala Val Val Leu Ala Ser
1 5

<210> SEQ ID NO 394
<211> LENGTH: 9
<212> TYPE: PRT
<213> ORGANISM: Homo sapiens

<400> SEQUENCE: 394

Leu Val Leu Met Ala Val Val Leu Ala
1 5

<210> SEQ ID NO 395
<211> LENGTH: 9
<212> TYPE: PRT
<213> ORGANISM: Homo sapiens

<400> SEQUENCE: 395

Leu Val Leu Lys Arg Cys Leu Leu His
1 5

<210> SEQ ID NO 396
<211> LENGTH: 9
<212> TYPE: PRT
<213> ORGANISM: Homo sapiens

<400> SEQUENCE: 396

Ile Tyr Arg Arg Arg Leu Met Lys Gln
1 5

<210> SEQ ID NO 397
<211> LENGTH: 9
<212> TYPE: PRT
<213> ORGANISM: Homo sapiens

<400> SEQUENCE: 397

Tyr Arg Arg Arg Leu Met Lys Gln Asp
1 5

<210> SEQ ID NO 398
<211> LENGTH: 9
<212> TYPE: PRT
<213> ORGANISM: Homo sapiens

<400> SEQUENCE: 398

Leu Tyr Pro Glu Trp Thr Glu Ala Gln
1 5

<210> SEQ ID NO 399

-continued

<211> LENGTH: 16
<212> TYPE: PRT
<213> ORGANISM: Homo sapiens

<400> SEQUENCE: 399

Trp Asn Arg Gln Leu Tyr Pro Glu Trp Thr Glu Ala Gln Arg Leu Asp
1 5 10 15

<210> SEQ ID NO 400
<211> LENGTH: 19
<212> TYPE: PRT
<213> ORGANISM: Homo sapiens

<400> SEQUENCE: 400

Ile Tyr Arg Arg Arg Leu Met Lys Gln Asp Phe Ser Val Pro Gln Leu
1 5 10 15

Pro His Ser

<210> SEQ ID NO 401
<211> LENGTH: 13
<212> TYPE: PRT
<213> ORGANISM: Homo sapiens

<400> SEQUENCE: 401

Ser Leu Ala Val Val Ser Thr Gln Leu Ile Met Pro Gly
1 5 10

<210> SEQ ID NO 402
<211> LENGTH: 15
<212> TYPE: PRT
<213> ORGANISM: Homo sapiens

<400> SEQUENCE: 402

Gly Arg Ala Met Leu Gly Thr His Thr Met Glu Val Thr Val Tyr
1 5 10 15

<210> SEQ ID NO 403
<211> LENGTH: 16
<212> TYPE: PRT
<213> ORGANISM: Homo sapiens

<400> SEQUENCE: 403

Gly Pro Thr Leu Ile Gly Ala Asn Ala Ser Phe Ser Ile Ala Leu Asn
1 5 10 15

<210> SEQ ID NO 404
<211> LENGTH: 24
<212> TYPE: PRT
<213> ORGANISM: Artificial Sequence
<220> FEATURE:
<223> OTHER INFORMATION: Description of Artificial Sequence: Synthetic
Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 404

Leu Arg Met Lys Xaa Ile Tyr Arg Arg Arg Leu Met Lys Gln Asp Phe
1 5 10 15

Ser Val Pro Gln Leu Pro His Ser
20

-continued

<210> SEQ ID NO 405
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 405

Leu Arg Met Lys Xaa Leu Val Leu Lys Arg Cys Leu Leu His
1 5 10

<210> SEQ ID NO 406
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 406

Leu Arg Met Lys Xaa Val Tyr Val Trp Lys Thr Trp Gly Gln
1 5 10

<210> SEQ ID NO 407
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 407

Leu Arg Met Lys Xaa Trp Val Glu Thr Thr Ala Arg Glu Leu
1 5 10

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 408

Leu Arg Met Lys Xaa Leu Tyr Arg Tyr Gly Ser Phe Ser Val
1 5 10

-continued

<210> SEQ ID NO 409
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 409

```
Leu Arg Met Lys Xaa Trp Asn Arg Gln Leu Tyr Pro Glu Trp Thr Glu
  1               5                  10                  15

Ala Gln Arg Leu Asp
             20
```

<210> SEQ ID NO 410
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 410

```
Leu Arg Met Lys Xaa Leu Tyr Pro Glu Trp Thr Glu Ala Gln
  1               5                  10
```

<210> SEQ ID NO 411
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 411

```
Leu Arg Met Lys Xaa Trp Asn Arg Gln Leu Tyr Pro Glu Trp Thr Glu
  1               5                  10                  15

Ala Gln Arg Leu Asp
             20
```

<210> SEQ ID NO 412
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:

-continued

<223> OTHER INFORMATION: C-term amidated

<400> SEQUENCE: 412

Leu Arg Met Lys Xaa Val Pro Leu Ile Val Gly Ile Leu Leu
1 5 10

<210> SEQ ID NO 413
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 413

Leu Arg Met Lys Xaa Val Gly Ile Leu Leu Val Leu Met Ala
1 5 10

<210> SEQ ID NO 414
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 414

Leu Arg Met Lys Xaa Val Leu Met Ala Val Val Leu Ala Ser
1 5 10

<210> SEQ ID NO 415
<211> LENGTH: 23
<212> TYPE: PRT
<213> ORGANISM: Artificial Sequence
<220> FEATURE:
<223> OTHER INFORMATION: Description of Artificial Sequence: Synthetic Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 415

Leu Arg Met Lys Xaa Val Pro Leu Ile Val Gly Ile Leu Leu Val Leu
1 5 10 15

Met Ala Val Val Leu Ala Ser
20

<210> SEQ ID NO 416
<211> LENGTH: 9
<212> TYPE: PRT
<213> ORGANISM: Homo sapiens

<400> SEQUENCE: 416

Arg Leu Met Lys Gln Asp Phe Ser Val

-continued

```
  1               5


<210> SEQ ID NO 417
<211> LENGTH: 9
<212> TYPE: PRT
<213> ORGANISM: Homo sapiens

<400> SEQUENCE: 417

Leu Pro Lys Glu Ala Cys Met Glu Ile
  1               5


<210> SEQ ID NO 418
<211> LENGTH: 9
<212> TYPE: PRT
<213> ORGANISM: Homo sapiens

<400> SEQUENCE: 418

Ile Leu Leu Val Leu Met Ala Val Val
  1               5


<210> SEQ ID NO 419
<211> LENGTH: 9
<212> TYPE: PRT
<213> ORGANISM: Homo sapiens

<400> SEQUENCE: 419

Arg Tyr Gly Ser Phe Ser Val Thr Leu
  1               5


<210> SEQ ID NO 420
<211> LENGTH: 9
<212> TYPE: PRT
<213> ORGANISM: Homo sapiens

<400> SEQUENCE: 420

Lys Thr Trp Gly Gln Tyr Trp Gln Val
  1               5


<210> SEQ ID NO 421
<211> LENGTH: 9
<212> TYPE: PRT
<213> ORGANISM: Homo sapiens

<400> SEQUENCE: 421

Ala Leu Leu Ala Val Gly Ala Thr Lys
  1               5


<210> SEQ ID NO 422
<211> LENGTH: 9
<212> TYPE: PRT
<213> ORGANISM: Homo sapiens

<400> SEQUENCE: 422

Leu Ile Tyr Arg Arg Arg Leu Met Lys
  1               5


<210> SEQ ID NO 423
<211> LENGTH: 9
<212> TYPE: PRT
<213> ORGANISM: Homo sapiens

<400> SEQUENCE: 423

Tyr Leu Glu Pro Gly Pro Val Thr Ala
  1               5
```

-continued

<210> SEQ ID NO 424
<211> LENGTH: 9
<212> TYPE: PRT
<213> ORGANISM: Homo sapiens

<400> SEQUENCE: 424

Ala Leu Leu Ala Val Gly Ala Thr Lys
1 5

<210> SEQ ID NO 425
<211> LENGTH: 9
<212> TYPE: PRT
<213> ORGANISM: Homo sapiens

<400> SEQUENCE: 425

Ile Thr Asp Gln Val Pro Phe Ser Val
1 5

<210> SEQ ID NO 426
<211> LENGTH: 9
<212> TYPE: PRT
<213> ORGANISM: Homo sapiens

<400> SEQUENCE: 426

Leu Ile Tyr Arg Arg Arg Leu Met Lys
1 5

<210> SEQ ID NO 427
<211> LENGTH: 9
<212> TYPE: PRT
<213> ORGANISM: Homo sapiens

<400> SEQUENCE: 427

Arg Leu Met Lys Gln Asp Phe Ser Val
1 5

<210> SEQ ID NO 428
<211> LENGTH: 9
<212> TYPE: PRT
<213> ORGANISM: Homo sapiens

<400> SEQUENCE: 428

Arg Leu Pro Arg Ile Phe Cys Ser Cys
1 5

<210> SEQ ID NO 429
<211> LENGTH: 9
<212> TYPE: PRT
<213> ORGANISM: Homo sapiens

<400> SEQUENCE: 429

Lys Thr Trp Gly Gln Tyr Trp Gln Val
1 5

<210> SEQ ID NO 430
<211> LENGTH: 10
<212> TYPE: PRT
<213> ORGANISM: Homo sapiens

<400> SEQUENCE: 430

Ala Met Leu Gly Thr His Thr Met Glu Val
1 5 10

<210> SEQ ID NO 431

-continued

```
<211> LENGTH: 10
<212> TYPE: PRT
<213> ORGANISM: Homo sapiens

<400> SEQUENCE: 431

Ser Leu Ala Asp Thr Asn Ser Leu Ala Val
  1               5                  10


<210> SEQ ID NO 432
<211> LENGTH: 9
<212> TYPE: PRT
<213> ORGANISM: Homo sapiens

<400> SEQUENCE: 432

Val Ser Asn Asp Gly Pro Thr Leu Ile
  1               5


<210> SEQ ID NO 433
<211> LENGTH: 9
<212> TYPE: PRT
<213> ORGANISM: Homo sapiens

<400> SEQUENCE: 433

Ala Leu Asn Phe Pro Gly Ser Gln Lys
  1               5


<210> SEQ ID NO 434
<211> LENGTH: 23
<212> TYPE: PRT
<213> ORGANISM: Artificial Sequence
<220> FEATURE:
<223> OTHER INFORMATION: Description of Artificial Sequence: Synthetic
      Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 434

Leu Arg Met Lys Xaa Leu Pro Lys Glu Ala Cys Met Glu Ile Leu Val
  1               5                  10                  15

Leu His Gln Ile Leu Lys Gly
             20


<210> SEQ ID NO 435
<211> LENGTH: 23
<212> TYPE: PRT
<213> ORGANISM: Artificial Sequence
<220> FEATURE:
<223> OTHER INFORMATION: Description of Artificial Sequence: Synthetic
      Ii-key/gp 100 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 435

Leu Arg Met Lys Xaa Ala Leu Leu Ala Val Gly Ala Thr Lys Leu Val
  1               5                  10                  15

Leu Lys Arg Cys Leu Leu His
             20


<210> SEQ ID NO 436
```

-continued

<211> LENGTH: 24
<212> TYPE: PRT
<213> ORGANISM: Artificial Sequence
<220> FEATURE:
<223> OTHER INFORMATION: Description of Artificial Sequence: Synthetic
Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 436

```
Leu Arg Met Lys Xaa Ser Leu Ala Asp Thr Asn Ser Leu Ala Val Val
  1               5                  10                  15

Ser Thr Gln Leu Ile Met Pro Gly
             20
```

<210> SEQ ID NO 437
<211> LENGTH: 20
<212> TYPE: PRT
<213> ORGANISM: Artificial Sequence
<220> FEATURE:
<223> OTHER INFORMATION: Description of Artificial Sequence: Synthetic
Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 437

```
Leu Arg Met Lys Xaa Gly Arg Ala Met Leu Gly Thr His Thr Met Glu
  1               5                  10                  15

Val Thr Val Tyr
             20
```

<210> SEQ ID NO 438
<211> LENGTH: 31
<212> TYPE: PRT
<213> ORGANISM: Artificial Sequence
<220> FEATURE:
<223> OTHER INFORMATION: Description of Artificial Sequence: Synthetic
Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 438

```
Leu Arg Met Lys Xaa Val Ser Asn Asp Gly Pro Thr Leu Ile Gly Ala
  1               5                  10                  15

Asn Ala Ser Phe Ser Ile Ala Leu Asn Phe Pro Gly Ser Gln Lys
             20                  25                  30
```

<210> SEQ ID NO 439
<211> LENGTH: 25
<212> TYPE: PRT
<213> ORGANISM: Artificial Sequence
<220> FEATURE:
<223> OTHER INFORMATION: Description of Artificial Sequence: Synthetic
Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 439

Leu Arg Met Lys Xaa Leu Ile Tyr Arg Arg Arg Leu Met Lys Gln Asp
1 5 10 15

Phe Ser Val Pro Gln Leu Pro His Ser
20 25

<210> SEQ ID NO 440
<211> LENGTH: 17
<212> TYPE: PRT
<213> ORGANISM: Artificial Sequence
<220> FEATURE:
<223> OTHER INFORMATION: Description of Artificial Sequence: Synthetic Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 440

Leu Arg Met Lys Xaa Val Tyr Val Lys Thr Trp Gly Gln Tyr Trp Gln
1 5 10 15

Val

<210> SEQ ID NO 441
<211> LENGTH: 16
<212> TYPE: PRT
<213> ORGANISM: Artificial Sequence
<220> FEATURE:
<223> OTHER INFORMATION: Description of Artificial Sequence: Synthetic Ii-key/gp 100 overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 441

Leu Arg Met Lys Xaa Leu Tyr Arg Tyr Gly Ser Phe Ser Val Thr Leu
1 5 10 15

<210> SEQ ID NO 442
<211> LENGTH: 519
<212> TYPE: PRT
<213> ORGANISM: Homo sapiens

<400> SEQUENCE: 442

Met Ser Pro Leu Trp Trp Gly Phe Leu Leu Ser Cys Leu Gly Cys Lys
1 5 10 15

Ile Leu Pro Gly Ala Gln Gly Gln Phe Pro Arg Val Cys Met Thr Val
20 25 30

Asp Ser Leu Val Asn Lys Glu Cys Cys Pro Arg Leu Gly Ala Glu Ser
35 40 45

Ala Asn Val Cys Gly Ser Gln Gln Gly Arg Gly Gln Cys Thr Glu Val
50 55 60

Arg Ala Asp Thr Arg Pro Trp Ser Gly Pro Tyr Ile Leu Arg Asn Gln
65 70 75 80

Asp Asp Arg Glu Leu Trp Pro Arg Lys Phe Phe His Arg Thr Cys Lys
85 90 95

-continued

```
Cys Thr Gly Asn Phe Ala Gly Tyr Asn Cys Gly Asp Cys Lys Phe Gly
            100                 105                 110

Trp Thr Gly Pro Asn Cys Glu Arg Lys Lys Pro Pro Val Ile Arg Gln
        115                 120                 125

Asn Ile His Ser Leu Ser Pro Gln Glu Arg Glu Gln Phe Leu Gly Ala
    130                 135                 140

Leu Asp Leu Ala Lys Lys Arg Val His Pro Asp Tyr Val Ile Thr Thr
145                 150                 155                 160

Gln His Trp Leu Gly Leu Leu Gly Pro Asn Gly Thr Gln Pro Gln Phe
                165                 170                 175

Ala Asn Cys Ser Val Tyr Asp Phe Phe Val Trp Leu His Tyr Tyr Ser
            180                 185                 190

Val Arg Asp Thr Leu Leu Gly Pro Gly Arg Pro Tyr Arg Ala Ile Asp
        195                 200                 205

Phe Ser His Gln Gly Pro Ala Phe Val Thr Trp His Arg Tyr His Leu
    210                 215                 220

Leu Cys Leu Glu Arg Asp Leu Gln Arg Leu Ile Gly Asn Glu Ser Phe
225                 230                 235                 240

Ala Leu Pro Tyr Trp Asn Phe Ala Thr Gly Arg Asn Glu Cys Asp Val
                245                 250                 255

Cys Thr Asp Gln Leu Phe Gly Ala Ala Arg Pro Asp Asp Pro Thr Leu
            260                 265                 270

Ile Ser Arg Asn Ser Arg Phe Ser Ser Trp Glu Thr Val Cys Asp Ser
        275                 280                 285

Leu Asp Asp Tyr Asn His Leu Val Thr Leu Cys Asn Gly Thr Tyr Glu
    290                 295                 300

Gly Leu Leu Arg Arg Asn Gln Met Gly Arg Asn Ser Met Lys Leu Pro
305                 310                 315                 320

Thr Leu Lys Asp Ile Arg Asp Cys Leu Ser Leu Gln Lys Phe Asp Asn
                325                 330                 335

Pro Pro Phe Phe Gln Asn Ser Thr Phe Ser Phe Arg Asn Ala Leu Glu
            340                 345                 350

Gly Phe Asp Lys Ala Asp Gly Thr Leu Asp Ser Gln Val Met Ser Leu
        355                 360                 365

His Asn Leu Val His Ser Phe Leu Asn Gly Thr Asn Ala Leu Pro His
    370                 375                 380

Ser Ala Ala Asn Asp Pro Ile Phe Val Val Leu His Ser Phe Thr Asp
385                 390                 395                 400

Ala Ile Phe Asp Glu Trp Met Lys Arg Phe Asn Pro Pro Ala Asp Ala
                405                 410                 415

Trp Pro Gln Glu Leu Ala Pro Ile Gly His Asn Arg Met Tyr Asn Met
            420                 425                 430

Val Pro Phe Phe Pro Pro Val Thr Asn Glu Glu Leu Phe Leu Thr Ser
        435                 440                 445

Asp Gln Leu Gly Tyr Ser Tyr Ala Ile Asp Leu Pro Val Ser Val Glu
    450                 455                 460

Glu Thr Pro Gly Trp Pro Thr Thr Leu Leu Val Val Met Gly Thr Leu
465                 470                 475                 480

Val Ala Leu Val Gly Leu Phe Val Leu Leu Ala Phe Leu Gln Tyr Arg
                485                 490                 495

Arg Leu Arg Lys Gly Tyr Thr Pro Leu Met Glu Thr His Leu Ser Ser
            500                 505                 510

Lys Arg Tyr Thr Glu Glu Ala
```

-continued

515

<210> SEQ ID NO 443
<211> LENGTH: 9
<212> TYPE: PRT
<213> ORGANISM: Homo sapiens

<400> SEQUENCE: 443

Tyr Val Ile Thr Thr Gln His Trp Leu
1 5

<210> SEQ ID NO 444
<211> LENGTH: 9
<212> TYPE: PRT
<213> ORGANISM: Homo sapiens

<400> SEQUENCE: 444

Leu Gly Tyr Ser Tyr Ala Ile Asp Leu
1 5

<210> SEQ ID NO 445
<211> LENGTH: 10
<212> TYPE: PRT
<213> ORGANISM: Homo sapiens

<400> SEQUENCE: 445

Val Arg Ala Asp Thr Arg Pro Trp Ser Gly
1 5 10

<210> SEQ ID NO 446
<211> LENGTH: 9
<212> TYPE: PRT
<213> ORGANISM: Homo sapiens

<400> SEQUENCE: 446

Leu Val Gly Leu Phe Val Leu Leu Ala
1 5

<210> SEQ ID NO 447
<211> LENGTH: 9
<212> TYPE: PRT
<213> ORGANISM: Homo sapiens

<400> SEQUENCE: 447

Leu Ile Ser Arg Asn Ser Arg Phe Ser
1 5

<210> SEQ ID NO 448
<211> LENGTH: 9
<212> TYPE: PRT
<213> ORGANISM: Homo sapiens

<400> SEQUENCE: 448

Phe Val Val Leu His Ser Phe Thr Asp
1 5

<210> SEQ ID NO 449
<211> LENGTH: 9
<212> TYPE: PRT
<213> ORGANISM: Homo sapiens

<400> SEQUENCE: 449

Trp His Arg Tyr His Leu Leu Cys Leu
1 5

-continued

<210> SEQ ID NO 450
<211> LENGTH: 9
<212> TYPE: PRT
<213> ORGANISM: Homo sapiens

<400> SEQUENCE: 450

Leu Arg Lys Gly Tyr Thr Pro Leu Met
1 5

<210> SEQ ID NO 451
<211> LENGTH: 9
<212> TYPE: PRT
<213> ORGANISM: Homo sapiens

<400> SEQUENCE: 451

Val Met Ser Leu His Asn Leu Val His
1 5

<210> SEQ ID NO 452
<211> LENGTH: 9
<212> TYPE: PRT
<213> ORGANISM: Homo sapiens

<400> SEQUENCE: 452

Leu Val Val Met Gly Thr Leu Val Ala
1 5

<210> SEQ ID NO 453
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/TRP-2 antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 453

Leu Arg Met Lys Xaa Tyr Val Ile Thr Thr Gln His Trp Leu
1 5 10

<210> SEQ ID NO 454
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/TRP-2 antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 454

Leu Arg Met Lys Xaa Leu Gly Tyr Ser Tyr Ala Ile Asp Leu
1 5 10

<210> SEQ ID NO 455
<211> LENGTH: 14
<212> TYPE: PRT
<213> ORGANISM: Artificial Sequence
<220> FEATURE:

-continued

```
<223> OTHER INFORMATION: Description of Artificial Sequence: Synthetic
      Ii-key/TRP-2 antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 455

Leu Arg Met Lys Xaa Val Arg Ala Asp Thr Arg Pro Ser Gly
  1               5                  10


<210> SEQ ID NO 456
<211> LENGTH: 9
<212> TYPE: PRT
<213> ORGANISM: Homo sapiens

<400> SEQUENCE: 456

Ser Arg Phe Ser Ser Trp Glu Thr Val
  1               5


<210> SEQ ID NO 457
<211> LENGTH: 9
<212> TYPE: PRT
<213> ORGANISM: Homo sapiens

<400> SEQUENCE: 457

Lys Arg Phe Asn Pro Pro Ala Asp Ala
  1               5


<210> SEQ ID NO 458
<211> LENGTH: 9
<212> TYPE: PRT
<213> ORGANISM: Homo sapiens

<400> SEQUENCE: 458

Ile Arg Asp Cys Leu Ser Leu Gln Lys
  1               5


<210> SEQ ID NO 459
<211> LENGTH: 9
<212> TYPE: PRT
<213> ORGANISM: Homo sapiens

<400> SEQUENCE: 459

Lys Arg Val His Pro Asp Tyr Val Ile
  1               5


<210> SEQ ID NO 460
<211> LENGTH: 9
<212> TYPE: PRT
<213> ORGANISM: Homo sapiens

<400> SEQUENCE: 460

Asn Arg Met Tyr Asn Met Val Pro Phe
  1               5


<210> SEQ ID NO 461
<211> LENGTH: 9
<212> TYPE: PRT
<213> ORGANISM: Homo sapiens

<400> SEQUENCE: 461

Gly Leu Phe Val Leu Leu Ala Phe Leu
  1               5
```

-continued

<210> SEQ ID NO 462
<211> LENGTH: 9
<212> TYPE: PRT
<213> ORGANISM: Homo sapiens

<400> SEQUENCE: 462

Ser Val Tyr Asp Phe Phe Val Trp Leu
1 5

<210> SEQ ID NO 463
<211> LENGTH: 9
<212> TYPE: PRT
<213> ORGANISM: Homo sapiens

<400> SEQUENCE: 463

Leu Ala Phe Leu Gln Tyr Arg Arg Leu
1 5

<210> SEQ ID NO 464
<211> LENGTH: 9
<212> TYPE: PRT
<213> ORGANISM: Homo sapiens

<400> SEQUENCE: 464

Asn Met Val Pro Phe Phe Pro Pro Val
1 5

<210> SEQ ID NO 465
<211> LENGTH: 9
<212> TYPE: PRT
<213> ORGANISM: Homo sapiens

<400> SEQUENCE: 465

Phe Val Trp Leu His Tyr Tyr Ser Val
1 5

<210> SEQ ID NO 466
<211> LENGTH: 9
<212> TYPE: PRT
<213> ORGANISM: Homo sapiens

<400> SEQUENCE: 466

Ser Val Tyr Asp Phe Phe Val Trp Leu
1 5

<210> SEQ ID NO 467
<211> LENGTH: 9
<212> TYPE: PRT
<213> ORGANISM: Homo sapiens

<400> SEQUENCE: 467

Gly Pro Gly Arg Pro Tyr Arg Ala Ile
1 5

<210> SEQ ID NO 468
<211> LENGTH: 9
<212> TYPE: PRT
<213> ORGANISM: Homo sapiens

<400> SEQUENCE: 468

Ala Ala Arg Pro Asp Asp Pro Thr Leu
1 5

-continued

<210> SEQ ID NO 469
<211> LENGTH: 9
<212> TYPE: PRT
<213> ORGANISM: Homo sapiens

<400> SEQUENCE: 469

Gly Phe Asp Lys Ala Asp Gly Thr Leu
1 5

<210> SEQ ID NO 470
<211> LENGTH: 9
<212> TYPE: PRT
<213> ORGANISM: Homo sapiens

<400> SEQUENCE: 470

Lys Arg Phe Asn Pro Pro Ala Asp Ala
1 5

<210> SEQ ID NO 471
<211> LENGTH: 9
<212> TYPE: PRT
<213> ORGANISM: Homo sapiens

<400> SEQUENCE: 471

His Tyr Tyr Ser Val Arg Asp Thr Leu
1 5

<210> SEQ ID NO 472
<211> LENGTH: 9
<212> TYPE: PRT
<213> ORGANISM: Homo sapiens

<400> SEQUENCE: 472

Leu Gln Lys Phe Asp Asn Pro Pro Phe
1 5

<210> SEQ ID NO 473
<211> LENGTH: 9
<212> TYPE: PRT
<213> ORGANISM: Homo sapiens

<400> SEQUENCE: 473

Ser Val Tyr Asp Phe Phe Val Trp Leu
1 5

<210> SEQ ID NO 474
<211> LENGTH: 9
<212> TYPE: PRT
<213> ORGANISM: Homo sapiens

<400> SEQUENCE: 474

Thr Leu Asp Ser Gln Val Met Ser Leu
1 5

<210> SEQ ID NO 475
<211> LENGTH: 9
<212> TYPE: PRT
<213> ORGANISM: Homo sapiens

<400> SEQUENCE: 475

Ser Leu Asp Asp Tyr Asn His Leu Val
1 5

<210> SEQ ID NO 476
<211> LENGTH: 9

<212> TYPE: PRT
<213> ORGANISM: Homo sapiens

<400> SEQUENCE: 476

Tyr Ala Ile Asp Leu Pro Val Ser Val
1 5

<210> SEQ ID NO 477
<211> LENGTH: 23
<212> TYPE: PRT
<213> ORGANISM: Artificial Sequence
<220> FEATURE:
<223> OTHER INFORMATION: Description of Artificial Sequence: Synthetic Ii-key/TRP-2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 477

Leu Arg Met Lys Xaa Tyr Val Ile Thr Thr Gln His Trp Leu Ser Val
1 5 10 15

Tyr Asp Phe Phe Val Trp Leu
20

<210> SEQ ID NO 478
<211> LENGTH: 18
<212> TYPE: PRT
<213> ORGANISM: Artificial Sequence
<220> FEATURE:
<223> OTHER INFORMATION: Description of Artificial Sequence: Synthetic Ii-key/TRP-2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 478

Leu Arg Met Lys Xaa Leu Gly Tyr Ser Tyr Ala Ile Asp Leu Pro Val
1 5 10 15

Ser Val

<210> SEQ ID NO 479
<211> LENGTH: 19
<212> TYPE: PRT
<213> ORGANISM: Artificial Sequence
<220> FEATURE:
<223> OTHER INFORMATION: Description of Artificial Sequence: Synthetic Ii-key/TRP-2 hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 479

Leu Arg Met Lys Xaa Thr Leu Asp Ser Gln Val Met Ser Leu His Asn
1 5 10 15

Leu Val His

<210> SEQ ID NO 480
<211> LENGTH: 10
<212> TYPE: PRT

-continued

<213> ORGANISM: Homo sapiens

<400> SEQUENCE: 480

Cys Leu Leu Trp Ser Phe Gln Thr Ser Ala
1               5                   10

<210> SEQ ID NO 481
<211> LENGTH: 9
<212> TYPE: PRT
<213> ORGANISM: Homo sapiens

<400> SEQUENCE: 481

Ile Met Asp Gln Val Pro Ser Phe Val
1               5

<210> SEQ ID NO 482
<211> LENGTH: 9
<212> TYPE: PRT
<213> ORGANISM: Homo sapiens

<400> SEQUENCE: 482

Tyr Met Asp Gly Thr Met Ser Gln Val
1               5

<210> SEQ ID NO 483
<211> LENGTH: 12
<212> TYPE: PRT
<213> ORGANISM: Homo sapiens

<400> SEQUENCE: 483

Asp Ala Glu Lys Ser Asp Ile Cys Thr Asp Glu Tyr
1               5                   10

<210> SEQ ID NO 484
<211> LENGTH: 9
<212> TYPE: PRT
<213> ORGANISM: Homo sapiens

<400> SEQUENCE: 484

Tyr Leu Glu Pro Gly Pro Val Thr Ala
1               5

<210> SEQ ID NO 485
<211> LENGTH: 9
<212> TYPE: PRT
<213> ORGANISM: Homo sapiens

<400> SEQUENCE: 485

Tyr Met Asp Gly Thr Met Ser Gln Val
1               5

<210> SEQ ID NO 486
<211> LENGTH: 9
<212> TYPE: PRT
<213> ORGANISM: Homo sapiens

<400> SEQUENCE: 486

Ala Leu Leu Ala Val Gly Ala Thr Lys
1               5

<210> SEQ ID NO 487
<211> LENGTH: 529
<212> TYPE: PRT
<213> ORGANISM: Homo sapiens -continued

<400> SEQUENCE: 487

```
Met Leu Leu Ala Val Leu Tyr Cys Leu Leu Trp Ser Phe Gln Thr Ser
  1               5                  10                  15

Ala Gly His Phe Pro Arg Ala Cys Val Ser Ser Lys Asn Leu Met Glu
             20                  25                  30

Lys Glu Cys Cys Pro Pro Trp Ser Gly Asp Arg Ser Pro Cys Gly Gln
         35                  40                  45

Leu Ser Gly Arg Gly Ser Cys Gln Asn Ile Leu Leu Ser Asn Ala Pro
     50                  55                  60

Leu Gly Pro Gln Phe Pro Phe Thr Gly Val Asp Asp Arg Glu Ser Trp
 65                  70                  75                  80

Pro Ser Val Phe Tyr Asn Arg Thr Cys Gln Cys Ser Gly Asn Phe Met
                 85                  90                  95

Gly Phe Asn Cys Gly Asn Cys Lys Phe Gly Phe Trp Gly Pro Asn Cys
            100                 105                 110

Thr Glu Arg Arg Leu Leu Val Arg Arg Asn Ile Phe Asp Leu Ser Ala
        115                 120                 125

Pro Glu Lys Asp Lys Phe Phe Ala Tyr Leu Thr Leu Ala Lys His Thr
    130                 135                 140

Ile Ser Ser Asp Tyr Val Ile Pro Ile Gly Thr Tyr Gly Gln Met Lys
145                 150                 155                 160

Asn Gly Ser Thr Pro Met Phe Asn Asp Ile Asn Ile Tyr Asp Leu Phe
                165                 170                 175

Val Trp Met His Tyr Tyr Val Ser Met Asp Ala Leu Leu Gly Gly Ser
            180                 185                 190

Glu Ile Trp Arg Asp Ile Asp Phe Ala His Glu Ala Pro Ala Phe Leu
        195                 200                 205

Pro Trp His Arg Leu Phe Leu Leu Arg Trp Glu Gln Glu Ile Gln Lys
    210                 215                 220

Leu Thr Gly Asp Glu Asn Phe Thr Ile Pro Tyr Trp Asp Trp Arg Asp
225                 230                 235                 240

Ala Glu Lys Cys Asp Ile Cys Thr Asp Glu Tyr Met Gly Gly Gln His
                245                 250                 255

Pro Thr Asn Pro Asn Leu Leu Ser Pro Ala Ser Phe Phe Ser Ser Trp
            260                 265                 270

Gln Ile Val Cys Ser Arg Leu Glu Glu Tyr Asn Ser His Gln Ser Leu
        275                 280                 285

Cys Asn Gly Thr Pro Glu Gly Pro Leu Arg Arg Asn Pro Gly Asn His
    290                 295                 300

Asp Lys Ser Arg Thr Pro Arg Leu Pro Ser Ser Ala Asp Val Glu Phe
305                 310                 315                 320

Cys Leu Ser Leu Thr Gln Tyr Glu Ser Gly Ser Met Asp Lys Ala Ala
                325                 330                 335

Asn Phe Ser Phe Arg Asn Thr Leu Glu Gly Phe Ala Ser Pro Leu Thr
            340                 345                 350

Gly Ile Ala Asp Ala Ser Gln Ser Ser Met His Asn Ala Leu His Ile
        355                 360                 365

Tyr Met Asn Gly Thr Met Ser Gln Val Gln Gly Ser Ala Asn Asp Pro
    370                 375                 380

Ile Phe Leu Leu His His Ala Phe Val Asp Ser Ile Phe Glu Gln Trp
385                 390                 395                 400

Leu Arg Arg His Arg Pro Leu Gln Glu Val Tyr Pro Glu Ala Asn Ala
                405                 410                 415
```

-continued

```
Pro Ile Gly His Asn Arg Glu Ser Tyr Met Val Pro Phe Ile Pro Leu
            420                 425                 430

Tyr Arg Asn Gly Asp Phe Phe Ile Ser Ser Lys Asp Leu Gly Tyr Asp
        435                 440                 445

Tyr Ser Tyr Leu Gln Asp Ser Asp Pro Asp Ser Phe Gln Asp Tyr Ile
    450                 455                 460

Lys Ser Tyr Leu Glu Gln Ala Ser Arg Ile Trp Ser Trp Leu Leu Gly
465                 470                 475                 480

Ala Ala Met Val Gly Ala Val Leu Thr Ala Leu Leu Ala Gly Leu Val
                485                 490                 495

Ser Leu Leu Cys Arg His Lys Arg Lys Gln Leu Pro Glu Glu Lys Gln
            500                 505                 510

Pro Leu Leu Met Glu Lys Glu Asp Tyr His Ser Leu Tyr Gln Ser His
        515                 520                 525

Leu


<210> SEQ ID NO 488
<211> LENGTH: 9
<212> TYPE: PRT
<213> ORGANISM: Homo sapiens

<400> SEQUENCE: 488

Leu Arg Arg His Arg Pro Leu Gln Glu
  1               5


<210> SEQ ID NO 489
<211> LENGTH: 9
<212> TYPE: PRT
<213> ORGANISM: Homo sapiens

<400> SEQUENCE: 489

Met His Tyr Tyr Val Ser Met Asp Ala
  1               5


<210> SEQ ID NO 490
<211> LENGTH: 9
<212> TYPE: PRT
<213> ORGANISM: Homo sapiens

<400> SEQUENCE: 490

Trp Leu Arg Arg His Arg Pro Leu Gln
  1               5


<210> SEQ ID NO 491
<211> LENGTH: 9
<212> TYPE: PRT
<213> ORGANISM: Homo sapiens

<400> SEQUENCE: 491

Leu Val Arg Arg Asn Ile Phe Asp Leu
  1               5


<210> SEQ ID NO 492
<211> LENGTH: 9
<212> TYPE: PRT
<213> ORGANISM: Homo sapiens

<400> SEQUENCE: 492

Leu His Ile Tyr Met Asn Gly Thr Met
  1               5
```

-continued

<210> SEQ ID NO 493
<211> LENGTH: 9
<212> TYPE: PRT
<213> ORGANISM: Homo sapiens

<400> SEQUENCE: 493

Ile Tyr Met Asn Gly Thr Met Ser Gln
1 5

<210> SEQ ID NO 494
<211> LENGTH: 9
<212> TYPE: PRT
<213> ORGANISM: Homo sapiens

<400> SEQUENCE: 494

Tyr Val Ser Met Asp Ala Leu Leu Gly
1 5

<210> SEQ ID NO 495
<211> LENGTH: 9
<212> TYPE: PRT
<213> ORGANISM: Homo sapiens

<400> SEQUENCE: 495

Val Ile Pro Ile Gly Thr Tyr Gly Gln
1 5

<210> SEQ ID NO 496
<211> LENGTH: 9
<212> TYPE: PRT
<213> ORGANISM: Homo sapiens

<400> SEQUENCE: 496

Phe Ser Phe Arg Asn Thr Leu Glu Gly
1 5

<210> SEQ ID NO 497
<211> LENGTH: 9
<212> TYPE: PRT
<213> ORGANISM: Homo sapiens

<400> SEQUENCE: 497

Leu Leu Cys Arg His Lys Arg Lys Gln
1 5

<210> SEQ ID NO 498
<211> LENGTH: 9
<212> TYPE: PRT
<213> ORGANISM: Homo sapiens

<400> SEQUENCE: 498

Met Leu Leu Ala Val Leu Tyr Cys Leu
1 5

<210> SEQ ID NO 499
<211> LENGTH: 9
<212> TYPE: PRT
<213> ORGANISM: Homo sapiens

<400> SEQUENCE: 499

Phe Asn Asp Ile Asn Ile Tyr Asp Leu
1 5

<210> SEQ ID NO 500

-continued

<211> LENGTH: 15
<212> TYPE: PRT
<213> ORGANISM: Homo sapiens

<400> SEQUENCE: 500

Gln Asn Ile Leu Leu Ser Asn Ala Pro Leu Gly Pro Gln Phe Pro
1 5 10 15

<210> SEQ ID NO 501
<211> LENGTH: 17
<212> TYPE: PRT
<213> ORGANISM: Homo sapiens

<400> SEQUENCE: 501

Ala Leu His Ile Tyr Met Asn Gly Thr Met Ser Gln Val Gln Gly Ser
1 5 10 15

Ala

<210> SEQ ID NO 502
<211> LENGTH: 20
<212> TYPE: PRT
<213> ORGANISM: Homo sapiens

<400> SEQUENCE: 502

Tyr Gly Gln Met Lys Asn Gly Ser Thr Pro Met Phe Asn Asp Ile Asn
1 5 10 15

Ile Tyr Asp Leu
20

<210> SEQ ID NO 503
<211> LENGTH: 20
<212> TYPE: PRT
<213> ORGANISM: Artificial Sequence
<220> FEATURE:
<223> OTHER INFORMATION: Description of Artificial Sequence: Synthetic Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 503

Leu Arg Met Lys Xaa Gln Asn Ile Leu Leu Ser Asn Ala Pro Leu Gly
1 5 10 15

Pro Gln Phe Pro
20

<210> SEQ ID NO 504
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 504

Leu Arg Met Lys Xaa Leu Val Arg Arg Asn Ile Phe Asp Leu
1 5 10

-continued

<210> SEQ ID NO 505
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 505

Leu Arg Met Lys Xaa Phe Ser Phe Arg Asn Thr Leu Glu Gly
  1               5                  10

<210> SEQ ID NO 506
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 506

Leu Arg Met Lys Xaa Leu Leu Cys Arg His Lys Arg Lys Gln
  1               5                  10

<210> SEQ ID NO 507
<211> LENGTH: 22
<212> TYPE: PRT
<213> ORGANISM: Artificial Sequence
<220> FEATURE:
<223> OTHER INFORMATION: Description of Artificial Sequence: Synthetic
      Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 507

Leu Arg Met Lys Xaa Ala Leu His Ile Tyr Met Asn Gly Thr Met Ser
  1               5                  10                  15

Gln Val Gln Gly Ser Ala
             20

<210> SEQ ID NO 508
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 508

-continued

Leu Arg Met Lys Xaa Leu His Ile Tyr Met Asn Gly Thr Met
1 5 10

<210> SEQ ID NO 509
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 509

Leu Arg Met Lys Xaa Ile Tyr Met Asn Gly Thr Met Ser Gln
1 5 10

<210> SEQ ID NO 510
<211> LENGTH: 17
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 510

Leu Arg Met Lys Xaa Ala Leu His Ile Tyr Met Asn Gly Thr Met Ser
1 5 10 15

Gln

<210> SEQ ID NO 511
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 511

Leu Arg Met Lys Xaa Tyr Val Ser Met Asp Ala Leu Leu Gly
1 5 10

<210> SEQ ID NO 512
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:

-continued

<223> OTHER INFORMATION: C-term amidated

<400> SEQUENCE: 512

```
Leu Arg Met Lys Xaa Met His Tyr Tyr Val Ser Met Asp Ala
  1               5                  10
```

<210> SEQ ID NO 513
<211> LENGTH: 17
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 513

```
Leu Arg Met Lys Xaa Met His Tyr Tyr Val Ser Met Asp Ala Leu Leu
  1               5                  10                  15

Gly
```

<210> SEQ ID NO 514
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 514

```
Leu Arg Met Lys Xaa Val Ile Pro Ile Gly Thr Tyr Gly Gln
  1               5                  10
```

<210> SEQ ID NO 515
<211> LENGTH: 25
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 515

```
Leu Arg Met Lys Xaa Tyr Gly Gln Met Lys Asn Gly Ser Thr Pro Met
  1               5                  10                  15

Phe Asn Asp Ile Asn Ile Tyr Asp Leu
             20                  25
```

<210> SEQ ID NO 516
<211> LENGTH: 14
<212> TYPE: PRT
<213> ORGANISM: Artificial Sequence
<220> FEATURE:
<223> OTHER INFORMATION: Description of Artificial Sequence: Synthetic -continued

```
      Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 516

Leu Arg Met Lys Xaa Phe Asn Asp Ile Asn Ile Tyr Asp Leu
  1               5                  10


<210> SEQ ID NO 517
<211> LENGTH: 31
<212> TYPE: PRT
<213> ORGANISM: Artificial Sequence
<220> FEATURE:
<223> OTHER INFORMATION: Description of Artificial Sequence: Synthetic
      Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 517

Leu Arg Met Lys Xaa Val Ile Pro Ile Gly Thr Tyr Gly Gln Met Lys
  1               5                  10                  15

Asn Gly Ser Thr Pro Met Phe Asn Asp Ile Asn Ile Tyr Asp Leu
             20                  25                  30


<210> SEQ ID NO 518
<211> LENGTH: 9
<212> TYPE: PRT
<213> ORGANISM: Homo sapiens

<400> SEQUENCE: 518

Lys Cys Asp Ile Cys Thr Asp Glu Tyr
  1               5


<210> SEQ ID NO 519
<211> LENGTH: 9
<212> TYPE: PRT
<213> ORGANISM: Homo sapiens

<400> SEQUENCE: 519

Tyr Met Asn Gly Thr Met Ser Gln Val
  1               5


<210> SEQ ID NO 520
<211> LENGTH: 9
<212> TYPE: PRT
<213> ORGANISM: Homo sapiens

<400> SEQUENCE: 520

Met Leu Leu Ala Val Leu Tyr Cys Leu
  1               5


<210> SEQ ID NO 521
<211> LENGTH: 9
<212> TYPE: PRT
<213> ORGANISM: Homo sapiens

<400> SEQUENCE: 521

Phe Leu Pro Trp His Arg Leu Phe Leu
  1               5
```

```
<210> SEQ ID NO 522
<211> LENGTH: 12
<212> TYPE: PRT
<213> ORGANISM: Homo sapiens

<400> SEQUENCE: 522

Asp Ala Glu Lys Ser Asp Ile Cys Thr Asp Glu Tyr
  1               5                  10


<210> SEQ ID NO 523
<211> LENGTH: 9
<212> TYPE: PRT
<213> ORGANISM: Homo sapiens

<400> SEQUENCE: 523

Tyr Met Asp Gly Thr Met Ser Gln Val
  1               5


<210> SEQ ID NO 524
<211> LENGTH: 11
<212> TYPE: PRT
<213> ORGANISM: Homo sapiens

<400> SEQUENCE: 524

Ser Ser Asp Tyr Val Ile Pro Ile Gly Thr Tyr
  1               5                  10


<210> SEQ ID NO 525
<211> LENGTH: 32
<212> TYPE: PRT
<213> ORGANISM: Artificial Sequence
<220> FEATURE:
<223> OTHER INFORMATION: Description of Artificial Sequence: Synthetic
      Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 525

Leu Arg Met Lys Xaa Asp Ala Glu Lys Ser Asp Ile Cys Thr Asp Glu
  1               5                  10                  15

Tyr Gln Asn Ile Leu Leu Ser Asn Ala Pro Leu Gly Pro Gln Phe Pro
             20                  25                  30


<210> SEQ ID NO 526
<211> LENGTH: 23
<212> TYPE: PRT
<213> ORGANISM: Artificial Sequence
<220> FEATURE:
<223> OTHER INFORMATION: Description of Artificial Sequence: Synthetic
      Ii-key/tyrosinase non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 526

Leu Arg Met Lys Xaa Phe Leu Pro Trp His Arg Leu Phe Leu Leu Arg
  1               5                  10                  15

Arg His Arg Pro Leu Gln Glu
             20
```

<210> SEQ ID NO 527
<211> LENGTH: 22
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 527

```
Leu Arg Met Lys Xaa Ala Leu His Ile Tyr Met Asn Gly Thr Met Ser
  1               5                  10                  15

Gln Val Gln Gly Ser Ala
             20
```

<210> SEQ ID NO 528
<211> LENGTH: 35
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 528

```
Leu Arg Met Lys Xaa Ser Ser Asp Tyr Val Ile Pro Ile Gly Thr Tyr
  1               5                  10                  15

Gly Gln Met Lys Asn Gly Ser Thr Pro Met Phe Asn Asp Ile Asn Ile
             20                  25                  30

Tyr Asp Leu
         35
```

<210> SEQ ID NO 529
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/tyrosinase overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 529

```
Leu Arg Met Lys Xaa Met Leu Leu Ala Val Leu Tyr Cys Leu
  1               5                  10
```

<210> SEQ ID NO 530
<211> LENGTH: 9
<212> TYPE: PRT
<213> ORGANISM: Homo sapiens

<400> SEQUENCE: 530

```
Ala Ala Gly Ile Gly Ile Leu Thr Val
```

-continued 1 5

<210> SEQ ID NO 531
<211> LENGTH: 118
<212> TYPE: PRT
<213> ORGANISM: Homo sapiens

<400> SEQUENCE: 531

Met Pro Arg Glu Asp Ala His Phe Ile Tyr Gly Tyr Pro Lys Lys Gly
1 5 10 15

His Gly His Ser Tyr Thr Thr Ala Glu Glu Ala Ala Gly Ile Gly Ile
20 25 30

Leu Thr Val Ile Leu Gly Val Leu Leu Leu Ile Gly Cys Trp Tyr Cys
35 40 45

Arg Arg Arg Asn Gly Tyr Arg Ala Leu Met Asp Lys Ser Leu His Val
50 55 60

Gly Thr Gln Cys Ala Leu Thr Arg Arg Cys Pro Gln Glu Gly Phe Asp
65 70 75 80

His Arg Asp Ser Lys Val Ser Leu Gln Glu Lys Asn Cys Glu Pro Val
85 90 95

Val Pro Asn Ala Pro Pro Ala Tyr Glu Lys Leu Ser Ala Glu Gln Ser
100 105 110

Pro Pro Pro Tyr Ser Pro
115

<210> SEQ ID NO 532
<211> LENGTH: 9
<212> TYPE: PRT
<213> ORGANISM: Homo sapiens

<400> SEQUENCE: 532

Leu Thr Val Ile Leu Gly Val Leu Leu
1 5

<210> SEQ ID NO 533
<211> LENGTH: 9
<212> TYPE: PRT
<213> ORGANISM: Homo sapiens

<400> SEQUENCE: 533

Val Ile Leu Gly Val Leu Leu Leu Ile
1 5

<210> SEQ ID NO 534
<211> LENGTH: 9
<212> TYPE: PRT
<213> ORGANISM: Homo sapiens

<400> SEQUENCE: 534

Val Val Pro Asn Ala Pro Pro Ala Tyr
1 5

<210> SEQ ID NO 535
<211> LENGTH: 9
<212> TYPE: PRT
<213> ORGANISM: Homo sapiens

<400> SEQUENCE: 535

Ile Gly Ile Leu Thr Val Ile Leu Gly
1 5

-continued

<210> SEQ ID NO 536
<211> LENGTH: 9
<212> TYPE: PRT
<213> ORGANISM: Homo sapiens

<400> SEQUENCE: 536

Ile Tyr Gly Tyr Pro Lys Lys Gly His
1 5

<210> SEQ ID NO 537
<211> LENGTH: 23
<212> TYPE: PRT
<213> ORGANISM: Homo sapiens

<400> SEQUENCE: 537

Arg Asn Gly Tyr Arg Ala Leu Met Asp Lys Ser Leu His Val Gly Thr
1 5 10 15

Gln Cys Ala Leu Thr Arg Arg
20

<210> SEQ ID NO 538
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/MART-1/Melan-1 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 538

Leu Arg Met Lys Xaa Val Val Pro Asn Ala Pro Pro Ala Tyr
1 5 10

<210> SEQ ID NO 539
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/MART-1/Melan-1 non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 539

Leu Arg Met Lys Xaa Ile Tyr Gly Tyr Pro Lys Lys Gly His
1 5 10

<210> SEQ ID NO 540
<211> LENGTH: 28
<212> TYPE: PRT
<213> ORGANISM: Artificial Sequence
<220> FEATURE:
<223> OTHER INFORMATION: Description of Artificial Sequence: Synthetic Ii-key/MART-1/Melan-1 non-overlapping hybrid peptide
<220> FEATURE:
<221> NAME/KEY: MOD_RES
<222> LOCATION: (5)
<223> OTHER INFORMATION: a-aminovaleric acid -continued
<220> FEATURE:
<223> OTHER INFORMATION: C-term amidated

<400> SEQUENCE: 540

Leu Arg Met Lys Xaa Arg Asn Gly Tyr Arg Ala Leu Met Asp Lys Ser
1 5 10 15

Leu His Val Gly Thr Gln Cys Ala Leu Thr Arg Arg
20 25

<210> SEQ ID NO 541
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/MART-1/Melan-1 overlapping
hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 541

Leu Arg Met Lys Xaa Leu Thr Val Ile Leu Gly Val Leu Leu
1 5 10

<210> SEQ ID NO 542
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/MART-1/Melan-1 overlapping
hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 542

Leu Arg Met Lys Xaa Val Ile Leu Gly Val Leu Leu Leu Ile
1 5 10

<210> SEQ ID NO 543
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/MART-1/Melan-1 overlapping
hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 543

Leu Arg Met Lys Xaa Ile Gly Ile Leu Thr Val Ile Leu Gly
1 5 10

<210> SEQ ID NO 544
<211> LENGTH: 19
<212> TYPE: PRT
<213> ORGANISM: Artificial Sequence -continued
<220> FEATURE:
<223> OTHER INFORMATION: Description of Artificial Sequence: Synthetic
      Ii-key/MART-1/Melan-1 overlapping
      hybrid peptide
<220> FEATURE:
<221> NAME/KEY: MOD_RES
<222> LOCATION: (5)
<223> OTHER INFORMATION: a-aminovaleric acid

<400> SEQUENCE: 544

Leu Arg Met Lys Xaa Ile Gly Ile Leu Thr Val Ile Leu Gly Val Leu
  1               5                  10                  15

Leu Leu Ile

<210> SEQ ID NO 545
<211> LENGTH: 9
<212> TYPE: PRT
<213> ORGANISM: Homo sapiens

<400> SEQUENCE: 545

Leu Leu Leu Ile Gly Cys Trp Tyr Cys
  1               5

<210> SEQ ID NO 546
<211> LENGTH: 9
<212> TYPE: PRT
<213> ORGANISM: Homo sapiens

<400> SEQUENCE: 546

Ala Leu Met Asp Lys Ser Leu His Val
  1               5

<210> SEQ ID NO 547
<211> LENGTH: 9
<212> TYPE: PRT
<213> ORGANISM: Homo sapiens

<400> SEQUENCE: 547

Glu Glu Ala Ala Gly Ile Gly Ile Leu
  1               5

<210> SEQ ID NO 548
<211> LENGTH: 9
<212> TYPE: PRT
<213> ORGANISM: Homo sapiens

<400> SEQUENCE: 548

Ala Glu Gln Ser Pro Pro Pro Tyr Ser
  1               5

<210> SEQ ID NO 549
<211> LENGTH: 9
<212> TYPE: PRT
<213> ORGANISM: Homo sapiens

<400> SEQUENCE: 549

Ala Ala Gly Ile Gly Ile Leu Thr Val
  1               5

<210> SEQ ID NO 550
<211> LENGTH: 9
<212> TYPE: PRT
<213> ORGANISM: Homo sapiens

<400> SEQUENCE: 550

-continued

```
Ile Leu Thr Val Ile Leu Gly Val Leu
  1               5

<210> SEQ ID NO 551
<211> LENGTH: 11
<212> TYPE: PRT
<213> ORGANISM: Homo sapiens

<400> SEQUENCE: 551

Ala Glu Glu Ala Ala Gly Ile Gly Ile Leu Thr
  1               5                  10

<210> SEQ ID NO 552
<211> LENGTH: 37
<212> TYPE: PRT
<213> ORGANISM: Artificial Sequence
<220> FEATURE:
<223> OTHER INFORMATION: Description of Artificial Sequence: Synthetic
      Ii-key/MART-1 hybrid peptide
<220> FEATURE:
<221> NAME/KEY: MOD_RES
<222> LOCATION: (5)
<223> OTHER INFORMATION: a-aminovaleric acid

<400> SEQUENCE: 552

Leu Arg Met Lys Xaa Ala Ala Gly Ile Gly Ile Leu Thr Val Arg Asn
  1               5                  10                  15

Gly Tyr Arg Ala Leu Met Asp Lys Ser Leu His Val Gly Thr Gln Cys
             20                  25                  30

Ala Leu Thr Arg Arg
         35

<210> SEQ ID NO 553
<211> LENGTH: 1255
<212> TYPE: PRT
<213> ORGANISM: Homo sapiens

<400> SEQUENCE: 553

Met Glu Leu Ala Ala Leu Cys Arg Trp Gly Leu Leu Leu Ala Leu Leu
  1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
     50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175
```

-continued

```
Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
```

-continued

```
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                1000                1005

Leu Glu Asp Asp Asp Met Gly Asp Leu Val Asp Ala Glu Glu Tyr Leu
   1010                1015                1020
```

-continued

```
Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
               1045                1050                1055

Gly Asp Leu Thr Leu Gly Leu Glu Pro Ser Glu Glu Glu Ala Pro Arg
           1060                1065                1070

Ser Pro Leu Ala Pro Ser Glu Gly Ala Gly Ser Asp Val Phe Asp Gly
       1075                1080                1085

Asp Leu Gly Met Gly Ala Ala Lys Gly Leu Gln Ser Leu Pro Thr His
   1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
               1125                1130                1135

Pro Glu Tyr Val Asn Gln Pro Asp Val Arg Pro Gln Pro Pro Ser Pro
           1140                1145                1150

Arg Glu Gly Pro Leu Pro Ala Ala Arg Pro Ala Gly Ala Thr Leu Glu
       1155                1160                1165

Arg Pro Lys Thr Leu Ser Pro Gly Lys Asn Gly Val Val Lys Asp Val
   1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
               1205                1210                1215

Phe Asp Asn Leu Tyr Tyr Trp Asp Gln Asp Pro Pro Glu Arg Gly Ala
           1220                1225                1230

Pro Pro Ser Thr Phe Lys Gly Thr Pro Thr Ala Glu Asn Pro Glu Tyr
       1235                1240                1245

Leu Gly Leu Asp Val Pro Val
   1250                1255


<210> SEQ ID NO 554
<211> LENGTH: 9
<212> TYPE: PRT
<213> ORGANISM: Homo sapiens

<400> SEQUENCE: 554

Phe Val Val Ile Gln Asn Glu Asp Leu
  1               5


<210> SEQ ID NO 555
<211> LENGTH: 9
<212> TYPE: PRT
<213> ORGANISM: Homo sapiens

<400> SEQUENCE: 555

Leu Arg Ile Val Arg Gly Thr Gln Leu
  1               5


<210> SEQ ID NO 556
<211> LENGTH: 9
<212> TYPE: PRT
<213> ORGANISM: Homo sapiens

<400> SEQUENCE: 556

Met Ile Met Val Lys Cys Trp Met Ile
  1               5
```

<210> SEQ ID NO 557
<211> LENGTH: 9
<212> TYPE: PRT
<213> ORGANISM: Homo sapiens

<400> SEQUENCE: 557

Leu Arg Arg Arg Phe Thr His Gln Ser
1 5

<210> SEQ ID NO 558
<211> LENGTH: 9
<212> TYPE: PRT
<213> ORGANISM: Homo sapiens

<400> SEQUENCE: 558

Tyr Thr Met Arg Arg Leu Leu Gln Glu
1 5

<210> SEQ ID NO 559
<211> LENGTH: 9
<212> TYPE: PRT
<213> ORGANISM: Homo sapiens

<400> SEQUENCE: 559

Val Val Leu Gly Val Val Phe Gly Ile
1 5

<210> SEQ ID NO 560
<211> LENGTH: 9
<212> TYPE: PRT
<213> ORGANISM: Homo sapiens

<400> SEQUENCE: 560

Met Val His His Arg His Arg Ser Ser
1 5

<210> SEQ ID NO 561
<211> LENGTH: 9
<212> TYPE: PRT
<213> ORGANISM: Homo sapiens

<400> SEQUENCE: 561

Leu Ser Val Phe Gln Asn Leu Gln Val
1 5

<210> SEQ ID NO 562
<211> LENGTH: 9
<212> TYPE: PRT
<213> ORGANISM: Homo sapiens

<400> SEQUENCE: 562

Leu Thr Leu Ile Asp Thr Asn Arg Ser
1 5

<210> SEQ ID NO 563
<211> LENGTH: 9
<212> TYPE: PRT
<213> ORGANISM: Homo sapiens

<400> SEQUENCE: 563

Phe Gly Ile Leu Ile Lys Arg Arg Gln
1 5

<210> SEQ ID NO 564

-continued

<211> LENGTH: 9
<212> TYPE: PRT
<213> ORGANISM: Homo sapiens

<400> SEQUENCE: 564

Leu Gln Val Phe Glu Thr Leu Glu Glu
1 5

<210> SEQ ID NO 565
<211> LENGTH: 9
<212> TYPE: PRT
<213> ORGANISM: Homo sapiens

<400> SEQUENCE: 565

Leu Thr Tyr Leu Pro Thr Asn Ala Ser
1 5

<210> SEQ ID NO 566
<211> LENGTH: 9
<212> TYPE: PRT
<213> ORGANISM: Homo sapiens

<400> SEQUENCE: 566

Tyr Met Ile Met Val Lys Cys Trp Met
1 5

<210> SEQ ID NO 567
<211> LENGTH: 9
<212> TYPE: PRT
<213> ORGANISM: Homo sapiens

<400> SEQUENCE: 567

Leu Arg Lys Val Lys Val Leu Gly Ser
1 5

<210> SEQ ID NO 568
<211> LENGTH: 9
<212> TYPE: PRT
<213> ORGANISM: Homo sapiens

<400> SEQUENCE: 568

Phe Gln Asn Leu Gln Val Ile Arg Gly
1 5

<210> SEQ ID NO 569
<211> LENGTH: 15
<212> TYPE: PRT
<213> ORGANISM: Homo sapiens

<400> SEQUENCE: 569

Val Pro Ile Lys Trp Met Ala Leu Glu Ser Ile Leu Arg Arg Arg
1 5 10 15

<210> SEQ ID NO 570
<211> LENGTH: 13
<212> TYPE: PRT
<213> ORGANISM: Homo sapiens

<400> SEQUENCE: 570

Gly Ser Pro Tyr Val Ser Arg Leu Leu Gly Ile Cys Leu
1 5 10

<210> SEQ ID NO 571
<211> LENGTH: 11
<212> TYPE: PRT

-continued

<213> ORGANISM: Homo sapiens

<400> SEQUENCE: 571

Gln Leu Gln Val Phe Glu Thr Leu Glu Glu Ile
1 5 10

<210> SEQ ID NO 572
<211> LENGTH: 13
<212> TYPE: PRT
<213> ORGANISM: Homo sapiens

<400> SEQUENCE: 572

Leu Cys Phe Val His Thr Val Pro Trp Asp Gln Leu Phe
1 5 10

<210> SEQ ID NO 573
<211> LENGTH: 12
<212> TYPE: PRT
<213> ORGANISM: Homo sapiens

<400> SEQUENCE: 573

Gly Ile Ser Trp Leu Gly Leu Arg Ser Leu Arg Glu
1 5 10

<210> SEQ ID NO 574
<211> LENGTH: 12
<212> TYPE: PRT
<213> ORGANISM: Homo sapiens

<400> SEQUENCE: 574

Glu Phe Ser Arg Met Ala Arg Asp Pro Gln Arg Phe
1 5 10

<210> SEQ ID NO 575
<211> LENGTH: 12
<212> TYPE: PRT
<213> ORGANISM: Homo sapiens

<400> SEQUENCE: 575

Phe Asp Gly Asp Leu Gly Met Ala Ala Lys Gly Leu
1 5 10

<210> SEQ ID NO 576
<211> LENGTH: 15
<212> TYPE: PRT
<213> ORGANISM: Homo sapiens

<400> SEQUENCE: 576

His Leu Asp Met Leu Arg His Leu Tyr Gln Gly Cys Gln Val Val
1 5 10 15

<210> SEQ ID NO 577
<211> LENGTH: 16
<212> TYPE: PRT
<213> ORGANISM: Homo sapiens

<400> SEQUENCE: 577

Leu Arg Ile Val Arg Gly Thr Gln Leu Phe Glu Asp Asn Tyr Ala Leu
1 5 10 15

<210> SEQ ID NO 578
<211> LENGTH: 18
<212> TYPE: PRT
<213> ORGANISM: Homo sapiens -continued

<400> SEQUENCE: 578

Thr Gln Arg Cys Glu Lys Cys Ser Lys Pro Cys Ala Arg Val Cys Tyr
1 5 10 15

Gly Leu

<210> SEQ ID NO 579
<211> LENGTH: 15
<212> TYPE: PRT
<213> ORGANISM: Homo sapiens

<400> SEQUENCE: 579

Leu Gly Ser Gly Ala Phe Gly Thr Val Tyr Lys Gly Ile Trp Ile
1 5 10 15

<210> SEQ ID NO 580
<211> LENGTH: 15
<212> TYPE: PRT
<213> ORGANISM: Homo sapiens

<400> SEQUENCE: 580

Pro Ala Arg Glu Ile Pro Asp Leu Leu Glu Lys Gly Glu Arg Leu
1 5 10 15

<210> SEQ ID NO 581
<211> LENGTH: 15
<212> TYPE: PRT
<213> ORGANISM: Homo sapiens

<400> SEQUENCE: 581

Thr Leu Glu Arg Pro Lys Thr Leu Ser Pro Gly Lys Asn Gly Val
1 5 10 15

<210> SEQ ID NO 582
<211> LENGTH: 17
<212> TYPE: PRT
<213> ORGANISM: Homo sapiens

<400> SEQUENCE: 582

Lys Lys Ile Phe Gly Ser Leu Ala Phe Leu Pro Glu Ser Phe Asp Gly
1 5 10 15

Asp

<210> SEQ ID NO 583
<211> LENGTH: 16
<212> TYPE: PRT
<213> ORGANISM: Homo sapiens

<400> SEQUENCE: 583

Arg Gln Gln Lys Ile Arg Lys Tyr Thr Met Arg Arg Leu Leu Gln Glu
1 5 10 15

<210> SEQ ID NO 584
<211> LENGTH: 14
<212> TYPE: PRT
<213> ORGANISM: Homo sapiens

<400> SEQUENCE: 584

Glu Leu Val Ser Glu Phe Ser Arg Met Ala Arg Asp Pro Gln
1 5 10

<210> SEQ ID NO 585
<211> LENGTH: 10
<212> TYPE: PRT

-continued

<213> ORGANISM: Homo sapiens

<400> SEQUENCE: 585

Leu Arg Ile Val Arg Thr Gly Thr Gln Leu
1 5 10

<210> SEQ ID NO 586
<211> LENGTH: 9
<212> TYPE: PRT
<213> ORGANISM: Homo sapiens

<400> SEQUENCE: 586

Leu Val Ser Glu Phe Ser Arg Met Ala
1 5

<210> SEQ ID NO 587
<211> LENGTH: 18
<212> TYPE: PRT
<213> ORGANISM: Artificial Sequence
<220> FEATURE:
<223> OTHER INFORMATION: Description of Artificial Sequence: Synthetic Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 587

Leu Arg Met Lys Xaa Gly Ser Pro Tyr Val Ser Arg Leu Leu Gly Ile
1 5 10 15

Cys Leu

<210> SEQ ID NO 588
<211> LENGTH: 16
<212> TYPE: PRT
<213> ORGANISM: Artificial Sequence
<220> FEATURE:
<223> OTHER INFORMATION: Description of Artificial Sequence: Synthetic Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 588

Leu Arg Met Lys Xaa Gln Leu Gln Val Phe Glu Thr Leu Glu Glu Ile
1 5 10 15

<210> SEQ ID NO 589
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 589

Leu Arg Met Lys Xaa Phe Val Val Ile Gln Asn Glu Asp Leu
1 5 10

-continued

<210> SEQ ID NO 590
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 590

Leu Arg Met Lys Xaa Leu Arg Ile Val Arg Gly Thr Gln Leu
1 5 10

<210> SEQ ID NO 591
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 591

Leu Arg Met Lys Xaa Leu Arg Arg Arg Phe Thr His Gln Ser
1 5 10

<210> SEQ ID NO 592
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 592

Leu Arg Met Lys Xaa Tyr Thr Met Arg Arg Leu Leu Gln Glu
1 5 10

<210> SEQ ID NO 593
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 593

Leu Arg Met Lys Xaa Met Val His His Arg His Arg Ser Ser

-continued

```
 1               5                   10


<210> SEQ ID NO 594
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 594

Leu Arg Met Lys Xaa Leu Val Ser Glu Phe Ser Arg Met Ala
  1               5                   10


<210> SEQ ID NO 595
<211> LENGTH: 25
<212> TYPE: PRT
<213> ORGANISM: Artificial Sequence
<220> FEATURE:
<223> OTHER INFORMATION: Description of Artificial Sequence: Synthetic
      Ii-key/Her-2/neu overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 595

Leu Arg Met Lys Xaa Val Pro Ile Lys Trp Met Ala Leu Glu Ser Ile
  1               5                   10                  15

Leu Arg Arg Arg Phe Thr His Gln Ser
             20                  25


<210> SEQ ID NO 596
<211> LENGTH: 20
<212> TYPE: PRT
<213> ORGANISM: Artificial Sequence
<220> FEATURE:
<223> OTHER INFORMATION: Description of Artificial Sequence: Synthetic
      Ii-key/Her-2/neu overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 596

Leu Arg Met Lys Xaa Val Val Leu Gly Val Val Phe Gly Ile Leu Ile
  1               5                   10                  15

Lys Arg Arg Gln
             20


<210> SEQ ID NO 597
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/Her-2/neu overlapping hybrid peptide
<220> FEATURE:
<221> NAME/KEY: MOD_RES
<222> LOCATION: (5)
```

<223> OTHER INFORMATION: a-aminovaleric acid
<220> FEATURE:
<223> OTHER INFORMATION: C-term amidated

<400> SEQUENCE: 597

Leu Arg Met Lys Xaa Tyr Met Ile Met Val Lys Cys Trp Met Ile
1 5 10 15

<210> SEQ ID NO 598
<211> LENGTH: 17
<212> TYPE: PRT
<213> ORGANISM: Artificial Sequence
<220> FEATURE:
<223> OTHER INFORMATION: Description of Artificial Sequence: Synthetic
Ii-key/Her-2/neu overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 598

Leu Arg Met Lys Xaa Leu Ser Val Phe Gln Asn Leu Gln Val Ile Arg
1 5 10 15

Gly

<210> SEQ ID NO 599
<211> LENGTH: 9
<212> TYPE: PRT
<213> ORGANISM: Homo sapiens

<400> SEQUENCE: 599

Ile Leu Leu Val Val Val Leu Gly Val
1 5

<210> SEQ ID NO 600
<211> LENGTH: 9
<212> TYPE: PRT
<213> ORGANISM: Homo sapiens

<400> SEQUENCE: 600

Lys Ile Phe Gly Ser Leu Ala Phe Leu
1 5

<210> SEQ ID NO 601
<211> LENGTH: 9
<212> TYPE: PRT
<213> ORGANISM: Homo sapiens

<400> SEQUENCE: 601

Ile Leu Trp Lys Asp Ile Phe His Lys
1 5

<210> SEQ ID NO 602
<211> LENGTH: 9
<212> TYPE: PRT
<213> ORGANISM: Homo sapiens

<400> SEQUENCE: 602

Thr Tyr Leu Pro Thr Asn Ala Ser Leu
1 5

<210> SEQ ID NO 603
<211> LENGTH: 9
<212> TYPE: PRT

-continued

<213> ORGANISM: Homo sapiens

<400> SEQUENCE: 603

Gln Leu Phe Glu Asp Asn Tyr Ala Leu
1 5

<210> SEQ ID NO 604
<211> LENGTH: 9
<212> TYPE: PRT
<213> ORGANISM: Homo sapiens

<400> SEQUENCE: 604

Glu Tyr Val Asn Ala Arg His Cys Leu
1 5

<210> SEQ ID NO 605
<211> LENGTH: 9
<212> TYPE: PRT
<213> ORGANISM: Homo sapiens

<400> SEQUENCE: 605

Ala Tyr Ser Leu Thr Leu Gln Gly Leu
1 5

<210> SEQ ID NO 606
<211> LENGTH: 9
<212> TYPE: PRT
<213> ORGANISM: Homo sapiens

<400> SEQUENCE: 606

Ser Tyr Gly Val Thr Val Trp Glu Leu
1 5

<210> SEQ ID NO 607
<211> LENGTH: 9
<212> TYPE: PRT
<213> ORGANISM: Homo sapiens

<400> SEQUENCE: 607

Glu Tyr Leu Val Pro Gln Gln Gly Phe
1 5

<210> SEQ ID NO 608
<211> LENGTH: 9
<212> TYPE: PRT
<213> ORGANISM: Homo sapiens

<400> SEQUENCE: 608

Arg Leu Leu Gln Glu Thr Glu Leu Val
1 5

<210> SEQ ID NO 609
<211> LENGTH: 9
<212> TYPE: PRT
<213> ORGANISM: Homo sapiens

<400> SEQUENCE: 609

Ile Leu Lys Glu Thr Glu Leu Arg Lys
1 5

<210> SEQ ID NO 610
<211> LENGTH: 9
<212> TYPE: PRT
<213> ORGANISM: Homo sapiens -continued

<400> SEQUENCE: 610

Val Leu Arg Glu Asn Thr Ser Pro Lys
1 5

<210> SEQ ID NO 611
<211> LENGTH: 9
<212> TYPE: PRT
<213> ORGANISM: Homo sapiens

<400> SEQUENCE: 611

Ile Leu Ile Lys Arg Arg Gln Gln Lys
1 5

<210> SEQ ID NO 612
<211> LENGTH: 9
<212> TYPE: PRT
<213> ORGANISM: Homo sapiens

<400> SEQUENCE: 612

Gln Leu Phe Glu Asp Asn Tyr Ala Leu
1 5

<210> SEQ ID NO 613
<211> LENGTH: 9
<212> TYPE: PRT
<213> ORGANISM: Homo sapiens

<400> SEQUENCE: 613

Lys Ile Phe Gly Ser Leu Ala Phe Leu
1 5

<210> SEQ ID NO 614
<211> LENGTH: 9
<212> TYPE: PRT
<213> ORGANISM: Homo sapiens

<400> SEQUENCE: 614

Arg Leu Leu Gln Glu Thr Glu Leu Val
1 5

<210> SEQ ID NO 615
<211> LENGTH: 9
<212> TYPE: PRT
<213> ORGANISM: Homo sapiens

<400> SEQUENCE: 615

Ile Leu His Asn Gly Ala Tyr Ser Leu
1 5

<210> SEQ ID NO 616
<211> LENGTH: 9
<212> TYPE: PRT
<213> ORGANISM: Homo sapiens

<400> SEQUENCE: 616

Val Val Leu Gly Val Val Phe Gly Ile
1 5

<210> SEQ ID NO 617
<211> LENGTH: 9
<212> TYPE: PRT
<213> ORGANISM: Homo sapiens

<400> SEQUENCE: 617

-continued

```
Tyr Met Ile Met Val Lys Cys Trp Met
  1               5


<210> SEQ ID NO 618
<211> LENGTH: 9
<212> TYPE: PRT
<213> ORGANISM: Homo sapiens

<400> SEQUENCE: 618

Ile Ile Ser Ala Val Val Gly Ile Leu
  1               5


<210> SEQ ID NO 619
<211> LENGTH: 10
<212> TYPE: PRT
<213> ORGANISM: Homo sapiens

<400> SEQUENCE: 619

Phe Leu Ser Ala Val Val Gly Ile Leu Val
  1               5                  10


<210> SEQ ID NO 620
<211> LENGTH: 10
<212> TYPE: PRT
<213> ORGANISM: Homo sapiens

<400> SEQUENCE: 620

Val Met Ala Gly Val Gly Ser Pro Tyr Val
  1               5                  10


<210> SEQ ID NO 621
<211> LENGTH: 9
<212> TYPE: PRT
<213> ORGANISM: Homo sapiens

<400> SEQUENCE: 621

Val Leu Arg Glu Asn Thr Ser Pro Lys
  1               5


<210> SEQ ID NO 622
<211> LENGTH: 23
<212> TYPE: PRT
<213> ORGANISM: Artificial Sequence
<220> FEATURE:
<223> OTHER INFORMATION: Description of Artificial Sequence: Synthetic
      Ii-key/MHC Class II epitope/MHC Class I epitope
      hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 622

Leu Arg Met Lys Xaa Val Met Ala Gly Val Gly Ser Pro Tyr Val Ser
  1               5                  10                  15

Arg Leu Leu Gly Ile Cys Leu
             20


<210> SEQ ID NO 623
<211> LENGTH: 25
<212> TYPE: PRT
<213> ORGANISM: Artificial Sequence
<220> FEATURE:
<223> OTHER INFORMATION: Description of Artificial Sequence: Synthetic
      Ii-key/MHC Class II epitope/MHC Class I epitope
```

-continued

```
      hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 623

Leu Arg Met Lys Xaa Gln Leu Gln Val Phe Glu Thr Leu Glu Glu Ile
  1               5                  10                  15

Lys Ile Phe Gly Ser Leu Ala Phe Leu
             20                  25


<210> SEQ ID NO 624
<211> LENGTH: 16
<212> TYPE: PRT
<213> ORGANISM: Artificial Sequence
<220> FEATURE:
<223> OTHER INFORMATION: Description of Artificial Sequence: Synthetic
      Ii-key/MHC Class II epitope/MHC Class I epitope
      hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 624

Leu Arg Met Lys Xaa Phe Gly Ile Leu Ile Lys Arg Arg Gln Gln Lys
  1               5                  10                  15


<210> SEQ ID NO 625
<211> LENGTH: 15
<212> TYPE: PRT
<213> ORGANISM: Homo sapiens

<400> SEQUENCE: 625

Thr Arg Thr Val Cys Ala Gly Gly Cys Ala Arg Cys Lys Gly Pro
  1               5                  10                  15


<210> SEQ ID NO 626
<211> LENGTH: 15
<212> TYPE: PRT
<213> ORGANISM: Homo sapiens

<400> SEQUENCE: 626

Cys Ala Gly Gly Cys Ala Arg Cys Lys Gly Pro Leu Pro Thr Asp
  1               5                  10                  15


<210> SEQ ID NO 627
<211> LENGTH: 15
<212> TYPE: PRT
<213> ORGANISM: Homo sapiens

<400> SEQUENCE: 627

Gln Phe Leu Arg Gln Glu Cys Val Glu Glu Cys Arg Val Leu Gln
  1               5                  10                  15


<210> SEQ ID NO 628
<211> LENGTH: 15
<212> TYPE: PRT
<213> ORGANISM: Homo sapiens

<400> SEQUENCE: 628

Val Leu Gln Gly Leu Pro Arg Glu Tyr Val Asn Ala Arg His Cys
```

-continued

```
  1               5                   10                  15


<210> SEQ ID NO 629
<211> LENGTH: 15
<212> TYPE: PRT
<213> ORGANISM: Homo sapiens

<400> SEQUENCE: 629

Asn Gly Ser Val Thr Cys Phe Gly Pro Glu Ala Asp Gln Cys Val
  1               5                   10                  15


<210> SEQ ID NO 630
<211> LENGTH: 37
<212> TYPE: PRT
<213> ORGANISM: Artificial Sequence
<220> FEATURE:
<223> OTHER INFORMATION: Description of Artificial Sequence: Synthetic
      Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 630

Leu Arg Met Lys Xaa Gly Ser Pro Tyr Val Ser Arg Leu Leu Gly Ile
  1               5                   10                  15

Cys Leu Thr Arg Thr Val Cys Ala Gly Gly Cys Ala Arg Cys Lys Gly
             20                  25                  30

Pro Leu Pro Thr Asp
         35


<210> SEQ ID NO 631
<211> LENGTH: 31
<212> TYPE: PRT
<213> ORGANISM: Artificial Sequence
<220> FEATURE:
<223> OTHER INFORMATION: Description of Artificial Sequence: Synthetic
      Ii-key/Her-2/neu non-overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 631

Leu Arg Met Lys Xaa Gln Leu Gln Val Phe Glu Thr Leu Glu Glu Ile
  1               5                   10                  15

Asn Gly Ser Val Thr Cys Phe Gly Pro Glu Ala Asp Gln Cys Val
             20                  25                  30


<210> SEQ ID NO 632
<211> LENGTH: 22
<212> TYPE: PRT
<213> ORGANISM: Artificial Sequence
<220> FEATURE:
<223> OTHER INFORMATION: Description of Artificial Sequence: Synthetic
      Ii-key/Her-2/neu overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 632
```

-continued

```
Leu Arg Met Lys Xaa Ser Gln Phe Leu Arg Gly Gln Glu Cys Val Glu
  1               5                  10                  15

Glu Cys Arg Val Leu Gln
             20
```

<210> SEQ ID NO 633
<211> LENGTH: 21
<212> TYPE: PRT
<213> ORGANISM: Artificial Sequence
<220> FEATURE:
<223> OTHER INFORMATION: Description of Artificial Sequence: Synthetic Ii-key/Her-2/neu overlapping hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 633

```
Leu Arg Met Lys Xaa Arg Val Leu Gln Gly Leu Pro Arg Glu Tyr Val
  1               5                  10                  15

Asn Ala Arg His Cys
             20
```

<210> SEQ ID NO 634
<211> LENGTH: 14
<212> TYPE: PRT
<213> ORGANISM: Artificial Sequence
<220> FEATURE:
<223> OTHER INFORMATION: Description of Artificial Sequence: Synthetic MHC Class II-presented LF epitope peptide

<400> SEQUENCE: 634

```
His Ile Ser Leu Glu Ala Leu Ser Asp Lys Lys Lys Ile Lys
  1               5                  10
```

<210> SEQ ID NO 635
<211> LENGTH: 15
<212> TYPE: PRT
<213> ORGANISM: Artificial Sequence
<220> FEATURE:
<223> OTHER INFORMATION: Description of Artificial Sequence: Synthetic MHC Class II-presented LF epitope peptide

<400> SEQUENCE: 635

```
Glu Gln Glu Ile Asn Leu Ser Leu Glu Glu Leu Lys Asp Gln Arg
  1               5                  10                  15
```

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic MHC Class II-presented LF epitope peptide

<400> SEQUENCE: 636

```
Asp Asp Ile Ile His Ser Leu Ser Gln Glu Glu Lys Glu Leu Leu
  1               5                  10                  15
```

<210> SEQ ID NO 637
<211> LENGTH: 776
<212> TYPE: PRT
<213> ORGANISM: Bacillus anthracis

<400> SEQUENCE: 637

-continued

```
Ala Gly Gly His Gly Asp Val Gly Met His Val Lys Glu Lys Glu Lys
  1               5                  10                  15

Asn Lys Asp Glu Asn Lys Arg Lys Asp Glu Glu Arg Asn Lys Thr Gln
             20                  25                  30

Glu Glu His Leu Lys Glu Ile Met Lys His Ile Val Lys Ile Glu Val
         35                  40                  45

Lys Gly Glu Glu Ala Val Lys Lys Glu Ala Ala Glu Lys Leu Leu Glu
     50                  55                  60

Lys Val Pro Ser Asp Val Leu Glu Met Tyr Lys Ala Ile Gly Gly Lys
 65                  70                  75                  80

Ile Tyr Ile Val Asp Gly Asp Ile Thr Lys His Ile Ser Leu Glu Ala
                 85                  90                  95

Leu Ser Glu Asp Lys Lys Lys Ile Lys Asp Ile Tyr Gly Lys Asp Ala
            100                 105                 110

Leu Leu His Glu His Tyr Val Tyr Ala Lys Glu Gly Tyr Glu Pro Val
        115                 120                 125

Leu Val Ile Gln Ser Ser Glu Asp Tyr Val Glu Asn Thr Glu Lys Ala
    130                 135                 140

Leu Asn Val Tyr Tyr Glu Ile Gly Lys Ile Leu Ser Arg Asp Ile Leu
145                 150                 155                 160

Ser Lys Ile Asn Gln Pro Tyr Gln Lys Phe Leu Asp Val Leu Asn Thr
                165                 170                 175

Ile Lys Asn Ala Ser Asp Ser Asp Gly Gln Asp Leu Leu Phe Thr Asn
            180                 185                 190

Gln Leu Lys Glu His Pro Thr Asp Phe Ser Val Glu Phe Leu Glu Gln
        195                 200                 205

Asn Ser Asn Glu Val Gln Glu Val Phe Ala Lys Ala Phe Ala Tyr Tyr
    210                 215                 220

Ile Glu Pro Gln His Arg Asp Val Leu Gln Leu Tyr Ala Pro Glu Ala
225                 230                 235                 240

Phe Asn Tyr Met Asp Lys Phe Asn Glu Gln Glu Ile Asn Leu Ser Leu
                245                 250                 255

Glu Glu Leu Lys Asp Gln Arg Met Leu Ser Arg Tyr Glu Lys Trp Glu
            260                 265                 270

Lys Ile Lys Gln His Tyr Gln His Trp Ser Asp Ser Leu Ser Glu Glu
        275                 280                 285

Gly Arg Gly Leu Leu Lys Lys Leu Gln Ile Pro Ile Glu Pro Lys Lys
    290                 295                 300

Asp Asp Ile Ile His Ser Leu Ser Gln Glu Glu Lys Glu Leu Leu Lys
305                 310                 315                 320

Arg Ile Gln Ile Asp Ser Ser Asp Phe Leu Ser Thr Glu Glu Lys Glu
                325                 330                 335

Phe Leu Lys Lys Leu Gln Ile Asp Ile Arg Asp Ser Leu Ser Glu Glu
            340                 345                 350

Glu Lys Glu Leu Leu Asn Arg Ile Gln Val Asp Ser Ser Asn Pro Leu
        355                 360                 365

Ser Glu Lys Glu Lys Glu Phe Leu Lys Lys Leu Lys Leu Asp Ile Gln
    370                 375                 380

Pro Tyr Asp Ile Asn Gln Arg Leu Gln Asp Thr Gly Gly Leu Ile Asp
385                 390                 395                 400

Ser Pro Ser Ile Asn Leu Asp Val Arg Lys Gln Tyr Lys Arg Asp Ile
                405                 410                 415

Gln Asn Ile Asp Ala Leu Leu His Gln Ser Ile Gly Ser Thr Leu Tyr
```

-continued

```
            420                 425                 430

Asn Lys Ile Tyr Leu Tyr Glu Asn Met Asn Ile Asn Asn Leu Thr Ala
        435                 440                 445

Thr Leu Gly Ala Asp Leu Val Asp Ser Thr Asp Asn Thr Lys Ile Asn
    450                 455                 460

Arg Gly Ile Phe Asn Glu Phe Lys Lys Asn Phe Lys Tyr Ser Ile Ser
465                 470                 475                 480

Ser Asn Tyr Met Ile Val Asp Ile Asn Glu Arg Pro Ala Leu Asp Asn
                485                 490                 495

Glu Arg Leu Lys Trp Arg Ile Gln Leu Ser Pro Asp Thr Arg Ala Gly
            500                 505                 510

Tyr Leu Glu Asn Gly Lys Leu Ile Leu Gln Arg Asn Ile Gly Leu Glu
        515                 520                 525

Ile Lys Asp Val Gln Ile Ile Lys Gln Ser Glu Lys Glu Tyr Ile Arg
    530                 535                 540

Ile Asp Ala Lys Val Val Pro Lys Ser Lys Ile Asp Thr Lys Ile Gln
545                 550                 555                 560

Glu Ala Gln Leu Asn Ile Asn Gln Glu Trp Asn Lys Ala Leu Gly Leu
                565                 570                 575

Pro Lys Tyr Thr Lys Leu Ile Thr Phe Asn Val His Asn Arg Tyr Ala
            580                 585                 590

Ser Asn Ile Val Glu Ser Ala Tyr Leu Ile Leu Asn Glu Trp Lys Asn
        595                 600                 605

Asn Ile Gln Ser Asp Leu Ile Lys Lys Val Thr Asn Tyr Leu Val Asp
    610                 615                 620

Gly Asn Gly Arg Phe Val Phe Thr Asp Ile Thr Leu Pro Asn Ile Ala
625                 630                 635                 640

Glu Gln Tyr Thr His Gln Asp Glu Ile Tyr Glu Gln Val His Ser Lys
                645                 650                 655

Gly Leu Tyr Val Pro Glu Ser Arg Ser Ile Leu Leu His Gly Pro Ser
            660                 665                 670

Lys Gly Val Glu Leu Arg Asn Asp Ser Glu Gly Phe Ile His Glu Phe
        675                 680                 685

Gly His Ala Val Asp Asp Tyr Ala Gly Tyr Leu Leu Asp Lys Asn Gln
    690                 695                 700

Ser Asp Leu Val Thr Asn Ser Lys Lys Phe Ile Asp Ile Phe Lys Glu
705                 710                 715                 720

Glu Gly Ser Asn Leu Thr Ser Tyr Gly Arg Thr Asn Glu Ala Glu Phe
                725                 730                 735

Phe Ala Glu Ala Phe Arg Leu Met His Ser Thr Asp His Ala Glu Arg
            740                 745                 750

Leu Lys Val Gln Lys Asn Ala Pro Lys Thr Phe Gln Phe Ile Asn Asp
        755                 760                 765

Gln Ile Lys Phe Ile Ile Asn Ser
    770                 775


<210> SEQ ID NO 638
<211> LENGTH: 9
<212> TYPE: PRT
<213> ORGANISM: Bacillus anthracis

<400> SEQUENCE: 638

Trp Arg Ile Gln Leu Ser Pro Asp Thr
  1               5
```

<210> SEQ ID NO 639
<211> LENGTH: 9
<212> TYPE: PRT
<213> ORGANISM: Bacillus anthracis

<400> SEQUENCE: 639

Tyr Ile Arg Ile Asp Ala Lys Val Val
1 5

<210> SEQ ID NO 640
<211> LENGTH: 9
<212> TYPE: PRT
<213> ORGANISM: Bacillus anthracis

<400> SEQUENCE: 640

Phe Arg Leu Met His Ser Thr Asp His
1 5

<210> SEQ ID NO 641
<211> LENGTH: 9
<212> TYPE: PRT
<213> ORGANISM: Bacillus anthracis

<400> SEQUENCE: 641

Leu Gln Arg Asn Ile Gly Leu Glu Ile
1 5

<210> SEQ ID NO 642
<211> LENGTH: 9
<212> TYPE: PRT
<213> ORGANISM: Bacillus anthracis

<400> SEQUENCE: 642

Leu Gln Ile Asp Ile Arg Asp Ser Leu
1 5

<210> SEQ ID NO 643
<211> LENGTH: 9
<212> TYPE: PRT
<213> ORGANISM: Bacillus anthracis

<400> SEQUENCE: 643

Ile Asn Leu Asp Val Arg Lys Gln Tyr
1 5

<210> SEQ ID NO 644
<211> LENGTH: 9
<212> TYPE: PRT
<213> ORGANISM: Bacillus anthracis

<400> SEQUENCE: 644

Leu Arg Asn Asp Ser Glu Gly Phe Ile
1 5

<210> SEQ ID NO 645
<211> LENGTH: 9
<212> TYPE: PRT
<213> ORGANISM: Bacillus anthracis

<400> SEQUENCE: 645

Leu Val Ile Gln Ser Ser Glu Asp Tyr
1 5

<210> SEQ ID NO 646

<211> LENGTH: 9
<212> TYPE: PRT
<213> ORGANISM: Bacillus anthracis

<400> SEQUENCE: 646

Tyr Leu Leu Asp Lys Asn Gln Ser Asp
1 5

<210> SEQ ID NO 647
<211> LENGTH: 9
<212> TYPE: PRT
<213> ORGANISM: Bacillus anthracis

<400> SEQUENCE: 647

Tyr Ser Ile Ser Ser Asn Tyr Met Ile
1 5

<210> SEQ ID NO 648
<211> LENGTH: 9
<212> TYPE: PRT
<213> ORGANISM: Bacillus anthracis

<400> SEQUENCE: 648

Leu Ile Asp Ser Pro Ser Ile Asn Leu
1 5

<210> SEQ ID NO 649
<211> LENGTH: 9
<212> TYPE: PRT
<213> ORGANISM: Bacillus anthracis

<400> SEQUENCE: 649

Ile Val Glu Ser Ala Tyr Leu Ile Leu
1 5

<210> SEQ ID NO 650
<211> LENGTH: 9
<212> TYPE: PRT
<213> ORGANISM: Bacillus anthracis

<400> SEQUENCE: 650

Phe Lys Tyr Ser Ile Ser Ser Asn Tyr
1 5

<210> SEQ ID NO 651
<211> LENGTH: 9
<212> TYPE: PRT
<213> ORGANISM: Bacillus anthracis

<400> SEQUENCE: 651

Phe Asn Tyr Met Asp Lys Phe Asn Glu
1 5

<210> SEQ ID NO 652
<211> LENGTH: 9
<212> TYPE: PRT
<213> ORGANISM: Bacillus anthracis

<400> SEQUENCE: 652

Phe Leu Lys Lys Leu Lys Leu Asp Ile
1 5

<210> SEQ ID NO 653
<211> LENGTH: 9
<212> TYPE: PRT

<213> ORGANISM: Bacillus anthracis

<400> SEQUENCE: 653

Val Val Pro Lys Ser Lys Ile Asp Thr
1 5

<210> SEQ ID NO 654
<211> LENGTH: 9
<212> TYPE: PRT
<213> ORGANISM: Bacillus anthracis

<400> SEQUENCE: 654

Tyr Tyr Glu Ile Gly Lys Ile Leu Ser
1 5

<210> SEQ ID NO 655
<211> LENGTH: 9
<212> TYPE: PRT
<213> ORGANISM: Bacillus anthracis

<400> SEQUENCE: 655

Ile Gln Asn Ile Asp Ala Leu Leu His
1 5

<210> SEQ ID NO 656
<211> LENGTH: 9
<212> TYPE: PRT
<213> ORGANISM: Bacillus anthracis

<400> SEQUENCE: 656

Leu Val Thr Asn Ser Lys Lys Phe Ile
1 5

<210> SEQ ID NO 657
<211> LENGTH: 9
<212> TYPE: PRT
<213> ORGANISM: Bacillus anthracis

<400> SEQUENCE: 657

Leu Ile Thr Phe Asn Val His Asn Arg
1 5

<210> SEQ ID NO 658
<211> LENGTH: 9
<212> TYPE: PRT
<213> ORGANISM: Bacillus anthracis

<400> SEQUENCE: 658

Leu Glu Ile Lys Asp Val Gln Ile Ile
1 5

<210> SEQ ID NO 659
<211> LENGTH: 9
<212> TYPE: PRT
<213> ORGANISM: Bacillus anthracis

<400> SEQUENCE: 659

Ile Tyr Leu Tyr Glu Asn Met Asn Ile
1 5

<210> SEQ ID NO 660
<211> LENGTH: 9
<212> TYPE: PRT
<213> ORGANISM: Bacillus anthracis -continued

<400> SEQUENCE: 660

Leu Glu Met Tyr Lys Ala Ile Gly Gly
1 5

<210> SEQ ID NO 661
<211> LENGTH: 9
<212> TYPE: PRT
<213> ORGANISM: Bacillus anthracis

<400> SEQUENCE: 661

Phe Ile His Glu Phe Gly His Ala Val
1 5

<210> SEQ ID NO 662
<211> LENGTH: 9
<212> TYPE: PRT
<213> ORGANISM: Bacillus anthracis

<400> SEQUENCE: 662

Phe Ile Asn Asp Gln Ile Lys Phe Ile
1 5

<210> SEQ ID NO 663
<211> LENGTH: 9
<212> TYPE: PRT
<213> ORGANISM: Bacillus anthracis

<400> SEQUENCE: 663

Val Tyr Tyr Glu Ile Gly Lys Ile Leu
1 5

<210> SEQ ID NO 664
<211> LENGTH: 9
<212> TYPE: PRT
<213> ORGANISM: Bacillus anthracis

<400> SEQUENCE: 664

His Tyr Gln His Trp Ser Asp Ser Leu
1 5

<210> SEQ ID NO 665
<211> LENGTH: 9
<212> TYPE: PRT
<213> ORGANISM: Bacillus anthracis

<400> SEQUENCE: 665

Leu Leu His Glu His Tyr Val Tyr Ala
1 5

<210> SEQ ID NO 666
<211> LENGTH: 9
<212> TYPE: PRT
<213> ORGANISM: Bacillus anthracis

<400> SEQUENCE: 666

Ser Thr Glu Glu Lys Glu Phe Leu Lys
1 5

<210> SEQ ID NO 667
<211> LENGTH: 9
<212> TYPE: PRT
<213> ORGANISM: Bacillus anthracis

<400> SEQUENCE: 667

-continued

Lys Leu Gln Ile Pro Ile Glu Pro Lys
1 5

<210> SEQ ID NO 668
<211> LENGTH: 9
<212> TYPE: PRT
<213> ORGANISM: Bacillus anthracis

<400> SEQUENCE: 668

Tyr Val Pro Glu Ser Arg Ser Ile Leu
1 5

<210> SEQ ID NO 669
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/MHC Class II epitope hybrid peptide
<220> FEATURE:
<223> OTHER INFORMATION: C-term amidated

<400> SEQUENCE: 669

Leu Arg Met Lys Trp Arg Ile Gln Leu Ser Pro Asp Thr
1 5 10

<210> SEQ ID NO 670
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/MHC Class II epitope hybrid peptide
<220> FEATURE:
<223> OTHER INFORMATION: C-term amidated

<400> SEQUENCE: 670

Leu Arg Met Lys Tyr Ile Arg Ile Asp Ala Lys Val Val
1 5 10

<210> SEQ ID NO 671
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/MHC Class II epitope hybrid peptide
<220> FEATURE:
<223> OTHER INFORMATION: C-term amidated

<400> SEQUENCE: 671

Leu Arg Met Lys Phe Arg Leu Met His Ser Thr Asp His
1 5 10

<210> SEQ ID NO 672
<211> LENGTH: 14
<212> TYPE: PRT
<213> ORGANISM: Artificial Sequence
<220> FEATURE:
<223> OTHER INFORMATION: Description of Artificial Sequence: Synthetic Ii-key/MHC Class II epitope hybrid peptide
<220> FEATURE:
<223> OTHER INFORMATION: C-term amidated

<400> SEQUENCE: 672

Leu Arg Met Lys Leu Ile Gln Arg Asn Ile Gly Leu Glu Ile
1 5 10

-continued

<210> SEQ ID NO 673
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/MHC Class II epitope hybrid peptide
<220> FEATURE:
<223> OTHER INFORMATION: C-term amidated

<400> SEQUENCE: 673

Leu Arg Met Lys Leu Gln Ile Asp Ile Arg Asp Ser Leu
1 5 10

<210> SEQ ID NO 674
<211> LENGTH: 17
<212> TYPE: PRT
<213> ORGANISM: Artificial Sequence
<220> FEATURE:
<223> OTHER INFORMATION: Description of Artificial Sequence: Synthetic
Ii-key/MHC Class II epitope hybrid peptide
<220> FEATURE:
<223> OTHER INFORMATION: C-term amidated

<400> SEQUENCE: 674

Leu Arg Met Lys Ile Asn Leu Asp Val Arg Lys Gln Tyr Lys Arg Asp
1 5 10 15

Ile

<210> SEQ ID NO 675
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/MHC Class II epitope hybrid peptide
<220> FEATURE:
<223> OTHER INFORMATION: C-term amidated

<400> SEQUENCE: 675

Leu Arg Met Lys Leu Arg Asn Asp Ser Glu Gly Phe Ile
1 5 10

<210> SEQ ID NO 676
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/MHC Class II epitope hybrid peptide
<220> FEATURE:
<223> OTHER INFORMATION: C-term amidated

<400> SEQUENCE: 676

Leu Arg Met Lys Tyr Glu Pro Val Gln Ser Ser Glu Asp Tyr
1 5 10

<210> SEQ ID NO 677
<211> LENGTH: 23
<212> TYPE: PRT
<213> ORGANISM: Artificial Sequence
<220> FEATURE:
<223> OTHER INFORMATION: Description of Artificial Sequence: Synthetic
Ii-key/anthrax lethal factor MHC Class II
epitope/ARD hybrid peptide
<220> FEATURE:
<223> OTHER INFORMATION: C-term amidated

<400> SEQUENCE: 677

-continued

```
Leu Arg Met Lys Pro Tyr Gln Lys Phe Leu Asp Val Leu Asn Thr Ile
  1               5                  10                  15

Lys Asn Ala Ser Asp Ser Asp
             20
```

<210> SEQ ID NO 678
<211> LENGTH: 28
<212> TYPE: PRT
<213> ORGANISM: Artificial Sequence
<220> FEATURE:
<223> OTHER INFORMATION: Description of Artificial Sequence: Synthetic Ii-key/anthrax lethal factor MHC Class II epitope/ARD hybrid peptide
<220> FEATURE:
<223> OTHER INFORMATION: C-term amidated

<400> SEQUENCE: 678

```
Leu Arg Met Lys Thr Asn Gln Leu Lys Glu His Pro Thr Asp Phe Ser
  1               5                  10                  15

Val Glu Phe Leu Glu Gln Asn Ser Asn Glu Val Gln
             20                  25
```

<210> SEQ ID NO 679
<211> LENGTH: 30
<212> TYPE: PRT
<213> ORGANISM: Artificial Sequence
<220> FEATURE:
<223> OTHER INFORMATION: Description of Artificial Sequence: Synthetic Ii-key/anthrax lethal factor MHC Class II epitope/ARD hybrid peptide
<220> FEATURE:
<223> OTHER INFORMATION: C-term amidated

<400> SEQUENCE: 679

```
Leu Arg Met Lys Asp Phe Ser Val Glu Phe Leu Glu Gln Asn Ser Asn
  1               5                  10                  15

Glu Val Gln Glu Val Phe Ala Lys Ala Phe Ala Tyr Tyr Ile
             20                  25                  30
```

<210> SEQ ID NO 680
<211> LENGTH: 19
<212> TYPE: PRT
<213> ORGANISM: Artificial Sequence
<220> FEATURE:
<223> OTHER INFORMATION: Description of Artificial Sequence: Synthetic Ii-key/anthrax lethal factor MHC Class II epitope/ARD hybrid peptide
<220> FEATURE:
<223> OTHER INFORMATION: C-term amidated

<400> SEQUENCE: 680

```
Leu Arg Met Lys Gln His Arg Asp Val Leu Gln Leu Tyr Ala Pro Glu
  1               5                  10                  15

Ala Phe Asn
```

<210> SEQ ID NO 681
<211> LENGTH: 764
<212> TYPE: PRT
<213> ORGANISM: Bacillus anthracis

<400> SEQUENCE: 681

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30
```

-continued

```
Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
```

-continued

```
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Val Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760


<210> SEQ ID NO 682
<211> LENGTH: 9
<212> TYPE: PRT
<213> ORGANISM: Bacillus anthracis

<400> SEQUENCE: 682

Tyr Asn Val Leu Pro Thr Thr Ser Leu
  1               5


<210> SEQ ID NO 683
<211> LENGTH: 9
<212> TYPE: PRT
<213> ORGANISM: Bacillus anthracis

<400> SEQUENCE: 683

Leu Ile Pro Leu Met Ala Leu Ser Thr
```

-continued 1 5

<210> SEQ ID NO 684
<211> LENGTH: 9
<212> TYPE: PRT
<213> ORGANISM: Bacillus anthracis

<400> SEQUENCE: 684

Tyr Val Asn Thr Gly Thr Ala Pro Ile
1 5

<210> SEQ ID NO 685
<211> LENGTH: 9
<212> TYPE: PRT
<213> ORGANISM: Bacillus anthracis

<400> SEQUENCE: 685

Tyr Ile Ser Asn Pro Asn Tyr Lys Val
1 5

<210> SEQ ID NO 686
<211> LENGTH: 9
<212> TYPE: PRT
<213> ORGANISM: Bacillus anthracis

<400> SEQUENCE: 686

Leu Arg Gln Asp Gly Lys Thr Phe Ile
1 5

<210> SEQ ID NO 687
<211> LENGTH: 9
<212> TYPE: PRT
<213> ORGANISM: Bacillus anthracis

<400> SEQUENCE: 687

Leu Ile Arg Asp Lys Arg Phe His Tyr
1 5

<210> SEQ ID NO 688
<211> LENGTH: 9
<212> TYPE: PRT
<213> ORGANISM: Bacillus anthracis

<400> SEQUENCE: 688

Ile Lys Leu Asn Ala Lys Met Asn Ile
1 5

<210> SEQ ID NO 689
<211> LENGTH: 9
<212> TYPE: PRT
<213> ORGANISM: Bacillus anthracis

<400> SEQUENCE: 689

Phe His Tyr Asp Arg Asn Asn Ile Ala
1 5

<210> SEQ ID NO 690
<211> LENGTH: 9
<212> TYPE: PRT
<213> ORGANISM: Bacillus anthracis

<400> SEQUENCE: 690

Ile Ile Leu Ser Lys Asn Glu Asp Gln
1 5

-continued

<210> SEQ ID NO 691
<211> LENGTH: 9
<212> TYPE: PRT
<213> ORGANISM: Bacillus anthracis

<400> SEQUENCE: 691

Val Ile Ser Ser Asp Asn Leu Gln Leu
1 5

<210> SEQ ID NO 692
<211> LENGTH: 9
<212> TYPE: PRT
<213> ORGANISM: Bacillus anthracis

<400> SEQUENCE: 692

Val Ile Asn Ser Ser Thr Glu Gly Leu
1 5

<210> SEQ ID NO 693
<211> LENGTH: 9
<212> TYPE: PRT
<213> ORGANISM: Bacillus anthracis

<400> SEQUENCE: 693

Phe Lys Leu Tyr Trp Thr Asp Ser Gln
1 5

<210> SEQ ID NO 694
<211> LENGTH: 9
<212> TYPE: PRT
<213> ORGANISM: Bacillus anthracis

<400> SEQUENCE: 694

Val Lys Asn Lys Arg Thr Phe Leu Ser
1 5

<210> SEQ ID NO 695
<211> LENGTH: 9
<212> TYPE: PRT
<213> ORGANISM: Bacillus anthracis

<400> SEQUENCE: 695

Phe Ile Lys Val Lys Lys Ser Asp Glu
1 5

<210> SEQ ID NO 696
<211> LENGTH: 9
<212> TYPE: PRT
<213> ORGANISM: Bacillus anthracis

<400> SEQUENCE: 696

Ile Leu Ile Phe Ser Lys Lys Gly Tyr
1 5

<210> SEQ ID NO 697
<211> LENGTH: 9
<212> TYPE: PRT
<213> ORGANISM: Bacillus anthracis

<400> SEQUENCE: 697

Leu Leu Gly Tyr Tyr Phe Ser Asp Leu
1 5

<210> SEQ ID NO 698

<211> LENGTH: 9
<212> TYPE: PRT
<213> ORGANISM: Bacillus anthracis

<400> SEQUENCE: 698

Ile Arg Lys Ile Leu Ser Gly Tyr Ile
1 5

<210> SEQ ID NO 699
<211> LENGTH: 9
<212> TYPE: PRT
<213> ORGANISM: Bacillus anthracis

<400> SEQUENCE: 699

Val Ala Ile Asp His Ser Leu Ser Leu
1 5

<210> SEQ ID NO 700
<211> LENGTH: 9
<212> TYPE: PRT
<213> ORGANISM: Bacillus anthracis

<400> SEQUENCE: 700

Ile Leu Ser Gly Tyr Ile Val Glu Ile
1 5

<210> SEQ ID NO 701
<211> LENGTH: 9
<212> TYPE: PRT
<213> ORGANISM: Bacillus anthracis

<400> SEQUENCE: 701

Ala Ile Trp Ser Gly Phe Ile Lys Val
1 5

<210> SEQ ID NO 702
<211> LENGTH: 9
<212> TYPE: PRT
<213> ORGANISM: Bacillus anthracis

<400> SEQUENCE: 702

Phe Leu Ser Pro Trp Ile Ser Asn Ile
1 5

<210> SEQ ID NO 703
<211> LENGTH: 9
<212> TYPE: PRT
<213> ORGANISM: Bacillus anthracis

<400> SEQUENCE: 703

Arg Leu Asn Ala Asn Ile Arg Tyr Val
1 5

<210> SEQ ID NO 704
<211> LENGTH: 9
<212> TYPE: PRT
<213> ORGANISM: Bacillus anthracis

<400> SEQUENCE: 704

Asn Ile Lys Asn Gln Leu Ala Glu Leu
1 5

<210> SEQ ID NO 705
<211> LENGTH: 9
<212> TYPE: PRT

-continued

<213> ORGANISM: Bacillus anthracis

<400> SEQUENCE: 705

Ser Leu Glu Val Glu Gly Tyr Thr Val
1 5

<210> SEQ ID NO 706
<211> LENGTH: 9
<212> TYPE: PRT
<213> ORGANISM: Bacillus anthracis

<400> SEQUENCE: 706

Lys Leu Asn Ala Lys Met Asn Ile Leu
1 5

<210> SEQ ID NO 707
<211> LENGTH: 9
<212> TYPE: PRT
<213> ORGANISM: Bacillus anthracis

<400> SEQUENCE: 707

Tyr Ile Ser Asn Pro Asn Tyr Lys Val
1 5

<210> SEQ ID NO 708
<211> LENGTH: 9
<212> TYPE: PRT
<213> ORGANISM: Bacillus anthracis

<400> SEQUENCE: 708

Val Ala Ala Tyr Pro Ile Val His Val
1 5

<210> SEQ ID NO 709
<211> LENGTH: 9
<212> TYPE: PRT
<213> ORGANISM: Bacillus anthracis

<400> SEQUENCE: 709

Leu Val Leu Gly Lys Asn Gln Thr Leu
1 5

<210> SEQ ID NO 710
<211> LENGTH: 12
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope hybrid peptide
<220> FEATURE:
<223> OTHER INFORMATION: C-term amidated

<400> SEQUENCE: 710

Leu Arg Met Lys Asn Val Leu Pro Thr Thr Ser Leu
1 5 10

<210> SEQ ID NO 711
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope hybrid peptide
<220> FEATURE:
<223> OTHER INFORMATION: C-term amidated -continued

<400> SEQUENCE: 711

Leu Arg Met Lys Leu Ile Pro Leu Met Ala Leu Ser Thr
1 5 10

<210> SEQ ID NO 712
<211> LENGTH: 12
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope hybrid peptide
<220> FEATURE:
<223> OTHER INFORMATION: C-term amidated

<400> SEQUENCE: 712

Leu Arg Met Lys Val Asn Thr Gly Thr Ala Pro Ile
1 5 10

<210> SEQ ID NO 713
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope hybrid peptide
<220> FEATURE:
<223> OTHER INFORMATION: C-term amidated

<400> SEQUENCE: 713

Leu Arg Met Lys Tyr Ile Ser Asn Pro Asn Tyr Lys Val
1 5 10

<210> SEQ ID NO 714
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope hybrid peptide
<220> FEATURE:
<223> OTHER INFORMATION: C-term amidated

<400> SEQUENCE: 714

Leu Arg Met Lys Leu Arg Gln Asp Gly Lys Thr Phe Ile
1 5 10

<210> SEQ ID NO 715
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope hybrid peptide
<220> FEATURE:
<223> OTHER INFORMATION: C-term amidated

<400> SEQUENCE: 715

Leu Arg Met Lys Leu Ile Arg Asp Lys Arg Phe His Tyr
1 5 10

<210> SEQ ID NO 716
<211> LENGTH: 13
<212> TYPE: PRT
<213> ORGANISM: Artificial Sequence

```
<220> FEATURE:
<223> OTHER INFORMATION: Description of Artificial Sequence: Synthetic
      Ii-key/anthrax protective antigen MHC Class II
      epitope hybrid peptide
<220> FEATURE:
<223> OTHER INFORMATION: C-term amidated

<400> SEQUENCE: 716

Leu Arg Met Lys Ile Lys Leu Asn Ala Lys Met Asn Ile
  1               5                  10


<210> SEQ ID NO 717
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/anthrax protective antigen MHC Class II
      epitope hybrid peptide
<220> FEATURE:
<223> OTHER INFORMATION: C-term amidated

<400> SEQUENCE: 717

Leu Arg Met Lys Phe His Tyr Asp Arg Asn Asn Ile Ala
  1               5                  10


<210> SEQ ID NO 718
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/anthrax protective antigen MHC Class II
      epitope hybrid peptide
<220> FEATURE:
<223> OTHER INFORMATION: C-term amidated

<400> SEQUENCE: 718

Leu Arg Met Lys Ile Ile Leu Ser Lys Asn Glu Asp Gln
  1               5                  10


<210> SEQ ID NO 719
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/anthrax protective antigen MHC Class II
      epitope hybrid peptide
<220> FEATURE:
<223> OTHER INFORMATION: C-term amidated

<400> SEQUENCE: 719

Leu Arg Met Lys Val Ile Ser Ser Asp Asn Leu Gln Leu
  1               5                  10


<210> SEQ ID NO 720
<211> LENGTH: 33
<212> TYPE: PRT
<213> ORGANISM: Artificial Sequence
<220> FEATURE:
<223> OTHER INFORMATION: Description of Artificial Sequence: Synthetic
      Ii-key/anthrax protective antigen MHC Class II
      epitope/anthrax protective antigen ARD hybrid
      peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated
```

-continued

<400> SEQUENCE: 720

Leu Arg Met Lys Xaa Val Ile Ser Ser Asp Asn Leu Gln Leu Pro Glu
1 5 10 15

Leu Lys Gln Lys Ser Ser Asn Ser Arg Lys Lys Arg Ser Thr Ser Ala
20 25 30

Gly

<210> SEQ ID NO 721
<211> LENGTH: 25
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope/anthrax protective antigen ARD hybrid peptide
<220> FEATURE:
<223> OTHER INFORMATION: C-term amidated

<400> SEQUENCE: 721

Leu Arg Met Lys Pro Asp Ser Leu Glu Val Glu Gly Tyr Thr Val Asp
1 5 10 15

Val Lys Asn Lys Arg Thr Phe Leu Ser
20 25

<210> SEQ ID NO 722
<211> LENGTH: 34
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope/anthrax protective antigen ARD hybrid peptide
<220> FEATURE:
<223> OTHER INFORMATION: C-term amidated

<400> SEQUENCE: 722

Leu Arg Met Lys Val Pro Asp Arg Asp Asn Asp Gly Ile Pro Asp Ser
1 5 10 15

Leu Glu Val Glu Gly Tyr Thr Val Asp Val Lys Asn Lys Arg Thr Phe
20 25 30

Leu Ser

<210> SEQ ID NO 723
<211> LENGTH: 26
<212> TYPE: PRT
<213> ORGANISM: Artificial Sequence
<220> FEATURE:
<223> OTHER INFORMATION: Description of Artificial Sequence: Synthetic Ii-key/anthrax protective antigen MHC Class II epitope/anthrax protective antigen ARD hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 723

Leu Arg Met Lys Xaa Ile Arg Lys Ile Leu Ser Gly Tyr Ile Val Glu
1 5 10 15

Ile Glu Asp Thr Glu Gly Leu Lys Glu Val
20 25

<210> SEQ ID NO 724
<211> LENGTH: 25
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<223> OTHER INFORMATION: C-term amidated

<400> SEQUENCE: 724

Leu Arg Met Lys Ile Asn Asp Arg Tyr Asp Met Leu Asn Ile Ser Ser
1 5 10 15

Leu Arg Gln Asp Gly Lys Thr Phe Ile
20 25

<210> SEQ ID NO 725
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<223> OTHER INFORMATION: C-term amidated

<400> SEQUENCE: 725

Leu Arg Met Lys Tyr Val Asn Thr Gly Thr Ala Pro Ile
1 5 10

<210> SEQ ID NO 726
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<223> OTHER INFORMATION: C-term amidated

<400> SEQUENCE: 726

Leu Arg Met Lys Tyr Val Asn Thr Gly Thr Ala Pro Ile
1 5 10

<210> SEQ ID NO 727
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 727

Leu Arg Met Lys Xaa Tyr Val Asn Thr Gly Thr Ala Pro Ile
1 5 10

-continued

<210> SEQ ID NO 728
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 728

Leu Arg Met Lys Xaa Tyr Val Asn Thr Gly Thr Ala Pro Ile
1 5 10

<210> SEQ ID NO 729
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 729

Leu Arg Met Lys Xaa Tyr Val Asn Thr Gly Thr Ala Pro Ile
1 5 10

<210> SEQ ID NO 730
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 730

Leu Arg Met Lys Xaa Tyr Val Asn Thr Gly Thr Ala Pro Ile
1 5 10

<210> SEQ ID NO 731
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/anthrax protective antigen MHC Class II
epitope/anthrax protective antigen ARD hybrid
peptide
<220> FEATURE:
<223> OTHER INFORMATION: C-term amidated

```
<400> SEQUENCE: 731

Leu Arg Met Lys Tyr Val Asn Thr Gly Thr Ala Pro Ile
  1               5                  10


<210> SEQ ID NO 732
<211> LENGTH: 21
<212> TYPE: PRT
<213> ORGANISM: Artificial Sequence
<220> FEATURE:
<223> OTHER INFORMATION: Description of Artificial Sequence: Synthetic
      Ii-key/anthrax protective antigen MHC Class II
      epitope/anthrax protective antigen ARD hybrid
      peptide
<220> FEATURE:
<223> OTHER INFORMATION: C-term amidated

<400> SEQUENCE: 732

Leu Arg Met Lys Asn Gly Ile Lys Lys Ile Leu Ile Phe Ser Lys Lys
  1               5                  10                  15

Gly Tyr Glu Ile Gly
             20


<210> SEQ ID NO 733
<211> LENGTH: 317
<212> TYPE: PRT
<213> ORGANISM: Variola virus

<400> SEQUENCE: 733

Met Lys Thr Ile Ser Val Val Thr Leu Leu Cys Val Leu Pro Ala Val
  1               5                  10                  15

Val Tyr Ser Thr Cys Thr Val Pro Thr Met Asn Asn Ala Lys Leu Thr
             20                  25                  30

Ser Thr Glu Thr Ser Phe Asn Asp Lys Gln Lys Val Thr Phe Thr Cys
         35                  40                  45

Asp Ser Gly Tyr Tyr Ser Leu Asp Pro Asn Ala Val Cys Glu Thr Asp
     50                  55                  60

Lys Trp Lys Tyr Glu Asn Pro Cys Lys Lys Met Cys Thr Val Ser Asp
 65                  70                  75                  80

Tyr Val Ser Glu Leu Tyr Asn Lys Pro Leu Tyr Glu Val Asn Ala Ile
                 85                  90                  95

Ile Thr Leu Ile Cys Lys Asp Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Ser Leu Gln Leu Asp His Gly Ser Cys Gln Pro Val Lys
    130                 135                 140

Glu Lys Tyr Ser Phe Gly Glu His Ile Thr Ile Asn Cys Asp Val Gly
145                 150                 155                 160

Tyr Glu Val Ile Gly Ala Ser Tyr Ile Thr Cys Thr Ala Asn Ser Trp
                165                 170                 175

Asn Val Ile Pro Ser Cys Gln Gln Lys Cys Asp Ile Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Ile Leu Thr Gly Ser Pro Ser Ser Thr
    210                 215                 220

Cys Ile Asp Gly Lys Trp Asn Pro Val Leu Pro Ile Cys Ile Arg Ser
225                 230                 235                 240
```

-continued

```
Asn Glu Glu Phe Asp Pro Val Glu Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asn
    290                 295                 300

Lys Asn Asn Asp Gln Tyr Lys Phe His Lys Leu Leu Leu
305                 310                 315
```

<210> SEQ ID NO 734
<211> LENGTH: 9
<212> TYPE: PRT
<213> ORGANISM: Variola virus

<400> SEQUENCE: 734

```
Val Ile Phe Leu Ile Ser Val Ile Val
  1               5
```

<210> SEQ ID NO 735
<211> LENGTH: 9
<212> TYPE: PRT
<213> ORGANISM: Variola virus

<400> SEQUENCE: 735

```
Ile Phe Leu Ile Ser Val Ile Val Leu
  1               5
```

<210> SEQ ID NO 736
<211> LENGTH: 9
<212> TYPE: PRT
<213> ORGANISM: Variola virus

<400> SEQUENCE: 736

```
Phe Leu Ile Ser Val Ile Val Leu Val
  1               5
```

<210> SEQ ID NO 737
<211> LENGTH: 9
<212> TYPE: PRT
<213> ORGANISM: Variola virus

<400> SEQUENCE: 737

```
Tyr Tyr Ser Leu Asp Pro Asn Ala Val
  1               5
```

<210> SEQ ID NO 738
<211> LENGTH: 9
<212> TYPE: PRT
<213> ORGANISM: Variola virus

<400> SEQUENCE: 738

```
Trp Asn Pro Val Leu Pro Ile Cys Ile
  1               5
```

<210> SEQ ID NO 739
<211> LENGTH: 9
<212> TYPE: PRT
<213> ORGANISM: Variola virus

<400> SEQUENCE: 739

-continued

Ile His Leu Ser Cys Lys Ser Gly Phe
1 5

<210> SEQ ID NO 740
<211> LENGTH: 9
<212> TYPE: PRT
<213> ORGANISM: Variola virus

<400> SEQUENCE: 740

Ile Val Ala Leu Thr Ile Met Gly Val
1 5

<210> SEQ ID NO 741
<211> LENGTH: 9
<212> TYPE: PRT
<213> ORGANISM: Variola virus

<400> SEQUENCE: 741

Ile Ile Ile Val Ala Leu Thr Ile Met
1 5

<210> SEQ ID NO 742
<211> LENGTH: 9
<212> TYPE: PRT
<213> ORGANISM: Variola virus

<400> SEQUENCE: 742

Phe Ile Leu Thr Gly Ser Pro Ser Ser
1 5

<210> SEQ ID NO 743
<211> LENGTH: 9
<212> TYPE: PRT
<213> ORGANISM: Variola virus

<400> SEQUENCE: 743

Trp Asn Val Ile Pro Ser Cys Gln Gln
1 5

<210> SEQ ID NO 744
<211> LENGTH: 9
<212> TYPE: PRT
<213> ORGANISM: Variola virus

<400> SEQUENCE: 744

Tyr Ser Leu Asp Pro Asn Ala Val Cys
1 5

<210> SEQ ID NO 745
<211> LENGTH: 9
<212> TYPE: PRT
<213> ORGANISM: Variola virus

<400> SEQUENCE: 745

Tyr His Ile Ile Ile Val Ala Leu Thr
1 5

<210> SEQ ID NO 746
<211> LENGTH: 9
<212> TYPE: PRT
<213> ORGANISM: Variola virus

<400> SEQUENCE: 746

Leu Thr Ile Met Gly Val Ile Phe Leu
1 5

-continued

<210> SEQ ID NO 747
<211> LENGTH: 9
<212> TYPE: PRT
<213> ORGANISM: Variola virus

<400> SEQUENCE: 747

Val Thr Leu Leu Cys Val Leu Pro Ala
1 5

<210> SEQ ID NO 748
<211> LENGTH: 9
<212> TYPE: PRT
<213> ORGANISM: Variola virus

<400> SEQUENCE: 748

Leu Tyr Asn Lys Pro Leu Tyr Glu Val
1 5

<210> SEQ ID NO 749
<211> LENGTH: 9
<212> TYPE: PRT
<213> ORGANISM: Variola virus

<400> SEQUENCE: 749

Val Ile Phe Leu Ile Ser Val Ile Val
1 5

<210> SEQ ID NO 750
<211> LENGTH: 16
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 750

Leu Arg Met Lys Xaa Val Ile Phe Leu Ile Ser Val Ile Val Leu Val
1 5 10 15

<210> SEQ ID NO 751
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 751

Leu Arg Met Lys Xaa Tyr Tyr Ser Leu Asp Pro Asn Ala Val
1 5 10

<210> SEQ ID NO 752
<211> LENGTH: 14
<212> TYPE: PRT
<213> ORGANISM: Artificial Sequence -continued
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 752

Leu Arg Met Lys Xaa Trp Asn Pro Val Leu Pro Ile Cys Ile
1 5 10

<210> SEQ ID NO 753
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 753

Leu Arg Met Lys Xaa Ile His Leu Ser Cys Lys Ser Gly Phe
1 5 10

<210> SEQ ID NO 754
<211> LENGTH: 16
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 754

Leu Arg Met Lys Xaa Ile Ile Ile Val Ala Leu Thr Ile Met Gly Val
1 5 10 15

<210> SEQ ID NO 755
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 755

Leu Arg Met Lys Xaa Phe Ile Leu Thr Gly Ser Pro Ser Ser
1 5 10

<210> SEQ ID NO 756
<211> LENGTH: 14
<212> TYPE: PRT

-continued

<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 756

Leu Arg Met Lys Xaa Trp Asn Val Ile Pro Ser Cys Gln Gln
1 5 10

<210> SEQ ID NO 757
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 757

Leu Arg Met Lys Xaa Tyr His Ile Ile Ile Val Ala Leu Thr
1 5 10

<210> SEQ ID NO 758
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 758

Leu Arg Met Lys Xaa Tyr His Ile Ile Ile Val Ala Leu Thr
1 5 10

<210> SEQ ID NO 759
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 759

Leu Arg Met Lys Xaa Leu Thr Ile Met Gly Val Ile Phe Leu
1 5 10

<210> SEQ ID NO 760
<211> LENGTH: 14

-continued

<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 760

Leu Arg Met Lys Xaa Val Thr Leu Leu Cys Val Leu Pro Ala
1 5 10

<210> SEQ ID NO 761
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 761

Leu Arg Met Lys Xaa Leu Tyr Asn Lys Pro Leu Tyr Glu Val
1 5 10

<210> SEQ ID NO 762
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/variola B5R epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 762

Leu Arg Met Lys Xaa Val Ile Phe Leu Ile Ser Val Ile Val
1 5 10

<210> SEQ ID NO 763
<211> LENGTH: 9
<212> TYPE: PRT
<213> ORGANISM: Variola virus

<400> SEQUENCE: 763

Phe Leu Ile Ser Val Ile Val Leu Val
1 5

<210> SEQ ID NO 764
<211> LENGTH: 9
<212> TYPE: PRT
<213> ORGANISM: Variola virus

<400> SEQUENCE: 764

Thr Leu Leu Cys Val Leu Pro Ala Val
1 5

-continued

<210> SEQ ID NO 765
<211> LENGTH: 9
<212> TYPE: PRT
<213> ORGANISM: Variola virus

<400> SEQUENCE: 765

Lys Met Cys Thr Val Ser Asp Tyr Val
1 5

<210> SEQ ID NO 766
<211> LENGTH: 9
<212> TYPE: PRT
<213> ORGANISM: Variola virus

<400> SEQUENCE: 766

Thr Ile Met Gly Val Ile Phe Leu Ile
1 5

<210> SEQ ID NO 767
<211> LENGTH: 9
<212> TYPE: PRT
<213> ORGANISM: Variola virus

<400> SEQUENCE: 767

Leu Leu Cys Val Leu Pro Ala Val Val
1 5

<210> SEQ ID NO 768
<211> LENGTH: 9
<212> TYPE: PRT
<213> ORGANISM: Variola virus

<400> SEQUENCE: 768

Val Leu Pro Ala Val Val Tyr Ser Thr
1 5

<210> SEQ ID NO 769
<211> LENGTH: 9
<212> TYPE: PRT
<213> ORGANISM: Variola virus

<400> SEQUENCE: 769

Val Ile Phe Leu Ile Ser Val Ile Val
1 5

<210> SEQ ID NO 770
<211> LENGTH: 9
<212> TYPE: PRT
<213> ORGANISM: Variola virus

<400> SEQUENCE: 770

Ile Val Ala Leu Thr Ile Met Gly Val
1 5

<210> SEQ ID NO 771
<211> LENGTH: 9
<212> TYPE: PRT
<213> ORGANISM: Variola virus

<400> SEQUENCE: 771

Thr Val Ser Asp Tyr Val Ser Glu Leu
1 5

<210> SEQ ID NO 772

-continued

<211> LENGTH: 9
<212> TYPE: PRT
<213> ORGANISM: Variola virus

<400> SEQUENCE: 772

Leu Ile Ser Gly Ser Thr Phe Ser Ile
1 5

<210> SEQ ID NO 773
<211> LENGTH: 16
<212> TYPE: PRT
<213> ORGANISM: Artificial Sequence
<220> FEATURE:
<223> OTHER INFORMATION: Description of Artificial Sequence: Synthetic Ii-key/MHC Class II-presented/MHC Class I-presented B5R hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 773

Leu Arg Met Lys Xaa Val Ile Phe Leu Ile Ser Val Ile Val Leu Val
1 5 10 15

<210> SEQ ID NO 774
<211> LENGTH: 20
<212> TYPE: PRT
<213> ORGANISM: Artificial Sequence
<220> FEATURE:
<223> OTHER INFORMATION: Description of Artificial Sequence: Synthetic Ii-key/MHC Class II-presented/MHC Class I-presented B5R hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 774

Leu Arg Met Lys Xaa Thr Ile Met Gly Val Ile Phe Leu Ile Ser Val
1 5 10 15

Ile Val Leu Val
20

<210> SEQ ID NO 775
<211> LENGTH: 22
<212> TYPE: PRT
<213> ORGANISM: Artificial Sequence
<220> FEATURE:
<223> OTHER INFORMATION: Description of Artificial Sequence: Synthetic Ii-key/MHC Class II-presented/MHC Class I-presented B5R hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 775

Leu Arg Met Lys Xaa Tyr His Ile Ile Ile Val Ala Leu Thr Ile Met
1 5 10 15

Gly Val Ile Phe Leu Ile
20

-continued

```
<210> SEQ ID NO 776
<211> LENGTH: 16
<212> TYPE: PRT
<213> ORGANISM: Artificial Sequence
<220> FEATURE:
<223> OTHER INFORMATION: Description of Artificial Sequence: Synthetic
      Ii-key/MHC Class II-presented/MHC Class I-presented
      B5R hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 776

Leu Arg Met Lys Xaa Val Thr Leu Leu Cys Val Leu Pro Ala Val Val
  1               5                  10                  15


<210> SEQ ID NO 777
<211> LENGTH: 251
<212> TYPE: PRT
<213> ORGANISM: Ebola virus

<400> SEQUENCE: 777

Met Ala Lys Ala Thr Gly Arg Tyr Asn Leu Ile Ser Pro Lys Lys Asp
  1               5                  10                  15

Leu Glu Lys Gly Val Val Leu Ser Asp Leu Cys Asn Phe Leu Val Ser
             20                  25                  30

Gln Thr Ile Gln Gly Trp Lys Val Tyr Trp Ala Gly Ile Glu Phe Asp
         35                  40                  45

Val Thr His Lys Gly Met Ala Leu Leu His Arg Leu Lys Thr Asn Asp
     50                  55                  60

Phe Ala Pro Ala Trp Ser Met Thr Arg Asn Leu Phe Pro His Leu Phe
 65                  70                  75                  80

Gln Asn Pro Asn Ser Thr Ile Glu Ser Pro Leu Trp Ala Leu Arg Val
                 85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
    130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Ile Thr Arg
            180                 185                 190

Thr Asn Met Gly Phe Leu Val Glu Leu Gln Glu Pro Asp Lys Ser Ala
        195                 200                 205

Met Asn Arg Lys Lys Pro Gly Pro Ala Lys Phe Ser Leu Leu His Glu
    210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250


<210> SEQ ID NO 778
<211> LENGTH: 9
```

-continued

<212> TYPE: PRT
<213> ORGANISM: Ebola virus

<400> SEQUENCE: 778

Leu Arg Val Ile Leu Ala Ala Gly Ile
1 5

<210> SEQ ID NO 779
<211> LENGTH: 9
<212> TYPE: PRT
<213> ORGANISM: Ebola virus

<400> SEQUENCE: 779

Val Val Leu Ser Asp Leu Cys Asn Phe
1 5

<210> SEQ ID NO 780
<211> LENGTH: 9
<212> TYPE: PRT
<213> ORGANISM: Ebola virus

<400> SEQUENCE: 780

Leu Ile Arg Ser Asn Ile Leu Lys Phe
1 5

<210> SEQ ID NO 781
<211> LENGTH: 9
<212> TYPE: PRT
<213> ORGANISM: Ebola virus

<400> SEQUENCE: 781

Leu Lys Met Leu Ser Leu Ile Arg Ser
1 5

<210> SEQ ID NO 782
<211> LENGTH: 9
<212> TYPE: PRT
<213> ORGANISM: Ebola virus

<400> SEQUENCE: 782

Leu Lys Phe Ile Asn Lys Leu Asp Ala
1 5

<210> SEQ ID NO 783
<211> LENGTH: 9
<212> TYPE: PRT
<213> ORGANISM: Ebola virus

<400> SEQUENCE: 783

Met Thr Arg Gln Arg Val Lys Glu Gln
1 5

<210> SEQ ID NO 784
<211> LENGTH: 9
<212> TYPE: PRT
<213> ORGANISM: Ebola virus

<400> SEQUENCE: 784

Val Asn Tyr Asn Gly Leu Leu Ser Ser
1 5

<210> SEQ ID NO 785
<211> LENGTH: 9
<212> TYPE: PRT
<213> ORGANISM: Ebola virus

-continued

<400> SEQUENCE: 785

Leu Leu His Glu Ser Thr Leu Lys Ala
1 5

<210> SEQ ID NO 786
<211> LENGTH: 9
<212> TYPE: PRT
<213> ORGANISM: Ebola virus

<400> SEQUENCE: 786

Trp Leu Leu Thr Thr Asn Thr Asn His
1 5

<210> SEQ ID NO 787
<211> LENGTH: 9
<212> TYPE: PRT
<213> ORGANISM: Ebola virus

<400> SEQUENCE: 787

Ile Ile Ile Thr Arg Thr Asn Met Gly
1 5

<210> SEQ ID NO 788
<211> LENGTH: 9
<212> TYPE: PRT
<213> ORGANISM: Ebola virus

<400> SEQUENCE: 788

Phe Leu Val Ser Gln Thr Ile Gln Gly
1 5

<210> SEQ ID NO 789
<211> LENGTH: 9
<212> TYPE: PRT
<213> ORGANISM: Ebola virus

<400> SEQUENCE: 789

Ile Gln Gly Trp Lys Val Tyr Trp Ala
1 5

<210> SEQ ID NO 790
<211> LENGTH: 5
<212> TYPE: PRT
<213> ORGANISM: Artificial Sequence
<220> FEATURE:
<223> OTHER INFORMATION: Description of Artificial Sequence: Synthetic
Ii-key motif

<400> SEQUENCE: 790

Leu Ile Val Phe Met
1 5

<210> SEQ ID NO 791
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/Ebola virus VP24 MHC Class II epitope
hybrid peptide
<220> FEATURE:
<223> OTHER INFORMATION: C-term amidated

<400> SEQUENCE: 791

Leu Arg Met Lys Val Val Leu Ser Asp Leu Cys Asn Phe

-continued 1 5 10

<210> SEQ ID NO 792
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/Ebola virus VP24 MHC Class II epitope hybrid peptide
<220> FEATURE:
<223> OTHER INFORMATION: C-term amidated

<400> SEQUENCE: 792

Leu Arg Met Lys Phe Leu Val Ser Gln Thr Ile Gln Gly
1 5 10

<210> SEQ ID NO 793
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/Ebola virus VP24 MHC Class II epitope hybrid peptide
<220> FEATURE:
<223> OTHER INFORMATION: C-term amidated

<400> SEQUENCE: 793

Leu Arg Met Lys Ile Gln Gly Trp Lys Val Tyr Trp Ala
1 5 10

<210> SEQ ID NO 794
<211> LENGTH: 19
<212> TYPE: PRT
<213> ORGANISM: Artificial Sequence
<220> FEATURE:
<223> OTHER INFORMATION: Description of Artificial Sequence: Synthetic Ii-key/Ebola virus VP24 MHC Class II epitope hybrid peptide
<220> FEATURE:
<223> OTHER INFORMATION: C-term amidated

<400> SEQUENCE: 794

Leu Arg Met Lys Phe Leu Val Ser Gln Thr Ile Gln Gly Trp Lys Val
1 5 10 15

Tyr Trp Ala

<210> SEQ ID NO 795
<211> LENGTH: 13
<212> TYPE: PRT
<213> ORGANISM: Artificial Sequence
<220> FEATURE:
<223> OTHER INFORMATION: Description of Artificial Sequence: Synthetic Ii-key/Ebola virus VP24 MHC Class II epitope hybrid peptide
<220> FEATURE:
<223> OTHER INFORMATION: C-term amidated

<400> SEQUENCE: 795

Leu Arg Met Lys Leu Lys Met Leu Ser Leu Ile Arg Ser
1 5 10

<210> SEQ ID NO 796
<211> LENGTH: 13
<212> TYPE: PRT
<213> ORGANISM: Artificial Sequence
<220> FEATURE:
<223> OTHER INFORMATION: Description of Artificial Sequence: Synthetic

```
      Ii-key/Ebola virus VP24 MHC Class II epitope
      hybrid peptide
<220> FEATURE:
<223> OTHER INFORMATION: C-term amidated

<400> SEQUENCE: 796

Leu Arg Met Lys Leu Ile Arg Ser Asn Ile Leu Lys Phe
  1               5                  10


<210> SEQ ID NO 797
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/Ebola virus VP24 MHC Class II epitope
      hybrid peptide
<220> FEATURE:
<223> OTHER INFORMATION: C-term amidated

<400> SEQUENCE: 797

Leu Arg Met Lys Leu Lys Phe Ile Asn Lys Leu Asp Ala
  1               5                  10


<210> SEQ ID NO 798
<211> LENGTH: 18
<212> TYPE: PRT
<213> ORGANISM: Artificial Sequence
<220> FEATURE:
<223> OTHER INFORMATION: Description of Artificial Sequence: Synthetic
      Ii-key/Ebola virus VP24 MHC Class II epitope
      hybrid peptide
<220> FEATURE:
<223> OTHER INFORMATION: C-term amidated

<400> SEQUENCE: 798

Leu Arg Met Lys Leu Lys Met Leu Ser Leu Ile Arg Ser Asn Ile Leu
  1               5                  10                  15

Lys Phe


<210> SEQ ID NO 799
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/Ebola virus VP24 MHC Class II epitope
      hybrid peptide
<220> FEATURE:
<223> OTHER INFORMATION: C-term amidated

<400> SEQUENCE: 799

Leu Arg Met Lys Val Asn Tyr Asn Gly Leu Leu Ser Ser
  1               5                  10


<210> SEQ ID NO 800
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/Ebola virus VP24 MHC Class II epitope
      hybrid peptide
<220> FEATURE:
<223> OTHER INFORMATION: C-term amidated

<400> SEQUENCE: 800

Leu Arg Met Lys Leu Leu His Glu Ser Thr Leu Lys Ala
  1               5                  10
```

-continued

<210> SEQ ID NO 801
<211> LENGTH: 4
<212> TYPE: PRT
<213> ORGANISM: Artificial Sequence
<220> FEATURE:
<223> OTHER INFORMATION: Description of Artificial Sequence: Synthetic
Ii-key/Ebola virus VP24 MHC Class II epitope
hybrid peptide
<220> FEATURE:
<223> OTHER INFORMATION: C-term amidated

<400> SEQUENCE: 801

Leu Arg Met Lys
1

<210> SEQ ID NO 802
<211> LENGTH: 9
<212> TYPE: PRT
<213> ORGANISM: Ebola virus

<400> SEQUENCE: 802

Val Leu Ser Asp Leu Cys Asn Phe Leu
1 5

<210> SEQ ID NO 803
<211> LENGTH: 9
<212> TYPE: PRT
<213> ORGANISM: Ebola virus

<400> SEQUENCE: 803

Leu Ile Leu Glu Phe Asn Ser Ser Leu
1 5

<210> SEQ ID NO 804
<211> LENGTH: 9
<212> TYPE: PRT
<213> ORGANISM: Ebola virus

<400> SEQUENCE: 804

Asn Ile Leu Lys Phe Ile Asn Lys Leu
1 5

<210> SEQ ID NO 805
<211> LENGTH: 9
<212> TYPE: PRT
<213> ORGANISM: Ebola virus

<400> SEQUENCE: 805

Ala Leu Gly Leu Ile Ser Asp Trp Leu
1 5

<210> SEQ ID NO 806
<211> LENGTH: 9
<212> TYPE: PRT
<213> ORGANISM: Ebola virus

<400> SEQUENCE: 806

Ser Gln Thr Ile Gln Gly Trp Lys Val
1 5

<210> SEQ ID NO 807
<211> LENGTH: 9
<212> TYPE: PRT
<213> ORGANISM: Ebola virus

-continued

<400> SEQUENCE: 807

Gln Leu Ser Leu Lys Met Leu Ser Leu
1 5

<210> SEQ ID NO 808
<211> LENGTH: 9
<212> TYPE: PRT
<213> ORGANISM: Ebola virus

<400> SEQUENCE: 808

Ser Leu Ile Glu Pro Leu Ala Gly Ala
1 5

<210> SEQ ID NO 809
<211> LENGTH: 9
<212> TYPE: PRT
<213> ORGANISM: Ebola virus

<400> SEQUENCE: 809

Leu Leu His Glu Ser Thr Leu Lys Ala
1 5

<210> SEQ ID NO 810
<211> LENGTH: 9
<212> TYPE: PRT
<213> ORGANISM: Ebola virus

<400> SEQUENCE: 810

Asn Leu Ile Ser Pro Lys Lys Asp Leu
1 5

<210> SEQ ID NO 811
<211> LENGTH: 9
<212> TYPE: PRT
<213> ORGANISM: Ebola virus

<400> SEQUENCE: 811

Met Leu Ser Leu Ile Arg Ser Asn Ile
1 5

<210> SEQ ID NO 812
<211> LENGTH: 9
<212> TYPE: PRT
<213> ORGANISM: Ebola virus

<400> SEQUENCE: 812

Leu Ile Ser Asp Trp Leu Leu Thr Thr
1 5

<210> SEQ ID NO 813
<211> LENGTH: 9
<212> TYPE: PRT
<213> ORGANISM: Ebola virus

<400> SEQUENCE: 813

Gly Leu Ile Ser Asp Trp Leu Leu Thr
1 5

<210> SEQ ID NO 814
<211> LENGTH: 14
<212> TYPE: PRT
<213> ORGANISM: Artificial Sequence
<220> FEATURE:
<223> OTHER INFORMATION: Description of Artificial Sequence: Synthetic
Ii-key/Ebola VP24 MHC Class II-predicted -continued

```
      epitope/Ebola VP24 MHC Class I-predicted epitope
      hybrid peptide
<220> FEATURE:
<223> OTHER INFORMATION: C-term amidated

<400> SEQUENCE: 814

Leu Arg Met Lys Val Val Leu Ser Asp Leu Cys Asn Phe Leu
  1               5                  10


<210> SEQ ID NO 815
<211> LENGTH: 20
<212> TYPE: PRT
<213> ORGANISM: Artificial Sequence
<220> FEATURE:
<223> OTHER INFORMATION: Description of Artificial Sequence: Synthetic
      Ii-key/Ebola VP24 MHC Class II-predicted
      epitope/Ebola VP24 MHC Class I-predicted epitope
      hybrid peptide
<220> FEATURE:
<223> OTHER INFORMATION: C-term amidated

<400> SEQUENCE: 815

Leu Arg Met Lys Val Leu Ser Asp Leu Cys Asn Phe Leu Val Ser Gln
  1               5                  10                  15

Thr Ile Gln Gly
             20


<210> SEQ ID NO 816
<211> LENGTH: 18
<212> TYPE: PRT
<213> ORGANISM: Artificial Sequence
<220> FEATURE:
<223> OTHER INFORMATION: Description of Artificial Sequence: Synthetic
      Ii-key/Ebola VP24 MHC Class II-predicted
      epitope/Ebola VP24 MHC Class I-predicted epitope
      hybrid peptide
<220> FEATURE:
<223> OTHER INFORMATION: C-term amidated

<400> SEQUENCE: 816

Leu Arg Met Lys Gly Leu Ile Ser Asp Trp Leu Leu Thr Thr Asn Thr
  1               5                  10                  15

Asn His


<210> SEQ ID NO 817
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/Ebola VP24 MHC Class II-predicted
      epitope/Ebola VP24 MHC Class I-predicted epitope
      hybrid peptide
<220> FEATURE:
<223> OTHER INFORMATION: C-term amidated

<400> SEQUENCE: 817

Leu Arg Met Lys Gln Leu Ser Leu Lys Met Leu Ser Ile Arg Ser
  1               5                  10                  15


<210> SEQ ID NO 818
<211> LENGTH: 18
<212> TYPE: PRT
<213> ORGANISM: Artificial Sequence
<220> FEATURE:
<223> OTHER INFORMATION: Description of Artificial Sequence: Synthetic
      Ii-key/Ebola VP24 MHC Class II-predicted
      epitope/Ebola VP24 MHC Class I-predicted epitope
      hybrid peptide
```

-continued

<220> FEATURE:
<223> OTHER INFORMATION: C-term amidated

<400> SEQUENCE: 818

Leu Arg Met Lys Gln Leu Ser Leu Lys Met Leu Ser Leu Ile Arg Ser
1 5 10 15

Asn Ile

<210> SEQ ID NO 819
<211> LENGTH: 15
<212> TYPE: PRT
<213> ORGANISM: Artificial Sequence
<220> FEATURE:
<223> OTHER INFORMATION: Description of Artificial Sequence: Synthetic
Ii-key/Ebola VP24 MHC Class II-predicted
epitope/Ebola VP24 MHC Class I-predicted epitope
hybrid peptide
<220> FEATURE:
<223> OTHER INFORMATION: C-term amidated

<400> SEQUENCE: 819

Leu Arg Met Lys Asn Ile Leu Lys Phe Ile Asn Lys Leu Asp Ala
1 5 10 15

<210> SEQ ID NO 820
<211> LENGTH: 19
<212> TYPE: PRT
<213> ORGANISM: Artificial Sequence
<220> FEATURE:
<223> OTHER INFORMATION: Description of Artificial Sequence: Synthetic
Ii-key/Ebola VP24 MHC Class II-predicted
epitope/Ebola VP24 MHC Class I-predicted epitope
hybrid peptide
<220> FEATURE:
<223> OTHER INFORMATION: C-term amidated

<400> SEQUENCE: 820

Leu Arg Met Lys Leu Ile Arg Ser Asn Ile Leu Lys Phe Ile Asn Lys
1 5 10 15

Leu Asp Ala

<210> SEQ ID NO 821
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/Ebola VP24 MHC Class II-predicted
epitope/Ebola VP24 MHC Class I-predicted epitope
hybrid peptide
<220> FEATURE:
<223> OTHER INFORMATION: C-term amidated

<400> SEQUENCE: 821

Leu Arg Met Lys Leu Leu His Glu Ser Thr Leu Lys Ala
1 5 10

<210> SEQ ID NO 822
<211> LENGTH: 12
<212> TYPE: PRT
<213> ORGANISM: Homo sapiens

<400> SEQUENCE: 822

Pro Val Val His Phe Phe Lys Asn Ile Val Thr Pro
1 5 10

<210> SEQ ID NO 823

-continued

<211> LENGTH: 16
<212> TYPE: PRT
<213> ORGANISM: Unknown Organism
<220> FEATURE:
<223> OTHER INFORMATION: Description of Unknown Organism: PL139-154
peptide

<400> SEQUENCE: 823

His Cys Leu Gly Lys Trp Leu Gly His Pro Asp Lys Phe Val Gly Ile
1 5 10 15

<210> SEQ ID NO 824
<211> LENGTH: 304
<212> TYPE: PRT
<213> ORGANISM: Homo sapiens

<400> SEQUENCE: 824

Met Gly Asn His Ala Gly Lys Arg Glu Leu Asn Ala Glu Lys Ala Ser
1 5 10 15

Thr Asn Ser Glu Thr Asn Arg Gly Glu Ser Glu Lys Lys Arg Asn Leu
20 25 30

Gly Glu Leu Ser Arg Thr Thr Ser Glu Asp Asn Glu Val Phe Gly Glu
35 40 45

Ala Asp Ala Asn Gln Asn Asn Gly Thr Ser Ser Gln Asp Thr Ala Val
50 55 60

Thr Asp Ser Lys Arg Thr Ala Asp Pro Lys Asn Ala Trp Gln Asp Ala
65 70 75 80

His Pro Ala Asp Pro Gly Ser Arg Pro His Leu Ile Arg Leu Phe Ser
85 90 95

Arg Asp Ala Pro Gly Arg Glu Asp Asn Thr Phe Lys Asp Arg Pro Ser
100 105 110

Glu Ser Asp Glu Leu Gln Thr Ile Gln Glu Asp Ser Ala Ala Thr Ser
115 120 125

Glu Ser Leu Asp Val Met Ala Ser Gln Lys Arg Pro Ser Gln Arg His
130 135 140

Gly Ser Lys Tyr Leu Ala Thr Ala Ser Thr Met Asp His Ala Arg His
145 150 155 160

Gly Phe Leu Pro Arg His Arg Asp Thr Gly Ile Leu Asp Ser Ile Gly
165 170 175

Arg Phe Phe Gly Gly Asp Arg Gly Ala Pro Lys Arg Gly Ser Gly Lys
180 185 190

Asp Ser His His Pro Ala Arg Thr Ala His Tyr Gly Ser Leu Pro Gln
195 200 205

Lys Ser His Gly Arg Thr Gln Asp Glu Asn Pro Val Val His Phe Phe
210 215 220

Lys Asn Ile Val Thr Pro Arg Thr Pro Pro Pro Ser Gln Gly Lys Gly
225 230 235 240

Arg Gly Leu Ser Leu Ser Arg Phe Ser Trp Gly Ala Glu Gly Gln Arg
245 250 255

Pro Gly Phe Gly Tyr Gly Gly Arg Ala Ser Asp Tyr Lys Ser Ala His
260 265 270

Lys Gly Phe Lys Gly Val Asp Ala Gln Gly Thr Leu Ser Lys Ile Phe
275 280 285

Lys Leu Gly Gly Arg Asp Ser Arg Ser Gly Ser Pro Met Ala Arg Arg
290 295 300

<210> SEQ ID NO 825

-continued

<211> LENGTH: 9
<212> TYPE: PRT
<213> ORGANISM: Homo sapiens

<400> SEQUENCE: 825

Leu Ser Lys Ile Phe Lys Leu Gly Gly
1 5

<210> SEQ ID NO 826
<211> LENGTH: 9
<212> TYPE: PRT
<213> ORGANISM: Homo sapiens

<400> SEQUENCE: 826

Arg Pro His Leu Ile Arg Leu Phe Ser
1 5

<210> SEQ ID NO 827
<211> LENGTH: 9
<212> TYPE: PRT
<213> ORGANISM: Homo sapiens

<400> SEQUENCE: 827

His Ala Gly Lys Arg Glu Leu Asn Ala
1 5

<210> SEQ ID NO 828
<211> LENGTH: 9
<212> TYPE: PRT
<213> ORGANISM: Homo sapiens

<400> SEQUENCE: 828

His Lys Gly Phe Lys Gly Val Asp Ala
1 5

<210> SEQ ID NO 829
<211> LENGTH: 9
<212> TYPE: PRT
<213> ORGANISM: Homo sapiens

<400> SEQUENCE: 829

Leu Gln Thr Ile Gln Glu Asp Ser Ala
1 5

<210> SEQ ID NO 830
<211> LENGTH: 9
<212> TYPE: PRT
<213> ORGANISM: Homo sapiens

<400> SEQUENCE: 830

Arg Asp Thr Gly Ile Leu Asp Ser Ile
1 5

<210> SEQ ID NO 831
<211> LENGTH: 9
<212> TYPE: PRT
<213> ORGANISM: Homo sapiens

<400> SEQUENCE: 831

Asp Ser Lys Arg Thr Ala Asp Pro Lys
1 5

<210> SEQ ID NO 832
<211> LENGTH: 9
<212> TYPE: PRT

<213> ORGANISM: Homo sapiens

<400> SEQUENCE: 832

Val His Phe Phe Lys Asn Ile Val Thr
1 5

<210> SEQ ID NO 833
<211> LENGTH: 9
<212> TYPE: PRT
<213> ORGANISM: Homo sapiens

<400> SEQUENCE: 833

Ala Ser Thr Met Asp His Ala Arg His
1 5

<210> SEQ ID NO 834
<211> LENGTH: 9
<212> TYPE: PRT
<213> ORGANISM: Homo sapiens

<400> SEQUENCE: 834

Lys Arg Asn Leu Gly Glu Leu Ser Arg
1 5

<210> SEQ ID NO 835
<211> LENGTH: 9
<212> TYPE: PRT
<213> ORGANISM: Homo sapiens

<400> SEQUENCE: 835

Gly Arg Phe Phe Gly Gly Asp Arg Gly
1 5

<210> SEQ ID NO 836
<211> LENGTH: 44
<212> TYPE: PRT
<213> ORGANISM: Homo sapiens

<400> SEQUENCE: 836

Met Gly Asn His Ala Gly Lys Arg Glu Leu Asn Ala Glu Lys Ala Ser
1 5 10 15

Thr Asn Ser Glu Thr Asn Arg Gly Glu Ser Glu Lys Lys Arg Asn Leu
20 25 30

Gly Glu Leu Ser Arg Thr Thr Ser Glu Asp Asn Glu
35 40

<210> SEQ ID NO 837
<211> LENGTH: 36
<212> TYPE: PRT
<213> ORGANISM: Homo sapiens

<400> SEQUENCE: 837

Ala Trp Gln Asp Ala His Pro Ala Asp Pro Gly Ser Arg Pro His Leu
1 5 10 15

Ile Arg Leu Phe Ser Arg Asp Ala Pro Gly Arg Glu Asp Asn Thr Phe
20 25 30

Lys Asp Arg Pro
35

<210> SEQ ID NO 838
<211> LENGTH: 15
<212> TYPE: PRT
<213> ORGANISM: Homo sapiens -continued

<400> SEQUENCE: 838

Leu Asp Val Met Ala Ser Gln Lys Arg Pro Ser Gln Arg His Gly
1 5 10 15

<210> SEQ ID NO 839
<211> LENGTH: 16
<212> TYPE: PRT
<213> ORGANISM: Homo sapiens

<400> SEQUENCE: 839

Pro Ser Gln Arg His Gly Ser Lys Tyr Leu Ala Thr Ala Ser Thr Met
1 5 10 15

<210> SEQ ID NO 840
<211> LENGTH: 20
<212> TYPE: PRT
<213> ORGANISM: Homo sapiens

<400> SEQUENCE: 840

Ala His Pro Ala Asp Pro Gly Ser Arg Pro His Leu Ile Arg Leu Phe
1 5 10 15

Ser Arg Asp Ala
20

<210> SEQ ID NO 841
<211> LENGTH: 14
<212> TYPE: PRT
<213> ORGANISM: Homo sapiens

<400> SEQUENCE: 841

Leu Ala Thr Ala Ser Thr Met Asp His Ala Arg His Gly Phe
1 5 10

<210> SEQ ID NO 842
<211> LENGTH: 9
<212> TYPE: PRT
<213> ORGANISM: Homo sapiens

<400> SEQUENCE: 842

Phe Ile Arg Leu Phe Ser Arg Asp Ala
1 5

<210> SEQ ID NO 843
<211> LENGTH: 9
<212> TYPE: PRT
<213> ORGANISM: Homo sapiens

<400> SEQUENCE: 843

Ile Arg Leu Phe Ser Arg Asp Ala Pro
1 5

<210> SEQ ID NO 844
<211> LENGTH: 9
<212> TYPE: PRT
<213> ORGANISM: Homo sapiens

<400> SEQUENCE: 844

Ile Gln Trp Asp Ser Ala Ala Thr Ala
1 5

<210> SEQ ID NO 845
<211> LENGTH: 9
<212> TYPE: PRT

-continued

```
<213> ORGANISM: Homo sapiens

<400> SEQUENCE: 845

Val Met Ala Ser Gln Lys Arg Pro Ser
  1               5


<210> SEQ ID NO 846
<211> LENGTH: 9
<212> TYPE: PRT
<213> ORGANISM: Homo sapiens

<400> SEQUENCE: 846

Leu Ala Thr Ala Ser Thr Met Asp His
  1               5


<210> SEQ ID NO 847
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/human MBP antigentic epitope hybrid
      peptide
<220> FEATURE:
<223> OTHER INFORMATION: C-term amidated

<400> SEQUENCE: 847

Leu Arg Met Lys Leu Ser Lys Ile Phe Lys Leu Gly Gly
  1               5                  10


<210> SEQ ID NO 848
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/human MBP antigentic epitope hybrid
      peptide
<220> FEATURE:
<223> OTHER INFORMATION: C-term amidated

<400> SEQUENCE: 848

Leu Arg Met Lys Arg Pro His Leu Ile Arg Leu Phe Ser
  1               5                  10


<210> SEQ ID NO 849
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/human MBP antigentic epitope hybrid
      peptide
<220> FEATURE:
<223> OTHER INFORMATION: C-term amidated

<400> SEQUENCE: 849

Leu Arg Met Lys His Ala Gly Lys Arg Glu Leu Asn Ala
  1               5                  10


<210> SEQ ID NO 850
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/human MBP antigentic epitope hybrid
      peptide
<220> FEATURE:
```

-continued

<223> OTHER INFORMATION: C-term amidated

<400> SEQUENCE: 850

Leu Arg Met Lys His Lys Gly Phe Lys Gly Val Asp Ala
1 5 10

<210> SEQ ID NO 851
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/human MBP antigentic epitope hybrid
peptide
<220> FEATURE:
<223> OTHER INFORMATION: C-term amidated

<400> SEQUENCE: 851

Leu Arg Met Lys His Lys Gly Phe Lys Gly Val Asp Ala
1 5 10

<210> SEQ ID NO 852
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/human MBP antigentic epitope hybrid
peptide
<220> FEATURE:
<223> OTHER INFORMATION: C-term amidated

<400> SEQUENCE: 852

Leu Arg Met Lys Phe Ile Arg Leu Phe Ser Arg Asp Ala
1 5 10

<210> SEQ ID NO 853
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/human MBP antigentic epitope hybrid
peptide
<220> FEATURE:
<223> OTHER INFORMATION: C-term amidated

<400> SEQUENCE: 853

Leu Arg Met Lys Ile Arg Leu Phe Ser Arg Asp Ala Pro
1 5 10

<210> SEQ ID NO 854
<211> LENGTH: 13
<212> TYPE: PRT
<213> ORGANISM: Artificial Sequence
<220> FEATURE:
<223> OTHER INFORMATION: Description of Artificial Sequence: Synthetic
Ii-key/human MBP antigentic epitope hybrid
peptide
<220> FEATURE:
<223> OTHER INFORMATION: C-term amidated

<400> SEQUENCE: 854

Leu Arg Met Lys Val Met Ala Ser Gln Lys Arg Pro Ser
1 5 10

<210> SEQ ID NO 855
<211> LENGTH: 13
<212> TYPE: PRT

-continued

```
<213> ORGANISM: Artificial Sequence
<220> FEATURE:
<223> OTHER INFORMATION: Description of Artificial Sequence: Synthetic
      Ii-key/human MBP antigentic epitope hybrid
      peptide
<220> FEATURE:
<223> OTHER INFORMATION: C-term amidated

<400> SEQUENCE: 855

Leu Arg Met Lys Leu Ala Thr Ala Ser Thr Met Asp His
  1               5                  10


<210> SEQ ID NO 856
<211> LENGTH: 16
<212> TYPE: PRT
<213> ORGANISM: Murine sp.

<400> SEQUENCE: 856

His Cys Leu Gly Lys Trp Leu Gly His Pro Asp Lys Phe Val Gly Ile
  1               5                  10                  15


<210> SEQ ID NO 857
<211> LENGTH: 14
<212> TYPE: PRT
<213> ORGANISM: Homo sapiens

<400> SEQUENCE: 857

Phe Asn Thr Trp Thr Thr Cys Asp Ser Ile Ala Phe Pro Ser
  1               5                  10


<210> SEQ ID NO 858
<211> LENGTH: 277
<212> TYPE: PRT
<213> ORGANISM: Homo sapiens

<400> SEQUENCE: 858

Met Gly Leu Leu Glu Cys Cys Ala Arg Cys Leu Val Gly Ala Pro Phe
  1               5                  10                  15

Ala Ser Leu Val Ala Thr Gly Leu Cys Phe Phe Gly Val Ala Leu Phe
             20                  25                  30

Cys Gly Cys Gly His Glu Ala Leu Thr Gly Thr Glu Lys Leu Ile Glu
         35                  40                  45

Thr Tyr Phe Ser Lys Asn Tyr Gln Asp Tyr Glu Tyr Leu Ile Asn Val
     50                  55                  60

Ile His Ala Phe Gln Tyr Val Ile Tyr Gly Thr Ala Ser Phe Phe Phe
 65                  70                  75                  80

Leu Tyr Gly Ala Leu Leu Leu Ala Glu Gly Phe Tyr Thr Thr Gly Ala
                 85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys His Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Asp Ser Ile Ala Phe Pro Ser Lys
            180                 185                 190
```

-continued

```
Thr Ser Ala Ser Ile Gly Ser Leu Cys Ala Asp Ala Arg Met Tyr Gly
        195                 200                 205

Val Leu Pro Trp Ile Ala Phe Pro Gly Lys Val Cys Gly Ser Asn Leu
    210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
            260                 265                 270

Arg Gly Thr Lys Phe
        275
```

<210> SEQ ID NO 859
<211> LENGTH: 9
<212> TYPE: PRT
<213> ORGANISM: Homo sapiens

<400> SEQUENCE: 859

```
Phe Phe Phe Leu Tyr Gly Ala Leu Leu
  1               5
```

<210> SEQ ID NO 860
<211> LENGTH: 9
<212> TYPE: PRT
<213> ORGANISM: Homo sapiens

<400> SEQUENCE: 860

```
Phe Val Gly Ala Ala Ala Thr Leu Val
  1               5
```

<210> SEQ ID NO 861
<211> LENGTH: 9
<212> TYPE: PRT
<213> ORGANISM: Homo sapiens

<400> SEQUENCE: 861

```
Phe His Leu Phe Ile Ala Ala Phe Val
  1               5
```

<210> SEQ ID NO 862
<211> LENGTH: 9
<212> TYPE: PRT
<213> ORGANISM: Homo sapiens

<400> SEQUENCE: 862

```
Leu Val Ser Leu Leu Thr Phe Met Ile
  1               5
```

<210> SEQ ID NO 863
<211> LENGTH: 9
<212> TYPE: PRT
<213> ORGANISM: Homo sapiens

<400> SEQUENCE: 863

```
Trp Leu Leu Val Phe Ala Cys Ser Ala
  1               5
```

<210> SEQ ID NO 864
<211> LENGTH: 9
<212> TYPE: PRT
<213> ORGANISM: Homo sapiens -continued

<400> SEQUENCE: 864

Ile Phe Gly Asp Tyr Lys Thr Thr Ile
1 5

<210> SEQ ID NO 865
<211> LENGTH: 9
<212> TYPE: PRT
<213> ORGANISM: Homo sapiens

<400> SEQUENCE: 865

Leu Cys Ala Asp Ala Arg Met Tyr Gly
1 5

<210> SEQ ID NO 866
<211> LENGTH: 9
<212> TYPE: PRT
<213> ORGANISM: Homo sapiens

<400> SEQUENCE: 866

Val Ile Tyr Gly Thr Ala Ser Phe Phe
1 5

<210> SEQ ID NO 867
<211> LENGTH: 9
<212> TYPE: PRT
<213> ORGANISM: Homo sapiens

<400> SEQUENCE: 867

Tyr Glu Tyr Leu Ile Asn Val Ile His
1 5

<210> SEQ ID NO 868
<211> LENGTH: 9
<212> TYPE: PRT
<213> ORGANISM: Homo sapiens

<400> SEQUENCE: 868

Val Gly Ile Thr Tyr Ala Leu Thr Val
1 5

<210> SEQ ID NO 869
<211> LENGTH: 16
<212> TYPE: PRT
<213> ORGANISM: Homo sapiens

<400> SEQUENCE: 869

His Cys Leu Gly Lys Trp Leu Gly His Pro Asp Lys Phe Val Gly Ile
1 5 10 15

<210> SEQ ID NO 870
<211> LENGTH: 18
<212> TYPE: PRT
<213> ORGANISM: Homo sapiens

<400> SEQUENCE: 870

Phe Val Gly Ile Thr Tyr Ala Leu Thr Val Val Trp Leu Leu Val Phe
1 5 10 15

Ala Cys

<210> SEQ ID NO 871
<211> LENGTH: 5
<212> TYPE: PRT
<213> ORGANISM: Artificial Sequence
<220> FEATURE:

-continued

<223> OTHER INFORMATION: Description of Artificial Sequence: Synthetic
      Ii-key motif

<400> SEQUENCE: 871

Leu Gly Lys Trp Leu
  1               5

<210> SEQ ID NO 872
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/PLP epitope hybrid peptide
<220> FEATURE:
<223> OTHER INFORMATION: C-term amidated

<400> SEQUENCE: 872

Leu Arg Met Lys Phe Phe Phe Leu Tyr Gly Ala Leu Leu
  1               5                  10

<210> SEQ ID NO 873
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/PLP epitope hybrid peptide
<220> FEATURE:
<223> OTHER INFORMATION: C-term amidated

<400> SEQUENCE: 873

Leu Arg Met Lys Phe Val Gly Ala Ala Ala Thr Leu Val
  1               5                  10

<210> SEQ ID NO 874
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/PLP epitope hybrid peptide
<220> FEATURE:
<223> OTHER INFORMATION: C-term amidated

<400> SEQUENCE: 874

Leu Arg Met Lys Phe His Leu Phe Ile Ala Ala Phe Val
  1               5                  10

<210> SEQ ID NO 875
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/PLP epitope hybrid peptide
<220> FEATURE:
<223> OTHER INFORMATION: C-term amidated

<400> SEQUENCE: 875

Leu Arg Met Lys Leu Val Ser Leu Leu Thr Phe Met Ile
  1               5                  10

<210> SEQ ID NO 876
<211> LENGTH: 22
<212> TYPE: PRT
<213> ORGANISM: Artificial Sequence
<220> FEATURE:
<223> OTHER INFORMATION: Description of Artificial Sequence: Synthetic -continued Ii-key/PLP epitope hybrid peptide
<220> FEATURE:
<223> OTHER INFORMATION: C-term amidated

<400> SEQUENCE: 876

Leu Arg Met Lys Phe Val Gly Ile Thr Tyr Ala Leu Thr Val Val Trp
1 5 10 15

Leu Leu Val Phe Ala Cys
20

<210> SEQ ID NO 877
<211> LENGTH: 247
<212> TYPE: PRT
<213> ORGANISM: Homo sapiens

<400> SEQUENCE: 877

Met Ala Ser Leu Ser Arg Pro Ser Leu Pro Ser Cys Leu Cys Ser Phe
1 5 10 15

Leu Leu Leu Leu Leu Leu Gln Val Ser Ser Ser Tyr Ala Gly Gln Phe
20 25 30

Arg Val Ile Gly Pro Arg His Pro Ile Arg Ala Leu Val Gly Asp Glu
35 40 45

Val Glu Leu Pro Cys Arg Ile Ser Pro Gly Lys Asn Ala Thr Gly Met
50 55 60

Glu Val Gly Trp Tyr Arg Pro Pro Phe Ser Arg Val Val His Leu Tyr
65 70 75 80

Arg Asn Gly Lys Asp Gln Asp Gly Asp Gln Ala Pro Glu Tyr Arg Gly
85 90 95

Arg Thr Glu Leu Leu Lys Asp Ala Ile Gly Glu Gly Lys Val Thr Leu
100 105 110

Arg Ile Arg Asn Val Arg Phe Ser Asp Glu Gly Gly Phe Thr Cys Phe
115 120 125

Phe Arg Asp His Ser Tyr Gln Glu Glu Ala Ala Met Glu Leu Lys Val
130 135 140

Glu Asp Pro Phe Tyr Trp Val Ser Pro Gly Val Leu Val Leu Leu Ala
145 150 155 160

Val Leu Pro Val Leu Leu Leu Gln Ile Thr Val Gly Leu Val Phe Leu
165 170 175

Cys Leu Gln Tyr Arg Leu Arg Gly Lys Leu Arg Ala Glu Ile Glu Asn
180 185 190

Leu His Arg Thr Phe Asp Pro His Phe Leu Arg Val Pro Cys Trp Lys
195 200 205

Ile Thr Leu Phe Val Ile Val Pro Val Leu Gly Pro Leu Val Ala Leu
210 215 220

Ile Ile Cys Tyr Asn Trp Leu His Arg Arg Leu Ala Gly Gln Phe Leu
225 230 235 240

Glu Glu Leu Arg Asn Pro Phe
245

<210> SEQ ID NO 878
<211> LENGTH: 9
<212> TYPE: PRT
<213> ORGANISM: Homo sapiens

<400> SEQUENCE: 878

Leu Val Leu Leu Ala Val Leu Pro Val
1 5

<210> SEQ ID NO 879
<211> LENGTH: 9
<212> TYPE: PRT
<213> ORGANISM: Homo sapiens

<400> SEQUENCE: 879

Phe Leu Arg Val Pro Cys Trp Lys Ile
1 5

<210> SEQ ID NO 880
<211> LENGTH: 9
<212> TYPE: PRT
<213> ORGANISM: Homo sapiens

<400> SEQUENCE: 880

Phe Arg Val Ile Gly Pro Arg His Pro
1 5

<210> SEQ ID NO 881
<211> LENGTH: 9
<212> TYPE: PRT
<213> ORGANISM: Homo sapiens

<400> SEQUENCE: 881

Leu Gly Pro Leu Val Ala Leu Ile Ile
1 5

<210> SEQ ID NO 882
<211> LENGTH: 9
<212> TYPE: PRT
<213> ORGANISM: Homo sapiens

<400> SEQUENCE: 882

Phe Val Ile Val Pro Val Leu Gly Pro
1 5

<210> SEQ ID NO 883
<211> LENGTH: 9
<212> TYPE: PRT
<213> ORGANISM: Homo sapiens

<400> SEQUENCE: 883

Phe Leu Leu Leu Leu Leu Leu Gln Val
1 5

<210> SEQ ID NO 884
<211> LENGTH: 9
<212> TYPE: PRT
<213> ORGANISM: Homo sapiens

<400> SEQUENCE: 884

Leu Val Gly Asp Glu Val Glu Leu Pro
1 5

<210> SEQ ID NO 885
<211> LENGTH: 9
<212> TYPE: PRT
<213> ORGANISM: Homo sapiens

<400> SEQUENCE: 885

Leu Leu Lys Asp Ala Ile Gly Glu Gly
1 5

<210> SEQ ID NO 886

-continued

```
<211> LENGTH: 9
<212> TYPE: PRT
<213> ORGANISM: Homo sapiens

<400> SEQUENCE: 886

Leu Arg Ile Arg Asn Val Arg Phe Ser
  1               5


<210> SEQ ID NO 887
<211> LENGTH: 9
<212> TYPE: PRT
<213> ORGANISM: Homo sapiens

<400> SEQUENCE: 887

Leu Leu Leu Gln Ile Thr Val Gly Leu
  1               5


<210> SEQ ID NO 888
<211> LENGTH: 9
<212> TYPE: PRT
<213> ORGANISM: Homo sapiens

<400> SEQUENCE: 888

Trp Val Ser Pro Gly Val Leu Val Leu
  1               5


<210> SEQ ID NO 889
<211> LENGTH: 9
<212> TYPE: PRT
<213> ORGANISM: Homo sapiens

<400> SEQUENCE: 889

Tyr Arg Leu Arg Gly Lys Leu Arg Ala
  1               5


<210> SEQ ID NO 890
<211> LENGTH: 9
<212> TYPE: PRT
<213> ORGANISM: Homo sapiens

<400> SEQUENCE: 890

Trp Leu His Arg Arg Leu Ala Gly Gln
  1               5


<210> SEQ ID NO 891
<211> LENGTH: 19
<212> TYPE: PRT
<213> ORGANISM: Homo sapiens

<400> SEQUENCE: 891

Leu Leu Gln Val Ser Ser Ser Tyr Ala Gly Gln Phe Arg Val Ile Gly
  1               5                  10                  15

Pro Arg His


<210> SEQ ID NO 892
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated

<400> SEQUENCE: 892
```

-continued

```
Leu Arg Met Lys Leu Val Leu Leu Ala Val Leu Pro Val
  1               5                   10


<210> SEQ ID NO 893
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated

<400> SEQUENCE: 893

Leu Arg Met Lys Phe Leu Arg Val Pro Cys Trp Lys Ile
  1               5                   10


<210> SEQ ID NO 894
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated

<400> SEQUENCE: 894

Leu Arg Met Lys Phe Arg Val Ile Gly Pro Arg His Pro
  1               5                   10


<210> SEQ ID NO 895
<211> LENGTH: 13
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated

<400> SEQUENCE: 895

Leu Arg Met Lys Phe Val Ile Val Pro Val Leu Gly Pro
  1               5                   10


<210> SEQ ID NO 896
<211> LENGTH: 17
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated

<400> SEQUENCE: 896

Leu Arg Met Lys Phe Leu Leu Leu Leu Leu Leu Gln Val Ser Ser Ser
  1               5                   10                  15

Tyr


<210> SEQ ID NO 897
<211> LENGTH: 16
<212> TYPE: PRT
<213> ORGANISM: Artificial Sequence
<220> FEATURE:
<223> OTHER INFORMATION: Description of Artificial Sequence: Synthetic
      Ii-key/MOG epitope hybrid peptide
<220> FEATURE:
<223> OTHER INFORMATION: C-term amidated
```

<400> SEQUENCE: 897

Leu Arg Met Lys Phe Arg Val Ile Gly Pro Arg His Pro Ile Arg Ala
1 5 10 15

<210> SEQ ID NO 898
<211> LENGTH: 16
<212> TYPE: PRT
<213> ORGANISM: Human immunodeficiency virus type 1

<400> SEQUENCE: 898

Asn Asp Ile Gln Lys Leu Val Gly Lys Leu Asn Trp Ala Ser Gln Ile
1 5 10 15

<210> SEQ ID NO 899
<211> LENGTH: 20
<212> TYPE: PRT
<213> ORGANISM: Human immunodeficiency virus type 1

<400> SEQUENCE: 899

Tyr Pro Gly Ile Lys Val Arg Gln Leu Cys Lys Leu Leu Arg Gly Thr
1 5 10 15

Lys Ala Leu Thr
20

<210> SEQ ID NO 900
<211> LENGTH: 15
<212> TYPE: PRT
<213> ORGANISM: Artificial Sequence
<220> FEATURE:
<223> OTHER INFORMATION: Description of Artificial Sequence: Synthetic
Ii-key/antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 900

Leu Arg Met Lys Xaa Ile Ala Tyr Leu Lys Gln Ala Thr Ala Lys
1 5 10 15

<210> SEQ ID NO 901
<211> LENGTH: 10
<212> TYPE: PRT
<213> ORGANISM: Artificial Sequence
<220> FEATURE:
<223> OTHER INFORMATION: Description of Artificial Sequence: Synthetic
antigenic epitope peptide
<220> FEATURE:
<223> OTHER INFORMATION: C-term amidated

<400> SEQUENCE: 901

Ile Ala Tyr Leu Lys Gln Ala Thr Ala Lys
1 5 10

<210> SEQ ID NO 902
<211> LENGTH: 16
<212> TYPE: PRT
<213> ORGANISM: Artificial Sequence
<220> FEATURE:
<223> OTHER INFORMATION: Description of Artificial Sequence: Synthetic
Ii-key/antigenic epitope hybrid peptide
<220> FEATURE:
<221> NAME/KEY: MOD_RES
<222> LOCATION: (5)..(6)
<223> OTHER INFORMATION: a-aminovaleric acid -continued

```
<220> FEATURE:
<223> OTHER INFORMATION: C-term amidated

<400> SEQUENCE: 902

Leu Arg Met Lys Xaa Xaa Ala Tyr Arg Ala Ile Arg His Ile Pro Arg
  1               5                  10                  15


<210> SEQ ID NO 903
<211> LENGTH: 15
<212> TYPE: PRT
<213> ORGANISM: Artificial Sequence
<220> FEATURE:
<223> OTHER INFORMATION: Description of Artificial Sequence: Synthetic
      Ii-key/antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 903

Leu Arg Met Lys Xaa Ala Tyr Arg Ala Ile Arg His Ile Pro Arg
  1               5                  10                  15


<210> SEQ ID NO 904
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/antigenic epitope hybrid peptide
<220> FEATURE:
<221> NAME/KEY: MOD_RES
<222> LOCATION: (5)
<223> OTHER INFORMATION: a-aminovaleric acid
<220> FEATURE:
<223> OTHER INFORMATION: C-term amidated

<400> SEQUENCE: 904

Leu Arg Met Lys Xaa Tyr Arg Ala Ile Arg His Ile Pro Arg
  1               5                  10


<210> SEQ ID NO 905
<211> LENGTH: 14
<212> TYPE: PRT
<213> ORGANISM: Artificial Sequence
<220> FEATURE:
<223> OTHER INFORMATION: Description of Artificial Sequence: Synthetic
      Ii-key/antigenic epitope hybrid peptide
<220> FEATURE:
<223> OTHER INFORMATION: C-term amidated

<400> SEQUENCE: 905

Leu Arg Met Lys Ala Tyr Arg Ala Ile Arg His Ile Pro Arg
  1               5                  10
```

II-KEY/ANTIGENIC EPITOPE HYBRID PEPTIDE VACCINES

Pursuant to 37 CFR 1.52(e) (5), materials contained on two compact discs is hereby incorporated-by-reference.

The name of the file on the compact disc is "REH-2015.APP", the date of creation is Nov. 26, 2002, the size of the document is 333,000 bytes and enclosed are two copies of the compact discs labeled "Copy 1" and "Copy 2".

BACKGROUND OF THE INVENTION

The immune system responds to foreign pathogens, to tumor cells, to autoimmune disease-inducing processes, to allergens, to grafts, through the recognition of the 'foreign' or 'abnormal' structures, as antigens. Most of those antigens are proteins, which are synthesized either by cells of the host, or by a pathogen. Such antigens are processed (proteolytically digested) into peptide fragments which come to be presented to the responding lymphocytes of the immune system, in a peptide-presenting structure on the surface of the antigen presenting cell. Those peptide presenting structures are called major histocompatibility complex (MHC) molecules. They obtained that name since they were first recognized as products of polymorphic, allelic genes in the MHC locus, which genes control graft rejection among inbred strains of mice.

The immune response to a specific antigen is mediated by T lymphocytes which recognize peptide fragments of those antigens in the MHC molecules. Within an antigen presenting cell (APC), peptide fragments of a proteolytically processed antigen become bound into the antigenic peptide binding site of major histocompatibility complex (MHC) molecules. These peptide-MHC complexes are then transported to the cell surface for recognition (of both the foreign peptide and the adjacent surface of the presenting MHC molecule) by T cell receptors on responding T lymphocytes. Those T lymphocytes can have either immunoregulatory functions (to help or suppress an immune response) or effector functions (to clear the pathogen or tumor, for example, through a cytotoxic immune response). The antigen-specific recognition event initiates the immune response cascade which leads to a protective immune response, or in the case of autoimmune processes, a deleterious immune response.

Two classes of MHC molecules function as immune system presenters of antigenic peptides to T cells. MHC class I molecules receive peptides from endogenously synthesized proteins, such as an infectious virus, in the endoplasmic reticulum about the time of synthesis of the MHC class I molecules. The MHC class I-bound antigenic peptides are presented at the cell surface to CD8-positive cytotoxic T lymphocytes, which then become activated and can directly kill the virus-expressing cells. In contrast, MHC class II molecules are synthesized in the endoplasmic reticulum with their antigenic peptide binding sites blocked by the invariant chain protein (Ii). These complexes of MHC class II molecules and Ii protein are transported from the endoplasmic reticulum to a post-Golgi compartment where Ii is released by proteolysis and a specific antigenic peptide becomes bound to the MHC class II molecule (Blum et al., *Proc. Natl. Acad. Sci. USA* 85: 3975 (1988); Riberdy et al., *Nature* 360: 474 (1992); Daibata et al., *Mol. Immunol.* 31: 255 (1994); Xu et al., *Mol. Immunol.* 31: 723 (1994); Xu et al., Antigen Processing and Presentation, Academic Press, NY p227 (1994); Kropshofer et al., *Science* 270: 1357 (1995); and Urban et al., *J. Exp. Med.* 180: 751 (1994)).

R. Humphreys (1996) U.S. Pat. No. 5,559,028, and Humphreys et al. (1999) U.S. Pat. No. 5,919,639 revealed the mechanisms by which Ii protein is cleaved, releasing fragments in the course of cleavage to regulate the binding and locking in of antigenic peptides within the antigenic peptide binding site of MHC class II molecules (Adams et al., *Eur. J. Immunol.* 25: 1693 (1995); Adams et al., *Arzneim. Forsch./Drug Research* 47: 1069 (1997); and Xu et al., *Arzneim. Forsch./Drug Research in press* (1999)). One segment of the Ii protein, Ii(77–92), was found to act at an allosteric site outside the antigenic peptide binding site near the end of that site holding the N-terminus of the antigenic peptide. The referenced patents, furthermore, disclosed novel therapeutic compounds and methods to control this initial regulatory, antigenic peptide recognizing event of the immune response by three classes of mechanisms. In the first mechanism, antigenic peptides are spilled from cell surface MHC class II molecules by the action of compounds of the invention.

In the second, the charging of the antigenic peptide binding site on those molecules is promoted with compounds of the invention for binding of other, synthetic peptides. Such inserted peptide sequences can be either antigenic epitopes or nonantigenic peptide sequences which nevertheless bind tightly to block the antigenic peptide binding site. The third mechanism involves altering the rates of association/dissociation of antigenic peptides from those complexes and the nature of the interaction of components of the trimolecular MHC molecule/antigenic peptide/T cell receptor complex, and furthermore the interaction of that trimolecular complex with auxiliary cell-to-cell interaction molecules, in a manner to regulate differentiation and function of the responding T lymphocytes.

The identification of the mechanisms referred to above opens new avenues of therapeutic intervention. New methods and compositions based on these discoveries offer the promise of epitope-specific therapies.

SUMMARY OF THE INVENTION

In one aspect, the present invention relates to a nucleic acid molecule comprising a first expressible sequence encoding a protein of interest or polypeptide of interest which contains an MHC Class II-presented epitope. In addition, the nucleic acid molecule comprises a second expressible nucleic acid sequence encoding an antigen presentation enhancing hybrid polypeptide. The antigen presentation enhancing hybrid polypeptide includes the following elements: i) an N-terminal element consisting essentially of 4–16 residues of the mammalian Ii-Key peptide LRMKLPKPPKPVSKMR (SEQ ID NO: 1) and non-N-terminal deletion modifications thereof that retain antigen presentation enhancing activity; ii) a C-terminal element comprising an MHC Class II-presented epitope in the form of a polypeptide or peptidomimetic structure which binds to the antigenic peptide binding site of an MHC class II molecule, the MHC Class II-presented epitope being contained in the protein of interest of step a); and iii) an intervening peptidyl structure linking the N-terminal and C-terminal elements of the hybrid, the peptidyl structure having a length of about 20 amino acids or less.

In preferred embodiments, the modifications of the I-Key peptide include deletion of amino acids from the C-terminus; N-terminal extensions; and amino acid substitutions. In other embodiments, the C-terminal element further comprises an MHC Class I-presented epitope, or a portion thereof, the amino acid residues comprising the MHC Class I-presented epitope or portion thereof being constituent residues of the MHC Class II-presented epitope.

Disclosed embodiments also include embodiments wherein the C-terminal element further comprises an antibody-recognized determinant, or a portion thereof. The amino acid residues comprising the antibody-recognized determinant, or a portion thereof, are preferably constituent residues of the MHC Class II-presented epitope. Embodiments are disclosed in which the infectious pathogen is selected from the group consisting of anthrax, EBOLA, HIV and influenza. In addition to the disclosed compositions, methods of use are also described.

DETAILED DESCRIPTION OF THE INVENTION

As discussed in the Background of the Invention section of the present disclosure, U.S. application Ser. No. 09/396,813 (now U.S. Pat. No. 6,432,409) discloses hybrid peptides useful in connection with modulation of the immune system (referred to herein as "the '813 enhancing hybrid peptide"). The disclosure was based on the discovery that an MHC Class II-restricted antigenic epitope which is covalently linked to a mammalian Ii key peptide by an appropriate intervening chemical structure, to form a hybrid polypeptide, is presented to T lymphocytes by antigen presenting cells with significantly higher efficacy than is the precursor antigenic epitope. The disclosure of U.S. Pat. No. 6,432,409 is incorporated herein by reference.

The hybrid polypeptide disclosed was referred to as an "MHC Class II antigen presentation enhancing hybrid polypeptide", or more simply as an "enhancing hybrid". In this disclosure, such peptides have also been referred to as "Ii-Key/antigenic epitope hybrids" or "hybrid peptides". Alternatively, short-hand designations based on functional elements may be used, particularly in the Exemplification section. For example, Ii-Key/MHC Class II-presented antigenic epitope hybrids, Ii-Key/MHC Class II-presented antigenic epitope/MHC Class I-presented antigenic epitope hybrids, Ii-Key/MHC Class II-presented antigenic epitope/antibody-recognized determinant (ARD) hybrids. The preceding listing of alternative terminology may not be comprehensive, but reference to such enhancing hybrids will be clear in context.

The '813 enhancing hybrid has an N-terminus comprised of a mammalian Ii-Key peptide, or a modification thereof, which retains antigen presentation enhancing activity. Covalently, but indirectly, linked to the Ii-Key peptide is the specific MHC Class II antigenic epitope to be presented.

Between the Ii-Key peptide and the antigenic epitope is an intervening chemical structure which covalently links the other two components. This intervening chemical structure was referred to simply as a "spacer". Necessary parameters of the spacer were described in detail.

The present disclosure specifically contemplates enhancing hybrid peptides containing antigenic epitopes/determinants in addition to the MHC Class II antigenic epitope disclosed in connection with the '813 enhancing hybrid. For example, the enhancing hybrids of the present invention may contain multiple MHC Class II epitopes. The inclusion of multiple MHC Class II epitopes enables a greater fraction of the human population to be immunized because the multiple epitopes are frequently presented by different alleles. In addition to a plurality of MHC Class II epitopes, the present invention also contemplates the inclusion of one or more MHC Class I epitopes and/or one or more ARDs (Antibody Recognized Determinants). The expressions "epitopes" and "determinants" are considered as synonyms by many skilled in the art. The use of the expression "epitope/determinant", as used herein, is intended to encompass MHC Class II epitopes, MHC Class I epitopes and ARDs.

The Exemplification section which follows provides numerous specific examples of experimentally-determined or predicted MHC Class II epitopes, MHC Class I epitopes and ARDs, which can be incorporated in enhancing hybrid peptides. The experimentally determined epitopes are preferred over algorithm-predicted epitopes for preclinical trials in animal models for human disease, in part, because a significant percentage of algorithm-predicted epitopes are not found to be biologically functional. Nevertheless, the "significant percentage" is sufficiently small that such epitopes are a source of sequences for the development of enhancing hybrids. In the context of a focus on a particular disease or condition, reference is made to the compounds and methods of use described in the corresponding Exemplification section which follows.

As will be discussed below, the use of the '813 enhancing hybrid peptide to enhance or augment an MHC Class II-mediated immune response, created an untapped immune reservoir. As will be discussed in greater detail below, the interaction of the '813 enhancing peptide with cells of the immune system greatly amplified a number of responsive cell types. Molecular input for a subset of these responsive cell types, in the form of the MHC Class II epitope component of the enhancing hybrid, were provided. However, large numbers of primed and responsive immune cell types were stimulated by the '813 peptide, but no provision for appropriate molecular inputs was provided. Such additional molecule inputs, in the form of MHC Class I epitopes and ARDs, is provided herein.

More specifically, the enhancement of the T helper cell stimulation mediated by the Class II epitope of the '813 peptide is substantially augmented (i.e., about 250 times) by the effect of the Ii-Key moiety. The clonal expansion of an immunoregulatory cell type, such as an activated T cell, has a cascading effect through the immune system. As discussed above, this can create an excess of immune capacity which has not been addressed in the prior art.

Ultimately, an MHC Class II-presented antigen which is an element of the hybrid peptide (either an enhancing hybrid peptide of the present invention or an '813 enhancing hybrid peptide), exerts its influence through presentation by an MHC Class II molecule on the surface of an antigen presenting cell. Two particularly important classes of antigen presenting cells are dendritic cells and macrophages. These antigen presenting cells have on their respective surfaces two types of special molecules that function in antigen presentation. These two types of molecules are MHC Class I and MHC Class II molecules. Antigenic peptides (e.g., MHC Class I or MHC Class II epitopes) are noncovalently bound to MHC Class I or MHC Class II molecules for subsequent presentation to antigen-specific receptors on T cells.

While not wishing to be bound by theory, it is thought that peptides containing MHC Class I and/or MHC Class II epitopes may be displayed on the surface of an antigen presenting cell in association with the cognate display molecule (i.e., MHC Class I molecules or MHC Class II molecules) through at least two mechanisms. For example, following contact with an antigen presenting cell, such peptides may be internalized by the antigen presenting cell and processed through classical channels. Alternatively, the MHC Class I or MHC Class II-presented antigen portion of such a peptide may bind directly to an MHC Class I or MHC Class II molecule on the surface of an antigen presenting cell. Thus, in both cases, the MHC Class I or MHC Class II-presented epitope of the peptide is displayed on the surface of an antigen presenting cell in association with its cognate MHC Class I or MHC Class II molecule.

Such an MHC Class II-associated display triggers a cascade of immune-mediated effects including the induction of T cells and the subsequent expansion of this induced population. T helper cells, stimulated in this manner, respond in a variety of ways. For example, stimulated T helper cells function by releasing cytokines that provide various activation signals for B cells. B cells produce a surface immunoglobulin which can recognize and specifically bind to an ARD element which is present, for example, on a protein or peptide which contacts the cell surface. The protein or peptide is then internalized and any processed MHC Class I or MHC Class II-presented epitopes present are subsequently displayed on the B cell surface in association with MHC Class I or MHC Class II molecules, respectively.

The example of an ARD-containing molecule provided in the preceding paragraph was a protein or peptide. In connection with the present invention, the ARD is provided as an element of an enhancing hybrid peptide. As was the case in the previous example, the enhancing hybrid peptide is internalized by the B cell and any MHC Class II epitopes present as an element of the enhancing hybrid are processed for display on the surface of the B cell in association with MHC Class II molecules. Such presentation further stimulates the helper T cell population resulting in proliferation and maturation of B lymphocytes to plasma cells which produce the antibody specific to the ARD.

The enhancing hybrid polypeptide of the present invention is comprised of 3 elements, as was the '813 enhancing hybrid. The 3 elements are: 1) an N-terminal element consisting essentially of 4–16 residues of the mammalian Ii-Key peptide LRMKLPKPPKPVSKMR (SEQ ID NO: 1 and non-N-terminal deletion modifications thereof that retain antigen presentation enhancing activity; 2) a C-terminal element comprising an MHC Class II-presented epitope in the form of a polypeptide or peptidomimetic structure which binds to the antigenic peptide binding site of an MHC Class II molecule; and 3) an intervening chemical structure covalently linking the N-terminal and C-terminal elements of the hybrid, the chemical structure being a covalently joined group of atoms which when arranged in a linear fashion forms a flexible chain which extends up to the length of 20 amino acids likewise arranged in a linear fashion.

The included additional epitope(s) or determinant(s) which distinguish the enhancing hybrid of the present invention from the '813 enhancing hybrid are preferably located within the C-terminal element or the linker element. Additionally, an epitope or determinant may overlap the C-terminal element and the linker element. In some circumstances it may be possible for an additional epitope or determinant to overlap between the linker element and the N-terminal Ii-Key moiety.

Generally speaking, MHC Class I and MHC Class II epitopes are comprised of from about 8 to about 12 amino acid residues. ARD elements are typically have a size range somewhat broader than MHC Class I and MHC Class II epitopes. A commonly cited size range for ARDs is from about 6 to about 16 amino acid residues. ARDs are recognized based on their 3-dimensional structure whereas MHC Class I and MHC Class II epitopes are recognized on the basis of their linear, primary amino acid structure.

To provide specificity to the options outlined in the preceding paragraph, it is necessary to discuss the anatomy of the enhancing peptide of the present invention in greater detail. The linker sequence has been described as an intervening chemical structure covalently linking the N-terminal and C-terminal elements of the hybrid, the chemical structure being a covalently joined group of atoms which when arranged in a linear fashion forms a flexible chain which extends up to the length of 20 amino acids likewise arranged in a linear fashion. Thus, to the extent that the linker sequence is comprised of amino acids (which is not a requirement), the disclosure of the present invention provides an additional functionality to the amino acid residues of the linker, above and beyond their required role as space occupiers.

The specified linker length (up to 20 amino acids arranged in a linear fashion) is long enough to contain a second complete MHC Class II epitope, a first complete MHC Class I epitope, or a first complete ARD or segments of such additional epitopes. Additionally, such a sequence length can accommodate a plurality of non-overlapping epitopes selected from the group consisting of MHC Class I epitopes, MHC Class II epitopes and ARDs.

It is known in the art that functional MHC Class I epitopes, MHC Class II epitopes and ARDs may be arranged in an overlapping manner while retaining full functionality of all represented epitopes. The respective functions of each epitope within a hybrid are not co-expressed at one point in time on a per peptide basis, because such peptides must be bound into MHC Class I or MHC Class II molecules and recognized in a folded structure by an antibody. Nevertheless, given a population of injected peptides with respective processing and/or binding to cell surface MHC molecules, all three classes of epitopes within any one Ii-Key enhancing hybrid can be effective immunogens within an immunized animal.

Minimum sequences are preferred for several reasons. These include simplicity and cost of synthesis, less opportunity for proteolytic degradation, less opportunity for metabolic change leading to clearance or adsorption. Thus, the linker element may contain a plurality of epitopes which overlap one another (i.e., an individual amino acid residues may be a components of more than one epitope). Similarly, the C-terminal element which includes an MHC Class II-presented epitope may also contain additional epitopes (MHC Class I, MHC Class II or ARD) in an overlapping or non-overlapping arrangement.

It is noted that the boundaries between the various elements of the enhancing hybrid peptide of the present invention are, within certain stated limits, somewhat arbitrary. Epitopes spanning the junctions between the various elements are encompassed within the scope of the present invention. Thus, for example, where a claim specifies that a portion of an epitope is contained within one of the enhancing hybrid peptide elements or domains (e.g., the linker region), this necessarily implies that the remaining portion is found in a contiguous portion of a flanking portion or domain. Partial (i.e., non-functional epitopes are of no utility in connection with the present invention).

Early work in this area demonstrated that the mammalian Ii key peptide LRMKLPKPPKPVSKMR (SEQ ID NO: 1), and a modified mammalian Ii-key peptide, YRMKLPKPPKPVSKMR (SEQ ID NO: 2), have the ability to alter presentation of certain MHC Class II-restricted, antigenic peptides to T lymphocyte-hybridomas which recognize those respective antigenic peptides (U.S. Pat. No. 5,559,028; U.S. Pat. No. 5,919,639, the disclosures of which are incorporated herein by reference). Previous experimentation with modified versions of the Ii-key peptide have indicated that a wide variety of modifications can be made to this polypeptide without detriment to activity. Indeed, modifications often enhanced antigen presentation activity of the polypeptide.

Results detailed in the Exemplification section of U.S. application Ser. No. 09/396,813, now U.S. Pat. No. 6,432,409, indicate that all modified Ii key peptides which retain antigen presentation enhancing activity will function in the enhancing hybrid of the present invention when appropriately incorporated. Modifications of the Ii key peptide include deletion of one or more amino acids from the C-terminus, protection of the N-terminus, amino acid substitutions, and introduction of cyclical peptides. Deletions of the Ii key peptide which retain at least 4 contiguous amino acids of the original sequence, or a substituted version thereof, exhibit functional activity. Various natural or non-natural amino acids may be substituted at respective residue positions. Some examples of molecules which may be substituted are peptidomimetic structures, D-isomer amino acids, N-methyl amino acids, L-isomer amino acids, modified L-isomer amino acids, and cyclized derivatives. In addition, procedures of medicinal chemistry may be applied by one skilled in the art using routine experimental methods to obtain additional modifications of the N-terminal segment of hybrids. Examples of such procedures are methods of rational drug design, molecular modeling based on structural information from X-ray diffraction data, nuclear magnetic resonance data, and other computational methods, and screening of products of combinatorial chemical syntheses, and isolations of natural products. Examples of modified versions of Ii key peptide which are known to retain high activity are LRMK (SEQ ID NO: 3), LRMKLPK (SEQ ID NO: 4), LRMKLPKS (SEQ ID NO: 5), LRMKLPKSAKP (SEQ ID NO: 6), and LRMKLPKSAKPVSK (SEQ ID NO: 7). Other modifications and modified versions of the Ii-key peptide are described in U.S. Pat. No. 5,919,639, and U.S. Pat. No. 5,559,028. A modified version of the Ii-key peptide (YRMKLPKPPKPVSKMR, SEQ ID NO: 2) which is known to retain activity is referred to herein as an 'Ii-key homolog'. The term Ii key homolog as used herein is inclusive of the Ii key peptide itself.

Such Ii-Key peptides were demonstrated by several experimental methods to bind to an allosteric site at the end of the antigenic peptide binding site of MHC Class II molecules holding the N-terminal end of an antigenic peptide. That process of binding to the allosteric site, facilitated the release and exchange of endogenously bound antigenic peptide with cell surface MHC Class II molecules.

Peptide homologs of the Ii-Key peptide act on murine or human MHC Class II molecules to promote the release of bound antigenic peptides and their replacement with synthetic peptides (Adams S. Arneimittelforschung. 1997 47:1069–1077; Xu M. Arneimittelforschung. 1999 49:791–9). Hybrid constructs of the Ii-Key peptide linked to an antigenic epitope peptide through either a simple polymethylene linker or the extended, natural sequence of the Ii protein, have 500 to 2000 times the potency of presentation versus the antigenic peptides (Humphreys R E. Vaccine. 2000 18:2693–2697). This property has great clinical utility in diagnosis, treatment monitoring and therapy of various diseases and conditions, as presented herein. This activity of the Ii-Key moiety within Ii-Key/antigenic epitope hybrids is found either in vitro or in vivo. This activity can be ascribed to interaction with cell surface MHC Class II molecules because the Ii-Key compounds were active in vitro with either living or paraformaldehyde-fixed antigen presenting cells (Adams S. Eur J. Immunol. 1995 25:1693–1702). However, since the compounds are potent in vivo, they may also be taken up by the pathway which processes exogenous antigens and bind to MHC Class II molecule sin the post-Golgi, antigen charging compartment.

The MHC Class I epitopes, MHC Class II epitopes and ARDs of the enhancing hybrid of the present invention have been discussed above. Such epitopes/determinants selected for use in the generation of an enhancing hybrid of the present invention may be further modified for use. That is to say, polypeptides of natural or modified sequence, peptidomimetic structures, and also chemical structures which are not natural or modified amino acids may be included in the epitope/determinant elements of the enhancing hybrids disclosed herein. In addition, various chemical modifications may be made to the antigenic epitope/determinant element of the enhancing hybrid. For example, the addition, in whole or in part, of non-natural amino acids, or of other backbone or side chain moieties, wherein the modifications preserve binding specificities of the antigenic epitope/determinant. Such chemical structures might bear moderate, little, or no apparent structural resemblance to any antigenic peptide which is derived from a natural protein sequence. Such modifications might or might not bear on recognition by T cell receptors. Modifications may increase recognition of the antigenic epitope (e.g. lead to recognition by previously non-recognizing subsets of T cell receptors).

The intervening chemical structure, or spacer, has been discussed above. Where the intervening chemical structure comprises one or more epitopes/determinants, the overall length within defined limits is dictated to a large extent by the identity and of the epitope/determinant. In the case in which the intervening chemical structure is antigenically neutral, the teachings of U.S. application Ser. No. 09/396,813, now U.S. Pat. No. 6,432,409, apply. As indicated, the spacer is preferably less than the length of a peptidyl backbone of 9 amino acids linearly arranged. Optimally, spacer length is the length of a peptidyl backbone of between 4 and 6 amino acids, linearly arranged. Preferably, the spacer is unable to hydrogen bond in any spatially distinct manner to other distinct elements of the enhancing hybrid peptide.

Again, with respect to antigenically neutral spacer elements, various chemical groups may be incorporated in the spacer segment instead of amino acids. Examples are described in U.S. Pat. No. 5,910,300, the contents of which are incorporated herein by reference. In a preferred embodiment the spacer is comprised of an aliphatic chain optimally interrupted by heteroatoms, for example a $C_2$–$C_6$ alkylene, or $=N-(CH_2)_{2-6}-N=$. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydroxyphobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A spacer may also contain repeating short aliphatic chains, such as polypropylene, isopropylene, butylene, isobutylene, pentamethlyene, and the like, separated by oxygen atoms.

Additional peptidyl sequences which can be used in a spacer are described in U.S. Pat. No. 5,856,456, the contents of which are incorporated herein by reference. In one embodiment, the spacer has a chemical group incorporated within which is subject to cleavage. Without limitation, such a chemical group may be designed for cleavage catalyzed by a protease, by a chemical group, or by a catalytic monoclonal antibody. In the case of a protease-sensitive chemical group, tryptic targets (two amino acids with cationic side chains), chymotryptic targets (with a hydrophobic side chain), and cathepsin sensitivity (B, D or S) are favored. The term 'tryptic target' is used herein to describe sequences of amino acids which are recognized by trypsin and trypsin-like enzymes. The term 'chymotryptic target' is used herein to describe sequences of amino acids which are recognized by chymotrypsin and chymotrypsin-like enzymes. In addition, chemical targets of catalytic monoclonal antibodies, and other chemically cleaved groups are well known to persons skilled in the art of peptide synthesis, enzymic catalysis, and organic chemistry in general, and can be designed into the hybrid structure and synthesized, using routine experimental methods.

Not all embodiments of the present invention include immunogenic neutrality of the intervening chemical structure, or spacer. That is, the present invention includes embodiments in which the intervening chemical structure, or spacer, is selected from the group consisting of: 1) an MHC Class I epitope, or a portion thereof; and 2) an antibody-recognized determinant, or a portion thereof. In particular, this embodiment is important in connection with the anticipated filing of a counterpart International Application for which the continuation-in-part provisions of the U.S. patent law are inapplicable.

The hybrids of the present invention vary from totally peptide in character to substantially non-peptide in character. In view of the fact that some homologs are substantially reduced or non-peptide in character, they will be more likely to have favorable properties, for example, penetration through cellular membranes, solubility, resistance to proteolysis, resistance to inactivation by conjugation, oral bioavailability, and longer half life in vivo.

Also included within the scope of this invention are pharmaceutically acceptable salts of the hybrid molecule, when an acidic or basic group is present in the structure. The term 'pharmaceutically acceptable salt' is intended to include all acceptable salts such as acetate, ammonium salt, benzenesulfonate, benzoate, borate, bromide, calcium edetate, camsylate, carbonate, chloride/dihydrochloride, citrate, clavulanate, edetate, edisylate, estolate, esylate, fumarate, hexylresorcinate, hydrabamine, hydroxynaphthoate, iodide, isothionate, lactate, lactobionate, laurate, mesylate, methylbromide, methylnitrate, methylsulfate, mucate, napsylate, nitrate, N-methylglucamide, oleaste, oxalate, pamoate, palmitate, panoate, pantothenate, phosphate/diphosphate, polygalacturonate, subacetate, sulfate, tartrate, tosylate, triethiodide, valerate, and the like. The pharmaceutically acceptable salt can be used as a dosage form for modifying the solubility or hydrolysis characteristics, or can be used in a sustained release or pro-drug formulation. Depending on the particular functionality for the compound of the present invention, pharmaceutically acceptable salts of the compounds of this invention may be formed from cations such as sodium, potassium, aluminum, calcium, lithium, magnesium, zinc and from bases such as ammonia, arginine, chloroprocaine, choline, diethanolamine, diethylamine, ethylenediamine, lysine, N-methyl-glutamine, ornithine, N,N'-dibenzylethylenediamine, N-benzylphenethylamine, piperazine, procaine, tris(hydroxymethyl)aminomethane, and tetramethylenediamine hydroxide, and the like. These salts may be prepared by standard procedures, for example, by reacting a free acid with suitable organic or inorganic base. When a basic group is present, such as an amino, and acidic salt, i.e., acetate, hydrobromide, hydrochloride, pamoate, and the like, can be used as the dosage form.

Also in the case of an acid (—COOH) or alcohol group being present, pharmaceutically acceptable esters can be employed, for example, acetate, maleate, pivaloyloxymethyl, and the like and those esters known in the art for modifying solubility or hydrolysis characteristics for use as sustained release or prodrug formulations.

The hybrid molecules of this present invention or components thereof may have chiral centers, and therefor may occur as racemates, racemic mixtures, and as individual enantiomers or diastereomers, with all such isomeric forms being included in the present invention as well as mixtures thereof. Furthermore, some of the crystalline forms of hybrid compounds of the present invention may exist as polymorphous and as such are intended to be included in the present invention. In addition, some of the compounds of the present invention may form solvates with water or common organic solvents. Such solvates are also encompassed within the scope of this invention.

The enhancing hybrid of the present invention may be composed of peptide or peptidomimetic or additional chemical groups which may be synthesized and selected by methods which have been developed for the synthesis and selection of antigenic peptides. Those methods and compounds are presented in the following patents: U.S. Pat. No. 4,708,871; U.S. Pat. No. 5,194,392; U.S. Pat. No. 5,270,170; U.S. Pat. No. 5,382,513; U.S. Pat. No. 5,539,084; U.S. Pat. No. 5,556,762; (1997) U.S. Pat. No. 5,595,915; U.S. Pat. No. 5,747,334; and U.S. Pat. No. 5,874,214, the contents of which are incorporated herein by reference.

The disclosure presented above relates primarily to antigen presentation enhancing hybrid peptides. In another aspect, the present invention relates to nucleic acid sequences which encode such enhancing peptides. It is noted that the scope of the enhancing hybrid peptide disclosure is somewhat broader than the corresponding nucleic acid sequence disclosure in light of the fact that enhancing hybrid peptides produced using recombinant DNA techniques from an encoding nucleic acid sequence must be produced from one of the 20 naturally occurring amino acids. A much broader range of substitutions is available when an enhancing hybrid peptide is produced by chemical synthetic techniques.

A wide variety of delivery systems are available for use in delivering the enhancing hybrid of the present invention to a target cell in vitro and in vivo. Such delivery systems include, for example, viral and non-viral systems. Examples of suitable viral systems include, for example, adenoviral vectors, adeno-associated virus, retroviral vectors, vaccinia, herpes simplex virus, HIV, the minute virus of mice, hepatitis B virus and influenza virus. Non-viral delivery systems may also be used, for example using, uncomplexed DNA, DNA-liposome complexes, DNA-protein complexes and DNA-coated gold particles, bacterial vectors such as *salmonella*, and other technologies such as those involving VP22 transport protein, Co-X-gene, and replicon vectors.

One option for expressing a nucleic acid sequence of interest in an animal cell is the adenovirus system. Adenovirus possesses a double-stranded DNA genome, and replicates independently of host cell division. Adenoviral vectors offer a variety of advantages relative to alternative methods for introducing expressible constructs into cells. For example, adenoviral vectors are capable of transducing a broad spectrum of human tissues and high levels of gene expression can be obtained in dividing and nondividing cells. Adenoviral vectors are characterized by a relatively short duration of transgene expression due to immune system clearance and dilutional loss during target cell division. Several routes of administration can be used including intravenous, intrabiliary, intraperitoneal, intravesicular, intracranial and intrathecal injection, and direct injection of a target organ or tissue. Thus, it is recognized in the art that targeting based on anatomical boundaries is achievable.

The adenoviral genome encodes about 15 proteins and infection involves a fiber protein which binds to a cell surface receptor. This receptor interaction results in internalization of the virus. Viral DNA enters the nucleus of the infected cell and transcription is initiated in the absence of cell division. Expression and replication is under control of the E1A and E1B genes (see Horwitz, M. S., In Virology, 2.sup.nd ed., 1990, pp. 1723–1740). Removal of E1 genes renders the virus replication-incompetent.

Adenoviral serotypes 2 and 5 have been extensively used for vector construction. Bett et al. (Proc. Nat. Acad. Sci. U.S.A., 1994, 91: 8802–8806) have used an adenoviral type 5 vector system with deletions of the E1 and E3 adenoviral genes. The 293 human embryonic kidney cell line has been engineered to express E1 proteins and can thus transcomplement the E1-deficient viral genome. The virus can be isolated from 293 cell media and purified by limiting dilution plaque assays (Graham, F. L. and Prevek, L. In Methods in Molecular Biology: Gene Transfer and Expression Protocols, Humana Press 1991, pp. 109–128). Recombinant virus can be grown in 293 cell line cultures and isolated by lysing infected cells and purification by cesium chloride density centrifugation. A problem associated with the 293 cells for manufacture of recombinant adenovirus is that due to additional flanking regions of the E1 genes, they may give rise to replication competent adenovirus (RCA) during the viral particle production. Although this material is only wild-type adenovirus, and is not replication competent recombinant virus, it can have significant effects on the eventual yield of the desired adenoviral material and lead to increased manufacturing costs, quality control issues for the production runs and acceptance of batches for clinical use. Alternative cell lines such as the PER.C6 which have more defined E1 gene integration than 293 cells (i.e. contain no flanking viral sequence) have been developed which do not allow the recombination events which produce RCA and thus have the potential to overcome above viral production issues.

Adeno-associated virus (AAV) (Kotin, R. M., Hum. Gene Ther., 1994, 5: 793–801) are single-stranded DNA, nonautonomous parvoviruses able to integrate into the genome of nondividing cells of a very broad host range. AAV has not been shown to be associated with human disease and does not elicit an immune response. AAV has two distinct life cycle phases. Wild-type virus will infect a host cell, integrate and remain latent. In the presence of adenovirus, the lytic phase of the virus is induced, which depends on the expression of early adenoviral genes, and leads to active virus replication. The AAV genome is composed of two open reading frames (called rep and cap) flanked by inverted terminal repeat (ITR) sequences. The rep region encodes four proteins which mediate AAV replication, viral DNA transcription, and endonuclease functions used in host genome integration. The rep genes are the only AAV sequences required for viral replication. The cap sequence encodes structural proteins that form the viral capsid. The ITRs contain the viral origins of replication, provide encapsidation signals, and participate in viral DNA integration. Recombinant, replication-defective viruses that have been developed for gene therapy lack rep and cap sequences. Replication-defective AAV can be produced by co-transfecting the separated elements necessary for AAV replication into a permissive 293 cell line. U.S. Pat. No. 4,797,368 contains relevant disclosure and such disclosure is incorporated herein by reference.

Retroviral vectors are useful for infecting dividing cells, and are composed of an RNA genome that is packaged in an envelope derived from host cell membrane and viral proteins. Retroviral gene expression involves a reverse transcription step in which its positive-strand RNA genome is employed as a template to direct the synthesis of double-stranded DNA, which is then integrated into the host cell DNA. The integrated provirus is able to use host cell machinery for gene expression.

Murine leukemia virus is a commonly employed retrovirus species (Miller et al., Methods Enzymol., 1993, 217: 581–599). Retroviral vectors are typically constructed by deletion of the gag, pol and env genes. The deletion of these sequences provides capacity for insertion of nucleic acid sequences of interest, and eliminates the replicative functions of the virus. Genes encoding antibiotic resistance often are included as a means of selection. Promoter and enhancer functions also may be included, for example, to provide for tissue-specific expression following in vivo administration. Promoter and enhancer functions contained in long terminal repeats may also be used.

Such viruses, and modifications of such viruses which carry an exogenous nucleic acid sequence of interest, can only be produced in viral packaging cell lines. The packaging cell line may be constructed by stably inserting the deleted viral genes (gag, pol and env) into the cell such that they reside on different chromosomes to prevent recombination. The packaging cell line is used to construct a producer cell line that will generate replication-defective retrovirus containing the nucleic acid sequence of interest by inserting the recombinant proviral DNA. Plasmid DNA containing the long terminal repeat sequences flanking a small portion of the gag gene that contains the encapsidation sequence and the genes of interest is transfected into the packaging cell line using standard techniques for DNA transfer and uptake (electroporation, calcium precipitation, etc.). Variants of this approach have been employed to decrease the likelihood of production of replication-competent virus (Jolly, D., Cancer Gene Therapy, 1994, 1; 51–64). The host cell range of the virus is determined by the envelope gene (env) and substitution of env genes with different cell specificities can be employed. Incorporation of appropriate ligands into the envelope protein may also be used for targeting.

Administration of recombinant retroviral vectors may be accomplished by any suitable technique. Such techniques include, for example, ex vivo transduction of patients' cells, direct injection of virus into tissue, and by the administration of the retroviral producer cells. ex vivo approaches require the isolation and maintenance in tissue culture of the patient's cells. In this context, a high ratio of viral particles to target cells can be achieved and thus improve the transduction efficiency (see, e.g., U.S. Pat. No. 5,399,346, the disclosure of which is incorporated herein by reference). U.S. Pat. No. 4,650,764 contains disclosure relevant to the use of retroviral expression systems and the disclosure of this referenced patent is incorporated herein by reference.

In some cases direct introduction of virus in vivo is necessary or preferred. Retroviruses have been used to treat brain tumors wherein the ability of a retrovirus to infect only dividing cells (tumor cells) may be particularly advantageous. The administration of a retrovirus producer cell line directly into a brain tumor in a patient has also been proposed (see e.g., Oldfield et al., Hum. Gene Ther., 1993, 4: 39–69). Such a producer cell would survive within the brain tumor for a period of days, and would secrete retrovirus capable of transducing the surrounding brain tumor.

Pox virus-based systems for expression have been described (Moss, B. and Flexner, C., Annu. Rev. Immunol., 1987, 5: 305–324; Moss, B., In Virology, 1990, pp. 2079–2111). Vaccinia, for example, are large, enveloped DNA viruses that replicate in the cytoplasm of infected cells. Nondividing and dividing cells from many different tissues are infected, and gene expression from a nonintegrated genome is observed. Recombinant virus can be produced by inserting the transgene into a vaccinia-derived plasmid and transfecting this DNA into vaccinia-infected cells where homologous recombination leads to the virus production. A significant disadvantage is that it elicits a host immune response to the 150 to 200 virally encoded proteins making repeated administration problematic.

The herpes simplex virus is a large, double-stranded DNA virus that replicates in the nucleus of infected cells. This virus is adaptable for use in connection with exogenous nucleic acid sequences (see Kennedy, P. G. E. and Steiner, I., Q. J. Med., 1993, 86: 697–702). Advantages include a broad host cell range, infection of dividing and nondividing cells, and large sequences of foreign DNA can be inserted into the viral genome by homologous recombination. Disadvantages are the difficulty in rendering viral preparations free of replication-competent virus and a potent immune response. Deletion of the viral thymidine kinase gene renders the virus replication-defective in cells with low levels of thymidine kinase. Cells undergoing active cell division (e.g., tumor cells) possess sufficient thymidine kinase activity to allow replication.

A variety of other viruses, including HIV, the minute virus of mice, hepatitis B virus, and influenza virus, have been disclosed as vectors for gene transfer (see Jolly, D., Cancer Gene Therapy, 1994, 1: 51–64). Nonviral DNA delivery strategies are also applicable. These DNA delivery strategies relate to uncomplexed plasmid DNA, DNA-lipid complexes, DNA-liposome complexes, DNA-protein complexes, DNA-coated gold particles and DNA-coated polylactide coglycolide particles. Purified nucleic acid can be injected directly into tissues and results in transient gene expression for example in muscle tissue, particularly effective in regenerating muscle (Wolff et al., Science, 1990, 247: 1465–1468). Davis et al. (Hum. Gene Ther., 1993, 4: 733–740) has published on direct injection of DNA into mature muscle (skeletal muscle is generally preferred).

Plasmid DNA on gold particles can be “fired” into cells (e.g. epidermis or melanoma) using a gene-gun. DNA is coprecipitated onto the gold particle and then fired using an electric spark or pressurized gas as propellant (Fynan et al., Proc. Natl. Acad. Sci. U.S.A., 1993, 90: 11478–11482). Electroporation has also been used to enable transfer of DNA into solid tumors using electroporation probes employing multi-needle arrays and pulsed, rotating electric fields (Nishi et al., in Cancer Res., 1996, 56:1050–1055). High efficiency gene transfer to subcutaneous tumors has been claimed with significant cell transfection enhancement and better distribution characteristics over intra-tumoral injection procedures.

Lipid-mediated transfections are preferred for both in vitro and in vivo transfections (Horton et al., J. Immunology, 162:6378, 1999). Lipid-DNA complexes are formed by mixing DNA and lipid 1 to 5 minutes before injection, using commercially available lipids such as DMRIE-C reagent.

Liposomes work by surrounding hydrophilic molecules with hydrophobic molecules to facilitate cell entry. Liposomes are unilamellar or multilamellar spheres made from lipids. Lipid composition and manufacturing processes affect liposome structure. Other molecules can be incorporated into the lipid membranes. Liposomes can be anionic or cationic. Nicolau et al. (Proc. Natl. Acad. Sci. U.S.A., 1983, 80: 1068–1072) has published work relating to insulin expression from anionic liposomes injected into rats. Anionic liposomes mainly target the reticuloendothelial cells of the liver, unless otherwise targeted. Molecules can be incorporated into the surface of liposomes to alter their behavior, for example cell-selective delivery (Wu, G. Y. and Wu, C. H., J. Biol. Chem., 1987, 262: 4429–4432).

Felgner et al. (Proc. Nat. Acad. Sci. U.S.A., 1987, 84: 7413–7417) has published work relating to cationic liposomes, demonstrated their binding of nucleic acids by electrostatic interactions and shown cell entry. Intravenous injection of cationic liposomes leads to transgene expression in most organs on injection into the afferent blood supply to the organ. Cationic liposomes can be administered by aerosol to target lung epithelium (Brigham et al., Am. J. Med. Sci., 1989, 298: 278–281). In vivo studies with cationic liposome transgene delivery have been published (see, e.g., Nabel, G., Rev. Hum. Gene Ther., 1994, 5: 79–92; Hyde et al., Nature, 1993, 362: 250–255 and; Conary et al., J. Clin. Invest., 1994, 93: 1834–1840).

Microparticles are being studied as systems for delivery of DNA to phagocytic cells such approaches have been reported by Pangaea Pharmaceuticals. Such a DNA microencapsulation delivery system has been used to effect more efficient transduction of phagocytic cells, such as macrophages, which ingest the microspheres. The microspheres encapsulate plasmid DNA encoding potentially immunogenic peptides which, when expressed, lead to peptide display via MHC molecules on the cell surface which can stimulate immune response against such peptides and protein sequences which contain the same epitopes. This approach is presently aimed towards a potential role in anti-tumor and pathogen vaccine development but may have other possible gene therapy applications.

Natural viral coat proteins which are capable of homogeneous self-assembly into virus-like particles (VLPs) have also been used to package DNA for delivery. The major structural coat protein (VP1) of human polyoma virus can be expressed as a recombinant protein and is able to package plasmid DNA during self-assembly into a VLP. The resulting particles can be subsequently used to transduce various cell lines.

Improvements in DNA vectors have also been made and are likely applicable to many of the non-viral delivery systems. These include the use of supercoiled minicircles (which do not have bacterial origins of replication nor antibiotic resistance genes and thus are potentially safer as they exhibit a high level of biological containment), episomal expression vectors (replicating episomal expression systems where the plasmid amplifies within the nucleus but outside the chromosome and thus avoids genome integration events) and T7 systems (a strictly a cytoplasmic expression vector in which the vector itself expresses phage T7 RNA polymerase and the therapeutic gene is driven from a second T7 promoter, using the polymerase generated by the first promoter). Other, more general improvements to DNA vector technology include use of cis-acting elements to effect high levels of expression, sequences derived from alphoid repeat DNA to supply once-per-cell-cycle replication and nuclear targeting sequences.

In other aspects, the present invention relates to methods for enhancing presentation of an MHC Class II-presented antigenic peptide to a T-lymphocyte. As discussed in U.S. Pat. No. 6,432,409, the MHC Class II-restricted antigenic epitope is appropriately incorporated into the C-terminus of an enhancing hybrid of the present invention, described above. The produced enhancing hybrid is then contacted under physiological conditions to an MHC Class II expressing antigen presenting cell which is in contact with or is then contacted to a I cell which is responsive to the presentation of the antigenic epitope by an MHC Class II molecule of the antigen presenting cell. This method is suitable for use with all antigenic epitopes which conform to the above listed description of an antigenic epitope. Examples of methods to assay such enhancement in vitro are detailed in the Exemplification section below, and in U.S. patents listed in the present disclosure.

In one aspect, the subject invention relates to a method to improve the potency of peptide vaccines containing MHC Class II-presented epitopes of antigens of interest to activate CD4+ immunoregulatory T cells for therapeutic or diagnostic purposes. A wide range of diseases and conditions in humans will benefit from the application of the compounds and methods of this invention to activate CD4+ immunoregulatory T cells. Such CD4+ immunoregulatory T cells can either augment or suppress the immune response to antigens of clinical interest in cancer, infectious disease, allergy, autoimmunity, graft rejection, and other clinical processes.

Antigens of clinical interest in the treatment or modification of various diseases and conditions as presented herein, are recognized by the T cells of the immune system as small peptide fragments, which are presented by Major Histocompatibility Complex (MHC) molecules on the surfaces of antigen presenting cells. MHC Class I molecules present such antigenic peptides to CD8+ cytotoxic or killer T cells. Most cells of the body express cell surface MHC Class I-presented peptides which have been drawn from the repertoire of cellular proteins and bound into the MHC Class I molecules of those cells at the time of their synthesis in the endoplasmic reticulum (the "immunological survey of self"). After viral infection or malignant transformation, the CD8+, cytotoxic T cells recognize the novel or "foreign" endogenously derived peptides in the MHC Class I molecules and kill the presenting cells.

MHC Class II molecules present antigenic peptides to CD4+ T immunoregulatory cells, which regulate the immune response by augmenting or suppressing various effector mechanisms of that response. Such effector mechanisms include, for example, cytotoxic T cell killing of target cells, antibody production by B cells and plasma cells, and dendritic cell activation. Because they regulate directly or indirectly almost all mechanisms in the immune response, CD4+ T immunoregulatory cells have been called the conductors of the immune response orchestra. MHC Class II molecules are expressed on only a subset of the cells of the body, such as macrophages, dendritic cells, and B-cells that have specialized mechanisms to internalize and process antigens of the environment. At the time of synthesis in the endoplasmic reticulum, the antigenic peptide-binding site of MHC Class II molecules is filled with the Ii protein. After transport of that complex to a post-Golgi, antigen charging compartment, the Ii protein is removed by proteases with the concerted insertion of antigenic peptides from foreign proteins, which have been internalized and processed by the antigen processing cells (Cresswell P. Cell. 1996 84:505–7; Hudson A W. Exp Cell Res. 2002 272:1–7; Bryant P W. Adv Immunol. 2002 80:71–114). The Ii-Key segment of the Ii protein interacts with an allosteric site on the MHC Class II molecule to induce lability of the antigenic peptide binding site during release of the Ii protein and binding of a selected antigenic peptide. After dissociation/destruction of the Ii-Key segment, the antigenic peptide is tightly bound in the MHC Class II molecule, for extended expression in the antigenic peptide binding site of those molecules. After transport to the cell surface, such MHC Class II-antigen peptide complexes are recognized by specialized receptors on CD4+T immunoregulatory cells. Activation of those cells regulates the immune response in various ways, which are considered later in terms of individual therapeutic objectives. In brief, subsets of CD4+ cells may be activated along Th1, Th2, or Th2 pathways, which are characterized by differential induction of cytokines and other genes. Those regulatory cells either induce or suppress immune responses in an antigen-specific manner. Furthermore, CD4+ T cells can be induced to be a long-lived population of memory T cells.

The allosteric site at which the Ii-Key segment of the Ii protein interacts is accessible to the environment in cell surface-expressed MHC Class II molecules. This fact is of considerable value clinically because Ii-Key/antigenic epitope hybrids peptides can be administered in a simple manner in a fluid phase, for example subcutaneously, intravenously, intrathecally, intraperitoneally, transmucosally and as an aerosol to the respiratory tract, and can contact the target MHC Class II molecules without traversing membranes or undergoing any special intracellular or metabolic processing or modification. Furthermore, the fact that the allosteric site of MHC Class II molecules is expressed on the surfaces of living, or even paraformaldehyde-fixed antigen presenting cells has facilitated in vitro studies of the mechanism of action of Ii-Key peptides and of Ii-Key/antigenic epitope hybrid peptides, as presented both herein and previously in U.S. Pat. No. 5,559,028 (1996) and U.S. Pat. No. 5,919,639 (1999).

In addition to the favored property of contacting cell surface-expressed with MHC Class II molecules after a simple fluid phase administration, the Ii-Key/antigenic epitope hybrid peptides can also be taken up in an antigen processing and presenting cell, such as a macrophage or dendritic cell, and contacted to MHC Class II molecules in the course of their transversing a post-Golgi, antigen charging compartment. Selective use of either these two, very different pathways for antigen to contact MHC Class II molecules is useful during the treatment of various diseases and conditions as described herein. For example, intravenous administration at a low concentrations over a long period of time, will favor epitope presentation in a manner yielding immunosuppression, which is favored for example in the case of peptide epitopes from antigens related to multiple sclerosis or rheumatoid arthritis. Or, on the other hand, in the case of augmenting the immune response to a subsequently administered DNA vaccine for an antigen relevant to therapy of either a cancer or an infectious disease, administration of an Ii-Key/antigenic epitope incorporating an epitope coded by the DNA vaccine with an adjuvant cytokine or other stimulant promotes development of a Th1-mediated response.

The method of enhancing presentation of an MHC Class II-restricted antigenic epitope to a T lymphocyte finds wide application in the diagnosis and therapy of diseases. T cell responses to diagnostic antigenic epitopes are often measured in the diagnosis of diseases, particularly with respect to etiological infectious agents. The use of enhancing hybrids of the present invention which have such diagnostic antigenic epitopes incorporated will increase substantially the sensitivity of these in vitro diagnostic assays. In the case of infectious diseases and cancer, antigenic epitopes which are identified as pathogen or cancer specific can be incorporated into an enhancing hybrid of the present invention and the hybrid then used to initiate a Th response to a pathogen or cancer specific MHC Class II-presented antigenic epitope. This response leads to activation and expansion of T helper cells which in turn activate or 'license' dendritic cells, to prime an effective MHC Class I restricted cytotoxic T lymphocyte response toward the invading organism. In the case of autoimmune diseases, allergy, and graft rejection, specific antigenic epitopes which trigger the pathogenic immune response are identified and then incorporated into an enhancing hybrid of the present invention. The hybrid is then used to stimulate T cells in a manner leading to a Th2 response which will down regulate T cell responses. In this case, stimulation of a suppressor cell response is used to down regulate a pathogenic immune response. Methods for identifying enhancing hybrids which specifically stimulate a predetermined subset of T lymphocytes are described below. Additional methods and utilities of such hybrids in the therapy of disease are considered below.

In another aspect, the Ii-Key antigenic epitope hybrids increase the repertoire of MHC Class II alleles, and therefore the reaction of individuals in the vaccinated population who can be immunized with any given MHC Class II-presented epitope. Since the potency of an antigenic epitope presented within an Ii-Key/antigenic epitope hybrid is much larger than that of the same epitope presented as a peptide, mammals with low responder MHC Class II alleles for that given epitope may be stimulated to a level equivalent to mammals with high responder MHC Class II alleles. The development of immunoregulatory T cell clones recognizing that epitope will lead to enhanced subsequent presentation of the same epitope from an antigen of interest, for example of a malignant or virus-infected cell. This expansion of the repertoire of MHC Class II alleles promoting a therapeutic response to any one epitope, leads to a greater portion of the population being protected by immunizing with any given epitope. Thus, a "basket of peptides" vaccine, i.e., one containing peptides with various epitopes, is not needed. That is, without the use of the Ii-Key/antigenic epitope hybrid, a much larger number of individual antigenic epitope peptides must be used in a T helper peptide vaccine.

In another aspect, Ii-Key/antigenic epitope hybrids enhance responses to DNA vaccines. Vaccines containing the cDNA sequence for one or more antigens from either a pathogen or a tumor specific or tumor-associated antigen are being tested clinically. However, in many instances, high levels of protective antibodies, or long duration immunological memory, or maximal cytotoxic T cell responses, are not found. This lack of potency has been ascribed to weak helper T cell responses to such immunization. T helper cells can therefore be primed with Ii-Key/antigenic epitope hybrids to MHC Class II-presented epitopes in the cDNA vaccine in a suitable temporal schedule to maximize immunization with the cDNA vaccine.

In another aspect, addition of the Ii-Key-linker to each of a member of a library of peptides, overlapping through the sequence of an antigen of interest, increases the sensitivity of picking up MHC Class II epitopes. Given the increased potency of presentation of epitope in such hybrids, weakly antigenic epitopes, and epitopes with other limitations in inducing a particular pathway of biological response, for example those mediated by IgE, might be better recognized. Furthermore, in the case of combinatorial libraries of peptides synthesized with homology to a given experimental antigenic epitope, or a sequence only partially identified, for example by HLPC separation and tandem mass spectrography, the potency of peptides in such libraries can be enhanced by synthesizing the Ii-Key motif and linker at the N-terminus of such peptides. The fact that the synthesis of such peptides proceeds from the C- to the N-termini is favorable because either, sequentially ava, then K, then M, then R, then L (LRMK in reverse)(SEQ ID NO: 8) can be added, or Ac-LRMK-ava (SEQ ID NO: 9) can be added terminally as a unit.

In another aspect Ii-Key/antigenic epitope technology can be applied in the discovery, validation and use of cryptic antigenic epitopes. Cryptic antigenic epitopes have been defined empirically to be those epitopes, which are recognized upon immunization of a mammal with a peptide from an antigenic protein, but not upon immunization of a genetically identical mammal with the intact antigenic protein. In extensive experimental studies by Sercarz and colleagues, a procedure was established to discover most cryptic epitopes in a given antigenic protein, with respect to a given strain of mice. A library of peptides, for example each 15 amino acids in length with overlapping terminal segment of 6 amino acids, was created through the primary amino acid sequence of an antigen protein of interest, for example hen egg lysozyme. One mouse of a given strain was immunized with lysozyme and the proliferative response of splenic T cells to each of the peptides in the lysozyme library was tested. The epitopes in peptides stimulating the proliferative response were termed dominant epitopes. When additional mice of that strain were immunized with each of the respective peptides of the library of lysozyme peptides, all of the dominant epitopes were found to be immunogenic in isolated peptides, but additional epitopes were also discovered. These additional experiments were termed cryptic epitopes. Sercarz and colleagues demonstrated a series of mechanisms by which cryptic epitopes are not immunogenic when presented within the intact proteins. The clinical value of cryptic epitopes lies in part in the fact that a given individual is very unlikely to have previously recognized such epitope immunologically and therefore has not been tolerized to that epitope. Upon presentation of such cryptic epitopes within Ii-Key hybrids, therefore, a robust immune response can be developed, if the dose, route, schedule and adjuvants are designed toward that end. In the case of cancer, and even in the case of some infectious agents, tolerance can be developed to one or more epitopes, with the end result being that an effective immune response of the host is blocked. Cryptic epitope offer a novel repertoire of antigenic epitopes for such therapeutic purposes. Likewise such epitopes from allergens offer targets to develop therapeutic Th1 response while an IgE-promoting Th2 response had been developed toward dominant epitopes of the allergen. In such cases, Ii-Key/antigenic epitope hybrids containing dominant epitopes might exacerbate the pathological allergic responses.

In another aspect, the Ii-Key/antigenic epitope hybrids are favored in clinical diagnostic or therapeutic immunizations of patient for responses to epitopes in antigen of interest.

That is, immunizing with Ii-Key/antigenic epitope hybrids as opposed to the epitope peptide, is favored because the dose required to obtain a clinically significant result is greatly reduced. Concomitantly the likelihood of a fatal anaphylactic response to the antigen, either in the case of an allergen, or otherwise, is reduced.

Additional assay systems can be used to measure the effect of incorporating an antigenic epitope other than a single MHC Class II epitope into an enhancing hybrid of the present invention. Assays with alternative readouts include, without limitation, measuring efficacy of immunoglobulin production from B cells, measuring efficacy of cytotoxic T cell generation, and the use of native T cells from animals which are outbred, inbred, congenic, transgenic for a T cell receptor or another biologically relevant molecule.

Methods for modulating the immune response of an individual finds application in the therapeutic treatment of an individual with a disease or condition. An antigenic epitope to which an enhanced immune response is considered to be beneficial in treatment of the patient is first selected. In one embodiment, the molecule from which the antigenic epitope is derived plays a role in pathogenesis. Alternatively, the antigenic epitope may be an epitope found on a harmful agent such as a pathogen, or on a pathogen infected cell. The term 'therapeutic treatment' as used herein is intended to include ameliorating the signs or symptoms of disease, or arresting the progression of disease in an individual identified or considered to be suffering from a disease. The term 'prevention' as used herein is intended to include ameliorating the underlying cause to, or associated factor predisposing to, a disease, in an individual who might not have begun to experience recognizable signs or symptoms of a disease.

The disease may be an infectious disease caused or associated with infection by a bacterium, a virus, a parasite, a fungus, a *rickettsia*, or other infectious agent, or combination of such agents. The therapy may be directed against the toxin of a disease or against a receptor for a toxin of a disease. Preferred toxins for epitope derivation include, without limitation, staphylococcal enterotoxins, toxic shock syndrome toxin, retroviral antigens (e.g. antigens derived from human immunodeficiency virus), streptococcal antigens, mycoplasma, mycobacterium, and herpes viruses. Highly preferred toxins are anthrax toxin (lethal factor, edema factor and protective antigen), SEA, SEB, $SE_{1-3}$, SED and SEE.

The disease or condition may be considered to be an autoimmune process, for example rheumatoid arthritis, multiple sclerosis, lupus erythematosus, diabetes mellitus, myasthenia gravis, autoimmune thyroiditis, scleroderma, dermatomyositis, pemphigus, and other similar processes. Examples of such model systems for autoimmune diseases which can be used to evaluate the effects of the compounds and methods of the present invention are systemic lupus erythematosus, myasthenia gravis, rheumatoid arthritis, insulin dependent diabetes mellitus, and experimental allergic encephalomyelitis. The procedures for conducting these experiments are presented in Clark et al., (1994) U.S. Pat. No. 5,284,935, the contents of which are incorporated herein by reference.

The disease or condition may be considered to be an allergic process, for example asthma, hayfever, allergic rhinitis, topical dermatitis, colitis, and other such processes initiated or associated with particular allergens or no defined allergen. Examples of such allergens are plant, animal, bacterial, parasitic allergens and metal-based allergens that cause contact sensitivity. Preferred allergens for use in the present invention are weed, grass, peanut, mite, flea and cat antigens.

Alternatively, the disease or condition may be a proliferative or malignant process, for example cancer, benign prostatic hypertrophy, psoriasis, adenomas or other cellular proliferations of intrinsic origin, or in response to a viral or other infectious, irritative, or environmental process.

The term 'mammal' as used herein is meant to encompass the human species as well as all other mammalian species. The compounds and methods of this invention may be applied in the treatment of diseases and conditions occurring in individuals of all mammalian species. The term 'individual' as used herein refers to one of any mammalian species, including the human species. The diseases and conditions occurring in individuals of the human species, and mentioned herein by way of example, shall include comparable diseases or conditions occurring in another species, whether caused by the same organism or pathogenic process, or by a related organism or pathogenic process, or by unknown or other known, organism and/or pathogenic process. The term 'physician' as used herein also encompasses veterinarians, or any individual participating in the diagnosis and/or treatment of an individual of a mammalian species.

The present invention also provides for the administration of a compound, as a drug, a prodrug of the compound, or a drug-metabolite of the compound, in a suitable pharmaceutical formulation. The terms 'administration of' or 'administering a' compound is understood to mean providing a compound of the invention, as a drug, a prodrug of the compound, or a drug-metabolite of the compound, to an individual in need of treatment or prevention of a disease. Such a drug which contains one or more of the hybrid polypeptides of the present invention, as the principal or member active ingredient, for use in the treatment or prevention of one or more of the above-noted diseases and conditions, can be administered in a wide variety of therapeutic dosage forms in the conventional vehicles for topical, oral, systemic, and parenteral administration. The route and regimen of administration will vary depending upon the disease or condition to be treated, and is to be determined by the skilled practitioner. For example, the compounds can be administered in such oral dosage forms for example as tablets, capsules (each including timed release and sustained release formulations), pills, powders, granules, elixirs, tinctures, solutions, suspensions, syrups and emulsions, or by injection. Likewise, they may also be administered in intravenous (either by bolus or infusion methods), intraperitoneal, subcutaneous, topical with or without occlusion, or intramuscular form. All of these forms are well known to those of ordinary skill in the pharmaceutical arts.

The daily dose of the products may be varied over a range from 0.001 to 1,000 mg per adult per day. For oral administration, the compositions are preferably provided in the form of tables containing from 0.001 to 1,000 mg, preferably 0.001, 0.01, 0.05, 0.1, 0.5, 1.0, 2.5, 10.0, 20.0, 50.0, 100.0 milligrams of active ingredient for the symptomatic adjustment of dosage according to signs and symptoms of the patient in the course of treatment. An effective amount of drug is ordinarily supplied at a dosage level of from about 0.0001 mg/kg to about 50 mg/kg of body weight per day. The range is more particular from about 0.0001 mg/kg to 7 mg/kg of body weight per day.

Advantageously, suitable formulations of the present invention may be administered in a single daily dose, or the total daily dosage may be administered in divided doses for example of two, three, or four times daily. The enhancing hybrid polypeptide of the present invention may be used to prepare a medicament or agent useful for the treatment of the diseases or conditions listed above. Furthermore, compounds of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, or course, be continuous rather than intermittent throughout the dosage regimen.

For treatment and prevention of disease, the hybrid polypeptide of the present invention may be administered in a pharmaceutical composition comprising the active compound in combination with a pharmaceutically acceptable carried adopted for topical administration. Topical pharmaceutical compositions may be, for example, in the form of a solution, cream, ointment, gel, lotion, shampoo, or aerosol formulation adapted for application to the skin. These topical pharmaceutical composition containing the compounds of the present invention ordinarily include about 0.005% to 5% by weight of the active compound in admixture with a pharmaceutically acceptable vehicle.

For the treatment and prevention of disease and conditions, for example listed above, the hybrid polypeptide of the present invention may be used together with other agents known to be useful in treating such diseases and conditions. For combination treatment with more than one active agent, where the active agents can be administered concurrently, the active agents can be administered concurrently, or they can be administered separately at staggered times.

The dosage regimen utilizing the compositions of the present invention is selected in accordance with a variety of factors, including for example type, species, age, weight, sex and medical condition of the patient, the severity of the condition to be treated, and the particular compound thereof employed. A physician of ordinary skill can readily determine and prescribe the effective amount of the drug required to prevent, counter, or arrest the progress of the disease or condition. Optimal precision in achieving concentration of drug with the range that yields efficacy either without toxicity or with acceptable toxicity requires a regimen based on the kinetics of the drug's availability to target sites. This process involves a consideration of the distribution, equilibrium, and elimination of the drug, an is within the ability of the skilled practitioner.

In the methods of the present invention, the compounds herein described in detail can form the active ingredient and are typically administered in admixture with suitable pharmaceutical diluents, excipients or carders (collectively referred to herein as 'carder materials') suitably selected with respect to the intended form of administration, that is, oral tablets, capsules, elixirs, syrups, and the like, and consistent with conventional pharmaceutical practices. For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethyl cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, aga, bentonite, xanthan gum and the like.

The liquid forms may be suitably flavored suspending or dispersing agents such as the synthetic and natural gums, for example, tragacanth, acacia, methyl cellulose and the like. Other dispersing agents which may be employed are glycerin and the like. For parental administration, sterile suspensions an solutions are desired. Isotonic predations which generally contain suitable preservatives are employed when intravenous administration is desired.

Topical preparations containing the active drug component can be admixed with a variety of carrier materials well known in the art, such as, for example, alcohols, aloe vera gel, allatoin, glycerine, vitamins A or E oils, mineral oil, PPG2 myristyl propionate, and the like, to form, for example, alcoholic solutions, topical cleansers, cleansing creams, skin gels, skin lotions, and shampoos in cream or gel formulations.

The hybrid polypeptide of the present invention can also be administered in the form of liposome delivery systems, such as small unilamellar vesicles, large unilameller vesicles and multilamellar vesicles. Liposomes can be formed from a variety of compounds, including for example cholesterol, stearylamine, and various phosphatidylcholines.

The hybrid polypeptide or formulation thereof of the present invention may be coupled to a class of biodegradable polymers useful in achieving controlled release of a drug, for example, polylactic acid, polyepsilon caprolactone, polyhydroxy butyric acid, polyorthoesters, polyacetals, polydihyrdo-pyrans, polycyanoacrylates, and cross-linked or amphipathic block copolymers of hydrogels.

The hybrid polypeptides of the present invention and formulations thereof can be prepared using readily available starting materials, reagents and conventional synthesis procedures. In these reactions, it is also possible to make use of variants which are themselves known to those of ordinary skill in this art, but are not mentioned in greater detail herein.

As an alternative to administering the enhancing hybrid of the present invention directly to an individual to enhance the MHC Class II presentation of an antigenic epitope to T lymphocytes of the individual, a population of antigen presenting cells may be obtained from the individual and treated ex vivo with the enhancing hybrid of the present invention. These cells are treated with the enhancing hybrid under conditions appropriate for binding of the hybrid to an MHC Class II molecule of the antigen presenting cells. Once treated, the antigen presenting cells are administered to the individual under conditions which promote physical contact of the treated cells with T lymphocytes of the individual. As described above, the effect on the immune response, enhancement or suppression, will depend upon which subset of T cells are preferentially stimulated by the enhancing hybrid. Enhancement of the immune response may have a favorable effect upon the cytotoxic response against, for example, either a cancer cell or an infectious organism. Alternately, enhancement of the T suppressor cell response may have the effect of suppressing the immune response to a specific molecule. Such suppression may have a therapeutic effect when utilizing antigenic epitopes from etiological antigens of autoimmune diseases, for example, rheumatoid arthritis, multiple sclerosis, myasthenia gravis, or lupus erythematosus. The methods and procedures for the ex vivo treatment of cells from a patient with the compounds and methods of the present invention may be adapted from the following patents, the contents of which are incorporated herein by reference: Rosenberg (1998) U.S. Pat. No. 5,126, 132; Chada et al., (1997) U.S. Pat. No. 5,693,522; Kriegler et al., (1998) U.S. Pat. No. 5,849,586; Gruber et al., (1999) U.S. Pat. No. 5,856,185; and Kriegler et al., (1999) U.S. Pat. No. 5,874,077.

In another respect, the compounds and methods of the present invention can be used under ex vivo conditions to promote the generation of cytotoxic T lymphocytes, using the compounds and methods described in Celis et al., (1998) U.S. Pat. No. 5,846,827, the contents of which are incorporated herein by reference.

As discussed above, a non-comprehensive discussion of specific examples of epitopes/determinants useful as elements in the enhancing hybrids of the present invention is provided in the Exemplification section. Also found in the corresponding Exemplification section is a discussion of methods for using an enhancing hybrid containing such an element. One skilled in the art, through the application of no more than routine experimentation, can incorporate experimentally-determined or predicted epitopes/determinants into an enhancing hybrid for application to a wide range of disease or conditions.

In another aspect this invention relates to a method to identify and exploit naturally occurring Ii-Key/MHC Class II antigenic epitopes which have in the sequence a primary sequence motif which functions during the processing and binding of such peptides to MHC Class II molecules in the classical exogenous pathway, as does the synthetic Ii-Key/antigenic epitope hybrids.

Given the identification of the presence or absence of such Ii-Key motifs comprising, one can modify the amino acid sequence of the protein in a manner to introduce such a motif when one was not present, or to delete such a motif when one was present. Such modifications are obtained for example trough manipulation of the genes coding of the antigenic protein in a manner to substitute a functionally accepted amino acid in the Ii-Key motif. In some instances a deletion or insertion of amino acids can obtain the same end, for example when the antigenic epitope occurs at or near the N-terminus of the protein. Such modifications to change the immunogenecity of the protein have favorable clinical properties. For example, vaccine promoters can behave increased potency. Certain therapeutic proteins can have decrease immunogenecity.

In another aspect, the present invention relates to methods for selecting biologically active MHC Class II-presented epitopes and altering the immune response to such epitopes in antigenic proteins or polypeptides. Specifically, this disclosure provides method to identify in the amino acid sequence of a protein the presence or absence of a Ii-Key immunoregulatory motif of 5 amino acids preceding an experimentally determined or algorithm-predicted, MHC Class II-presented, antigenic epitope. This immunoregulatory Ii-Key motif enhances charging of the antigenic epitope, which follows it into the antigenic peptide binding site of MHC Class II molecules. Given predictions of antigenic epitopes within a protein, identifying the subset of those epitopes preceded by an Ii-Key motif improves greatly the efficiency of vaccine peptide selection. Also, by modifying the sequence of a protein or polypeptide, for example, either to introduce or to eliminate an Ii-Key motif before selected MHC Class II-presented epitopes, the immunological response to that protein can be altered.

Adverse immunological responses to a therapeutic protein can limit the use of such a protein. Such adverse immunological responses can be lessened either by decreasing immunogenecity of some of the MHC Class II-presented epitopes or by inducing immunosuppression. For either case, insertion or alteration(s) at the location of an Ii-Key motif appropriately spaced before an MHC Class II epitope can achieve that endpoint without alteration of the MHC Class II epitope itself. It may not be possible to alter residues within the MHC Class II-epitope without loss of the biological function of the therapeutic protein. The following procedure is followed in designing sequence modifications in a therapeutic protein of interest to alter its immunogenecity and/or the immune response to that protein.

The sequence of a protein, or a fragment thereof, is established by one of several methods. The protein or fragment thereof can be experimentally sequenced, or the sequence can be deduced from either the sequence of either the gene coding for the protein or a cDNA created from the RNA coding for the protein. Given that primary amino acid sequence, the experimentally determined or algorithm-predicted MHC Class II epitopes are specified. The experimentally determined epitopes are known from prior investigations. The algorithm-predicted epitopes are found by several methods, such as the ProPred MHC Class-II Binding Peptide Prediction Server (Raghava G P. Nat Biotechnol. 1999 17:555–61); Singh, H. Bioinformatics 2001 17:1236–7 (access via: http://www.imtech.res.in/raghava/propred/index.html)). An alternative program is the SYFPEITHI program (Rammensee H G. Immunogenetics 1999 50: 213–219 (access via: http://134.2.96.221/scripts/MHCServer.dll/Ep.html)). These epitopes are also characterized with respect to the MHC Class II alleles, which are either known or predicted to present them to the immune system of humans or an experimental animal such as the mouse. Thus, differing sets of predicted epitopes are obtained, according to the relevant presenting MHC Class II allele. Some epitopes are presented by multiple MHC Class II alleles and are, therefore, preferred.

This disclosure presents a method for the identification of an Ii-Key immunoregulatory motif. Specifically, in the sequence of a protein, the immunoregulatory, Ii-Key motif is a segment of 5 contiguous amino acids containing at least two amino acids of the group comprising Leu, Ile, Val, Phe, and Met, and at least one of the group comprising His, Lys, and Arg, where that contiguous 5 amino acid segment is separated by 5 to 11 amino acids from the N-terminal residue of the MHC Class II-presented epitope.

The subset of such antigenic epitopes with the presence of an appropriately spaced Ii-Key motif lead to vaccine peptides to enhance the potency of the CD4+ T cell immune response. Such epitopes are considered to be more likely to be dominant or biologically active. Peptides with such epitopes are favored as vaccine protect against infectious diseases and cancer, and to immunosuppressive vaccines to allergy. The compositions and methods of the present invention relate to non-naturally occurring proteins or polypeptides which contain: 1) a C-terminal element comprising an MHC Class II-presented epitope; 2) an N-terminal element comprising an Ii-key motif; and 3) an intervening element comprising a sequence from about 4 to about 11 amino acid residues. The use of the term non-naturally occurring is intended to require that the protein or polypeptide is modified. Generally, the modification is by recombinant DNA techniques, and the modification or modifications take place within elements 2) or 3) as defined above. The designations "N- and C-terminal" are meant to refer only to the relationship of these elements in the 3-part segment specifically recited. One of skill in the art will recognize that if such a 3-part segment is located within a protein, it is likely that additional residues will extend in the C-terminal direction from the C-terminal element, and in the N-terminal direction from the N-terminal element. In addition to proteins or polypeptides as described above, the present application is also directed toward expressible nucleic acid sequences which encode such proteins or polypeptides.

In preferred embodiments, the non-naturally occurring protein or polypeptide is a modified form of a naturally occurring protein or polypeptide. Therapeutic proteins represent a particularly important class. Such modified proteins or polypeptides stimulate an immune response which differs from that induced by their non-modified, naturally-occurring counterparts. Such products include therapeutic proteins, such as hormones, cytokines, or other molecules interacting with cell surface receptors. Modifications of an Ii-Key motif can be made to eliminate its function, or a site N-terminal to a putative antigenic epitope can be modified to introduce an Ii-Key motif. Such modifications suppress a deleterious immune response to the therapeutic protein. Such products include the therapeutic protein, and fragments thereof, and genetic constructs leading to their expression.

Modifications most likely not to disturb the biological function of a therapeutic protein to be engineered to alter immunogenecity include the following. Presence is scored of sequences, and even individual amino acid residues, which are known from the crystallographic structure of the protein to be superficially exposed on the protein, and thus more likely to accept a mutation without loss of function. In the case of therapeutic proteins for which the three dimensional structure has not been determined, various methods are applied to predicting acceptance of mutations to engineer an Ii-Key box appropriately spaced from an antigenic epitope. Distances from the N-terminus and from the C-terminus of the protein are determined. Upon modestly denaturing conditions, N-terminal and C-terminal antigenic epitopes can be presented by MHC Class II molecules. Epitopes at the N-terminus of the protein are favored over epitopes at the C-terminus, in part because the to-be-designed Ii-Key box is more distal. Also sequence alterations are more likely to be accepted in a sequence, which is predicted to be on the surface of the protein, preferably in relatively loose configuration. Such segments can be identified in homologous proteins with a relatively higher frequency of naturally occurring mutations. Segments are identified containing residues, which in site-directed mutational studies, have been shown to accept amino acid substitutions. By the preceding and additional methods, one skilled in the art will predict segments of a protein that are more likely to accept without loss of function, amino acid substitutions at residue positions resulting in the creation of Ii-Key box motifs at appropriate N-terminal displacements from the N-terminus of an antigenic epitope. The following peptide sequences are targeted for Ii-Key box manipulations, in rank order: epitopes known to be MHC Class II-presented, epitopes predicted to be MHC Class II-presented by MHC Class II alleles present either in the highest frequency among humans or in the animal strain of experimental interest. Some of these methods are presented in U.S. Pat. No. 5,679,527 (1997), the content of which is incorporated herein by reference.

In addition to the above site-specific engineered replacements, one skilled in the art will use additional combinatorial molecular biological methods to generate mutations within sets of residue positions to create an Ii-Key box motif spaced 4 to 8 amino acids N-terminal to a selected, either known or putative antigenic epitope. Such methods may encompass the preparations of multiple products, which are screened for altered immunogenecity with or without retention of biological activity.

Each experimentally determined or algorithm-predicted epitope in the protein of interest is examined for the presence in its primary sequence of a segment of 5 contiguous amino acids containing at least two amino acids of the group comprising Leu, Ile, Val, Phe, and Met, and at least one of the group comprising His, Lys, and Arg, where that contiguous 5 amino acid segment is separated by 4 to 12 amino acids from the N-terminal residue of a MHC Class II-presented epitope. The subset of all experimentally or algorithm-predicted epitopes meeting these criteria are preferred for developmental work, including for example synthesis of peptide vaccines, chemical modifications of those vaccines for a favorable therapeutic effect, experimental study in animals, and clinical studies. In this disclosure the standard single letter nomenclature of the International Union of Pure and Applied Chemists is used to identify amino acids within the sequence of proteins or peptides.

More preferable is the set of experimentally or algorithm-predicted epitopes with a 4 to 8 amino acids separation from the N-terminal residue of the MHC Class II-presented epitope, of the segment of 5 contiguous amino acids containing at least two amino acids of the group comprising Leu, Ile, Val, Phe, and Met, and at least one of the group comprising His, Lys, and Arg. This set constitutes a subset of the set of experimentally or algorithm-predicted epitopes with a 0 to 12 amino acids separation from the N-terminal residue of the MHC Class II-presented epitope, of the segment of 5 contiguous amino acids containing at least two amino acids of the group comprising Leu, Ile, Val, Phe, and Met, and at least one of the group comprising His, Lys, and Arg. An important utility in this method is the reduction in the number of candidate epitopes subject to study toward therapeutic or diagnostic development objectives. In each of the Exemplification Tables of this disclosure presenting either experimentally determined or algorithm-predicted epitopes, the presence of an Ii-Key box separated by 4–10 amino acids from the N-terminus of the MHC Class II-presented epitope is indicated, with the number of intervening residue positions. Among these, preference is ranked according to the length of the separating interval, with shorter being better, among spacers of 4 or more amino acids.

Peptides which are chosen for synthesis have within the natural primary sequence of the protein, an MHC Class II-presented epitope and a segment of 5 contiguous amino acids containing at least two amino acids of the group comprising Leu, Ile, Val, Phe, and Met, and at least one of the group comprising His, Lys, and Arg, the intervening segment of 0 to 12 amino acids, and the antigenic epitope, comprising a total length of 12 to 34 amino acids. More preferred is a synthetic peptide synthesized according to the primary sequence of the protein, including the segment of 5 contiguous amino acids containing at least two amino acids of the group comprising Leu, Ile, Val, Phe, and Met, and at least one of the group comprising His, Lys, and Arg, the intervening segment of 4 to 11 amino acids, and the antigenic epitope, comprising a total length of 15 to 25 amino acids. The sequence of the synthetic peptide will usually be the natural sequence of a mammalian protein, but also the protein may be a non-natural sequence, such as that generated by methods using a combinatorial library with selections for a useful function. Furthermore, the sequence of the protein may include modifications of the sequence of natural protein, including for example substitution, insertion, or deletion of one or more amino acids, including the use of non-natural amino acids.

The selected peptides, including the segment of 5 contiguous amino acids containing at least two amino acids of the group comprising Leu, Ile, Val, Phe, and Met, and at least one of the group comprising His, Lys, and Arg, the intervening segment of 4 to 8 amino acids, and the antigenic epitope, comprising a total length of 12 to 34 amino acids will be modified to obtain favorable biological and pharmacokinetic properties. These medications are selected from the group consisting of: a) acetylation of the N-terminus, b) amidation of the C-terminus; c) replacement of an amino acid with another natural or synthetic amino acid, d) replacement of an L-amino acid with a D-amino acid, e) inversion of the amino acid sequence and use of D-amino acids in each residue positions, f) modifications to limit proteolysis or clearance (inactivation), and g) modifications to improve solubility, transport and half-life. Methods of chemical modification of therapeutic peptides for favorable therapeutic properties are presented, for example, in U.S. Pat. No. 5,679,527, the disclosure of which is incorporated herein by reference.

The method to design such modifications start with a list of identified epitopes, ranked according to each of several characteristics in order to identify segments of the therapeutic protein, which are more likely to accept without loss of function, amino acid substitutions which create an Ii-Key box motif appropriately spaced from the N-terminus of an antigenic epitope. The characteristics by which the epitopes are ranked include, without limitation, the following. Presence is scored of sequences, and even individual amino acid residues, which are known from the crystallographic structure of the protein to be superficially exposed on the protein, and thus more likely to accept a mutation without loss of function. In the case of therapeutic proteins for which the three dimensional structure has not been determined, various methods are applied to predicting acceptance of mutations to engineer an Ii-Key box appropriately spaced from an antigenic epitope. Distances from the N-terminus and from the C-terminus of the protein are determined. Upon modestly denaturing conditions, N-terminal and C-terminal antigenic epitopes can be presented by MHC Class II molecules. Epitopes at the N-terminus of the protein are favored over epitopes at the C-terminus, in part because the to-be-designed Ii-Key box is more distal. Presence in a sequence motif, which is predicted to be on the surface of the protein, preferably in relatively loose configuration. Segments are identified which in homologous proteins have a relatively higher frequency of naturally occurring mutations. Segments are identified containing residues, which in site-directed mutational studies have been shown to accept amino acid substitutions. By the preceding and additional methods, one skilled in the art will predict segments of a protein which are more likely to accept without loss of function, amino acid substitutions at residue positions which create Ii-Key box motifs at appropriate N-terminal displacements from the N-terminus of an antigenic epitope which is highly ranked according to the following ranking scheme: epitopes known to be MHC Class II-presented, epitopes predicted to be MHC Class II-presented by MHC Class II alleles present either in the highest frequency among humans or in the animal strain of experimental interest. Some of these methods are presented in U.S. Pat. No. 5,679,527 (1997) the disclosures of which are incorporated herein by reference.

The Ii-Key box/spacer identifying algorithm is applied within the amino acid sequence of the protein to examine regions N-terminal to each of the above experimentally determined or predicted MHC Class II-presented epitopes, in a manner to identify three categories: a) presence of an Ii-Key box motif spaced by 4 to 8 amino acids, N-terminal to the antigenic epitope, b) presence of an Ii-Key box motif spaced by 4 to 8 amino acids, N-terminal to the antigenic epitope if one or more amino acids were exchanged for a member of the group Leu, Ile, Val, Phe, Met and/or one or more amino acids were exchanged for a member of the group His, Lys and Arg in the primary sequence.

In addition to the above site-specific engineered replacements, one skilled in the art will use additional combinatorial molecular biological methods to generate mutations within sets of residue positions to create an Ii-Key box motif spaced 4 to 8 amino acids N-terminal to a selected, either known or putative antigenic epitope. Such methods may encompass the preparations of multiple products, which are screened for altered immunogenecity with or without retention of biological activity.

Many uses of Ii-Key antigenic epitope hybrids can be described with respect to individual antigenic proteins. Such uses are presented in the Examples, in varying degrees of detail. The concepts, which are presented in the context of one Example, apply nevertheless in the cases of all Examples when appropriate, even when they are not repeated in the context of each individual Example. While such specific examples well present methods to design and synthesize Ii-Key antigenic epitope hybrids of specific proteins by which such Ii-Key antigenic epitope hybrids can be created and used with respect to other proteins of interest, as the need might arise from to time.

In another aspect, this invention relates to the use of Ii-Key/antigenic epitope hybrids to enhance protective immune responses to a subsequently administered DNA vaccine or against an attenuated infectious pathogen vaccine. Such adjuvant vaccine preparations can be referred to as PreVaccines™. One example is the use of Ii-Key antigenic epitope hybrids in vaccination protocols to protect against variola. Uses in protecting against smallpox virus are considered in relatively greater detail in a corresponding section of the Exemplification section which follows. Considerations detailed herein also serve to model applications directed toward other pathogens. In the case of smallpox vaccination, Ii-Key antigenic epitope hybrids are used to elicit a Th1 response to one or more MHC Class II-presented epitopes of the gp42 extracellular envelope protein coded by the B5R viral gene of vaccinia. Individuals so vaccinated will have an anamnestic response which is more rapid and of higher potency in terms of antibody titers and isotype an affinity maturation, CTL and memory responses to challenge by cDNA vaccines for the B5R gene, by vaccinia, or by variola. In a related application, such PreVaccines™ can be used before vaccination with recombinant vaccinia virus containing either Ii-RGC genes or CIITA plus Ii-RGC genes. The recombinant vaccinia virus containing an Ii-RGC gene, upon infection within a professional antigen presenting cell such as a dendritic cell, will lead to MHC Class II-restricted T helper cell responses in those cells as described. In the case of recombinant vaccinia virus containing both an Ii-RGC gene and a CIITA gene, such a virus upon infecting cells which do not normally express MHC Class II molecules, such as dendritic cells, will express MHC Class II molecules without Ii protein. A wide repertoire of MHC Class II-presented epitopes are thus represented and the response to those epitopes is further enhanced by prior expansion of responses to the MHC Class II epitope in the PreVaccine™. Such a use can be further augmented by prior immunization of mammals with Ii-Key antigenic epitope hybrids in an appropriate dose, vehicle, route and schedule. Ii-Key/antigenic epitope hybrids can thus be used either as a stand-alone protective vaccine or as a PreVaccine™ used in conjunction with vaccines for other viruses and infectious pathogens, for example, without limitation, HIV, *Bacillus anthracis*, EBOLA virus and Marburg virus.

EXEMPLIFICATION

Example 1

Ii-Key/Ara h 1 Antigenic Epitope Hybrids

In one aspect this invention relates to therapeutic modulation of pathological allergic responses of some humans to peanuts and other edible nuts. Such responses include potentially fatal asthmatic or anaphylactic reactions. Good progress has been made in identifying and sequencing the principal protein allergens in peanuts and other nuts mediating these pathological responses. Crossed-radioimmunoelectrophoresis has identified 16 allergenic fractions in raw peanut and sodium dodecylsulfate polyacrylamide gel electrophoresis has revealed 32 protein bands (Barnett D. J Allergy Clin Immunol. 1983 72:61–68). Three major allergens have been identified. Ara h 1 of 64.5 kDa is a member of the vicilin family of seed storage proteins (Burks A W. J Allergy and Clin Immunol. 1991 88:172–9). Ara h 2 of 17.5 kDa is a member of the conglutin family of seed storage proteins (Burks A W. J Allergy and Clin Immunol. 1992 90:962–9). Ara h 3 of 60 kDa, a preproglobulin, is a member of the glycinin-like seed storage proteins (Rabjohn P. J Clin Invest. 1999 103:535–42). For Ara h 1, 23 IgE-recognized epitopes have been mapped, with 4 being dominant. For Ara h 2, 10 IgE-recognized epitopes have been mapped, with 3 being dominant. For Ara h 3, 4 IgE-recognized epitopes have been mapped, with 1 being dominant. For each of these three allergens, the respective cDNAs have been isolated and expressed. The deduced protein sequences are presented below (Tables 1.1, 2.1 and 3.1).

Development of allergy-inducing IgE antibodies is regulated by a subset of CD4+ T cells, the receptors of which recognize antigenic peptides presented by MHC Class II-molecules. The recognition of such epitopes by CD4+ T cells can lead either to a Th1 response, in which the responding T cells are characterized by synthesis of predominantly certain cytokines such as IFN-γ, or to a Th2 response, in which the responding T cells are characterized by synthesis of predominantly other cytokines such as IL-4 and IL-10. In patients with allergen-induced asthma, a Th2 pattern of response enhances synthesis of IgE molecules recognizing many different surface epitopes of the offending allergen(s). Binding of IgE to such allergens activates a cascade of biological mediators resulting in the asthmatic symptoms. The compounds and methods of the invention can be applied to the modification of responses in a Th1 or Th2 pathway-specific manner to obtain clinically desired effects. Such modifications can be illustrated for the control of asthma.

In animal studies of asthmatic allergic responses to protein antigens, it was discovered that substitution of one or more amino acids within the MHC Class II antigenic epitope leads to potential therapeutic agents inducing an altered T cell immune response. Specifically, such altered antigenic peptides modified a predominantly Th2 response, which promotes asthmatic responses, to a predominantly Th1 response (Janssen E. J Immunol. 2000 164:1580–8; Janssen E M. J Immunol. 2000 165:7207–14). Such immunodeviation from a Th2 to a Th1 pattern functionally suppresses the asthmatic response. However replacement of individual amino acids in a MHC Class II-presented epitope of an offending allergen is expected to alter potency of binding of the antigenic peptides in the antigenic peptide binding site as well as the repertoire of T cell receptors responding to the antigenic peptide. Affinity of the antigenic epitope peptide for a patient's MHC Class II alleles can be decreased by such structural manipulations. One significant advantage of the method of this invention is the ability to immunodeviate the pattern of Th subset activation from the Th2 pathway, to the Th1 pathway, without changing the sequence of the antigenic epitope. Since MHC Class II molecules demonstrate allele-specific preferences for some antigenic peptides and not for other antigenic peptides (which might nevertheless be well presented by other MHC Class II alleles), there is no issue of potentially decreased potency of Ii-Key/antigenic epitope hybrids. In fact, given the increase in potency of presentation of epitopes within Ii-Key/antigenic epitope hybrids, one can expect presentation by a wider range of MHC Class II alleles. Another clinically preferred characteristic of the Ii-Key/antigenic epitope hybrids over sequence-modified antigenic epitope peptides is that the dose required to achieve immunodeviation is much less (by a factor of 10 to 100) and therefore potentially fatal anaphylaxis is much less likely to occur.

In another aspect, this invention relates to the design of Ii-Key/Ara h 1 antigenic epitope hybrids. Such Ii-Key/Ara h 1 antigenic epitope hybrids comprise the Ii-Key motif LRMK (SEQ ID NO: 31 and acceptable modifications, linked through a simple, flexible linker to a MHC Class II-presented epitopes of the *Arachis hypogaea* 1 (Ara h 1) major allergen protein found in peanuts and some additional edible nuts. The amino acid sequence of this allergen (626 amino acids) is presented in Table 1.1. The sequence of Ara h 1 was taken from GenBank entry gi/11683gi/allergen Ara h 1. MHC Class II-presented epitopes within this protein sequence were identified with the Singh ProPred MHC Class-II Binding Peptide Prediction Server (Raghava G P. Nat Biotechnol. 1999 17:555–61; Singh, H. Bioinformatics 2001 17:1236–7 (access via: http://www.imtech.res.in/raghava/propred/index.html)). The ProPred program evaluates sequences for presentation by many common MHC Class II alleles. An alternative program is the SYFPEITHI program (Rammensee H G. Immunogenetics 1999 50: 213–219 (access via: http://www.uni-tuebingen.de/uni/kxi/)). Epitopes with highest scores were identified for their presentation by 51 HLA-DR alleles, that cover more than 90% of the MHC Class II alleles. The highest scoring epitopes predicted with the ProPred program are likely to be experimentally antigenic. The peptides listed in Table 1.2 have the highest scoring epitopes, in the ProPred program analysis for Ara h 1. Ii-Key/Ara h 1 hybrids containing some of the predicted MHC Class II-presented Ara h 1 epitopes of Table 1.2 are listed in Table 1.3. Experimentally defined IgE-binding Ara h 1 epitopes which overlap with predicted MHC Class II-presented Ara h 1 epitopes are listed in Table 1.4. Ii-Key/Ara h 1 hybrids containing predicted MHC Class II Ara h 1 epitopes and experimentally determined IgE-binding Ara h 1 epitopes are listed in Table 1.5.

TABLE 1.1

| (SEQ ID NO: 10) Deduced amino acid sequence of Ara h 1. | | | | | |
|---|---|---|---|---|---|
| 1 | mrgrvsplml | llgilvlasv | sathaksspy | qkktenpcaq | rclqscqqep |
| 51 | ddlkqkaces | rctkleydpr | cvydprghtg | ttnqrsppge | rtrgrqpgdy |
| 101 | dddrrqpree | eggrwgpagp | rerereedwr | qpredwrrps | hqqprkirpe |
| 151 | gregeqewgt | pgshvreets | rnnpfyfpsr | rfstrygnqn | grirvlqrfd |
| 201 | qrsrqfqnlq | nhrivqieak | pntlvlpkha | dadnilviqq | ggatvtvang |
| 251 | nnrksfnlde | ghalripsgf | isyilnrhdn | qnlrvakism | pvntpggfed |
| 301 | ffpassrdqs | sylqgfsrnt | leaafnaefn | eirrvlleen | aggeqeergq |
| 351 | rrwstrssen | negvivkvsk | ehveeltkha | ksvskkgsee | egditnpinl |
| 401 | regepdlsnn | fgklfevkpd | kknpqlqdld | mmltcveike | galmlphfns |
| 451 | kamvivvvnk | gtgnlelvav | rkeqqqrgrr | eeeededeee | egsnrevrry |
| 501 | tarlkegdvf | impaahpval | nasselhllg | fginaennhr | iflagdkdnv |
| 551 | idqiekqakd | lafpgsgeqv | ekliknqkes | hfvsarpqsq | sqspsspeke |
| 601 | spekedqeee | ngggkgplls | ilkafn | | |

TABLE 1.2

Predicted MHC Class II-presented epitopes of Ara h 1.

| PEPTIDE NO: | Pos. | Sequence | Score | Ii-Key | SEQ ID NO: |
|---|---|---|---|---|---|
| 1.2.1 | 417 | V K P D K K N P Q | 6.00 | — | 11 |
| 1.2.2 | 193 | I R V L Q R F D Q | 6.00 | — | 12 |
| 1.2.3 | 313 | L Q G F S R N T L | 6.00 | — | 13 |
| 1.2.4 | 453 | M V I V V V N K G | 6.00 | 3 | 14 |
| 1.2.5 | 457 | V V N K G T G N L | 5.20 | — | 15 |
| 1.2.6 | 498 | V R R Y T A R L K | 5.30 | — | 16 |
| 1.2.7 | 209 | L Q N H R I V Q I | 5.30 | 8 | 17 |
| 1.2.8 | 206 | F Q N L Q N H R I | 4.40 | 5 | 18 |
| 1.2.9 | 9 | M L L L G I L V L | 5.30 | 3 | 19 |
| 1.2.10 | 11 | L L G I L V L A S | 5.50 | 4 | 20 |
| 1.2.11 | 1 | M R G R V S P L M | 4.25 | — | 21 |
| 1.2.12 | 15 | L V L A S V S A T | 4.20 | — | 22 |
| 1.2.13 | 429 | L D M M L T C V E | 5.10 | 9 | 23 |
| 1.2.14 | 264 | L R I P S G F I S | 5.00 | 5 | 24 |
| 1.2.15 | 270 | F I S Y I L N R H | 4.48 | —/11 | 25 |
| 1.2.16 | 275 | L N R H D N Q N L | 4.10 | 6 | 26 |
| 1.2.17 | 325 | F N A E F N E I R | 4.30 | — | 27 |
| 1.2.18 | 329 | F N E I R R V L L | 4.60 | — | 28 |
| 1.2.19 | 335 | V L L E E N A G G | 4.20 | — | 29 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. IL-Key is the number of residue positions intervening between an Ii-Key motif and the first residue of the antigenic epitope.

In Table 1.2, PEPTIDES: 1.2.1, 1.2.3, 1.2.6, 1.2.5, and 1.2.18 overlap to some degree with experimentally defined IgE-binding epitopes of Table 1.4. PEPTIDES 1.2.9, 1.2.10, 1.2.11, 1.2.12 are peptides with altered amino acid sequences in a recombinant, mutated Ara h 1 (Burks A W. Eur J. Immunol. 1997 245:334–9). IgE epitopes were defined further in the work of Shin et al. (J Biol. Chem. 1998 273:13753–9).

TABLE 1.3

Ii-Key/Ara h 1 hybrids containing some of the predicted MHC Class II-presented Ara h 1 epitopes of Table 1.2.

| PEPTIDE | Pos. | Sequence | SEQ ID NO: |
|---|---|---|---|
| 1.3.1 | 192 | Ac-LRMK-ava-IRVLQRFDQ-$NH_2$ | 30 |
| 1.3.2 | 1 | Ac-LRMK-ava-MRGRVSPLM-$NH_2$ | 31 |
| 1.3.3 | 1/8/10/14 | Ac-LRMK-ava-MRGRVSPLML LLGILVLASV SAT-$NH_2$ | 32 |
| 1.3.4 | 205 | Ac-LRMK-ava-FQNLQNHRI-$NH_2$ | 33 |
| 1.3.5 | 205/208 | Ac-LRMK-ava-FQNLQNHRIVQI-$NH_2$ | 34 |
| 1.3.6 | 428 | Ac-LRMK-ava-LDMMLTCVE-$NH_2$ | 35 |

TABLE 1.3-continued

Ii-Key/Ara h 1 hybrids containing some of the predicted MHC Class II-presented Ara h 1 epitopes of Table 1.2.

| PEPTIDE | Pos. | Sequence | SEQ ID NO: |
|---|---|---|---|
| 1.3.7 | 263 | Ac-LRMK-ava-LRIPSGFIS-$NH_2$ | 36 |
| 1.3.8 | 263/269/274 | Ac-LRMK-ava-LRIPSGFISYILNRHDNQNL-$NH_2$ | 37 |

Pos. is the residue position in the primary sequence of the first amino acid in the antigenic epitope. Sequence is the amino acid sequence of a hybrid peptide containing a MHC Class II epitope of Table 1.2. Ii-Key is the number of residue positions intervening between an Ii-Key motif and the first residue of the antigenic epitope.

The activity of additional Ii-Key/Ara h antigenic epitope hybrids are tested with one residue of ä-aminovaleric acid as a spacer because, in previous studies of a series of hybrids with systematic variation of spacer structures, the hybrid with one ava residue was no less active than any hybrid with a more complex spacer sequence. In the Ara h hybrids, the Ii-Key-spacer (LRMK-ava) (SEQ ID NO: 9) sequence was linked to the first amino acid of the ProPred-identified peptide, which amino acid is thought to fit into pocket 1 of the antigenic peptide-binding site of the MHC Class II molecules.

The peptides of Table 1.3 are characterized as follows. PEPTIDE 1.3.1 contains the ProPred-predicted MHC Class II-presented epitope PEPTIDE 1.2.2. PEPTIDE 1.3.2 is a composite of the first two MHC Class II-presented epitopes (PEPTIDE 1.2.9; PEPTIDE 1.2.11), overlapping by two amino acids. PEPTIDE 1.3.3 is a composite of the first four MHC Class II-presented epitopes (PEPTIDE 1.2.11, PEPTIDE 1.2.9, PEPTIDE 1.2.10, PEPTIDE 1.2.12). PEPTIDES 1.3.2 and 1.3.3 are peptides with altered amino acid sequences in the recombinant, mutated Ara h 1 (Burks A W. Eur J. Immunol. 1997 245:334–9). PEPTIDE 1.3.4 contains the ProPred-predicted MHC Class II-presented epitopes PEPTIDE 1.2.8. PEPTIDE 1.3.5 is the composite of two MHC Class II-predicted epitopes (PEPTIDE 1.2.7 and PEPTIDE 1.2.8), overlapping by six amino acids. PEPTIDE 1.3.6 contains the ProPred-predicted MHC Class II-presented epitope PEPTIDE 1.2.13. PEPTIDE 1.3.7 contains the ProPred-predicted MHC Class II-presented epitope PEPTIDE 1.2.14. PEPTIDE 1.3.8 is the composite of three MHC Class II-predicted epitopes (PEPTIDE 1.2.14 PEPTIDE 1.2.15 and PEPTIDE 1.2.16), overlapping by three and four amino acids, respectively.

TABLE 1.4

Experimentally defined IgE-binding Ara h 1 epitopes which overlap with predicted MHC Class II-presented Ara h 1 epitopes.

| PEPTIDE | Pos. | Sequence | SEQ ID NO: |
|---|---|---|---|
| 1.4.1 | 409 | NNFGKLFEVK | 38 |
| 1.4.2 | 311 | SYLQEFSRNT | 39 |
| 1.4.3 | 498 | RRYTARLKEG | 40 |

TABLE 1.4-continued

Experimentally defined IgE-binding Ara h 1 epitopes which overlap with predicted MHC Class II-presented Ara h 1 epitopes.

| PEPTIDE | Pos. | Sequence | SEQ ID NO: |
|---|---|---|---|
| 1.4.4 | 325 | FNAEFNEIRR | 41 |
| 1.4.5 | 461 | GTGNLELVAV | 42 |

Pos. is the residue position in the primary sequence of the first amino acid in the antigenic epitope. Sequence is the amino acid sequence of the predicted MHC Class II-presented epitope. Ii-Key is the number of residue positions intervening between an Ii-Key motif and the first residue of the antigenic epitope.

TABLE 1.5

Ii-Key/Ara h 1 hybrids containing predicted MHC Class II Ara h 1 epitopes and experimentally determined IgE-binding Ara h 1 epitopes.

| PEPTIDE | Pos. | Sequence | SEQ ID NO: |
|---|---|---|---|
| 1.5.1 | 416 | Ac-LRMK-ava-NNFGKLFEVKPDKKNPQ-$NH_2$ | 43 |
| 1.5.2 | 312 | Ac-LRMK-ava-LQGFSRNTL-$NH_2$ | 44 |
| 1.5.3 | 496 | Ac-LRMK-ava-VRRYTARLK-$NH_2$ | 45 |
| 1.5.4 | 452 | Ac-LRMK-ava-MVIVVVNKG-$NH_2$ | 46 |
| 1.5.5 | 456 | Ac-LRMK-ava-VVNKGTGNL-$NH_2$ | 47 |
| 1.5.6 | 452 | Ac-LRMK-ava-MVIVVVNKGTGNLELVAV-$NH_2$ | 48 |
| 1.5.7 | 324 | Ac-LRMK-ava-FNAEFNEIR-$NH_2$ | 49 |
| 1.5.8 | 328 | Ac-LRMK-ava-FNEIRRVLL-$NH_2$ | 50 |
| 1.5.9 | 334 | Ac-LRMK-ava-VLLEENAGG-$NH_2$ | 51 |
| 1.5.10 | 324/328/334 | Ac-LRMK-ava-FNAEFNEIRRVLLEENAGG-$NH_2$ | 52 |

Pos. is the residue position in the primary sequence of the first amino acid in the antigenic epitope. Sequence is the amino acid sequence of the proposed hybrid containing a predicted MHC Class II-presented epitope of Table 1.2 and an IgE binding epitope of Table 1.4. Ii-Key is the number of residue positions intervening between an Ii-Key motif and the first residue of the antigenic epitope.

The PEPTIDES of Table 1.5 are characterized as follows. PEPTIDES 1.5.1, 1.5.6, and 1.5.10 include residues of an experimentally defined, IgE-binding epitope. PEPTIDES 1.5.1, 1.5.2, 1.5.4, 1.5.6, 1.5.9, and 1.5.10 have residues of a ProPred-predicted MHC Class II-presented epitopes. PEPTIDES 1.5.2, 1.5.3, 1.5.4, 1.5.5, 1.5.6, 1.5.7, 1.5.8 and 1.5.10 share amino acids between overlapping IgE binding and MHC Class II-presented epitopes. PEPTIDES 1.5.4, 1.5.5, 1.5.6, 1.5.8, 1.5.9, and 1.5.10 share amino acids between overlapping MHC Class II-presented epitopes.

The peptides of Table 1.5 are characterized as follows. PEPTIDE 1.5.1 is the composite of MHC Class II-presented epitope with the highest ProPred predictive binding score (PEPTIDE 1.2.1) and IgE binding epitope (PEPTIDE 1.4.1), overlapping by 2 amino acids. PEPTIDE 1.5.2 is the composite of MHC Class II-presented epitope SEQ ID NO 44 and IgE binding epitope PEPTIDE 1.4.2, overlapping by 8 amino acids. PEPTIDE 1.5.3 is the composite of MHC Class II-presented epitope PEPTIDE 1.2.6 and IgE binding epitope PEPTIDE 1.4.3, overlapping by 8 amino acids. PEPTIDE 1.5.4 contains MHC Class II-predicted epitope PEPTIDE 1.2.4 and an IgE binding epitope PEPTIDE 1.4.5, overlapping by 1 amino acid. PEPTIDE 1.5.5 contains MHC Class II-predicted epitope PEPTIDE 1.5 and an IgE binding epitope PEPTIDE 1.4.5, overlapping by 5 amino acids. PEPTIDE 1.5.6 is the composite of the two MHC Class II-predicted epitopes, PEPTIDE 1.2.4 and PEPTIDE 1.2.5, overlapping by 5 amino acids. Additionally, there is a 5 amino acids overlap with IgE binding epitope (PEPTIDE 1.4.5). PEPTIDE 1.5.7 contains MHC Class II-predicted epitope PEPTIDE 1.2.17 and an IgE binding epitope PEPTIDE 1.4.4, overlapping by 9 amino acids. PEPTIDE 1.5.8 contains MHC Class II-predicted epitope PEPTIDE 1.18 and an IgE binding epitope PEPTIDE 1.4.4, overlapping by 6 amino acids. PEPTIDE 1.5.9 contains MHC Class II-predicted epitope PEPTIDE 1.2.19. PEPTIDE 1.5.10 is the composite of the three MHC Class II-predicted epitopes PEPTIDES 1.2.17, 1.2.18, and 1.2.19 and IgE binding epitope PEPTIDE 3.1.5. PEPTIDE 1.5.5 is the composite of three MHC Class II-predicted epitopes (PEPTIDES 1.2.17, 1.2.18 and 1.2.19), overlapping by 5 and 3 amino acids, respectively. Additionally, there is a 9 amino acid overlap with IgE binding epitope (PEPTIDE 1.4.4).

Example 2

Ii-Key/Ara h 2 Peanut Antigenic Epitope Hybrids

In another aspect, this invention relates to the design of Ii-Key/Ara h 2 antigenic epitope hybrids. Sampson, WO 0052154, a series of Ara h 2 MHC Class II-presented epitopes, which had been experimentally identified by Burks A W. (J Allergy Clin Immunol. 1992 90:962–7). Ara h 2-specific T cell lines were established from the peripheral blood of 12 atopic and 4 nonatopic individuals. All of the T cell lines were predominantly CD 4+T cells. Reactivity of each of these T cell line s was tested against individual peptides from a library of overlapping Ara h 2 peptides. Four immunodominant T cell epitopes were identified for Ara h 2: epitope 1 (amino acids 18–28), epitope 2 (amino acids 45–55), epitope 3 (amino acids 95–108), and epitope 4 (amino acids 134–144). Epitopes 1, 2, and 4 have overlapping sequences with IgE antibody-recognized epitopes while epitope 3 does not overlap IgE binding epitopes. Bannon and colleagues suggested that such sequences provide for the possibility for the development of a non-anaphylactic, T cell-directed immunotherapeutic (Bannon G A. Int Arch Allergy Immunol. 2001 124:70–72). The sequence of Ara h 2 in Table 2.1 was taken from GenBank gi/15418705/allergen II [*Arachis hypogaea*]. Experimentally defined MHC Class II-presented Ara h 2 epitopes are listed in Table 2.2. Ii-Key/Ara h 2 hybrids containing some of the experimentally defined MHC Class II-presented Ara h 2 epitopes of Table 2.2 are listed in Table 2.3. Predicted MHC Class II epitopes of Ara h 2 are listed in Table 2.4. Ii-Key/Ara h 2 hybrids containing some of the predicted MHC Class II-presented Ara h 2 epitopes of Table 2.4 are listed in Table 2.5. Experimentally defined IgE-binding Ara h 2 epitopes, which overlap with predicted MHC Class II-presented Ara h 2 epitopes from Table 2.4 are listed in Table 2.6. Hybrids containing predicted MHC Class II Ara h 2 epitopes and overlapping experimentally determined IgE-binding Ara h 2 epitopes are listed in Table 2.7.

TABLE 2.1

| Deduced amino acid sequence of Ara h 2. (SEQ ID NO:53) | |
|---|---|
| 1 | makltilval alfllaahas arqqwelqgd rrcqsqlera nlrpceqhlm |
| 51 | qkiqrdedsy erdpyspsqd pyspspydrr gagssqhqer ccnelnefen |
| 101 | nqrcmcealq qimenqsdrl qgrqqeqqfk relrnlpqqc glrapqrcdl |
| 151 | dvesgg |

TABLE 2.2

Experimentally defined MHC Class II-presented Ara h 2 epitopes.

| PEPTIDE | Pos. | Sequence | Ii-Key | SEQ ID NO: |
|---|---|---|---|---|
| 2.2.1 | 22 | RQQWE LQGDRRCQSQ | 3 | 54 |
| 2.2.2 | 42 | LRPCEQHLMQKIQRDEDSYE | — | 55 |
| 2.2.3 | 7 | HQERCCNELN | — | 56 |
| 2.2.4 | 102 | QRCMCEALQQ | — | 57 |
| 2.2.5 | 137 | PQQCGLRAPQ | — | 58 |

Pos. is the residue position in the primary sequence of the first amino acid in the antigenic epitope. Sequence is the amino acid sequence of an experimentally determined MHC Class II-presented epitope. Ii-Key is the number of residue positions intervening between an Ii-Key motif and the first residue of the antigenic epitope.

The PEPTIDES of Table 2.2 are characterized as follows. PEPTIDES 2.2.1, 2.2.2, 2.2.4, and 2.2.5 are ProPred-predicted MHC Class II-presented sequences. PEPTIDE 2.2.1 contains an IgE binding epitopes. PEPTIDES 2.2.1 and 2.2.2 have overlapping amino acids of the IgE binding epitope and MHC Class II-presented epitope. Pos. is the residue number in the primary amino acid sequence of the first amino acid of the epitope. Many of the experimentally predicted epitopes are also predicted with the ProPred algorithm, either entirely or partially.

TABLE 2.3

| Ii-Key/Ara h 2 hybrids containing some of the experimentally defined MHC Class IT-presented Ara h 2 epitopes of Table 2.2. | | | |
|---|---|---|---|
| PEPTIDE | Pos. | Sequence | SEQ ID NO: |
| 2.3.1 | 19 | Ac-LRMK-ava-RQQWE LQGDRRCQSQ-$NH_2$ | 59 |
| 2.3.2 | 39 | Ac-LRMK-ava-LRPCEQHLMQKIQRDEDSYE-$NH_2$ | 60 |
| 2.3.3 | 84 | Ac-LRMK-ava-HQERCCNELN-$NH_2$ | 61 |
| 2.3.4 | 99 | Ac-LRMK-ava-QRCMCEALQQ-$NH_2$ | 62 |
| 2.3.5 | 135 | Ac-LRMK-ava-PQQCGLRAPQ-$NH_2$ | 63 |

Pos. is the residue position in the primary sequence of the first amino acid in the antigenic epitope. Sequence is the amino acid sequence of a hybrid peptide containing a MHC Class II epitope of Table 2.2. Score is the score reported by the ProPred program, for the relative likelihood of being presented by many common HLA-DR alleles. Ii-Key is the number of residue positions intervening between an Ii-Key motif and the first residue of the antigenic epitope.

The PEPTIDES of Table 2.3 are characterized as follows. PEPTIDE 2.3.1 contains an experimentally defined, IgE-binding epitope. PEPTIDES 2.3.1 and 2.3.2 share amino acids between overlapping IgE binding and MHC Class II-presented epitopes. PEPTIDES 2.3.2 and 2.3.3 are peptides with altered amino acid sequences in the modified Ara h 1 of Burks and colleagues (Burks A W. Eur J. Immunol. 1997 245:334–9). Pos. is the residue number in the primary amino acid sequence of the first amino acid of the epitope.

TABLE 2.4

| Predicted MHC Class II epitopes of Ara h 2. | | | | | |
|---|---|---|---|---|---|
| PEPTIDE | Pos. | Sequence | Score | Ii-key | SEQ ID NO: |
| 2.4.1 | 5 | I L V A L A L F L | 6.10 | — | 64 |
| 2.4.2 | 26 | L Q G D R R C Q S | 5.80 | 8 | 65 |
| 2.4.3 | 3 | L T I L V A L A L | 5.30 | — | 66 |
| 2.4.4 | 49 | L M Q K I Q R D E | 4.10 | — | 67 |
| 2.4.5 | 12 | L F L L A A H A S | 3.30 | 4 | 68 |
| 2.4.6 | 7 | L V A L A L F L L | 4.70 | — | 69 |
| 2.4.7 | 42 | L R P C E Q H L M | 3.60 | — | 70 |
| 2.4.8 | 10 | L A L F L L A A H | 3.30 | 2 | 71 |
| 2.4.9 | 133 | L R N L P Q Q C G | 2.70 | — | 72 |
| 2.4.10 | 37 | L E R A N L R P C | 2.20 | — | 73 |
| 2.4.11 | 13 | F L L A A H A S A | 1.90 | 5 | 74 |
| 2.4.12 | 77 | Y D R R G A G S S | 1.90 | — | 75 |
| 2.4.13 | 98 | F E N N Q R C M C | 1.70 | — | 76 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

The PEPTIDES of Table 2.4 are characterized as follows. PEPTIDES 2.4.1, 2.4.5, 2.4.6, 2.4.8, and 2.4.11 are peptides not preserved in an Ara h 2 modified to decrease allergic IgE binding. In PEPTIDE 2.4.4 R54 is replaced by A. In PEPTIDE 2.4.7 P43 and Q46 are each replaced by A. PEPTIDES 2.4.2, 2.4.4, 2.4.9, 2.4.10, and 2.4.13 are experimentally defined T cell epitopes. PEPTIDES 2.4.2, 2.4.4, 2.4.7, 2.4.10, and 2.4.11 have amino acids of an IgE binding epitope.

TABLE 2.5

| Ii-Key/Ara h 2 hybrids containing some of the predicted MHC Class II-presented Ara h 2 epitopes of Table 2.4. | | | |
|---|---|---|---|
| PEPTIDE | Pos. | Sequence | SEQ ID NO: |
| 2.5.1 | 5 | Ac-LRMK-ava-ILVALALFL-$NH_2$ | 77 |
| 2.5.2 | 3 | Ac-LRMK-ava-LTILVALAL-$NH_2$ | 78 |
| 2.5.3 | 6 | Ac-LRMK-ava-LVALALFLL-$NH_2$ | 79 |
| 2.5.4 | 3/5/6 | Ac-LRMK-ava-LTILVALALFLL-$NH_2$ | 80 |
| 2.5.5 | 132 | Ac-LRMK-ava-LRNLPQQCG-$NH_2$ | 81 |
| 2.5.6 | 76 | Ac-LRMK-ava-YDRRGAGSS-$NH_2$ | 82 |
| 2.5.7 | 97 | Ac-LRMK-ava-FENNQRCMC-$NH_2$ | 83 |

Pos. is the residue position in the primary sequence of the first amino acid in the antigenic epitope. Sequence is the amino acid sequence of a hybrid peptide containing a MHC Class II epitope of Table 2.4. Ii-Key is the number of residue positions intervening between an Ii-Key motif and the first residue of the antigenic epitope.

The PEPTIDES of Table 2.5 are characterized as follows. PEPTIDES 2.5.1, 2.5.2, 2.5.3, 2.5.4 are peptides not preserved in the modified Ara h 2. PEPTIDES 2.5.5 and 2.5.7 are experimentally defined CD4+ T cell epitopes.

In another aspect, this invention provides for the immunodeviation of an allergic patient's antibody response from an IgE pattern to an IgG or IgG subtype pattern. The decrease synthesis of IgE antibodies to the allergen and/or the synthesis of IgG antibodies, which block the binding of IgE antibodies, has a desired therapeutic effect. To this end MHC Class II epitopes of the allergen are joined with an IgE binding peptide sequence in an Ii-Key/MHC Class II epitope/IgE epitope hybrid peptide. The sequences so combined may be taken from different segments of the primary amino acid sequence of the allergen. For example, a MHC Class II epitope with a high ProPred score can be coupled to a peptide from an IgE-recognized site on the allergen. Preferably, however, those two respective MHC Class II-presented and IgE-recognized sites overlap in the primary sequence of the allergen. Such hybrids combining MHC Class II-presented Ara h2 2 epitopes from Table 2.4 and experimentally determined IgE binding epitopes of Table 2.6 are presented in Table 2.7.

TABLE 2.6

Experimentally defined IgE-binding Ara h 2 epitopes, which overlap with predicted MHC Class II-presented Ara h 2 epitopes from Table 2.4.

| PEPTIDE | Pos. | SEQUENCE | Ii-Key | SEQ ID NO: |
|---|---|---|---|---|
| 2.6.1 | 18 | HASARQQWEL | 10 | 84 |
| 2.6.2 | 24 | QWELQGDRRC | 5 | 85 |
| 2.6.3 | 30 | DRRCQSQLER | 11 | 86 |
| 2.6.4 | 42 | LRPCEQHLMO | — | 87 |
| 2.6.5 | 52 | KIQRDEDSYE | — | 88 |
| 2.6.6 | 130 | KRELRNLPQQ | — | 89 |

Pos. is the residue position in the primary sequence of the first amino acid in the antigenic epitope. Sequence is the amino acid sequence of an experimentally determined IgE binding epitope. Ii-Key is the number of residue positions intervening between an Ii-Key motif and the first residue of the antigenic epitope.

TABLE 2.7

Hybrids containing predicted MHC Class II Ara h 2 epitopes and overlapping experimentally determined IgE-binding Ara h 2 epitopes.

| PEPTIDE | Pos. | Sequence | SEQ ID NO: |
|---|---|---|---|
| 2.7.1 | 26 | Ac-LRMK-ava-LQGDRRCQS-$NH_2$ | 90 |
| 2.7.2 | 48 | Ac-LRMK-ava-LMQKIQRDE-$NH_2$ | 91 |
| 2.7.3 | 41 | Ac-LRMK-ava-LRPCEQHLM-$NH_2$ | 92 |
| 2.7.4 | 41/48 | Ac-LRMK-ava-LRPCEQHLMOKIQRDE-$NH_2$ | 93 |
| 2.7.5 | 36 | Ac-LRMK-ava-LERANLRPCEQHLMO-$NH_2$ | 94 |
| 2.7.6 | 12 | Ac-LRMK-ava-FLLAAHASARQQWEL-$NH_2$ | 95 |

Pos. is the residue position in the primary sequence of the first amino acid in the antigenic epitope. Sequence is the amino acid sequence of a hybrid peptide containing a MHC Class II epitope of Table 2.4 and an IgE binding epitope of Table 2.6. Ii-Key is the number of residue positions intervening between an Ii-Key motif and the first residue of the antigenic epitope.

The PEPTIDES of Table 2.7 are characterized as follows. PEPTIDE 2.7.1 contains predicted and experimentally defined MHC Class II epitope PEPTIDE 7.2, which coincides with IgE binding epitope PEPTIDES 2.6.2 and 2.6.3. PEPTIDE 2.7.2 contains predicted and experimentally defined MHC Class II epitope PEPTIDE 7.4, which coincides with IgE binding epitope PEPTIDES 2.6.4 and 2.6.5. PEPTIDE 2.7.3 contains predicted MHC Class II epitope PEPTIDE 7.7, which coincides with IgE binding epitope PEPTIDE 2.6.4. PEPTIDE 2.7.4 contains MHC Class II epitopes PEPTIDE 7.4 and 7.7, and IgE binding epitopes PEPTIDE 2.6.4 and 2.6.5. PEPTIDE 2.7.5 contains MHC Class II epitope PEPTIDE 7.10 overlapping with IgE binding epitope PEPTIDE 2.6.4. PEPTIDE 2.7.6 contains MHC Class II epitope PEPTIDE 7.11, overlapping with IgE binding epitope PEPTIDE 2.6.1.

Example 3

Ii-Key/Ara h 3 Peanut Antigenic Epitope Hybrids

In another aspect, this invention relates to the design of Ii-Key/Ara h 3 antigenic epitope hybrids. Rabjohn et al. reported the molecular cloning and T cell epitope analysis of the peanut allergen Ara h3 (J Clin Invest. 1999 103:535–42). The sequence of Ara h 3 in Table 3.1 was taken from GenBank gi/3703107/glycin. Predicted MHC Class II epitopes of Ara h 3 are listed in Table 3.2. Ii-Key/Ara h 3 hybrids containing some of the MHC Class II-presented epitopes of Table 3.2 are listed in Table 3.3. Experimentally defined IgE-binding Ara h 3 epitope, overlapping with a predicted MHC Class II-presented Ara h 3 epitope are listed in Table 3.4. Hybrids containing predicted MHC Class II Ara h 3 epitopes overlapping experimentally defined IgE-binding epitopes Table 3.5.

TABLE 3.1

(SEQ ID NO: 96)
Deduced amino acid sequence of Ara h 3.

| | | | | | |
|---|---|---|---|---|---|
| 1 | rqqpeenacq | fqrlnaqrpd | nrieseggyi | etwnpnnqef | ecagvalsrl |
| 51 | vlrrnalrrp | fysnapqeif | igggrgyfgl | ifpgcprhye | ephtggrrsq |
| 101 | sqrpprrlqg | edqsqqqrds | hqkvhrfdeg | dliavptgva | fwlyndhdtd |
| 151 | vvavsltdtn | nndnqldqfp | rrfnlagnte | qeflryqqqs | rqsrrrslpy |
| 201 | spyspqsqpr | qeerefsprg | qhsrreragq | eeeneggnif | sgftpefleq |
| 251 | afqvddrqiv | qnlrgetses | eegaivtvrg | glrilspdrk | rradeeeeyd |
| 301 | edeyeydeed | rrrgrgsrgr | gngieetict | asakknigrn | rspdiynpqa |
| 351 | gslktandln | llilrwlgps | aeygnlyrna | lfvahyntna | hsiiyrlrgr |
| 401 | ahvqvvdsng | nrvydeelqe | ghvlvvpqnf | avagksqsen | feyvafktds |

TABLE 3.1-continued

| (SEQ ID NO: 96) Deduced amino acid sequence of Ara h 3. |
|---|
| 451 rpsianlage nsvidnlpee vvansyglqr eqarqlknnn pfkffvppsq |
| 501 qsprava |

TABLE 3.2

Predicted MHC Class II epitopes of Ara h 3.

| PEPTIDE | Pos. | Sequence | Score | Ii-Key | SEQ ID NO: |
|---|---|---|---|---|---|
| 3.2.1 | 395 | Y R L R G R A H V | 6.10 | — | 97 |
| 3.2.2 | 393 | I I Y R L R G R A | 4.70 | 6 | 98 |
| 3.2.3 | 446 | F K T D S R P S I | 5.70 | — | 99 |
| 3.2.4 | 278 | V R G G L R I L S | 5.40 | — | 100 |
| 3.2.5 | 274 | I V T V R G G L R | 5.00 | 10 | 101 |
| 3.2.6 | 282 | L R I L S P D R K | 4.70 | — | 102 |
| 3.2.7 | 252 | F Q V D D R Q I V | 5.20 | — | 103 |
| 3.2.8 | 364 | L R W L G P S A E | 5.00 | — | 104 |
| 3.2.9 | 362 | L I L R W L G P S | 4.80 | — | 105 |
| 3.2.10 | 173 | F N L A G N T E Q | 4.80 | — | 106 |
| 3.2.11 | 424 | L V V P Q N F A V | 4.70 | — | 107 |
| 3.2.12 | 403 | V Q V V D S N G N | 4.50 | 4 | 108 |
| 3.2.13 | 405 | V V D S N G N R V | 4.10 | 6 | 109 |
| 3.2.14 | 382 | F V A H Y N T N A | 4.40 | — | 110 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 3.3

Ii-Key/Ara h 3 hybrids containing some of the MHC Class II-presented epitopes of Table 3.2.

| PEPTIDE | Pos. | Sequence | SEQ ID NO: |
|---|---|---|---|
| 3.3.1 | 393 | Ac-LRMK-ava-IIYRLRGRA-$NH_2$ | 111 |
| 3.3.2 | 395 | Ac-LRMK-ava-YRLRGRAHV-$NH_2$ | 112 |
| 3.3.3 | 393/395 | Ac-LRMK-ava-IIYRLRGRAHV-$NH_2$ | 113 |
| 3.3.4 | 446 | Ac-LRMK-ava-FKTDSRPSI-$NH_2$ | 114 |
| 3.3.5 | 362 | Ac-LRMK-ava-FKTDSRPSI-$NH_2$ | 115 |
| 3.3.6 | 364 | Ac-LRMK-ava-LRWLGPSAE-$NH_2$ | 116 |

TABLE 3.3-continued

Ii-Key/Ara h 3 hybrids containing some of the MHC Class II-presented epitopes of Table 3.2.

| PEPTIDE | Pos. | Sequence | SEQ ID NO: |
|---|---|---|---|
| 3.3.7 | 362/364 | Ac-LRMK-ava-LILRWLGPSAE-$NH_2$ | 117 |
| 3.3.8 | 252 | Ac-LRMK-ava-FQVDDRQIV-$NH_2$ | 118 |
| 3.3.9 | 173 | Ac-LRMK-ava-FNLAGNTEQ-$NH_2$ | 119 |
| 3.3.10 | 424 | Ac-LRMK-ava-LVVPQNFAV-$NH_2$ | 120 |
| 3.3.11 | 403 | Ac-LRMK-ava-VQVVDSNGN-$NH_2$ | 121 |
| 3.3.12 | 405 | Ac-LRMK-ava-VVDSNGNRV-$NH_2$ | 122 |
| 3.3.13 | 403/405 | Ac-LRMK-ava-VQVVDSNGNRV-$NH_2$ | 123 |
| 3.3.14 | 382 | Ac-LRMK-ava-FVAHYNTNA-$NH_2$ | 124 |

Pos. is the residue position in the primary sequence of the first amino acid in the antigenic epitope. Sequence is the amino acid sequence of a hybrid peptide containing a MHC Class II epitope of Table 3.2.

PEPTIDE 3.3.1 contains the ProPred-predicted MHC Class II-presented epitope PEPTIDE 3.2.2. PEPTIDE 3.3.2 contains the ProPred-predicted MHC Class II-presented epitope PEPTIDE 3.2.1. PEPTIDE 3.3.3 is a composite of two ProPred-predicted MHC Class II-presented epitopes (PEPTIDES 3.2.1 and 3.2.2), overlapping by 7 amino acids. PEPTIDE 3.3.4 contains the ProPred-predicted MHC Class II-presented epitope PEPTIDE 3.2.3. PEPTIDE 3.3.5 contains the ProPred-predicted MHC Class II-presented epitope PEPTIDE 3.3.6. PEPTIDE 3.2.6 contains the ProPred-predicted MHC Class II-presented epitope PEPTIDE 3.2.8. PEPTIDE 3.3.7 is a composite of two ProPred-predicted MHC Class II-presented epitopes (PEPTIDES 3.2.9 and 3.2.8), overlapping by 7 amino acids. PEPTIDE 3.3.8 contains the ProPred-predicted MHC Class II-presented epitope PEPTIDE 3.2.7. PEPTIDE 3.3.9 contains the ProPred-predicted MHC Class II-presented epitope PEPTIDE 3.2.10. PEPTIDE 3.3.10 contains the ProPred-predicted MHC Class II-presented epitope PEPTIDE 3.2.11. PEPTIDE 3.3.11 contains the ProPred-predicted MHC Class II-presented epitope PEPTIDE 3.2.11. PEPTIDE 3.3.12 contains the ProPred-predicted MHC Class II-presented epitope PEPTIDE 3.2.13. PEPTIDE 3.3.13 is a composite of two ProPred-predicted MHC Class II-presented epitopes (PEPTIDES 3.2.12 and 3.2.13), overlapping by 7 amino acids. PEPTIDE 3.3.14 contains the ProPred-predicted MHC Class II-presented epitope PEPTIDE 3.2.14.

TABLE 3.4

Experimentally defined IgE-binding Ara h 3 epitope, overlapping with a predicted MHC Class II-presented Ara h 3 epitope.

| PEPTIDE | Pos. | Sequence | Ii Key | SEQ ID NO: |
|---|---|---|---|---|
| 3.4.1 | 276 | VTVRGGLRILSPDRK | 11 | 125 |

Pos. is the residue position in the primary sequence of the first amino acid in the antigenic epitope. Ii-Key is the number of residue positions intervening between an Ii-Key motif and the first residue of the antigenic epitope.

TABLE 3.5

Hybrids containing predicted MHC Class II Ara h 3 epitopes overlapping experimentally defined IgE-binding epitopes.

| PEP-TIDE | POS. | Sequence | SEQ ID NO: |
|---|---|---|---|
| 3.5.1 | 274 | Ac-LRMK-ava-IVTVRGGLR-$NH_2$ | 126 |
| 3.5.2 | 277 | Ac-LRMK-ava-VRGGLRILS-$NH_2$ | 127 |
| 3.5.3 | 281 | Ac-LRMK-ava-IVTVRGGLRILSPDRK-$NH_2$ | 128 |
| 3.5.4 | 274/ 277/281 | Ac-LRMK-ava-IVTVRGGLRILSPDRK-$NH_2$ | 129 |

Pos. is the residue position in the primary sequence of the first amino acid in the antigenic epitope. Sequence is the amino acid sequence of a hybrid peptide containing a MHC Class II epitope of Table 3.2 and an IgE binding epitope of Table 3.4.

The PEPTIDES of Table 3.5 are characterized as follows. PEPTIDES 3.5.1–3.5.4 share amino acids between IgE binding and MHC Class II-presented epitopes. PEPTIDE 3.5.1 contains the predicted MHC Class II epitope PEPTIDE 3.2.5, which coincides with experimentally defined IgE binding epitope PEPTIDE 13.1. PEPTIDE 3.5.2 contains the predicted MHC Class II epitope PEPTIDE 3.5.4, which coincides with experimentally defined IgE binding epitope PEPTIDE 3.4.1. PEPTIDE 3.4.3 contains the predicted MHC Class II epitope PEPTIDE 3.2.6, which coincides with experimentally defined IgE binding epitope PEPTIDE 3.4.1. PEPTIDE 3.4.4 is a composite of three ProPred-predicted MHC Class II-presented epitopes (PEPTIDE 3.2.4, 3.2.5 and 3.2.6), which coincide with IgE binding epitope PEPTIDE 3.4.1.

Example 4

Ii-Key/Fel d 1 Cat Dander Antigenic Epitope Hybrids

In another aspect, this invention relates to the design of Ii-Key/Fel d 1 antigenic epitope hybrids. Such Ii-Key/Fel d 1 antigenic epitope hybrids comprise the Ii-Key motif LRMK. (SEQ ID NO: 3) and modifications, joined through a functionally acceptable linker to a MHC Class II-presented epitopes of the F1 d 1 major allergen protein of cat dander. The amino acid sequences of Fel d 1 chains 1 and 2 in Table 4.1 were taken from GenBank gi/1082945/chain 1 and gi/1082946/chain 2 (Morgenstern J P. Proc Natl Acad Sci USA. 1991 88:9640–4). The MHC Class II-presented epitopes of Fel d 1 (chain 1) listed in Table 4.2 include those with the highest scores in the ProPred program analysis. Table 4.3 presents Ii-Key/Fel d 1 (chain 1) hybrids containing some of the predicted MHC Class II-presented epitopes of Table 2. Table 4.4 presents Fel d 1 (chain 1) MHC Class II-presented peptides which elicit allergic responses in cat dander-atopic humans (Haselden B M. J Exp Med. 1999 189: 1885–94). Table 4.5 presents Ii-Key/Fel d 1 (chain 1) hybrids containing some of the experimentally defined MHC Class II-presented epitopes of Table 4.4. Table 4.6 presents predicted MHC Class II-presented epitopes of Fel d 1 (chain 2). Table 4.7 presents designed Ii-Key/Fel d 1 (chain 2) hybrids containing some of the MHC Class II-presented epitopes of Table 4.6. Table 4.8 presents Fel d 1 (chain 2) MHC Class II-presented peptides which elicit allergic responses in cat dander-atopic humans (Haselden B M. J Exp Med. 1999 189: 1885–94). Table 4.9. presents designed Ii-Key/Fel d 1 (chain 2) hybrids containing some of the MHC Class II-presented epitopes of Table 4.8. Since some of the epitope peptides alone can induce hyporesponsiveness to cat dander allergen challenge in the clinic (Oldfield W L. J. Immunol. 2001 167:1734–9; Mazzarella G. Allergy 2000 61:6–9), the corresponding hybrids will be more potent and less susceptible to induce anaphylaxis during clinical testing or therapy. Methods for such analyses and therapy are presented in Larche M. WO99/34826 and U.S. Pat. No. 6,120,769 (2000), which are incorporated herein by reference.

Asthma is a complex inflammatory disease of the lung characterized by variable airflow obstruction, bronchial hyper-responsiveness, and airway inflammation. Inflammation in asthma consists of airway infiltration by mast cells, lymphocytes, and eosinophils. There is accumulating evidence that CD4+ cells with a Th2-cytokine pattern play a pivotal role in the pathogenesis of asthma. These cells orchestrate the recruitment and activation of the primary effector cells of the allergic response (mast cells and eosinophils), through the release of cytokines such as IL-4, IL-5, and IL-13. Allergic inflammation is also implicated in airway epithelium changes, although the mechanisms by which inflammatory cells and, in particular, T cells interact with the epithelium are not completely clarified.

Treatment of mice in an ovalbumin-induced asthmatic response with superagonistic Th1-skewing peptide 336E-A (ISQAVHAAHAEINAAGR) (SEQ ID NO: 130) resulted in a Th1-like cytokine profile and a significant decrease in airway eosinophilia and OVA-specific IL-4 and IL-5 production (Janssen E. J. Immunol. 2000 164:1580–8; Janssen E M. J. Immunol. 2000 165:7207–14). In these studies the wild type sequence (ISQAVHAAHAEINEAGR) (SEQ ID NO: 131) was modified in homologs each with a single alanine substitutions at all non-alanine residue positions.

In extension of the principles of this study Pene et al. examined the effects of immunotherapy with Fel d 1 peptides on the response to bronchial provocation tests with a standardized Fel d 1 cat extract on Fel d 1-specific serum IgE and IgG levels and in vitro IL-4 and IFN-ã production (Pene J. J Allergy Clin Immunol. 1998; 102:571–8). Patients allergic to cats received 6 weekly injections of low dose, medium dose, or high dose of Fel d 1 peptides or a placebo. Six weeks after ending immunotherapy, posttreatment $PD_{20}$Forced Expiratory Volume/$_{1sec}$ was not significantly different between the treated and placebo groups. However, in the medium- and high-dose groups there was a significant improvement between baseline and posttreatment days. IL-4 release was significantly reduced in the high dose-treated group whereas it was unchanged in the low or medium dose-and in the placebo-treated groups. In all groups, IFN-γ, IgE, and IgG levels remained unchanged. The investigators concluded there was no correlation between the improvement of $PD_{20}FEV_1$ and the decrease in IL-4 production. They suggested that peptide immunotherapy might act by shifting the Fel d 1-induced response of peripheral blood mononuclear cells in vitro from the $T_{h2}$-like to the $T_{h0}$-like phenotype. The Ii-Key/antigenic epitope hybrids presented below include some of the experimentally tested MHC Class II epitopes of these investigators and can be predicted to be of greater potency and have a wider margin of safety in diagnostic and therapeutic applications, for reasons presented previously

.

The preceding studies followed the preparation of ALLERVAX CAT, a peptide vaccine containing two peptides of 27 amino acids containing regions of multiple MHC Class II-presented epitopes from the *Felis domesticus* cat allergen Fel d1 chain I were produced FC1P1, LFLTGTPDEYVEQVAQY (SEQ ID NO: 132); FC1P2, EQVAQYKALPVVLENA (SEQ ID NO: 133); and FC1P3, KALP-VVLENARILKNCV (SEQ ID NO: 134).

The deduced amino acid sequence of Fel d 1 Chain 1 and Chain 2 are presented in Table 4.1 (>gi|1082945|pir||B56413 major allergen Fel d1 chain 1 short form—cat; >gi|1082946|pir||C56413 major allergen Fel d1 chain 2 precursor—cat). Predicted MHC Class-II-presented epitopes of Fel d 1 (chain 1) are listed in Table 4.3. Designed Ii-Key/Fel d 1 (chain 1) hybrids containing some of the predicted MHC Class II-presented epitopes of Table 4.2 are listed in Table 4.3. Experimentally defined Fel d 1 chain 1 MHC Class II-presented epitopes are listed in Table 4.4. Designed Ii-Key/Fel d 1 (chain 1) hybrids containing some of the MHC Class II-presented epitopes of Table 4.4 are listed I Table 4.5. Predicted MHC Class II-presented epitopes of Fel d 1 (chain 2) are listed in Table 4.6. Designed Ii-Key/Fel d (chain 2) hybrids containing some of the MHC Class II-presented epitopes of Table 4.6 are listed in Table 4.7. Experimentally determined/Fel d 1 (chain 2) MHC Class II-presented epitopes are listed in Table 4.8. Designed Ii-Key/Fel d 1 (chain 2) hybrids containing some of the MHC Class II-presented epitopes of Table 4.8 are listed in Table 4.9.

TABLE 4.1

Deduced amino acid sequence of Fel d 1.

Chain 1.

>gi|1082945|pir| |B56413 major allergen Fel dI chain 1 short form - cat (SEQ ID NO:135)
1mldaalppcp tvaatadcei cpavkrdvdl fltgtpdeyv eqvaqykalp 51vvlenarilk ncvdakmtee dkenalslld kiytsplc Chain 2.

>gi|1082946|pir| |C56413 major allergen Fel dl chain 2 precursor - cat (SEQ ID NO:136)
1mrgallvlal lvtqalgvkm aetcpifydv ffavangnel lldlsltkvn 51atepertamk kiqdcyveng lisrvldglv mttissskdc mgeavqntve 101dlklntlgr

TABLE 4.2

Predicted MHC ClassII-presented epitopes of Fel d 1 (chain 1)

| PEPTIDE | Pos. | Sequence | Score | Ii-Key | SEQ ID NO: |
|---|---|---|---|---|---|
| 4.2.1 | 46 | Y K A L P V V L E | 4.20 | — | 137 |
| 4.2.2 | 51 | V V L E N A R I L | 4.80 | — | 138 |
| 4.2.3 | 43 | V A Q Y K A L P V | 4.70 | — | 139 |
| 4.2.4 | 39 | Y V E Q V A Q Y K | 3.60 | 8 | 140 |
| 4.2.5 | 24 | V K R D V D L F L | 3.4 | — | 141 |
| 4.2.6 | 20 | I C P A V K R D V | 3.1 | — | 142 |
| 4.2.7 | 76 | L S L L D K I Y T | 2.70 | 8 | 143 |
| 4.2.8 | 79 | L D K I Y T S P L | 2.52 | 11 | 144 |
| 4.2.9 | 30 | L F L T G T P D E | 2.40 | — | 145 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 4.3

Designed Ii-Key/Fel d 1 (chain 1) hybrids containing some of the predicted MHC Class II-presented epitopes of Table 4.2.

| PEPTIDE | Pos. | Sequence | SEQ ID NO: |
|---|---|---|---|
| 4.3.1 | 43 | Ac-LRMK-ava-VAQYKALPV-$NH_2$ | 146 |
| 4.3.2 | 46 | Ac-LRMK-ava-YKALPVVLE-$NH_2$ | 147 |

TABLE 4.3-continued

Designed Ii-Key/Fel d 1 (chain 1) hybrids containing some of the predicted MHC Class II-presented epitopes of Table 4.2.

| PEPTIDE | Pos. | Sequence | SEQ ID NO: |
|---|---|---|---|
| 4.3.3 | 51 | Ac-LRMK-ava-VVLENARIL-$NH_2$ | 148 |
| 4.3.4 | 39 | Ac-LRMK-ava-YVEQVAQYK-$NH_2$ | 149 |
| 4.3.5 | 39/43/46/51 | Ac-LRMK-ava-YVEQVAQYKALPVVLENARIL-$NH_2$ | 150 |
| 4.3.6 | 20 | Ac-LRMK-ava-ICPAVKRDV-$NH_2$ | 151 |
| 4.3.7 | 24 | Ac-LRMK-ava-VKRDVDLFL-$NH_2$ | 152 |
| 4.3.8 | 30 | Ac-LRMK-ava-LFLTGTPDE-$NH_2$ | 153 |
| 4.3.9 | 20/24/30 | Ac-LRMK-ava-ICPAVKRDVDLFLTGTPDE-$NH_2$ | 154 |
| 4.3.10 | 76 | Ac-LRMK-ava-LSLLDKIYT-$NH_2$ | 155 |
| 4.3.11 | 79 | Ac-LRMK-ava-LDKIYTSPL-$NH_2$ | 156 |
| 4.3.12 | 76/79 | Ac-LRMK-ava-LSLLDKIYTSPL-$NH_2$ | 157 |

Pos. is the residue position in the primary sequence of the first amino acid in the antigenic epitope. Ii-Key is the number of residue positions intervening between an Ii-Key motif and the first residue of the antigenic epitope.

TABLE 4.4

Experimentally defined Fel d 1 chain 1 MHC Class II-presented epitopes.

| PEPTIDE | Pos. | Sequence | Ii-Key | SEQ ID NO: |
|---|---|---|---|---|
| 4.4.1 | 20 | EICPAVKRDVDLFLTGT | — | 158 |
| 4.4.2 | 30 | LFLTGTPDEYVEQVAQY | — | 159 |
| 4.4.3 | 41 | EQVAQYKALPVVLENA | 10 | 160 |
| 4.4.4 | 47 | KALPVVLENARILKNCV | — | 161 |
| 4.4.5 | 57 | RILKNCVDAKMTEEDKE | 5 | 162 |
| 4.4.6 | 66 | KMTEEDKENALSLLDK | 2 | 163 |
| 4.4.7 | 72 | KENALSVLDKIYTSPL | — | 164 |

Pos. is the residue position in the primary sequence of the first amino acid in the antigenic epitope. Sequence is the amino acid sequence of certain peptides found to elicit responses in patients with allergy to cat dander (Haselden B M. J Exp Med. 1999 189: 1885–94). Ii-Key is the number of residue positions intervening between an Ii-Key motif and the first residue of the antigenic epitope. PEPTIDE 4.4.2 is from FC1P1; PEPTIDE 4.4.3 is from FC1P2; PEPTIDE 4.4.4 is from FC1P3 (Haselden B M. J Exp Med. 1999 189:1885–94).

TABLE 4.5

Designed Ii-Key/Fel d 1 (chain 1) hybrids containing some of the MHC Class II-presented epitopes of Table 4.4.

| PEPTIDE | Pos. | Sequence | SEQ ID NO: |
|---|---|---|---|
| 4.5.1 | 30 | Ac-LRMK-ava-LFLTGTPDEYVEQVAQY-$NH_2$ | 165 |
| 4.5.2 | 41 | Ac-LRMK-ava-EQVAQYKALPVVLENA-$NH_2$ | 166 |
| 4.5.3 | 47 | Ac-LRMK-ava-KALPVVLENARILKNCV-$NH_2$ | 167 |
| 4.5.4 | 57 | Ac-LRMK-ava-RILKNCVDAKMTEEDKE-$NH_2$ | 168 |
| 4.5.5 | 41/47/57 | Ac-LRMK-ava-QVAQYKALPVVLENARILKNCVDAKM-TEEDKE-$NH_2$ | |

Pos. is the residue position in the primary sequence of the first amino acid in the antigenic epitope. Ii-Key is the number of residue positions intervening between an Ii-Key motif and the first residue of the antigenic epitope.

TABLE 4.6

Predicted MHC Class II-presented epitopes of Fel d 1 (chain 2)

| PEPTIDE | Pos. | Sequence | Score | Ii-Key | SEQ ID NO: |
|---|---|---|---|---|---|
| 4.6.1 | 10 | LLVTQALGV | 6.10 | 3 | 170 |
| 4.6.2 | 40 | LLLDLSLTK | 4.60 | — | 171 |
| 4.6.3 | 79 | LVMTTISSS | 4.37 | — | 172 |
| 4.6.4 | 18 | VKMAETCPI | 4.80 | 11 | 173 |
| 4.6.5 | 5 | LVLALLVTQ | 4.50 | — | 174 |
| 4.6.6 | 4 | LLVLALLVT | 3.90 | — | 175 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 4.7

Designed Ii-Key/Fel d (chain 2) hybrids containing some of the MHC Class II-presented epitopes of Table 4.6.

| PEPTIDE | Pos. | Sequence | SEQ ID NO: |
|---|---|---|---|
| 4.7.1 | 9 | Ac-LRMK-ava-LLVTQALGV-$NH_2$ | 176 |
| 4.7.2 | 5 | Ac-LRMK-ava-LVLALLVTQ-$NH_2$ | 177 |

TABLE 4.7-continued

Designed Ii-Key/Fel d (chain 2) hybrids containing some of the MHC Class II-presented epitopes of Table 4.6.

| PEPTIDE | Pos. | Sequence | SEQ ID NO: |
|---|---|---|---|
| 4.7.3 | 4 | Ac-LRMK-ava-LLVLALLVT-$NH_2$ | 178 |
| 4.7.4 | 4/5/9 | Ac-LRMK-ava-LLVLALLVTQALGV-$NH_2$ | 179 |
| 4.7.5 | 17 | Ac-LRMK-ava-VKMAETCPI-$NH_2$ | 180 |
| 4.7.6 | 39 | Ac-LRMK-ava-LLLDLSLTK-$NH_2$ | 181 |
| 4.7.7 | 78 | Ac-LRMK-ava-LVMTTISSS-$NH_2$ | 182 |

Pos. is the residue position in the primary sequence of the first amino acid in the antigenic epitope.

TABLE 4.8

Experimentally determined Fel d 1 (chain 2) MHC Class II-presented epitopes.

| PEPTIDE | Pos. | Sequence | Ii-Key | SEQ ID NO: |
|---|---|---|---|---|
| 4.8.1 | 46 | LTKVNATEPERTAMKK | — | 183 |
| 4.8.2 | 57 | TAMKKIQDCYVENGLI | 6 | 184 |
| 4.8.3 | 65 | CYVENGLISRVLDGLV | — | 185 |
| 4.8.4 | 84 | ISSSKDCMGEAVQNTV | 5 | 186 |
| 4.8.5 | 94 | AVQNTVEDLKLNTLGR | — | 187 |

Pos. is the residue position in the primary sequence of the first amino acid in the antigenic epitope. Sequence is the amino acid sequence of an experimentally determined MHC Class II-presented epitope. Ii-Key is the number of residue positions intervening between an Ii-Key motif and the first residue of the antigenic epitope.

TABLE 4.9

Designed Ii-Key/Fel d 1 (chain 2) hybrids containing some of the MHC Class II-presented epitopes of Table 4.8.

| PEPTIDE | Pos. | Sequence | SEQ ID NO: |
|---|---|---|---|
| 4.9.1 | 46 | Ac-LRMK-ava-LTKVNATEPERTAMKK-$NH_2$ | 188 |
| 4.9.2 | 57 | Ac-LRMK-ava-TAMKKIQDCYVENGLI-$NH_2$ | 189 |
| 4.9.3 | 65 | Ac-LRMK-ava-CYVENGLISRVLDGLV-$NH_2$ | 190 |
| 4.9.4 | 84 | Ac-LRMK-ava-ISSSKDCMGEAVQNTV-$NH_2$ | 191 |
| 4.9.5 | 57/65 | Ac-LRMK-ava-TAMKKIQDCYVENGLISRVLDGLV-$NH_2$ | 192 |

Pos. is the residue position in the primary sequence of the first amino acid in the antigenic epitope.

Example 5

Ii-Key/Ph1 p 1 Pollen Antigenic Epitope Hybrids

In another aspect this invention relates to the design and use of Ii-Key/Ph1 p 1 pollen antigenic epitope hybrids. Laffer and colleagues obtained the cDNA for the major allergen Phl p I from timothy grass (*Phleum pratense*) and found that the recombinant protein Phl p I inhibits IgE binding to group I allergens prepared form eight different grass species (Laffer S. J Allergy Clin Immunol. 1994 94:689–98). In a study of the T-cell epitopes of Phl p 1, major pollen allergen of timothy grass (*Phleum pratense*) Schenk S. and colleagues found evidence for crossreacting and non-crossreacting T-cell epitopes within grass group I allergens (Schenk S. J Allergy Clin Immunol. 1995 96:986–96). Immunological characterization of various purified recombinant timothy grass pollen (*Phleum pratense*) allergens (Phl p 1, Phl p2, Phl p 5) were characterized with respect to such cross reactions (Vrtala S. J Allergy Clin Immunol. 1996 97:781–7). Various nonanaphylactic synthetic peptides were obtained from antibody-recognized epitopes of the major grass pollen allergen, Phl p 1, for allergy vaccination (Focke M. FASEB J. 2001 15:2042–4). Some of these epitopes are incorporated in the Ii-Key/MHC Class II epitope/IgG epitope hybrids of Tables 5.7. In related work, Blaher et al. identified MHC Class II-presented epitopes of Lol p 9, a major allergen of ryegrass (*Lolium perenne*) pollen (Blaher B. J Allergy Clin Immunol. 1996 98:124–32).

The sequence of Phl p I allergen [*Phleum pratense*] in Table 5.1 was taken from GenBank 473360, Phl p I allergen. Predicted MHC class-II-presented epitopes of Phl p 1 are listed in Table 5.2. Ii-Key/Phl p 1 hybrids containing some of the MHC Class II-presented Phl p 1 epitopes of Table 5.2 are listed in Table 5.3. Experimentally defined MHC Class II-presented epitopes of Phl p 1 are listed in Table 5.4. Ii-Key/Phl p 1 hybrids containing some of the experimentally defined MHC Class II-presented epitopes of Table 5.4 are listed in Table 5.5. Experimentally defined IgE-binding epitopes of Phl p 1 overlapping with MHC Class II-presented Pnl p 1 epitopes are listed in Table 5.6. A hybrid peptide including an experimentally defined MHC Class II and IgE binding Php 1 epitope is listed in Table 5.7.

TABLE 5.1

| Deduced amino acid sequence of Phi p 1 pollen protein. |
|---|
| 1 massssvllv vvlfavflgs aygipkvppg pnitatygdk wldakstwyg |
| 51 kptgagpkdn ggacgykdvd kppfsgmtgc gntpifksgr gcgscfeikc |
| 101 tkpeacsgep vvvhitddne epiapyhfdl sghafgamak kgdeqklrsa |
| 151 gelelqfrrv kckypegtkv tfhvekgsnp nylallvkyv ngdgdvvavd |
| 201 ikekgkdkwi elkeswgaiw ridtpdkltg pftvrytteg gtkteaedvi |
| 251 pegwkadtsy esk |

TABLE 5.2

Predicted MHC class II-presented epitopes of Phl p 1.

| PEPTIDE | Pos. | Sequence | Score | Ii-Key | SEQ ID NO: |
|---|---|---|---|---|---|
| 5.2.1 | 0 | MASSSSVLL | 6.30 | — | 194 |
| 5.2.2 | 220 | WRIDTPDKL | 5.86 | 5 | 195 |
| 5.2.3 | 9 | VVVLFAVFL | 5.80 | — | 196 |
| 5.2.4 | 10 | VVLFAVLG | 6.00 | — | 197 |
| 5.2.5 | 6 | VLLVVVLFA | 5.10 | — | 198 |
| 5.2.6 | 96 | FEIKCTKPE | 5.80 | 6 | 199 |
| 5.2.7 | 15 | VFLGSAYGI | 4.80 | — | 200 |
| 5.2.8 | 186 | LVKYVNGDG | 4.50 | 9 | 201 |
| 5.2.9 | 185 | LLVKYVNGD | 4.50 | 8 | 202 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 5.3

Ii-Key/Phi p 1 hybrids containing some of the MHC Class II-presented Phi p 1 epitopes of Table 5.2.

| PEPTIDE | Pos. | Sequence | SEQ ID NO: |
|---|---|---|---|
| 5.3.1 | 0 | Ac-LRMK-ava-MASSSSVLL-$NH_2$ | 203 |
| 5.3.2 | 6 | Ac-LRMK-ava-VLLVVVLFA-$NH_2$ | 204 |
| 5.3.3 | 9 | Ac-LRMK-ava-VVVLFAVFL-$NH_2$ | 205 |
| 5.3.4 | 10 | Ac-LRMK-ava-VVLFAVFLG-$NH_2$ | 206 |
| 5.3.5 | 0/6/9/10 | Ac-LRMK-ava-MASSSSVLLVVVLFAVFLG-$NH_2$ | 207 |
| 5.3.6 | 219 | Ac-LRMK-ava-WRIDTPDKL-$NH_2$ | 208 |
| 5.3.7 | 95 | Ac-LRMK-ava-FEIKCTKPE-$NH_2$ | 209 |
| 5.3.8 | 15 | Ac-LRMK-ava-VFLGSAYGI-$NH_2$ | 210 |
| 5.3.9 | 184 | Ac-LRMK-ava-LLVKYVNGD-$NH_2$ | 211 |
| 5.3.10 | 185 | Ac-LRMK-ava-LVKYVNGDG-$NH_2$ | 212 |
| 5.3.11 | 184/185 | Ac-LRMK-ava-LLVKYVNGDG-$NH_2$ | 213 |

Pos. is the residue position in the primary sequence of the first amino acid in the antigenic epitope.

TABLE 5.4

Experimentally defined MHC Class II-presented epitopes of Phl p 1.

| PEPTIDE | Pos. | Sequence | Ii-Key | SEQ ID NO: |
|---|---|---|---|---|
| 5.4.1 | 96 | F E I K C T K P E A C S | 6 | 214 |
| 5.4.2 | 123 | I A P Y H F D L S G H A | 5 | 215 |

Pos. is the residue position in the primary sequence of the first amino acid in the antigenic epitope. Ii-Key is the number of residue positions intervening between an Ii-Key motif and the of residue of the antigenic epitope.

The experimentally defined MHC Class II epitopes of Phl p 1, cross react within grass group I allergens—Lol p 1 (ryegrass, *Lolium perenne*), Sec c 1 (rye, *secale cereale*) (Schenk S. J Allergy Clin Immunol. 1995 96:986–96). Specifically the epitope of PEPTIDE 5.4.1 cross reacts with Lol p 1 (A97 is replaced by S97) and cross reacts with Sec c 1 (I89 is replaced by L89). The epitope of PEPTIDE 5.4.2 cross reacts with Lol p 1 and sec c 1 (A124 is replaced by D124).

TABLE 5.5

| Ii-Key/Phi p 1 hybrids containing some of the experimentally defined MHC Class II-presented epitopes of Table 3. | | | |
|---|---|---|---|
| PEPTIDE | Pos. | Sequence | SEQ ID NO: |
| 5.4.1 | 96 | Ac-LRMK-ava-FEIKCTKPEACS-$NH_2$ | 216 |
| 5.4.2 | 123 | Ac-LRMK-ava-IAPYHFDLSGHA-$NH_2$ | 217 |

Pos. is the residue position in the primary sequence of the first amino acid in the antigenic epitope. Ii-Key is the number of residue positions intervening between an Ii-Key motif and the first residue of the antigenic epitope.

TABLE 5.6

| Experimentally defined IgE-binding epitopes of Phl p 1 overlapping with MHC Class II-presented Phi p 1 epitopes. | | | |
|---|---|---|---|
| PEPTIDE | Pos. | Sequence | SEQ ID NO: |
| 5.6.1 | 24 | IPKVPPG PNITATYGDK WLDAKSTWYG KPT | 218 |
| 5.6.2 | 65 | GYKDVD KPPFSGMTGC GNTPIFKSGR G | 219 |
| 5.6.3 | 109 | EP VVVHITDDNE EPIAPYHFDL SGHAFGAMA | 220 |
| 5.6.4 | 173 | HVEKGSNP NYLALLVKYV NGDGDVVAV | 221 |
| 5.6.5 | 235 | RYTTEG GTKTEAEDVI PEGWKADTSY ESK | 222 |

Pos. is the residue position in the primary sequence of the first amino acid in the antigenic epitope. Ii-Key is the number of residue positions intervening between an Ii-Key motif and the first residue of the antigenic epitope. The peptides containing IgE-binding epitopes were defined by Focke and colleagues (Focke M. FASEB J. 2001 15:2042–4). PEPTIDE 5.6.3 includes experimentally defined MHC Class II epitopes of Phl p 1 (Schenk S. J Allergy Clin Immunol. 1995 96:986–96) overlapping with IgE epitope containing peptides (Focke M. FASEB J. 2001 15:2042–4).

TABLE 5.7

| A hybrid peptide including an experimentally defined MHC Class II and IgE binding Php 1 epitope. | | | |
|---|---|---|---|
| PEPTIDE | Pos. | Sequence | SEQ ID NO: |
| 5.7.1 | 109 | Ac-LRMK-ava-FEIKCTKPEACSGEPVVVHITDDNEEPIAPYHFDLSGHAFGAMA-$NH_2$ | 223 |

Pos. is the residue position in the primary sequence of the first amino acid in the antigenic epitope. Ii-Key is the number of residue positions intervening between an Ii-Key motif and the first residue of the antigenic epitope. PEPTIDE 5.7.1 includes Phl p 1 experimentally defined IgE epitopes (Focke M. FASEB J. 2001 15:2042–4) and experimentally defined MHC Class II epitopes of Phl p 1 (Schenk S. J Allergy Clin Immunol. 1995 96:986–96).

Example 6

Ii-Key/Phl p 5a Birch Pollen Antigenic Epitope Hybrids

In another aspect this invention relates to the design and use of Ii-Key/Phl p 5a birch pollen antigenic epitope hybrids. Multiple T cell epitopes on Bet v I, the major birch pollen allergen, have been determined using specific T cell clones and overlapping peptides (Ebner C. J. Immunol. 1993 150:1047–54). Vrtala and colleagues found that the major birch pollen allergen, Bet v 1, can be divided into two fragments each of which contained nonanaphylactic T cell epitopes and are candidates for suppressive immunotherapy (Vrtala S. Int Arch Allergy Immunol. 1997 113:246–8; Vrtala S. J Clin Invest. 1997 99:1673–81). Friedl-Hajek R. and colleagues characterized a highly promiscuous, HLA allele-specific T-cell epitope in the birch major allergen Bet v 1Five Bet v 1-specific T cell clones derived from two birch pollen-allergic individuals and specific for Bet v 1 (Friedl-Hajek R. Clin Exp Allergy. 1999 29:478–87). One of these T cell clones reacted with a Bet v 1 peptide containing amino acid residues 21–33 (BP21), the other two T cell clones reacted with a minimal peptide containing residues 37–45 (BP37). While BP37-specific T cell clones were restricted by a HLA-DQA1*0301/DQB1*0603 heterodimer, BP21 was recognized in a highly promiscuous manner. T cell clones recognizing this sequence were restricted by HLA-DPB1*0201, a HLA-DQA1*0201/DQB1*0201 heterodimer, or HLA-DRB3*0101.

The sequence of Phl p 5a birch pollen protein in Table 6.1 was taken from GenBank 2851456 (Bufe A. J Allergy Clin Immuno. 1994 94:173–81). Predicted MHC Class II-presented epitopes of Phl p 5a are listed in Table 6.2. Experimentally defined, cross reacting MHC Class II isoepitopes of Phl p 5a and Phl p 5b are listed in Table 6.3 (Muller W. Clin Exp Allergy. 1998 28:1538–48). Designed Ii-Key/antigenic epitope hybrids containing Phl p 5 MHC Class II-presented epitopes are listed in Table 6.4.

TABLE 6.1

| Deduced amino acid sequence of Phl p 5a birch pollen. (SEQ ID NO 224) |
|---|
| 1 adlgygpatp aapaagytpa tpaapagada agkatteeqk liekinagfk |
| 51 aalagagvqp adkyrtfvat fgpasnkafa eglsgepkga aessskaalt |

TABLE 6.1-continued

| Deduced amino acid sequence of Phl p 5a birch pollen. (SEQ ID NO 224) |
|---|
| 101 skldaaykla yktaegatpe akydayvatl sealriiagt levhavkpaa |
| 151 eevkvipage lqviekvdaa fkvaataana apandkftvf eaafndeika |
| 201 stggayesyk fipaleaavk qayaatvata pevkytvfet alkkaitams |
| 251 eaqkaakpaa aatatataav gaatgaataa tggykv |

TABLE 6.2

Predicted MHC Class II-presented epitopes of Phl p 5a.

| PEPTIDE | Pos. | Sequence | Score | Ii-Key | SEQ ID NO: |
|---|---|---|---|---|---|
| 6.2.1 | 126 | Y V A T L S E A L | 8.40 | — | 225 |
| 6.2.2 | 153 | V K V I P A G E L | 5.10 | 5 | 226 |
| 6.2.3 | 134 | L R I I A G T L E | 5.00 | — | 227 |
| 6.2.4 | 209 | Y K F I P A L E A | 4.80 | — | 228 |
| 6.2.5 | 206 | Y E S Y K F I P A | 4.00 | — | 229 |
| 6.2.6 | 171 | F K V A A T A A N | 4.10 | 2 | 230 |
| 6.2.7 | 64 | Y R T F V A T F G | 4.00 | — | 231 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 6.3

Experimentally defined, cross reacting MHC Class II isoepitopes of Phi p 5a and Phi p 5b.

| PEPTIDE | Pos. | Sequence | Ii-Key | SEQ ID NO: |
|---|---|---|---|---|
| 6.3.1 | 209 | Y K F I P A L E A A V K | — | 232 |
| 6.3.2 | 161 | L Q V I E K V D A A F K | 2 | 233 |

Pos. is the residue position in the primary sequence of the first amino acid in the antigenic epitope. Sequence is the amino acid sequence of an experimentally determined MHC Class II-presented epitope. Ii-Key is the number of residue positions intervening between an Ii-Key motif and the first residue of the antigenic epitope. PEPTIDE 6.3.1 corresponds to peptide Phl p 5b(184–195; YKCIPSLEAAVK) (SEQ ID NO: 234) and PEPTIDE 6.3.2 corresponds to peptide Phl p 5b(136–147; LQIIDKIDAAFK (SEQ ID NO: 235) (Muller W. Clin Exp Allergy. 1998 28:1538–48).

TABLE 6.4

Hybrids containing Phi p 5 MHC Class II-presented epitopes.

| PEPTIDE | Pos. | Sequence | SEQ ID NO: |
|---|---|---|---|
| | | A. Non-overlapping epitopes. | |
| 6.4.1 | 126 | Ac-LRMK-ava-YVATLSEAL-$NH_2$ | 236 |
| 6.4.2 | 153 | Ac-LRMK-ava-VKVIPAGEL-$NH_2$ | 237 |
| 6.4.3 | 134 | Ac-LRMK-ava-LRIIAGTLE-$NH_2$ | 238 |
| 6.4.4 | 64 | Ac-LRMK-ava-YRTFVATFG-$NH_2$ | 239 |
| | | B. Overlapping epitopes | |
| 6.4.5 | 209 | Ac-LRMK-ava-YKFIPALEA-$NH_2$ | 240 |
| 6.4.6 | 206 | Ac-LRMK-ava-YESYKFIPA-$NH_2$ | 241 |
| 6.4.7 | 206/209 | Ac-LRMK-ava-YESYKFIPALEA-$NH_2$ | 242 |
| 6.4.8 | 161 | Ac-LRMK-ava-LQVIEKVDAAFK-$NH_2$ | 243 |
| 6.4.9 | 171 | Ac-LRMK-ava-FKVAATAAN-$NH_2$ | 244 |
| 6.4.10 | 161/171 | Ac-LRMK-ava-LQVIEKVDAAFKVAATAAN-$NH_2$ | 245 |

Pos. is the residue position in the primary sequence of the first amino acid in the antigenic epitope. Ii-Key is the number of residue positions intervening between an Ii-Key motif and the first residue of the antigenic epitope.

Example 7

Ii-Key/Phospholipase A-2 Bee Venom Antigenic Epitope Hybrids

In another aspect this invention relates to the design and use of Ii-Key/Phospholipase A-2 bee venom antigenic epitope hybrids. Muller and colleagues successful induced specific T-cell anergy in patients allergic to bee venom with immunotherapy with T-cell recognized peptides of bee venom phospholipase A2 (Muller U. J Allergy Clin Immunol. 1998 101:747–54). Five patients with IgE-mediated systemic allergic reactions to bee stings were treated with a mixture of three T-cell epitope peptides of PLA. Ten patients allergic to BV receiving whole BV immunotherapy served as control subjects. Increasing doses of the peptide mixture, up to a maintenance dose of 100 micrograms, were administered subcutaneously within 2 months. The patients were then challenged with PLA and 1 week later with a bee sting. The cellular and humoral immune response was measured in vitro. No allergic side effects were caused by the peptide immunotherapy, and all patients tolerated the challenge with PLA without systemic allergic symptoms. Two patients developed mild systemic allergic reactions after the bee sting challenge. After peptide immunotherapy, specific proliferative responses to PLA and the peptides in peripheral blood mononuclear cells were decreased in successfully treated patients. The production of TH2 and TH1 cytokines was inhibited, and B cells were not affected in their capacity to produce specific IgE and IgG4 antibodies. Their levels increased after allergen challenge in favor of IgG4. The investigators concluded that immunotherapy of BV allergy with short T-cell peptides of PLA induces epitope-specific anergy in peripheral T cells and changes the specific isotype ratio in a fashion similar to that of conventional immunotherapy in successfully treated patients. Additional MHC Class II-presented candidate epitopes have been identified (Texier C. J Immunol 2000 164:3177–84).

The sequence of bee venom phospholipase A-2 in Table 7.1 was taken from GenBank 129501 allergen Api m1 (Kuchler K. Eur J. Biochem. 1989 184:249–54). Predicted MHC Class II-presented epitopes of the major bee venom allergen phospholipase A-2 are listed in Table 7.2. Table 7.3. Experimentally defined MHC Class II-presented epitopes of the major bee venom allergen phospholipase A-2 are listed in Table 7.3. Ii-Key/PHL A2 hybrids containing some of the MHC Class II-presented PHL A2 epitopes of Table 1 and 2 (nonoverlapping and overlapping epitopes) are listed in Table 7.4.

TABLE 7.1

Deduced amino acid sequence of Phospholipase A-2 bee venom.

| | |
|---|---|
| 1 | gslfllllst shgwqirdri gdneleerii ypgtlwcghg nkssgpnelg |
| 51 | rfkhtdaccr thdmcpdvms ageskhgltn tashtrlscd cddkfydclk |
| 101 | nsadtissyf vgkmyfnlid tkcyklehpv tgcgertegr clhytvdksk |
| 151 | pkvyqwfdlr ky |

TABLE 7.2 predicted MHC Class II-presented epitopes of the major bee venom allergen Phospholipase A-2.

| PEPTIDE | Pos. | Sequence | Score | Ii-Key | SEQ ID NO: |
|---|---|---|---|---|---|
| 7.2.1 | 14 | W Q I R D R I G D | 7.80 | — | 247 |
| 7.2.2 | 4 | F L L L L S T S H | 5.70 | — | 248 |
| 7.2.3 | 110 | F V G K M Y F N L | 5.50 | — | 249 |
| 7.2.4 | 118 | L I D T K C Y K L | 5.30 | — | 250 |
| 7.2.5 | 6 | L L L S T S H G W | 4.80 | — | 251 |
| 7.2.6 | 116 | F N L I D T K C Y | 4.50 | — | 252 |
| 7.2.7 | 5 | L L L L S T S H G | 4.40 | — | 253 |

TABLE 7.2-continued predicted MHC Class II-presented epitopes of the major bee venom allergen Phospholipase A-2.

| PEPTIDE | Pos. | Sequence | Score | Ii-Key | SEQ ID NO: |
|---|---|---|---|---|---|
| 7.2.8 | 52 | F K H T D A C C R | 4.10 | — | 254 |
| 7.2.9 | 124 | Y K L E H P V T G | 4.08 | — | 255 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 7.3

Experimentally defined MHC Class II-presented epitopes of the major bee venom allergen Phospholipase A-2.

| PEPTIDE | Pos. | Sequence | Ii-Key | SEQ ID NO: |
|---|---|---|---|---|
| 7.3.1 | 113 | K M Y F N L I D T K C Y K | — | 256 |

TABLE 7.3-continued

Experimentally defined MHC Class II-presented epitopes of the major bee venom allergen Phospholipase A-2.

| PEPTIDE | Pos. | Sequence | Ii-Key | SEQ ID NO: |
|---|---|---|---|---|
| 7.3.2 | 122 | K C Y K L E H P V T G C G | 4 | 257 |
| 7.3.3 | 109 | Y F V G K M Y F N L I D T | — | 258 |
| 7.3.4 | 141 | C L H Y T V D K S K P K | 10 | 259 |
| 7.3.5 | 73 | E S K H G L T N T A S H T RLSCD | — | 260 |

Pos. is the residue position in the primary sequence of the first amino acid in the antigenic epitope. Sequence is the amino acid sequence of an experimentally determined MHC Class II-presented epitope. Ii-Key is the number of residue positions intervening between an Ii-Key motif and the first residue of the antigenic epitope. The above epitopes were defined by Texier and colleagues and Carballido and colleagues (Texier C. J. Immunol. 2000 164:3177–84; Carballido J. J. Immunol. 1993 150:3582–91).

TABLE 7.4

Ii-Key/PHL A2 hybrids containing some of the MHC Class II-presented PHL A2 epitopes of Table 1 and 2.

| PEPTIDE | Pos. | Sequence | SEQ ID NO: |
|---|---|---|---|
| | | Nonoverlapping epitopes | |
| 7.4.1 | 14 | Ac-LRMK-ava-WQIRDRIGD-$NH_2$ | 261 |
| 7.4.2 | 52 | Ac-LRMK-ava-FKHTDACCR-$NH_2$ | 262 |
| | | Overlapping epitopes | |
| 7.4.3 | 4 | Ac-LRMK-ava-FLLLLSTSH-$NH_2$ | 263 |
| 7.4.4 | 5 | Ac-LRMK-ava-LLLLSTSHG-$NH_2$ | 264 |
| 7.4.5 | 6 | Ac-LRMK-ava-LLLSTSHGW-$NH_2$ | 265 |
| 7.4.6 | 4/5/6 | Ac-LRMK-ava-FLLLLSTSHGW-$NH_2$ | 266 |
| 7.4.7 | 110 | Ac-LRMK-ava-FVGKMYFNL-$NH_2$ | 267 |
| 7.4.8 | 116 | Ac-LRMK-ava-FNLIDTKCY-$NH_2$ | 268 |
| 7.4.9 | 118 | Ac-LRMK-ava-LIDTKCYKL-$NH_2$ | 269 |
| 7.4.10 | 110/116/118 | Ac-LRMK-ava-FVGKMYFNLIDTKCYKL-$NH_2$ | 270 |

Pos. is the residue position in the primary sequence of the first amino acid in the antigenic epitope. Ii-Key is the number of residue positions intervening between an Ii-Key motif and the first residue of the antigenic epitope.

Example 8

Bla g 5 Glutathione-S-Transferase (GST) Cockroach Antigenic Epitope Hybrids

In another aspect this invention relates to the design and use of Ii-Key/Bla g 5 glutathione-S-transferase (GST) cockroach antigenic epitope hybrids. Sensitization to cockroach allergens is associated with the development of asthma. This antigenic protein was found to induce positive skin test reactions in 70% of patients who are allergic to cockroaches. A 23-kDa allergen, glutathione S-transferase (EC 2.5.1.18; GST) was purified from German cockroach (*Blattella germanica*) by glutathione affinity chromatography (Arruda L K. J Biol. Chem. 1997 272:20907–12). The purified protein and recombinant protein had a high level of IgE antibody binding activity. This GST caused positive immediate skin tests in cockroach-allergic patients using as little as 3 pg of recombinant protein. Bla g 1 and has a molecular structure composed of multiple tandem amino-acid repeats. Two consecutive repeats are not identical but form a duplex that constitutes a basic molecular unit of Bla g 1 (Pomes A. Am J Respir Crit Care Med, 2002 165:391–7). The presence of two repeats was not a requirement for IgE antibody binding (Pomes A. Eur J. Biochem. 2002 269:3086–3092). That fact supports the view that single linear chains of one repeat in the antigen can be found to express IgE binding epitopes. Bla g 2 is one of the most potent cockroach allergens (prevalence of IgE responses of 60 to 80%) and shows homology to the aspartic proteinase family of enzymes. Mutational destruction of the enzymatic activity did not alter allergenicity (Pomes A. Am J Respir Crit Care Med, 2002 165:391–7). Recombinant proteins of cockroach allergens Bla g 2, Bla g 4 and Bla g 5 and mite group 5 allergens were produced in bacterial expression vectors and demonstrated strong immediate skin and serum IgE antibody responses in cockroach-allergic patients (Chapman M D. Int Arch Allergy Immunol. 1997 113:102–4). Each of the recombinant allergens retained biologic activity and the investigators suggested that cocktails of two to four recombinant allergens could be used for diagnostic or therapeutic purposes. No dominant linear IgE-binding epitopes have been reported, but when they become determined, Ii-Key/Bla g MHC Class II epitope/BLA g IgE-recognized hybrid peptides can be designed and tested.

The sequence of cockroach allergen BLA g 5 in Table 8.1 was taken from GenBank 6225491 (Arruda L K. J Biol. Chem. 1997 272:20907–12). Predicted MHC Class II epitopes of cockroach allergen Bla g 5 are presented in Table 8.2. Experimentally defined MHC Class II epitopes of Bla g 5 (Papouchado B G. Tissue Antigens. 2000 55:303–11) are presented in Table 8.3.

TABLE 8.1

Deduced amino acid sequence of cockroach allergen Bla g 5. (SEQ ID NO:271)

| | |
|---|---|
| 1 | mapsykltyc pvkalgepir fllsygekdf edyrfqegdw pnlkpsmpfg |
| 51 | ktpvleidgk qthqsvaisr ylgkqfglsg kddwenleid mivdtisdfr |
| 151 | aaianyhyda denskqkkwd plkketipyy tkkfdevvka nggylaagkl |
| 201 | twadfyfvai ldylnhmake dlvanqpnlk alrekvlglp aikawvakrp |
| 251 | ptdl |

TABLE 8.2

Predicted MHC Class II-presented epitopes of cockroach allergen Bla g 5.

| PEPTIDE NO: | Pos. | Sequence 1 2 3 4 5 6 7 8 9 | Score | Ii-Key | SEQ ID NO: |
|---|---|---|---|---|---|
| 8.2.1 | 49 | F G K T P V L E I | 7.60 | — | 272 |

TABLE 8.2-continued

Predicted MHC Class II-presented epitopes of cockroach allergen Bla g 5.

| PEPTIDE NO: | Pos. | Sequence 1 2 3 4 5 6 7 8 9 | Score | Ii-Key | SEQ ID NO: |
|---|---|---|---|---|---|
| 8.2.2 | 245 | W V A K R P P T D | 5.85 | — | 273 |
| 8.2.3 | 91 | M I V D T I S D F | 5.57 | — | 274 |
| 8.2.4 | 205 | F Y F V A I L D Y | 5.40 | — | 275 |
| 8.2.5 | 19 | I R F L L S Y G E | 5.10 | 2 | 276 |
| 8.2.6 | 55 | L E I D G K Q T H | 4.60 | 7 | 277 |
| 8.2.7 | 99 | F R A A I A N Y H | 4.20 | — | 278 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 8.3

Experimentally defined MHC Class II epitopes of Bla g 5.

| PEPTIDE NO: | Pos. | Sequence | Ii-Key | SEQ ID NO: |
|---|---|---|---|---|
| 8.3.1 | 92 | IVDTISDFRAAIANYHYDAD | — | 279 |
| 8.3.1 | 212 | DYLNHMAKEDLVANQPNLKA | — | 280 |

Pos. is the residue position in the primary sequence of the first amino acid in the antigenic epitope. Sequence is the amino acid sequence of an experimentally determined MHC Class II-presented epitope. Ii-Key is the number of residue positions intervening between an Ii-Key motif and the first residue of the antigenic epitope.

Example 9

Ii-Key/CEA Antigenic Epitope Hybrids

Carcinoembryonic antigen (CEA) is a tumor associated antigen (TAA) that is expressed in tumors including colon, breast and pancreas. The protein and the cDNA have been used for therapeutic tumor vaccines. A recombinant vaccinia-CEA vaccine has been used to generation cytotoxic T cells specific for human carcinoembryonic antigen epitopes (Tsang K Y. J Natl Cancer Inst. 1995 87:982–90). Ii-Key hybrids can be used to develop T helper cell responses to this tumor-associated antigen prior to DNA vaccines of any form. Thus, the clinical value of such a recombinant vaccinia-CEA construct can be enhanced substantially with the products and methods of this invention, as described in this disclosure. Additional CEA vaccination procedures, in which Ii-Key/CEA antigenic epitope hybrids can be applied, are presented below.

Reisfeld and colleagues demonstrated that an oral DNA vaccine against human CEA prevented growth and dissemination of Lewis lung carcinoma in CEA transgenic mice (Niethammer A G. Vaccine 2001 20:421–9). A DNA vaccine encoding human CEA broke peripheral T-cell tolerance toward this antigen expressed by Lewis lung carcinoma stably transduced with CEA in C57BL/6J mice transgenic for CEA. The vaccine was delivered by oral gavage with an attenuated strain of *Salmonella typhimurium* (SL7207), and boosted with an antibody-IL2 fusion protein. Both CTL and antigen-presenting dendritic cells were activated as indicated by a decisive increase in their respective activation markers CD2, CD25, CD28 as well as CD48 and CD80.

Stevenson and colleagues demonstrated that DNA fusion vaccine including MHC Class II epitopes of tetanus toxoid along with a tumor antigen of interest (here CEA) induced cytotoxic T cell responses against defined peptides. Fusion of the fragment C of tetanus toxin to a CEA sequence promoted antibody and CD4+ T cell responses against tested B cell tumors. Using only the first domain of tetanus toxoid, which contains a "universal" helper epitope, followed by two known CTL-recognized epitopes of CEA, they found strong CTL responses to each CTL-recognized peptide to be induced by the engineered construct.

Diagnostic assays with Ii-Key/antigenic epitope hybrids can be used to monitor therapy and predict outcomes in patients with CEA-positive tumors, as indicated from the following study. PBMC from two CEA-based vaccine clinical trials were analyzed for T cell responses to the same CEA peptide and to an influenza (Flu) control peptide (Arlen P. Cancer Immunol Immunother. 2000 49:517–29). The first trial consisted of three monthly vaccinations of CEA peptide (designated PPP) in adjuvant. The second trial consisted of cohorts receiving three monthly vaccinations of avipox-CEA recombinant (designated AAA) or cohorts receiving a primary vaccination with recombinant vaccinia-CEA followed by two monthly vaccinations with avipox-CEA (designated VAA). Few, if any, CEA-specific T cell responses were seen in patients receiving PPP vaccinations, while the majority of patients receiving the poxvirus CEA recombinants demonstrated increases in CEA-specific T cell responses and no increases in Flu-specific responses. CEA-specific IgG responses developed in patients following recombinant CEA poxvirus vaccinations. T cell responses to the CEA peptide were significantly increased after immunization with the recombinant poxvirus vaccine, as compared with the peptide vaccine (p=0.028). Clearly poxvirus recombinant-based vaccines are more potent in initiating tumor-antigen-specific T cell responses than are peptide vaccines. Their activity can be further enhanced, by prior vaccination with Ii-Key/CEA antigenic epitope hybrids.

In the case of tumor antigens such as CEA, Ii-Key/MHC Class II-presented antigenic epitope hybrids create T helper cell responses that augment the development of immune responses to CEA MHC Class I epitopes, for example through dendritic cell licensing. Such CTL activation by MHC Class I epitopes can be generated also by incorporating such MHC Class I epitopes in an Ii-Key MHC Class II-presented hybrids. Several MHC Class I epitope of CEA have been experimentally determined (Kawashima I. Hum Immunol. 1998 59:1–14; Nukaya I. Int J Cancer. 1999 80:92–7; Table 5). Such peptides have been discovered by various techniques. Nested deletions of the cDNA for the antigen of interest lead to protein products, which can be assayed for stimulation of CD8+ cells lines, which recognize the antigen. Given various cell lines recognizing individual epitopes, the localization of T cell epitopes can be approximated within the primary sequence, by analyzing the reactions of each T cell clone to the nested deletion cDNA constructs. Then a library of overlapping peptides through biologically active target regions can be assayed to define exactly the individual determinants. The binding of such peptides to immunopurified MHC Class I molecules can also be assayed, for example by inhibition of binding of a radiolabeled standard peptide to MHC molecules (Kawashima I. Hum Immunol. 1998 59:1–14). The MHC Class I molecules can be immunopurified and bound into microtiter plates, in which the various components of the assay are added sequentially, with appropriate washings. Alternatively the MHC Class I molecules can be detergent-solubilized without purification, for example from a microsomal membrane preparation of a cultured lymphoblastoid cell line, and the complexes separated in a gel filtration column, with the bound radioactive peptide being separated in the protein complexes from the unbound, free peptide. In the work of Kawashima, initial studies were performed with HLA-A2.1 molecules. The highly reactive peptide 9.5.2, which induced vigorous anti-tumor CTL responses, also bound tightly to other common HLA alleles of the A2 supertype (A2.2, A2.3, A2.6 and A6802), thus demonstrating a potential in providing broad and not ethnically biased population coverage. CTL lines were used to identify peptides 9.5.4 and 9.5.6, which elicited CTL lines that lysed tumor cells expressing HLA-A24 and CEA. The cytotoxicity to tumor cells by the CTL lines was antigen-specific since it was inhibited by peptide-pulsed cold target cells as well as by monoclonal antibodies to MHC Class I and CD3 molecules. Similar methods can be used to characterize the biological responses induced by Ii-Key/MHC Class II epitope/MHC Class I epitope hybrids of this disclosure.

Alternatively, such peptides are identified with algorithms for the prediction of MHC Class I and Class II T cell-recognized epitopes (Lu J. Cancer Res. 2000 60:5223–7). These computer-based predictive algorithms, which are available on the Internet (Parker K C. J. Immunol. 1992 149:3580–7; Rammensee H G. Immunogenetics. 1995 41:178–228), were used to identify HL4-B7-restricted CTL epitopes for carcinoembryonic antigen (CEA). Of three candidate peptides, CEA9(632) (IPQQHTQVL) (SEQ ID NO: 281) induced primary CTL responses in lymphocytes from HLA-B7+normal blood donors when dendritic cells were used as antigen-presenting cells. These CTLs were efficient in killing tumor cells that expressed HLA-B7 and produced CEA.

Cell lines reflecting the natural T-cell response against MHC Class I epitopes of epithelial cell adhesion molecule, Her-2/neu, and carcinoembryonic antigen in patients with colorectal cancer have been used to identify the respective antigenic epitopes (Nagorsen D. Cancer Res. 2000 60:4850–4). Antigens of epithelial cell adhesion molecule (Ep-CAM), her-2/neu, and CEA were potential targets in antigen-specific vaccination-based cancer therapy. The investigators tested whether a natural specific T-cell response against these antigens already exists in patients with colorectal carcinoma. The IFN-gamma ELISPOT assay was used to detect circulating TAA-reactive T cells directly ex vivo in unstimulated peripheral blood mononuclear cells. They determined that seven of 22 patients, but none of the 8 healthy subjects, had T cells specifically secreting IFN-gamma in response to antigen peptides (n=4, Ep-CAM; n=5, her-2/neu; n=6, CEA). T-cell responses occurred only in patients with metastatic disease (Dukes' stages C and D). The results of this study indicate that natural T-cell responses against tumor antigens occur in approximately one-half of colorectal carcinoma patients with involvement of lymph nodes or distant metastases, but not in colorectal carcinoma patients with disease confined to the bowel tract. Ii-Key/antigenic epitope hybrids containing MHC Class II epitopes can be used to vaccinate patients with localized and metastatic disease against their tumors.

The amino acid sequence of CEA was obtained from GenBank as 11386171 carcinoembryonic antigen-related cell adhesion molecule 5; carcinoembryonic antigen [*Homo sapiens*] (Table 1). The primary sequence of human carcinoembryonic antigen (CEA) was deduced from cDNA sequence (Oikawa S. Biochem Biophys Res Commun. 1987 142:511–8). The carcinoembryonic antigen (CEA) contains multiple immunoglobulin-like domains (Oikawa S. Biochem Biophys Res Commun. 1987 144:634–42). Predicted MHC Class II-presented epitopes of CEA are listed in Table 9.2. Designed Ii-Key/CEA hybrids containing some of the MHC Class II-presented epitopes of CEA in Table 9.2 are listed in Table 9.3. Predicted MHC Class I-presented CEA epitopes are listed in Table 9.4. Experimentally defined MHC Class I epitopes of CEA are listed in Table 9.5. Ii-Key/MHC Class II/MHC Class I CEA hybrids are listed in Table 9.6.

TABLE 9.1

(SEQ ID NO: 282)
Deduced amino acid sequence of CEA.

| | | | | | |
|---|---|---|---|---|---|
| 1 | mespsapphr | wcipwqrlll | taslltfwnp | pttaklties | tpfnvaegke |
| 51 | vlllvhnlpq | hlfgyswykg | ervdgnrqii | gyvigtqqat | pgpaysgrei |
| 101 | iypnaslliq | niiqndtgfy | tlhviksdlv | neeatgqfrv | ypelpkpsis |
| 151 | snnskpvedk | davaftcepe | tqdatylwwv | nnqslpvspr | lqlsngnrtl |
| 201 | tlfnvtrndt | asykcetqnp | vsarrsdsvi | lnvlygpdap | tisplntsyr |
| 251 | sgenlnlsch | aasnppaqys | wfvngtfqqs | tqelfipnit | vnnsgsytcq |
| 301 | ahnsdtglnr | ttvttitvya | eppkpfitsn | nsnpvededa | valtcepeiq |
| 351 | nttylwwvnn | qslpvsprlq | lsndnrtltl | lsvtrndvgp | yecgiqnels |
| 401 | vdhsdpviln | vlygpddpti | spsytyyrpg | vnlslschaa | snppaqyswl |
| 451 | idgniqqhtq | elfisnitek | nsglytcqan | nsasghsrtt | vktitvsael |

TABLE 9.1-continued

| (SEQ ID NO: 282) Deduced amino acid sequence of CEA. |
|---|
| 501 pkpsissnns kpvedkdava ftcepeaqnt tylwwvngqs lpvsprlqls |
| 551 ngnrtltlfn vtrndarayv cgiqnsvsan rsdpvtldvl ygpdtpiisp |
| 601 pdssylsgan lnlschsasn pspqyswrin gipqqhtqvl fiakitpnnn |
| 651 gtyacfvsnl atgrnnsivk sitvsasgts pglsagatvg imigvlvgva |
| 701 li |

TABLE 9.2

Predicted MHC Class II-presented epitopes of CEA.

| PEPTIDE | Pos. | Sequence | Score | Ii-Key | SEQ ID NO: |
|---|---|---|---|---|---|
| 9.2.1 | 427 | YRPGVNLSL | 6.40 | — | 283 |
| 9.2.2 | 535 | WVNGQSLPV | 6.30 | — | 284 |
| 9.2.3 | 179<br>357 | WVNNQSLPV | 5.50<br>6.30 | — | 285 |
| 9.2.4 | 627 | WRINGIPQQ | 5.80 | — | 286 |
| 9.2.5 | 249 | YRSGENLNL | 5.50 | — | 287 |
| 9.2.6 | 52 | LLLVHNLPQ | 5.40 | — | 288 |
| 9.2.7 | 449 | WLIDGNIQQ | 5.10<br>5.78 | 12 | 289 |
| 9.2.8 | 591 | YGPDTPIIS | 5.10 | — | 290 |
| 9.2.9 | 119 | FYTLHVIK S | 5.10 | — | 291 |
| 9.2.10 | 79 | IIGYVIGTQ | 5.00 | — | 292 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 9.3

Designed Ii-Key/CEA hybrids containing some of the MHC Class II-presented epitopes of CEA in Table 9.2. A. Non-overlapping epitopes

| PEPTIDE | Pos. | Sequence | SEQ ID NO: |
|---|---|---|---|
| 9.3.1 | 179<br>357<br>535 | Ac-LRMK-ava-WVNNQSLPV-$NH_2$ | 294 |
| 9.3.2 | 427 | Ac-LRMK-ava-YRPGVNLSL-$NH_2$ | 294 |
| 9.3.3 | 627 | Ac-LRMK-ava-WRINGIPQQ-$NH_2$ | 295 |
| 9.3.4 | 249 | Ac-LRMK-ava-YRSGENLNL-$NH_2$ | 296 |

Pos. is the residue position in the primary sequence of the first amino acid in the antigenic epitope. Sequence is the amino acid sequence of a hybrid peptide containing a MHC Class II epitope of Table 9.2. CEA contains seven extracellular domains, which are strikingly homologous to each other. This fact explains the repeated identical epitopes that starts at positions 178, 356, and 534 in this Table (Oikawa S. Biochem Biophys Res Commun. 187 144:634–42).

TABLE 9.4

Predicted MHC Class I-presented CEA epitopes.

| PEPTIDE | Pos. | Sequence | Score | SEQ ID NO: |
|---|---|---|---|---|
| 9.4.1 | 61 | HLFGYSWYK | 1350 | 297 |
| 9.4.2 | 425 | TYYRPGVNL | 200 | 298 |
| 9.4.3 | 652 | TYACFVSNL | 200 | 299 |
| 9.4.4 | 691 | IMIGVLVGV | 196 | 300 |
| 9.4.5 | 605 | YLSGANLNL | 98 | 301 |

Pos. is the residue position in the primary sequence of the first amino acid in the antigenic epitope. Sequence is the amino acid sequence of the predicted MHC Class I-presented epitope. Score is the $T_{1/2}$ of disassociation of a peptide containing this subsequence (Tsang K Y. J Natl Cancer Inst. 1995 87:982–90). Peptide 9.3.1 are presented by HLA-A3. Peptides 9.3.2 and 9.3.2 are presented by HLA-A24. Peptides 9.3.4 and 9.3.5 are presented by HLA-A2.1. The MHC Class I-presented epitopes of this Table were predicted with the use of the online program at (http://bimas.dcrt.nih.gov/molbio/hla_bind/).

TABLE 9.5

Experimentally defined MHC Class I epitopes of CEA.

| PEPTIDE | Pos. | Sequence | SEQ ID NO: |
|---|---|---|---|
| 9.5.1 | 691 | IMIGVLVGV | 302 |
| 9.5.2 | 24 | LMTFWNPPV | 303 |
| 9.5.3 | 605 | YLSGANLNL | 304 |
| 9.5.4 | 268 | QYSWFVNGTF | 305 |
| 9.5.5 | 652 | TYACFVSNL | 306 |
| 9.5.6 | 61 | HLFYSWYK | 307 |

Pos. is the residue position in the primary sequence of the first amino acid in the antigenic epitope. Sequence is the amino acid sequence of the experimentally defined MHC Class I-presented epitope. Peptides 9.5.1, 9.5.2, 9.5.3 are presented by HLA-A2.1 and 9.5.6 is presented by HLA-A3 (Kawashima I. Hum Immunol. 1998 59:1–14). Peptides 9.5.4 and 9.5.5 are presented by HLA-A24 (Nukaya I. Int J Cancer. 1999 80:92–7). Peptide 9.5.2 is presented by HLA-A2.1 and it and LLTFWNPPV (SEQ ID NO: 308) are engineered CEA epitopes with respect to the wild type sequence LLTFWNPPT (SEQ ID NO: 309).

TABLE 9.6

Ii-Key/MHC Class II/MHC Class I CEA hybrids.

| PEP-TIDE | Pos. | Sequence | SEQ ID NO: |
|---|---|---|---|
| 9.6.1 | II:179, 357, 535, I:691 | Ac-LRMK-ava-WVNNQSLPV-IMIGVLVGV-NH₂ | 310 |
| 9.6.2 | II:427, I:425 | Ac-LRMK-ava-TYYRPGVNLSL-NH₂ | 311 |
| 9.6.3 | II:249, I:268 | Ac-LRMK-ava-YRSGENLNL-QYSWFVNGTF-NH₂ | 312 |
| 9.6.4 | II:52, I:61 | Ac-LRMK-ava-LLLVHNLPQ-HLFYSWYK-NH₂ | 313 |

Ii-Key/MHC Class II/MHC Class I CEA hybrids. The sequence position of the MHC Class II epitope is indicated: II: residue position of first epitope amino acid, and of the MHC Class I epitope is indicated: I: residue position of first epitope amino acid.

Example 10

Ii-Key/Ca-125 Cancer Antigenic Epitope Hybrids

The ovarian cancer antigen CA-125 is used in immunotherapeutic vaccinations. In one case, vaccination with a mixed vaccine of autogenous and allogeneic breast cancer cells and tumor associated antigens including the breast cancer antigen CA15.3, the carcinoembryonic antigen (CEA) and the ovarian cancer antigen CA125, resulted in immune and clinical responses in breast cancer patients (Jiang X P. Cancer Biother Radiopharm. 2000 15:495–505). The vaccine induced a significant increase in post-vaccination lymphocyte proliferative responses to AUTOC, CA15.3, CEA and CA125 but not ALLOC, compared to pre-vaccination ($p<0.05$, $p<0.01$, $p<0.05$, $p<0.01$ and $p>0.05$, respectively, a paired t Test).

The amino acid sequence of CA125 ovarian cancer antigen mucin 16 [*Homo sa* . . . [gi:14971110] as listed in Genebank is presented in Table 10.1. Predicted MHC Class II-presented epitopes of CA125, ovarian cancer antigen are listed in Table 10.2. Ii-Key/CA125 hybrids containing some of the MHC Class II-presented epitopes of Table 10.2 are listed in Table 10.3. Predicted MHC Class I-presented epitopes of CA 125 are listed in Table 10.4. Ii-Key/MHC II epitope/MHC I epitope hybrids are listed in Table 10.5.

TABLE 10.1

Deduced amino acid sequence of CA125 ovarian cancer antigen (SEQ ID NO: 314)

```
  1 rvdpigpgld rerlywelsq ltnsitelgp ytldrdslyv ngfnpwssvp
 51 ttstpgtstv hlatsgtpss lpghtapvpl lipftlnfti tnlhyeenmq
101 hpgsrkfntt ervlqgllkp lfkstsvgpl ysgcrltllr pekhgaatgv
151 daictlrldp tgpgldrerl ywelsqltns vtelgpytld rdslyvngft
201 hrssvpttsi pgtsavhlet sgtpaslpgh tapgpllvpf tlnftitnlq
251 yeedmrhpgs rkfnttervl qgllkplfks tsvgplysgc rltllrpekr
301 gaatgvdtic thrldplnpg ldreqlywel skltrgiiel gpylldrgsl
351 yvngfthrnf vpitstpgts tvhlgtsetp sslprpivpg pllvpftlnf
401 titnlqyeea mrhpgsrkfn ttervlqgll rplfkntsig plysscrltl
451 lrpekdkaat rvdaicthhp dpqspglnre qlywelsqlt hgitelgpyt
501 ldrdslyvdg fthwspiptt stpgtsivnl gtsgippslp ettatgpllv
551 pftlnftitn lqyeenmghp gsrkfnites vlqgllkplf kstsvgplys
601 gcrltllrpe kdgvatrvda icthrpdpki pgldrqqlyw elsqlthsit
651 elgpytldrd slyvngftqr ssvpttstpg tftvqpetse tpsslpgpta
701 tgpvllpftl nftiinlqye edmhrpgsrk fnttervlqg llmplfknts
751 vsslysgcrl tllrpekdga atrvdavcth rpdpkspgld rerlywklsq
801 lthgitelgp ytldrhslyv ngfthqssmt ttrtpdtstm hlatsrtpas
851 lsgpttaspl lvlftinfti tnlryeenmh hpgsrkfntt ervlqgllrp
901 vfkntsvgpl ysgcrltllr pkkdgaatkv daictyrpdp kapgldreql
```

TABLE 10.1-continued

Deduced amino acid sequence of CA125 ovarian cancer antigen (SEQ ID NO: 314)

```
 951 ywelsqlths itelgpytld rdslyvngft qrssvpttsi pgtptvdlgt
1001 agtpvskpgp saaspllvlf tlnftitnlr yeenmqhpgs rkfnttervl
1051 qgllrslfks tsvgplysgc rltllrpekd gtatgvdaic thhpdpkspr
1101 ldreqlywel sqlthnitel gpyaldndsl fvngfthrss vsttstpgtp
1151 tvylgasktp asifgpsaas hllilftlnf titnlryeen mwpgsrkfnt
1201 tervlqgllr plfkntsvgp lysgcrltll rpekdgeatg vdaicthrpd
1251 ptgpgldreq lylelsqlth sitelgpytl drdslyvngf thrssvptts
1301 tgvvseepft lnftinnlry madmgqpgsl kfnitdnvmq hllsplfqrs
1351 slgarytgcr vialrsvkng aetrvdllct ylqplsgpgl pikqvfhels
1401 qqthgitrlg pysldkdsly lngynepgpd eppttpkpat tflpplseat
1451 tamgyhlktl tlnftisnlq yspdmgkgsa tfnstegvlq hllrplfqks
1501 smgpfylgcq lislrpekdg aatgvdttct yhpdpvgpgl diqqlywels
1551 qlthgvtqlg fyvldrdslf ingyapqnls irgeyqinfh ivnwnlsnpd
1601 ptsseyitll rdiqdkvttl ykgsqlhdtf rfclvtnltm dsvlvtvkal
1651 fssnldpslv eqvfldktln asfhwlgsty qlvdihvtem essvyqptss
1701 sstqhfypnf titnlpysqd kaqpgttnyq rnkrniedal nqlfrnssik
1751 syfsdcqvst frsvpnrhht gvdslcnfsp larrvdrvai yeeflrmtrn
1801 gtqlqnftld rssvlvdgys pnrnepltgn adlpfwavil iglagllgli
1851 tclicgvlvt trrrkkegey nvqqqcpgyy qshldledlq
```

TABLE 10.2

Predicted MHC Class II-presented epitopes of CA125, ovarian cancer antigen.

| PEPTIDE | Pos. | Sequence | Score | Ii-Key | SEQ ID NO: |
|---|---|---|---|---|---|
| 10.2.1 | 1630 | FRFCLVTNL | 7.40 | 9 | 315 |
| 10.2.2 | 1018 | VLFTLNFTI | 7.10 | – | 316 |
| 10.2.3 | 1174 | ILFTLNFTI | 7.10 | – | 317 |
| 10.2.4 | 156 | LRLDPTGPG | 6.80 | – | 318 |
| 10.2.5 | 1017 | LVLFTLNFT | 6.20 | – | 319 |
| 10.2.6 | 861 | LVLFTINFT | 6.05 | – | 320 |
| 10.2.7 | 527 | IVNLGTSGI | 5.70 | – | 321 |
| 10.2.8 | 1318 | LRYMADMGQ | 5.70 | – | 322 |
| 10.2.9 | 1029 | LRYEENMQH | 5.68 | – | 323 |
| 10.2.10 | 873 | LRYEENMHH | 5.68 | – | 324 |
| 10.2.11 | 1663 | VFLDKTLNA | 5.60 | 10 | 325 |
| 10.2.12 | 1172 | LLILFTLNF | 5.60 | – | 326 |
| 10.2.13 | 936 | YRPDPKSPG | 5.57 | 2 | 327 |
| 10.2.14 | 393 | LVPFTLNFT | 5.50 | 3 | 328 |
| 10.2.15 | 430 | LRPLFKNTS | 5.40 | – | 329 |
| 10.2.16 | 1185 | LRYEENMWP | 5.30 | 9 | 330 |
| 10.2.17 | 1634 | LVTNLTMDS | 5.30 | – | 331 |
| 10.2.18 | 360 | FVPITSTPG | 5.20 | 11 | 332 |
| 10.2.19 | 1209 | LRPLFKNTS | 5.10 | – | 333 |
| 10.2.20 | 898 | LRPVFKNTS | 5.10 | – | 334 |
| 10.2.21 | 1531 | YHPDPVGPG | 5.10 | – | 335 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope. Because CA 125/MUC 16 is characterized by nine partially conserved tandem repeats (156 amino acids each) in an N-terminal region, similar predicted epitopes have different starting positions (e.g., start position 1017, 1173, 860, or 897, 1208, or 1184, 872, 1028).

TABLE 10.3

Ii-Key/CA125 hybrids containing some of the MHC Class II-presented epitopes of Table 10.2.

| PEPTIDE | Pos. | Sequence | SEQ ID NO: |
|---|---|---|---|
| A. Conserved tandem-repeats epitopes | | | |
| 10.3.1 | 1017 | Ac-LRMK-ava-VLFTLNFTI-$NH_2$ | 336 |
| 10.3.2 | 1173 | Ac-LRMK-ava-ILFTLNFTI-$NH_2$ | 337 |
| 10.3.3 | 860 | Ac-LRMK-ava-LVLFTINFT-$NH_2$ | 338 |
| 10.3.4 | 1028 | Ac-LRMK-ava-LRYEENMQH-$NH_2$ | 339 |
| 10.3.5 | 872 | Ac-LRMK-ava-LRYEENMHH-$NH_2$ | 340 |
| 10.3.6 | 1184 | Ac-LRMK-ava-LRYEENMWP-$NH_2$ | 341 |
| B. Overlapping MHC II epitopes | | | |
| 10.3.7 | 1629 | Ac-LRMK-ava-FRFCLVTNL-$NH_2$ | 342 |
| 10.3.8 | 1633 | Ac-LRMK-ava-LVTNLTMDS-$NH_2$ | 343 |
| 10.3.9 | 1629/ 1633 | Ac-LRMK-ava-FRFCLVTNLTMDS-$NH_2$ | 344 |

Pos. is the residue position in the primary sequence of the first amino acid in the antigenic epitope. Sequence is the amino acid sequence of a hybrid peptide containing a MHC Class II epitope of Table 10.2.

TABLE 10.4

Predicted MHC Class I-presented epitopes of CA 125.

| PEPTIDE | Pos. | Sequence | Score | SEQ ID NO: |
|---|---|---|---|---|
| 10.4.1 | 1675 | WLGSTYQLV | 478 | 345 |
| 10.4.2 | 1018 | VLFTLNFTI | 381 | 346 |
| 10.4.3 | 1174 | ILFTLNFTI | 381 | 347 |
| 10.4.4 | 862 | VLFTINFTI | 381 | 348 |
| 10.4.5 | 344 | LLDRGSLYV | 260 | 349 |
| 10.4.6 | 1506 | YLGCQLISL | 226 | 350 |
| 10.4.7 | 1668 | TLNASFHWL | 223 | 351 |
| 10.4.8 | 1555 | GVTQLGFYV | 194 | 352 |
| 10.4.9 | 1845 | GLLGLITCL | 182 | 353 |
| 10.4.10 | 32 | KLTRGIIEL | 172 | 354 |

Pos. is the residue position in the primary sequence of the first amino acid in the antigenic epitope. Sequence is the amino acid sequence of the predicted HLA-A2.1-resented epitope. Score is the $T_{1/2}$ of disassociation of a peptide containing this subsequence (Tsang K Y. J Natl Cancer Inst. 1995 87:982–90). The MHC Class I-presented epitopes of this Table were predicted with the use of the online program at (http://bimas.dcrt.nih.gov/molbio/hla_bind/).

TABLE 10.5

Ii-Key/MHC II epitope/MHC I epitope hybrids. Ii-Key/MHC Class

| PEPTIDE | Pos. | Sequence | SEQ ID NO: |
|---|---|---|---|
| 10.5.1 | 1630 | Ac-LRMK-ava-FRFCLVTNL-$NH_2$ | 355 |
| 10.5.2 | II:392 I:394, 238, 82, 550 | Ac-LRMK-ava-LVPFTLNFTI-$NH_2$ | 356 |

Ii-Key/MHC Class II/MHC Class I CEA hybrids. The sequence position of the MHC Class II epitope is indicated: II: residue position of first epitope amino acid, and of the MHC Class I epitope is indicated: I: residue position of first epitope amino acid. In peptide 10.5.1 the MHC Class II-predicted and the MHC Class I-predicted epitopes overlap precisely. In peptide 10.5.2 an MHC Class-predicted epitope starting at residue position 392 overlaps with the sequence of a MHC Class I-predicted epitope which starts (and is repeated at) residue positions 394, 238, 82, 550.

Example 11

Ii-Key/PSA Antigenic Epitope Hybrids

The identification of T cell specific epitopes within the coding sequence of PSA has led to the development of various vaccine strategies that target PSA in an attempt to treat established prostate cancer (Kaufman H L. Expert Opin Biol Ther. 2002 2:395–408). These strategies have included HLA-restricted PSA peptides, dendritic cells pulsed with PSA, recombinant viruses expressing PSA and combinations with different cytokines and cell interaction molecules. Many of these methods are enhanced by use of the products and methods of this disclosure.

PSA-recombinant pox vaccine constructs are immunogenic and induce antibody responses to a multitude of surface antigens on prostate tumor cell lines by epitope or determinant spreading after stimulation of the immune system by PSA immunization (Cavacini L A. Clin Cancer Res. 2002 8:368–73). Determinant spreading in the antibody responses to prostate cell surface antigens was observed in patients immunized with prostate-specific antigen encoded by recombinant pox vectors. The serum IgG response to cell surface antigens expressed on LNCAP (PSA-positive) and PC-3 (PSA-negative) prostate cancer cell lines were analyzed in individuals with advanced disease receiving vaccinia- or fowlpox-expressed PSA (v-PSA or f-PSA, respectively). Sera from all seven patients in a Phase I study of v-PSA, collected prior to the third immunization, reacted with both prostate tumor cell lines. The majority of individuals (n=12) in a Phase II trial of v-PSA and f-PSA developed sustainable antibody responses to cell surface antigens on the prostate tumor cell lines. The magnitude and kinetics of these responses depended on the immunization schedule.

Whiteside and colleagues demonstrated recovery of zeta-chain expression and changes in spontaneous IL-10 production after PSA-based vaccines in patients with prostate cancer (Meidenbauer N. Br J Cancer. 2002 86:168–78). In order to determine a mechanism by which circulating T lymphocytes of patients with prostate cancer have been reported to have functional deficits, including low or absent zeta-chain expression, 10 patients treated with recombinant human prostate specific antigen plus GM-CSF and eight others receiving PSA plus oil emulsion were evaluated. Prior to therapy, the patients had significantly lower zeta-chain expression in circulating CD3+ cells and a higher percentage of zeta-chain negative CD3+ and CD4+ cells than normal donors. The patients' peripheral blood mononuclear cells spontaneously produced more IL-10 ex vivo than those of normal controls. After vaccination, recovery of zeta-chain expression was observed in 50% of patients in both clinical trials. Also, spontaneous IL-10 secretion by peripheral blood mononuclear cells decreased following immunotherapy in patients treated with PSA and GM-CSF. Such therapies will be greatly augmented by products and methods of this disclosure.

Mann and colleagues demonstrated enhanced CD4+ and CD8+ cell responses after exposure to PSA alone, PSA targeted to the mannose receptor (mannosylated PSA (PSA-m)), or PSA targeted to Fc receptors by combining PSA with an anti-PSA antibody (AR47.47) (Berlyn K A. Clin Immunol. 2001 101:276–83). PSA and PSA-m are processed primarily through pathways that favor MHC Class II presentation, while the PSA/anti-PSA immune complexes are processed through both Class I and Class II pathways in monocyte-derived dendritic cells.

Gilboa and colleagues demonstrated that autologous dendritic cells transfected with PSA RNA stimulate CTL responses against metastatic prostate tumors (Heiser A. J Clin Invest. 2002 109:409–17). Autologous dendritic cells transfected with mRNA encoding prostate-specific antigen (PSA) stimulate potent, T cell-mediated antitumor immune responses in vitro. A phase I trial evaluated this strategy for safety, feasibility, and efficacy to induce T cell responses against the PSA in patients with metastatic prostate cancer. In 13 subjects, escalating doses of PSA mRNA-transfected dendritic cells were administered with no evidence of dose-limiting toxicity or adverse effects, including autoimmunity. Induction of PSA-specific T cell responses was consistently detected in all patients, suggesting in vivo bioactivity of the vaccine. Vaccination was further associated with a significant decrease in the log slope of serum PSA levels in six of seven subjects.

Schlom and colleagues characterized an agonist epitope designated PSA-3A ("A" for agonist) of the PSA-3 CTL epitope which demonstrated enhanced binding to the HLA-A2 allele and enhanced stability of the peptide-MHC complex (Terasawa H. Clin Cancer Res. 2002 8:41–53). T-cell lines generated with either the PSA-3 or the PSA-3A peptide showed higher levels of lysis of targets pulsed with the PSA-3A peptide than those targets pulsed with the PSA-3 peptide. T cells stimulated with dendritic cells (dendritic cells) pulsed with PSA-3A peptide produced higher levels of IFN-gamma than did dendritic cells pulsed with PSA-3 peptide. Dendritic cells infected with a recombinant vaccinia virus containing the agonist amino acid change within the entire PSA gene (designated rV-PSA-3A) were more effective than dendritic cells infected with the rV-PSA vector in enhancing IFN-gamma production by T cells. Finally, the PSA-3A agonist was shown to induce higher levels of T-cell activation, compared with the PSA-3 peptide, in an in vivo model using HLA-A2.1/K(b) transgenic mice. These studies thus demonstrated the potential use of the PSA-3A agonist epitope in both peptide- and vector-mediated immunotherapy protocols for prostate cancer. Such results can be bettered with the products and methods of this disclosure.

Recombinant PSA proteins incorporating 6xHis (SEQ ID NO: 357) residues were synthesized for magnetic bead attachment allowing antigen isolation and delivery to APC for processing and presentation (Turner M J. J Immunol Meth. 1998 256:107–19). PSA deletion constructs were generated by amplifying 3' deletions of PSA using a constant 5' primer and five individual 3' primers starting at 736 bp, 610 bp, 505 bp, and 394 bp. The recombinant PSA proteins encoded 261, 231, 189, 154 and 117 amino acids. PSA-specific Class I- and II-restricted T cell hybridomas were generated by fusing Thy-1+ tumor infiltrating lymphocytes (TIL) isolated from BALB/c mice challenged with Line 1/PSA/IL-2 tumors to the T cell fusion partner BWZ.36. MHC Class I (PSA 188–197) and Class II (PSA 238–253) T cell epitopes were identified.

The amino acid sequence of prostate specific antigen (PSA) as obtained from GenBank 45021731 kallikrein 3 is presented in Table 11.1. A cDNA vaccine for this antigen is available (Kim J J. Oncogene. 1998 17:3125–35). Predicted MHC Class II-presented epitopes of PSA are listed in Table 11.2. Experimentally defined MHC Class II-presented epitopes of PSA are listed in Table 11.3. Ii-Key/PSA hybrids containing some of the MHC Class II-presented epitopes of Tables 11.2 and 11.3 are listed in Table 11.4. Predicted MHC Class I-presented epitopes of PSA are listed in Table 11.5. Experimentally defined MHC Class I-presented epitopes of PSA are listed in Table 11.6. Ii-Key/PSA MHC II-presented epitope/PSA MHC I-presented epitope hybrids are listed in Table 11.7.

TABLE 11.1

| (SEQ ID NO: 358) Deduced amino acid sequence of PSA. |
|---|
| 1 mwvpvvfltl svtwigaapl ilsrivggwe cekhsqpwqv lvasrgravc |
| 51 ggvlvhpqwv ltaahcirnk svillgrhsl fhpedtgqvf qvshsfphpl |
| 101 ydmsllknrf lrpgddsshd lmllrlsepa eltdavkvmd lptqepalgt |
| 151 tcyasgwgsi epeefltpkk lqcvdlhvis ndvcaqvhpq kvtkfmlcag |
| 201 rwtggkstcs gdsggplvcn gvlggitswg sepcalperp slytkvvhyr |
| 251 kwikdtivan p |

TABLE 11.2

Predicted MHC Class II-presented epitopes of PSA.

| PEPTIDE | Pos. | Sequence | Score | Ii-Key | SEQ ID NO: |
|---|---|---|---|---|---|
| 11.2.1 | 59 | WVLTAAHCI | 8.80 | — | 359 |
| 11.2.2 | 2 | WVPVVFLTL | 8.10 | — | 360 |
| 11.2.3 | 124 | LRLSEPAEL | 6.60 | — | 361 |
| 11.2.4 | 67 | IRNKSVILL | 5.40 | 8 | 362 |
| 11.2.5 | 74 | LLGRHSLFH | 5.20 | — | 363 |
| 11.2.6 | 72 | VILLGRHSL | 4.70 | — | 364 |
| 11.2.7 | 223 | LQGITSWGS | 4.58 | — | 365 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 11.3

Experimentally defined MHC Class II-presented epitopes of PSA.

| PEPTIDE | Pos. | Sequence | Ii-Key | SEQ ID NO: |
|---|---|---|---|---|
| 11.3.1 | 238 | ERPSLYTKVVHYRKWI | — | 366 |

Pos. is the residue position in the primary sequence of the first amino acid in the antigenic epitope. Sequence is the amino acid sequence of the experimentally defined MHC Class II-presented epitope. Ii-Key is the number of residue positions intervening between an Ii-Key motif and the first residue of the antigenic epitope. Peptide 11.3.1 was experimentally defined (Turner M J. J Immunol Meth. 2001 256:107–19).

TABLE 11.4

Ii-Key/PSA hybrids containing some of the MHC Class II-presented epitopes of Tables 11.2 and 11.3.

| PEPTIDE | Pos. | Sequence | SEQ ID NO: |
|---|---|---|---|
| | | A. Non-overlapping epitopes | |
| 11.4.1 | 2 | Ac-LRMK-ava-WVPVVFLTL-$NH_2$ | 367 |
| 11.4.2 | 124 | Ac-LRMK-ava-LRLSEPAEL-$NH_2$ | 368 |
| 11.4.3 | 223 | Ac-LRMK-ava-LQGITSWGS-$NH_2$ | 369 |
| | | B. Overlapping epitopes | |
| 11.4.4 | 59 | Ac-LRMK-ava-WVLTAAHCI-$NH_2$ | 370 |
| 11.4.5 | 67 | Ac-LRMK-ava-IRNKSVILL-$NH_2$ | 371 |

TABLE 11.4-continued

Ii-Key/PSA hybrids containing some of the MHC Class II-presented epitopes of Tables 11.2 and 11.3.

| PEPTIDE | Pos. | Sequence | SEQ ID NO: |
|---|---|---|---|
| 11.4.6 | 72 | Ac-LRMK-ava-VILLGRHSL-$NH_2$ | 372 |
| 11.4.7 | 74 | Ac-LRMK-ava-LLGRHSLFH-$NH_2$ | 373 |
| 11.4.8 | 59, 67, 72, 74 | Ac-LRMK-ava-WVLTAAHCIRNKSVILLGRHSLFH-$NH_2$ | 374 |

Pos. is the residue position in the primary sequence of the first amino acid in the antigenic epitope. Sequence is the amino acid sequence of a hybrid peptide containing a MHC Class II epitope of Table 11.2 and 11.3. Peptide 11.4.8 contains several MHC Class II-presented epitopes each beginning at residue positions 59, 67, 72 and 74.

TABLE 11.5

Predicted MHC Class I-presented epitopes of PSA.

| PEPTIDE | Pos. | Sequence | Score | SEQ ID NO: |
|---|---|---|---|---|
| 11.5.1 | 46 | GRAVCGVL | 2000 | 375 |
| 11.5.2 | 67 | IRNKSVILL | 2000 | 376 |
| 11.5.3 | 124 | LRLSEPAEL | 2000 | 377 |
| 11.5.4 | 18 | APLILSRIV | 660 | 378 |
| 11.5.5 | 7 | FLTLSVTWI | 607 | 379 |
| 11.5.6 | 249 | YRKWIKDTI | 600 | 380 |

Pos. is the residue position in the primary sequence of the first amino acid in the antigenic epitope. Sequence is the amino acid sequence of the predicted MHC Class I-presented epitope. The MHC Class I-presented epitopes were predicted with the use of the online program at (http://bimas.dcrt.nih.gov/molbio/hla_bind/). Score is the $T_{1/2}$ of disassociation of a peptide containing this subsequence (Tsang K Y. J Natl Cancer Inst. 1995 87:982–90). Peptides 11.5.1, 11.5.2, 11.5.3 and 11.5.6 are presented optimally by HLA-B*2705. Peptide 11.5.4 is presented best by HLA-B*5102 and Peptide 11.5.5 is presented best by HLA-A*0201.

TABLE 11.6

| Experimentally defined MHC Class I-presented epitopes of PSA. | | | |
|---|---|---|---|
| PEPTIDE | Pos. | Sequence | SEQ ID NO: |
| 11.6.1 | 188 | HPQKVTKFML | 381 |

Pos. is the residue position in the primary sequence of the first amino acid in the antigenic epitope. Sequence is the amino acid sequence of the experimentally defined MHC Class I-presented epitope.

TABLE 11.7

| Ii-Key/PSA MHC II-presented epitope/PSA MHC I-presented epitope hybrids. A Overlapping epitopes | | | |
|---|---|---|---|
| PEPTIDE | Pos. | Sequence | SEQ ID NO: |
| 11.7.1 | 2 | Ac-LRMK-ava-WVPVVFLTLSVTWI-$NH_2$ | 382 |
| 11.7.2 | 67 | Ac-LRMK-ava-IRNKSVILL-$NH_2$ | 383 |
| 11.7.3 | 124 | Ac-LRMK-ava-LRLSEPAEL-$NH_2$ | 384 |

Pos. is the residue position in the primary sequence of the first amino acid in the antigenic epitope. Sequence is the amino acid sequence of a hybrid peptide containing a MHC Class II epitope of Table 11.2 and a MHC Class I epitope of Table 11.5. In each of the example the sequences of the predicted MHC Class II and MHC Class I peptides overlap precisely. The residue position of the first amino acid in the predicted MHC Class II epitopes are reported.

Example 12

Ii-Key/Melanocyte Protein Pmel 17 Antigenic Epitope Hybrids

Melanoma is a leading target in the development of therapeutic peptide and DNA vaccines because several specific tumor-associated antigens have been identified, efficiency of vaccinating mice with peptide or DNA vaccines in treating melanoma is proved, and use of comparable vaccines in the clinic has had occasionally promising results. The use of Ii-Key/melanoma antigenic epitope hybrids in melanoma vaccination is considered in respective Examples concerning melanocyte protein Pmel17, gp100, tyrosinase, and tyrosinase-s related protein.

Storkus and colleagues identified several MHC Class II-presented epitopes of gp 100/pmel17 and tyrosinase melanocyte-associated antigens and tested the response of tumor-reactive human CD4+ T cells from various melanoma patients against these peptides (Kierstead L S. Br J Cancer. 2001 85:1738–45). Two known and three novel CD4+ T cell epitopes were found using an IFN-gamma ELISPOT assay. Often freshly-isolated PBMC from HLA-DR4+ melanoma patients that are currently disease-free reveal elevated Th1-type CD4+ T-cells that recognize these peptides. Ii-Key/antigenic epitope hybrids incorporating these epitopes are presented in this Disclosure.

One problem in tumor immunotherapy is the fact that hosts can be tolerized to self proteins of the tumor. Intracutaneous immunization of C57BL/6 mice with a human Pmel17/gp100 DNA vaccine, but not the murine DNA, induces T cell-mediated B16 melanoma protection in vivo (Wagner S N. J Invest Dermatol. 2000 115:1082–7). This state of unresponsiveness to the autoantigen Pmel17/gp100 was broken by immunization with a plasmid DNA construct encoding the autologous form of the molecule. Mice receiving of Pmel17/gp100 DNA mounted an antigen-specific cytotoxic T lymphocyte response to M3 melanoma. Furthermore M3 tumors growing in immunized mice lost expression of this melanoma-associated antigen whereas M3 melanomas appearing in control-vector-treated animals were still Pmel17/gp100-positive. Ii-Key/antigenic epitope hybrids with appropriate immunization schemes and adjuvants can preferentially induce a Th1 or Th2 pattern of response thereby breaking tolerance.

The amino acid sequence of melanocyte protein Pmel17 was obtained at NCBI, >gi|1125063|gb|AAB00386.1| melanocyte protein Pmel 17 [*Homo sapiens*] =>gi|639590|gb|AAC60634.1| gp100 *[Homo sapiens*].

TABLE 12.1

| (SEQ ID NO: 385) Deduced amino acid sequence of gp 100/pmel. |
|---|
| 1 mdlvlkrcll hlavigalla vgatkvprnq dwlgvsrqlr tkawnrqlyp |
| 51 ewteaqrldc wrggqvslkv sndgptliga nasfsialnf pgsqkvlpdg |
| 101 viwvnntii ngsqvwggqp vypqetddac ifpdggpcps gswsqkrsfv |
| 151 yvwktwgqyw qvlggpvsgl sigtgramlg thtmevtvyh rrgsrsyvpl |
| 201 ahsssaftit dqvpfsvsvs qlraldggnk hflrnqpltf alqlhdpsgy |
| 251 laeadlsytw dfgdssgtli sralvvthty lepgpvtaqv vlqaaiplts |
| 301 cgsspvpgtt dghrptaeap nttagqvptt evvgttpgqa ptaepsgtts |
| 351 vqvpttevis tapvqmptae stgmtpekvp vsevmgttla emstpeatgm |
| 401 tpaevsivvl sgttaaqvtt tewvettare lpipepegpd assimstesi |
| 451 tgslgplldg tatlrlvkrq vpldcvlyry gsfsvtldiv ggiesaeilq |

TABLE 12.1-continued (SEQ ID NO: 385)
Deduced amino acid sequence of gp 100/pmel.

```
501 avpsgegdaf eltvscqggl pkeacmeiss pgcqppaqrl cqpvlpspac
551 qlvlhqilkg gsgtyclnvs ladtnslavv stqlimpgqe aglgqvpliv
601 gillvlmavv lasliyrrrl mkqdfsvpql phssshwlrl prifcscpig
651 enspllsgqq v
```

TABLE 12.2

Predicted MHC Class II-presented epitopes of gp 100.

| PEPTIDE | Pos. | Sequence | Score | Ii-Key | SEQ ID NO: |
|---|---|---|---|---|---|
| 12.2.1 | 150 | VYVWKTWGQ | 6.80 | — | 386 |
| 12.2.2 | 423 | WVETTREL | 6.40 | — | 387 |
| 12.2.3 | 277 | LYRYGSFSV | 6.40 | 3 | 388 |
| 12.2.4 | 290 | VVLQAAIPL | 6.40 | 10 | 389 |
| 12.2.5 | 552 | LVLHQILKG | 6.10 | — | 390 |
| 12.2.6 | 596 | VPLIVGILL | 5.80 | — | 391 |
| 12.2.7 | 600 | VGILLVLMA | 5.80 | — | 392 |
| 12.2.8 | 605 | VLMAVVLAS | 5.80 | — | 393 |
| 12.2.9 | 604 | LVLMAVVLA | 5.70 | — | 394 |
| 12.2.10 | 3 | LVLKRCLLH | 5.40–7.20 | — | 395 |
| 12.2.11 | 615 | IYRRRLMKQ | 5.10–5.70 | — | 396 |
| 12.2.12 | 616 | YRRRLMKQD | 4.50 | — | 397 |
| 12.2.13 | 48 | LYPEWTEAQ | 4.30 | 8 | 398 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 12.3

Experimentally defined MHC Class II-presented epitopes of gp100.

| PEPTIDE | Pos. | Sequence | Ii-Key | SEQ ID NO: |
|---|---|---|---|---|
| 12.3.1 | 44 | WNRQLYPEWTEAQRLD | 4 | 399 |
| 12.3.2 | 615 | IYRRRLMKQDFSVPQLPHS | — | 400 |
| 12.3.3 | 576 | SLAVVSTQLIMPG | — | 401 |
| 12.3.4 | 175 | GRAMLGTHTMEVTVY | — | 402 |
| 12.3.5 | 74 | GPTLIGANASFSIALN | — | 403 |

Pos. is the residue position in the primary sequence of the first amino acid in the antigenic epitope. Sequence is the amino acid sequence of the experimentally defined MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope. DR*0401 best presented peptide 12.3.1 (Storkus W. Forum (Genova). 2000 10:256–70) and peptide 12.3.2 (Kierstead L. Brit J Cancer. 2001 85:1738–45). The remaining peptides of this Table were identified by Kobayashi H. (Cancer Res. 2001 61:7577–84).

TABLE 12.4

Ii-Key/gp 100 hybrids containing some of the MHC Class II-presented epitopes of Table 12.2 and 12.3.

| PEPTIDE | Pos. | Sequence | SEQ ID NO: |
|---|---|---|---|
| A. Non-overlapping epitopes ||||
| 12.4.1 | 615 | Ac-LRMK-ava-IYRRRLMKQDFSVPQLPHS-NH$_2$ | 404 |
| 12.4.2 | 3 | Ac-LRNK-ava-LVLKRCLLH-NH$_2$ | 405 |
| 12.4.3 | 150 | Ac-LRMK-ava-VYVWKTWGQ-NH$_2$ | 406 |
| 12.4.5 | 423 | Ac-LRMK-ava-WVETTAREL-NH$_2$ | 407 |
| 12.4.6 | 477 | Ac-LRMK-ava-LYRYGSFSV-NH$_2$ | 408 |
| B. Overlapping epitopes ||||
| 12.4.7 | 44 | Ac-LRMK-ava-WNRQLYPEWTEAQRLD-NH$_2$ | 409 |
| 12.4.8 | 48 | Ac-LRMK-ava-LYPEWTEAQ-NH$_2$ | 410 |
| 12.4.9 | 44, 48 | Ac-LRMK-ava-WNRQLYPEWTEAQRLD-NH$_2$ | 411 |
| 12.4.10 | 596 | Ac-LRMK-ava-VPLIVGILL-NH$_2$ | 412 |

TABLE 12.4-continued

Ii-Key/gp 100 hybrids containing some of the MHC Class II-presented epitopes of Table 12.2 and 12.3.

| PEPTIDE | Pos. | Sequence | SEQ ID NO: |
|---|---|---|---|
| 12.4.11 | 600 | Ac-LRMK-ava-VGILLVLMA-$NH_2$ | 413 |
| 12.4.12 | 605 | Ac-LRMK-ava-VLMAVVLAS-$NH_2$ | 414 |
| 12.4.13 | 596, 600, 605 | Ac-LRMK-ava-VPLIVGILLVLMAVVLAS-$NH_2$ | 415 |

Pos. is the residue position in the primary sequence of the first amino acid in the antigenic epitope. Sequence is the amino acid sequence of a hybrid peptide containing a MHC Class II epitope of Table 1.2.

TABLE 12.5

Predicted MHC Class I-presented epitopes of gp 100.

| PEPTIDE | Pos. | Sequence | Score | SEQ ID NO: |
|---|---|---|---|---|
| 12.5.1 | 619 | RLMKQDFSV | 1495 | 416 |
| 12.5.2 | 520 | LPKEACMEI | 629 | 417 |
| 12.5.3 | 602 | ILLVLMAVV | 412 | 418 |
| 12.5.4 | 479 | RYGSFSVTL | 400 | 419 |
| 12.5.5 | 154 | KTWGQYWQV | 315 | 420 |
| 12.5.6 | 17 | ALLAVGATK | 45 | 421 |
| 12.5.7 | 614 | LIYRRRLMK | 20 | 422 |

Pos. is the residue position in the primary sequence of the first amino acid in the antigenic epitope. Sequence is the amino acid sequence of the predicted MHC Class I-presented epitope. The MHC Class I-presented epitopes were predicted with the use of the online program at (http://bimas.dcrt.nih.gov/molbio/hla_bind/). Score is the $T_{1/2}$ of disassociation of a peptide containing this subsequence (Tsang K Y. J Natl Cancer Inst. 1995 87:982–90). Peptides 12.5.1, 12.5.3 and 12.5.5 are presented by HLA-A*0201. Peptide 12.5.2 is presented by HLA-B*5101. Peptides 12.5.4 is presented by HLA-A*24. Peptides 12.5.6 and 12.5.7 are presented by HLA-A3.

TABLE 12.6

Experimentally defined MHC Class I-presented epitopes of gp100.

| PEPTIDE | Pos. | Sequence | SEQ ID NO: |
|---|---|---|---|
| 12.6.1 | 280 | YLEPGPVTA | 423 |
| 12.6.2 | 17 | ALLAVGATK | 424 |
| 12.6.3 | 209 | ITDQVPFSV | 425 |
| 12.6.4 | 614 | LIYRRRLMK | 426 |
| 12.6.5 | 619 | RLMKQDFSV | 427 |

TABLE 12.6-continued

Experimentally defined MHC Class I-presented epitopes of gp100.

| PEPTIDE | Pos. | Sequence | SEQ ID NO: |
|---|---|---|---|
| 12.6.6 | 639 | RLPRIFCSC | 428 |
| 12.6.7 | 154 | KTWGQYWQV | 429 |
| 12.6.8 | 177 | AMLGTHTMEV | 430 |
| 12.6.9 | 570 | SLADTNSLAV | 431 |
| 12.6.10 | 70 | VSNDGPTLI | 432 |
| 12.6.11 | 87 | ALNFPGSQK | 433 |

Pos. is the residue position in the primary sequence of the first amino acid in the antigenic epitope. Sequence is the amino acid sequence of the predicted MHC Class I-presented epitope. Peptide 12.6.1 is presented by HLA-A2 (Slingluff C. Clin Cancer Res. 2001 7:3012–24). Peptide 12.6.2 is presented by HLA-A3 (Yamshchikov G. Int j Cancer. 2001 92:703–11). Peptides 12.6.3, 12.6.5, 12.6.6 and 12.6.7 are presented by HLA-A*02012 (Kawakami Y. Proc Natl Acad Sci USA 1998). Peptide 12.6.8 and 12.6.9 are presented by HLA-A*0201 (Tsai V. J. Immunol. 1997 158:1796–802). Peptide 12.6.10 is presented by HLA-Cw8 (Castelli C. J. Immunol. 1999 162:1739–48). Peptide 12.6.11 is presented by HLA-A3 and HLA-A11.

TABLE 12.7

Designed Ii-Key/gp 100 hybrids containing some of the MHC Class I- and Class II-presented epitopes of Tables 4 and 5.

| PEPTIDE | Pos. | Sequence | SEQ ID NO: |
|---|---|---|---|
| | | A. Non-overlapping epitopes | |
| 12.7.1 | II:520, I:552 | Ac-LRMK-ava-LPKEACMEI-LVLHQILKG-$NH_2$ | 434 |
| 12.7.2 | II:17, I:3 | Ac-LRMK-ava-ALLAVGATK-LVLKRCLLH-$NH_2$ | 435 |
| | | B. Overlapping epitopes | |
| 12.7.3 | II:570, I:576 | Ac-LRMK-ava-SLADTNSLAVVSTQLIMPG-$NH_2$ | 436 |
| 12.7.4 | II:177, I: 175 | Ac-LRMK-ava-GRAMLGTHTMEVTVY-$NH_2$ | 437 |
| 12.7.5 | II:70, II87, I:74 | Ac-LRMK-ava-VSNDGPTLIGANASFSIALNFPGSQK-$NH_2$ | 438 |
| 12.7.6 | II:614 (619), I:615 | Ac-LRMK-ava-LIYRRRLMKQDFSVPQLPHS-$NH_2$ | 439 |
| 12.7.7 | II:154, I:150 | Ac-LRMK-ava-VYVKTWGQYWQV-$NH_2$ | 440 |
| 12.7.8 | II:479, I:477 | Ac-LRMK-ava-LYRYGSFSVTL-$NH_2$ | 441 |

Pos. is the residue position in the primary sequence of the first amino acid in the antigenic epitope, with MHC Class II indicated as I:, and MHC Class II indicated as II:. Sequence is the amino acid sequence of a hybrid peptide containing a MHC Class II epitope of Table 1.2. Peptides 12.7.3, 12.7.4 and 12.7.5 have been already proposed (Kabayashi H. Cancer Res. 2001 61:7577–84). Peptide 12.7.6-amino acid sequence of both MHC Class I— and II-presented gp 100 epitopes are experimentally defined and coincide.

Example 13

Ii-Key/Tyrosinase-Related Protein 2 Antigenic Epitope Hybrids

The amino acid sequence of tyrosinase-related protein 2 as given in GenBank gi|731026|sp|P40126|TYR2_HUMAN Dopachrome tautomerase precursor (DT) (DCT) (Dopachrome delta-isomerase) (Tyrosinase-related protein 2) (TRP-2) (TRP2) is presented in Table 13.1. Predicted MHC Class II-presented epitopes of TRP-2 are listed in Table 13.2. Designed Ii-Key/TRP-2 antigenic epitope hybrids containing some of the MHC Class II-presented epitopes of Table 13.2 are listed in Table 13.3. Predicted MHC Class-I presented epitopes of TRP-2 are listed in Table 13.4. Experimentally defined MHC Class I-presented TRP-2 epitopes are listed in Table 13.5. Designed Ii-Key/TRP-2 hybrids containing some of the MHC Class I— and II-presented epitopes of Tables 13.2, 13.3, 13.4 and 13.5 are listed in Table 13.6.

TABLE 13.2-continued

Predicted MHC Class II-presented epitopes of TRP-2.

| PEPTIDE | Pos. | Sequence | Score | Ii-Key | SEQ ID NO: |
|---|---|---|---|---|---|
| 13.2.5 | 272 | LISRNSRFS | 5.70 | — | 447 |
| 13.2.6 | 392 | FVVLHSFTD | 5.50 | — | 448 |
| 13.2.7 | 219 | WHRYHLLCL | 5.40 | — | 449 |
| 13.2.8 | 498 | LRKGYTPLM | 5.30 | — | 450 |
| 13.2.9 | 365 | VMSLHNLVH | 5.20 | — | 451 |
| 13.2.10 | 474 | LVVMGTLVA | 5.10 | — | 452 |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 13.1

Deduced amino acid sequence of melanocyte protein Pmel 17. (SEQ ID NO: 442)

| | |
|---|---|
| 1 | msplwwgfll sclgckilpg aqgqfprvcm tvdslvnkec cprlgaesan |
| 51 | vcgsqggrgq ctevradtrp wsgpyilrnq ddrelwprkf fhrtckctgn |
| 101 | fagyncgdck fgwtgpncer kkppvirqni hslspqereq flgaldlakk |
| 151 | rvhpdyvitt qhwlgllgpn gtqpqfancs vydffvwlhy ysvrdtllgp |
| 201 | grpyraidfs hqgpafvtwh ryhllclerd lqrlignesf alpywnfatg |
| 251 | rnecdvctdq lfgaarpddp tlisrnsrfs swetvcdsld dynhlvtlcn |
| 301 | gtyegllrrn qmgrnsmklp tlkdirdcls lqkfdnppff qnstfsfrna |
| 351 | legfdkadgt ldsqvmslhn lvhsflngtn alphsaandp ifvvlhsftd |
| 401 | aifdewmkrf nppadawpqe lapighnrmy nmvpffppvt neelfltsdq |
| 451 | lgysyaidlp vsveetpgwp ttllvvmgtl valvglfvll aflqyrrlrk |
| 501 | gytplmethl sskryteea |

TABLE 13.2

Predicted MHC Class II-presented epitopes of TRP-2.

| PEPTIDE | Pos. | Sequence | Score | Ii-Key | SEQ ID NO: |
|---|---|---|---|---|---|
| 13.2.1 | 156 | YVITTQHWL | 8.20 | 9 | 443 |
| 13.2.2 | 451 | LGYSYAIDL | 7.60 | — | 444 |
| 13.2.3 | 64 | VRADTRPWSG | 6.60 | — | 445 |
| 13.2.4 | 483 | LVGLFVLLA | 6.10 | — | 446 |

TABLE 13.3

Designed Ii-Key/TRP-2 antigenic epitope hybrids containing some of the MHC Class II-presented epitopes of Table 13.2.

| PEPTIDE | Pos. | Sequence | Score | SEQ ID NO: |
|---|---|---|---|---|
| 13.3.11 | 156 | Ac-LRMK-ava-YVITTQHWL-$NH_2$ | | 453 |
| 13.3.12 | 451 | Ac-LRMK-ava-LGYSYAIDL-$NH_2$ | | 454 |

TABLE 13.3-continued

Designed Ii-Key/TRP-2 antigenic epitope hybrids containing some of the MHC Class II-presented epitopes of Table 13.2.

| PEPTIDE | Pos. | Sequence | Score | SEQ ID NO: |
|---|---|---|---|---|
| 13.3.13 | 64 | Ac-LRMK-ava-VRADTRPSG-$NH_2$ | | 455 |

Pos. is the residue position in the primary sequence of the first amino acid in the antigenic epitope. Sequence is the amino acid sequence of a hybrid peptide containing a MHC Class II epitope of Table 13.2.

TABLE 13.4

Predicted MHC Class-I presented epitopes of TRP 2.

| PEPTIDE | Pos. | Sequence | Score | SEQ ID NO: |
|---|---|---|---|---|
| 13.4.1 | 277 | SRFSSWETV | 3000 | 456 |
| 13.4.2 | 408 | KRFNPPADA | 3000 | 457 |
| 13.4.3 | 325 | IRDCLSLQK | 2000 | 458 |
| 13.4.4 | 150 | KRVHPDYVI | 1800 | 459 |
| 13.4.5 | 427 | NRMYNMVPF | 1000 | 460 |
| 13.4.6 | 485 | GLFVLLAFL | 999 | 461 |
| 13.4.7 | 180 | SVYDFFVWL | 973 | 462 |
| 13.4.8 | 490 | LAFLQYRRL | 665 | 463 |
| 13.4.9 | 431 | NMVPFFPPV | 363 | 464 |
| 13.4.10 | 185 | FVWLHYYSV | 348 | 465 |
| 13.4.11 | 180 | SVYDFFVWL | 504 | 466 |
| 13.4.12 | 199 | GPGRPYRAI | 440 | 467 |
| 13.4.13 | 264 | AARPDDPTL | 360 | 468 |
| 13.4.14 | 353 | GFDKADGTL | 330 | 469 |
| 13.4.15 | 408 | KRFNPPADA | 300 | 470 |
| 13.4.16 | 189 | HYYSVRDTL | 280 | 471 |
| 13.4.17 | 331 | LQKFDNPPF | 240 | 472 |

Pos. is the residue position in the primary sequence of the first amino acid in the antigenic epitope. Sequence is the amino acid sequence of the predicted MHC Class II-presented epitope. The MHC Class I-presented epitopes of Table 9.4 were predicted with the use of the online program at (http://bimas.dcrt.nih.gov/molbio/hla_bind/). Score is the $T_{1/2}$ of disassociation of a peptide containing this subsequence (Tsang K Y. J Natl Cancer Inst. 1995 87:982–90). Peptides 13.4.1, 13.4.2, 13.4.3, 13.4.4 and 13.4.5 are presented by HLA-B*2705. Peptides 13.4.6, 13.4.7, 13.4.9 and 13.4.10 are presented by HLA-A*0201. Peptides 13.4.8 is presented by HLA-B*5102. Peptide 13.4.11 is presented by HLA-A*0205. Peptides 13.4.12 is presented by HLA-B5101 and HLA-B*5102. Peptide 13.4.13 is presented by HLA-B7. Peptides 13.4.14 is presented by Cw*0401. Peptide 13.4.15 is presented by HLA-B*2702. Peptide 13.4.16 is presented by HLA-A24. Peptide 13.4.17 is presented by HLA-B62.

TABLE 13.5

Experimentally defined MHC Class I-presented TRP-2 epitopes.

| PEPTIDE | Pos. | Sequence | SEQ ID NO: |
|---|---|---|---|
| 13.5.1 | 180 | SVYDFFVWL | 473 |
| 13.5.2 | 360 | TLDSQVMSL | 474 |
| 13.5.3 | 288 | SLDDYNHLV | 475 |
| 13.5.4 | 455 | YAIDLPVSV | 476 |

Pos. is the residue position in the primary sequence of the first amino acid in the antigenic epitope. Sequence is the amino acid sequence of the experimentally defined MHC Class I-presented epitope. Peptide 13.5.1 is presented by HLA-A2 (Parkhurst M R. Cancer Res. 1998 58:4895–901). Peptides 13.5.2 and 13.5.3 are presented by HLA-A2.1 (Noppen C. Int J Cancer. 2000 87:241–6). Peptide 13.5.4 is presented by HLA-A2.1 (Harada M. Cancer Res. 2001 61:1089–94).

TABLE 13.6

Designed Ii-Key/TRP-2 hybrids containing some of the MHC Class I and II-presented epitopes of Tables 13.2, 13.3, 13.4 and 13.5.

| PEPTIDE | Pos. | Sequence | SEQ ID NO: |
|---|---|---|---|
| 13.6.1 | I:180; II:156 | Ac-LRMK-ava-YVITTQHWL-SVYDFFVWL-$NH_2$ | 477 |
| 13.6.2 | I:455; II: 451 | Ac-LRMK-ava-LGYSYAIDLPVSV-$NH_2$ | 478 |
| 13.6.3 | I:360; II:365 | Ac-LRMK-ava-TLDSQVMSLHNLVH-$NH_2$ | 479 |

Pos. is the residue position in the primary sequence of the first amino acid in the antigenic epitope. Sequence is the amino acid sequence of a hybrid peptide containing a MHC Class II epitope of Table 13.2 and a MHC Class I epitope of Table 13.4.

Example 14

Ii-Key/Melanoma Tyrosinase Antigenic Epitope Hybrids

Tyrosinase has many advantages as a target antigen for the immunotherapy of patients with melanoma because it is expressed in nearly all melanoma specimens with a high degree of cellular homogeneity, and its distribution in normal tissues is limited to melanocytes. Several MHC Class I-presented epitopes have been identified and used clinically, and MHC Class II-presented epitopes have been discovered. The following summaries of the current state-of-the-art in identification and use of peptide vaccines, DNA vaccines, and dendritic cell charging with peptide preparations (tumor cell lysates) are presented in part to illustrate the value of the products and methods of this Disclosure to improving these procedures.

Rosenberg and colleagues identified a HLA-A2.1-presented restricted melanoma tyrosinase epitope (tyrosinase8–17; CLLWSFQTSA) (SEQ ID NO: 480) (Riley J P. J Immunother. 2001 24:212–20). In this study, the comparative binding to HLA-A2.1 of a series of algorithm-predicted peptides versus that of a standard peptide with an intermediate binding affinity was determined. Twelve peptides with binding affinities within 80% of that of the standard peptide stimulated peripheral blood mononuclear cells (PBMC) in vitro from three HLA-A2.1+ patients with metastatic melanoma. PBMC from 23 HLA-A2.1+ patients were stimulated in vitro with tyrosinase: 8–17. Eleven bulk T-cell cultures demonstrated specific peptide recognition, and six of these also recognized HLA-A2.1+ tyrosinase+ melanoma cells. This epitope can be incorporated in an Ii-Key/MHC Class II-presented epitope/MHC Class I-presented epitope hybrid.

Weber and colleagues found that patients with resected melanoma mounted an immune response against gp100 (209–217)(210M) (IMDQVPSFV) (SEQ ID NO: 481) and tyrosinase(368–376)(370D) (YMDGTMSQV) (SEQ ID NO: 482), emulsified with incomplete Freund's adjuvant (Lee P. J Clin Oncol. 2001 19:3836–47). Patients received peptides/IFA with or without IL-12 (30 ng/kg) to evaluate the toxicities and immune responses. Immunizations were administered every 2 weeks for 8 weeks, then every 4 weeks for 12 weeks, and then once 8 weeks later. Thirty-four of 40 patients developed a positive skin test response to the gp100 peptide but none responded to the tyrosinase peptide. Immune responses were measured by release of gamma-interferon in an enzyme-linked immunosorbent assay (ELISA) by effector cells in the presence of peptide-pulsed antigen-presenting cells or by an antigen-specific tetramer flow cytometry assay. Thirty-three of 38 patients demonstrated an immune response by ELISA after vaccination, as did 37 of 42 patients by tetramer assay. Twenty-four of 48 patients relapsed with a median follow-up of 20 months, and 10 patients in this high-risk group have died.

Slingluff and colleagues evaluated peptide vaccine immunogenicity of several peptides restricted to different HLA-A alleles in draining lymph nodes and peripheral blood of melanoma patients because vaccine trials have been limited mostly to those associated with HLA-A2, and immune responses have been detected inconsistently (Yamshchikov G V. Int J Cancer. 2001 92:703–11). They vaccinated stage IV melanoma patients with a mixture of gp100 and tyrosinase peptides restricted by HLA-A1 (DAEKSDICTDEY) (SEQ ID NO: 483), HLA-A2(YLEPGPVTA (SEQ ID NO: 484) and YMDGTMSQV (SEQ ID NO: 485)) and HLA-A3 (ALLAVGATK) (SEQ ID NO: 486) in an emulsion with GM-CSF and Montanide ISA-51 adjuvant. CTL responses to vaccinating peptides were found in a lymph node draining a vaccine site (sentinel immunized node, SIN) in 5/5 patients (100%) in PBLs of 2/5 patients (40%). Peptides restricted by HLA-A1 and -A3 and HLA-A2 restricted peptide, YMDGTMSQV (SEQ ID NO: 485), were immunogenic.

Cytotoxic T lymphocytes against melanoma-associated antigens were induced by a recombinant vaccinia virus vector expressing multiple immunodominant epitopes and costimulatory molecules in vivo (Oertli D. Hum Gene Ther. 2002 13:569–75). Patients received psoralen-UV-treated and replication-incompetent recombinant vaccinia virus encoding the three immunodominant HLA-A*0201-restricted epitopes Melan-A(27–35), gp100(280–288), and tyrosinase (1–9) together with two costimulatory molecules, B7.1 and B7.2, in the context of systemic granulocyte-macrophage colony-stimulating factor (GM-CSF) treatment. Subsequent boosts used corresponding synthetic nona-peptides and GM-CSF. Within 12 days of injection of the recombinant vector, cytotoxic T cell responses specific for engineered epitopes were detected in three of three patients. During the vaccination treatment, antigen-specific CTL frequencies exceeding 1:10,000 peripheral CD8+ T cells could be observed.

Two stage IV melanoma patients vaccinated with an HLA-A2- or HLA-A24-restricted tyrosinase peptide, and GM-CSF had long-term freedom from recurrence (Scheibenbogen C. Int J Cancer. 2002 99:403–8). While the patients had experienced 9 and 12 relapses (mostly subcutaneous), respectively, during the 3 years before vaccination, they experienced freedom from relapse for more than 2 years after vaccination. T-cell responses to the vaccine peptide were found in the peripheral blood of both patients using an IFN-gamma ELISPOT assay.

Mule and colleagues found that addition of keyhole limpet hemocyanin (KLH) augmented the efficacy of both tumor lysate-pulsed dendritic cells and peptide-pulsed dendritic cells immunizations for immune priming and rejection of established metastases of the D5 subline of B16 melanoma in vivo (Shimizu K. Cancer Res. 2001 61:2618–24). Interleukin 2 further augmented the enhancement afforded by KLH, as measured by cure rates and overall survival, in the absence of autoimmune depigmentation. KLH added to dendritic cells immunizations markedly enhances tumor-specific T cell production of IFN-gamma. D5 melanoma exposed to similar levels of IFN-gamma results in substantial expression of MHC Class I molecules. Immunization with dendritic cells pulsed with KLH and mouse tyrosinase-related protein-2 peptide results in enhanced reduction of B16 melanoma metastases; the effect is most pronounced in a setting where tyrosinase-related protein-2 peptide-pulsed dendritic cells alone are completely ineffective.

Therapeutic efficacy of a tumor cell-based vaccine against B16 melanoma requires disruption of either of two immunoregulatory mechanisms that control autoreactive T cell responses: the cytotoxic T lymphocyte-associated antigen (CTLA)-4 pathway or the CD25+regulatory T cells. Combination of CTLA-4 blockade and depletion of CD25+T cells results in maximal tumor rejection (Sutmuller R P. J Exp Med. 2001 194:823–32). Efficacy of the antitumor therapy correlates with the extent of autoimmune skin depigmentation as well as with the frequency of tyrosinase-related protein 2(180–188)-specific CTLs detected in the periphery. Furthermore, tumor rejection is dependent on the CD8+ T cell subset. The CTL response against melanoma antigens is an important component of the therapeutic antitumor response, and the reactivity of these CTLs can be augmented through interference with immunoregulatory mechanisms. The synergism in the effects of CTLA-4 blockade and depletion of CD25+T cells indicates that CD25+T cells and CTLA-4 signaling represent two alternative pathways for suppression of autoreactive T cell immunity. Simultaneous intervention with both regulatory mechanisms is, therefore, a promising concept for the induction of therapeutic antitumor immunity.

The amino acid sequence of tyrosinase as given in GenBank 4507753|ref|NP_000363.1| tyrosinase (oculocutaneous albinism IA); Tyrosinase [*Homo sapiens*] is listed in Table 14.1. Predicted MHC Class II-presented epitopes of tyrosinase are listed in Table 14.2. Experimentally defined MHC Class II-presented epitopes of tyrosinase are listed in Table 14.3. Designed Ii-Key/tyrosinase hybrids containing some of the MHC Class II-presented epitopes of Table 14.2 and 14.3 are listed in Table 14.4. Predicted MHC Class I-presented epitopes of tyrosinase are listed in Table 14.5. The experimental identification of MHC Class I-presented epitopes of tyrosinase (Pos. 240, 368, 146) is described in the gp100 example. Experimentally defined MHC Class I-presented epitopes of tyrosinase are listed in Table 14.6. Designed Ii-Key/tyrosinase hybrids containing some of the MHC Class I— and MHC Class II-presented epitopes of Tables 14.2, 14.3, 14.4 and 14.5 are listed in Table 14.7.

TABLE 14.1

| (SEQ ID NO: 487) Deduced amino acid sequence of tyrosinase. | | | | | |
|---|---|---|---|---|---|
| 1 | mllavlycll | wsfqtsaghf | pracvssknl | mekeccppws | gdrspcgqls |
| 51 | grgscqnill | snaplgpqfp | ftgvddresw | psvfynrtcq | csgnfmgfnc |
| 101 | gnckfgfwgp | ncterrllvr | rnifdlsape | kdkffayltl | akhtissdyv |
| 151 | ipigtygqmk | ngstpmfndi | niydlfvwmh | yyvsmdallg | gseiwrdidf |
| 201 | aheapaflpw | hrlfllrweq | eiqkltgden | ftipywdwrd | aekcdictde |
| 251 | ymggqhptnp | nllspasffs | swqivcsrle | eynshqslcn | gtpegplrrn |
| 301 | pgnhdksrtp | rlpssadvef | clsltqyesg | smdkaanfsf | rntlegfasp |
| 351 | ltgiadasqs | smhnalhiym | ngtmsqvqgs | andpifllhh | afvdsifeqw |
| 401 | lrrhrplqev | ypeanapigh | nresymvpfi | plyrngdffi | sskdlgydys |
| 451 | ylqdsdpdsf | qdyiksyleq | asriwswllg | aamvgavlta | llaglvsllc |
| 501 | rhkrkqlpee | kqpllmeked | yhslyqshl | | |

TABLE 14.2

Predicted MHC Class II-presented epitopes of tyrosinase.

| PEPTIDE | Pos. | Sequence | Score | Ii-Key | SEQ ID NO: |
|---|---|---|---|---|---|
| 14.2.1 | 401 | LRRHRPLQE | 6.60 | 6 | 488 |
| 14.2.2 | 179 | MHYYVSMDA | 6.40 | — | 489 |
| 14.2.3 | 400 | WLRRHRPLQ | 6.25 | 5 | 490 |
| 14.2.4 | 118 | LVRRNIFDL | 5.70 | 9 | 491 |
| 14.2.5 | 366 | LHIYMNGTM | 5.50 | — | 492 |
| 14.2.6 | 368 | IYMNGTMSQ | 5.40 | — | 493 |
| 14.2.7 | 182 | YVSMDALLG | 5.50 | — | 494 |
| 14.2.8 | 150 | VIPIGTYGQ | 5.50 | 7 | 495 |
| 14.2.9 | 338 | FSFRNTLEG | 5.40 | — | 496 |
| 14.2.10 | 498 | LLCRHKRKQ | 5.30 | — | 497 |
| 14.2.11 | 1 | MLLAVLYCL | 5.20 | — | 498 |
| 14.2.12 | 167 | FNDINIYDL | 5.20 | — | 499 |

Pos. is the residue position in the primary sequence of the first amino acid in the antigenic epitope. Sequence is the amino acid sequence of the predicted MHC Class II-presented epitope. Score is the score reported by the ProPred many common HLA-DR alleles. Ii-Key is the number of residue positions intervening between an Ii-Key motif and the first residue of the antigenic epitope.

TABLE 14.3

Experimentally defined MHC Class II-presented epitopes of tyrosinase.

| PEPTIDE | Pos. | Sequence | Ii-Key | SEQ ID NO: |
|---|---|---|---|---|
| 14.3.1 | 56 | QNILLSNAPLGPQFP | — | 500 |
| 14.3.2 | 365 | ALHIYMNGTMSQVQGSA | — | 501 |
| 14.3.3 | 156 | YGQMKNGSTPMFNDINIYDL | — | 502 |

Pos. is the residue position in the primary sequence of the first amino acid in the antigenic epitope. Sequence is the amino acid sequence of the experimentally defined MHC Class II-presented epitope. Ii-Key is the number of residue positions intervening between an Ii-Key motif and the first residue of the antigenic epitope. Peptide 14.3.1 is presented by HLA-DR*0401 (Storkus W. Forum (Genova). 2000 10:256–270). Peptides 14.3.2 and 14.3.3 are presented by HLA-DR*0401 (Kierstead L. Brit J Cancer. 2001 85:1738–45). Peptide 14.3.2 contains an N-glycosylation site.

TABLE 14.4

Designed Ii-Key/tyrosinase hybrids containing some of the MHC Class II-presented epitopes of Table 14.2 and 14.3.

| PEPTIDE | Pos. | Sequence | SEQ ID NO: |
|---|---|---|---|
| | | Non-overlapping | |
| 14.4.1 | 56 | Ac-LRMK-ava-QNILLSNAPLGPQFP-$NH_2$ | 503 |

TABLE 14.4-continued

Designed Ii-Key/tyrosinase hybrids containing some of the MHC Class II-presented epitopes of Table 14.2 and 14.3.

| PEPTIDE | Pos. | Sequence | SEQ ID NO: |
|---|---|---|---|
| 14.4.2 | 118 | Ac-LRMK-ava-LVRRNIFDL-$NH_2$ | 504 |
| 14.4.3 | 338 | Ac-LRMK-ava-FSFRNTLEG-$NH_2$ | 505 |
| 14.4.4 | 498 | Ac-LRMK-ava-LLCRHKRKQ-$NH_2$ | 506 |
| | | Overlapping epitopes | |
| 14.4.5 | 365 | Ac-LRMK-ava-ALHIYMNGTMSQVQGSA-$NH_2$ | 507 |
| 14.4.6 | 366 | Ac-LRMK-ava-LHIYMNGTM-$NH_2$ | 508 |
| 14.4.7 | 368 | Ac-LRMK-ava-IYMNGTMSQ-$NH_2$ | 509 |
| 14.4.8 | 365 366 and 368 | Ac-LRMK-ava-ALHIYMNGTMSQ-$NH_2$ | 510 |
| 14.4.9 | 182 | Ac-LRMK-ava-YVSMDALLG-$NH_2$ | 511 |
| 14.4.10 | 179 | Ac-LRMK-ava-MHYYVSMDA-$NH_2$ | 512 |
| 14.4.11 | 179 and 182 | Ac-LRMK-ava-MHYYVSMDALLG-$NH_2$ | 513 |
| 14.4.12 | 150 | Ac-LRMK-ava-VIPIGTYGQ-$NH_2$ | 514 |
| 14.4.13 | 156 | Ac-LRMK-ava-YGQMKNGSTPMFNDINIYDL-$NH_2$ | 515 |
| 14.4.14 | 167 | Ac-LRMK-ava-FNDINIYDL-$NH_2$ | 516 |
| 14.4.15 | 150 156 and 167 | Ac-LRMK-ava-VIPIGTYGQMKNGSTPMFN-DINIYDL-$NH_2$ | 517 |

Pos. is the residue position in the primary sequence of the first amino acid in the antigenic epitope. Sequence is the amino acid sequence of a hybrid peptide containing a MHC Class II epitope of Table 1.2.

TABLE 14.5

Predicted MHC Class I-presented epitopes of tyrosinase.

| PEPTIDE | Pos. | Sequence | Score | SEQ ID NO: |
|---|---|---|---|---|
| 14.5.1 | 243 | KCDICTDEY | 25.0 | 518 |
| 14.5.2 | 369 | YMNGTMSQV | 531.4 | 519 |
| 14.5.3 | 1 | MLLAVLYCL | 309.1 | 520 |
| 14.5.4 | 207 | FLPWHRLFL | 540.5 | 521 |

Pos. is the residue position in the primary sequence of the first amino acid in the antigenic epitope. Sequence is the amino acid sequence of the predicted MHC Class II-presented epitope. The MHC Class I-presented epitopes of Table 9.4 were predicted with the use of the online program at (http://bimas.dcrt.nih.gov/molbio/hla_bind/). Score is the $T_{1/2}$ of disassociation of a peptide containing this subsequence (Tsang K Y. J Natl Cancer Inst. 1995 87:982–90). Peptide 14.4.1 is presented by HLA-A1. Peptides 14.5.2, 14.5.3 and 14.5.4 are presented by HLA*A0201.

TABLE 14.6

Experimentally defined MHC Class I-presented epitopes of tyrosinase.

| PEPTIDE | Pos. | Sequence | SEQ ID NO: |
|---|---|---|---|
| 14.6.1 | 240 | DAEKSDICTDEY | 522 |
| 14.6.2 | 368 | YMDGTMSQV | 523 |
| 14.6.3 | 146 | SDYVIPIGTY | 524 |

Pos. is the residue position in the primary sequence of the first amino acid in the antigenic epitope. Sequence is the amino acid sequence of the experimentally defined MHC Class II-presented epitope. Peptide 14.6.1 is presented by HLA-A1 (Yamshchikov G. Int J Cancer. 2001 92:703–11). Peptide 14.6.2 is presented by HLA-A2 (Yamshchikov G. Int J Cancer. 2001 92:703–11). Peptide 14.6.3 is presented by HLA-A1 (Kawakami Y. J. Immunol. 1998 161:6985–92).

TABLE 14.7

Designed Ii-Key/tyrosinase hybrids containing some of the MHC Class I- and MHC Class II-presented epitopes of Tables 14.2, 14.3, 14.5, and 14.6).

| PEPTIDE | Pos. | Sequence | SEQ ID NO: |
|---|---|---|---|
| | | Non-overlapping epitopes | |
| 14.7.1 | 240 and 56 | Ac-LRMK-ava-DAEKSDICTDEY-QNILLSNAPLGPQFP-$NH_2$ | 525 |
| 14.7.2 | 207 and 401 | Ac-LRMK-ava-FLPWHR-LFL-LRRHRPLQE-$NH_2$ | 526 |
| | | Overlapping epitopes | |
| 14.7.3 | 368 (371D) and 365 (366, 368) | Ac-LRMK-ava-ALHIYMNGTMSQVQGSA-$NH_2$ | 527 |
| 14.7.4 | 146 and 156 | Ac-LRMK-ava-SSDYVIPIGTYGQMKNGSTPMFNDINIYDL-$NH_2$ | 528 |
| 14.7.5 | 1 and 1 | Ac-LRMK-ava-MLLAVLYCL-$NH_2$ | 529 |

Pos. is the residue position in the primary sequence of the first amino acid in the antigenic epitope. Sequence is the amino acid sequence of a hybrid peptide containing a MHC Class II epitope of Table 14.2. PEPTIDE 14.7.5 includes amino acid sequences of both MHC Class I— and II-presented epitope of tyrosinase, which are experimentally defined and coincide.

Example 15

Ii-Key/Melanoma Antigen MART-1 Antigenic Epitope Hybrids

Rosenberg and colleagues immunized metastatic melanoma patients with autologous dendritic cells presenting epitopes derived from the melanoma-associated antigens MART-1 and gp100 (Panelli M C. J Immunother. 2000 23:487–98). The DCs were generated by 5- to 7-day incubation in interleukin-4 (1,000 U/mL) and granulocyte-macrophage colony-stimulating factor (1,000 U/mL) of peripheral blood monocytes obtained by leukapheresis. Before administration, the DCs were pulsed separately with the HLA-A*0201-associated melanoma epitopes MART-1 (27–35) and gp-100-209-2M. The DCs were administered four times at 3-week intervals. A first cohort of patients (n=3) was treated with $6\times10^7$ DCs and a second cohort (n=5) with $2\times10^8$ DCs (in either case, one half of the DCs were pulsed with MART-1(27–35) and the other half was pulsed with gp-100-209-2M). In a final cohort under accrual (n=2) $2\times10^8$ DCs were administered in combination with interleukin-2 (720,000 IU/kg every 8 hours). The recovery of DCs after in vitro culture ranged from 3% to 35% (mean, 15%) of the original peripheral blood monocytes. Administration of DCs caused no symptoms at any of the doses, and the concomitant administration of interleukin-2 did not cause toxicity other than that expected for interleukin-2 alone. Monitoring of patients' cytotoxic T lymphocyte reactivity before and after treatment revealed enhancement of cytotoxic T lymphocyte reactivity only in one of five patients tested. Of seven patients evaluated for response, one had a transient partial response with regression of pulmonary and cutaneous metastases.

Ioannides and colleagues demonstrated reduced recognition of metastatic melanoma cells by autologous MART-1 specific CTL correlated to TAP deficiency (Murray J L. J Immunother. 2000 23:28–35). Class I expression in context with T-cell receptor expression is crucial for peptide presentation and induction of CD8+ cytotoxic T lymphocytes (CTL). Presentation of MHC class I bound peptides depends on transporter-associated proteins (TAP) expression and function. Tumor infiltrating lymphocytes from a patient with melanoma were isolated, expanded in vitro in the presence of interleukin-2, and tested for cytotoxicity against HLA-A2 positive, MART-1 positive autologous tumor cells, an HLA-A2-positive, MART-1 positive melanoma cell line (Mel-501), and HLA-A2-negative melanoma cells. Significant killing occurred against both A2-positive cell lines (63% and 65%, respectively), but not against the A2-negative line (18%) or A2-positive autologous tumor (1.5%). These CTL preferentially recognized the MART-1 peptide F119, 27–35, and gp100 peptide F125, 280–288, resulting in a 30% to 60% enhancement of lysis when autologous tumor or major histocompatibility complex class I "empty" T2 cells were pulsed with either peptide. To address whether the deficiency in autologous tumor recognition might be related to a deficiency in Ag presentation, screening for the presence of TAP1 and TAP2 transcripts by polymerase chain reaction, Southern blotting, and scanning densitometry using sequence-specific primers and probes. Both TAP1 and TAP2 expression levels in the autologous tumor were minimal, yet were upregulated 7- to 18-fold, respectively, by interferon-gamma. Despite this increase, a similar increase in cytotoxicity did not occur. In short, deficiencies in TAP presentation may have functional significance for tumor escape from immunosurveillance and with respect to impending vaccine trials.

Slingluff and colleagues demonstrated terminal modifications inhibit proteolytic degradation of an immunogenic MART-1(27–35) peptide (Brinckerhoff L H. Int J Cancer 1999 Oct. 29;83(3):326–34). The stability of the immunogenic peptide MART-1(27–35) in fresh normal human plasma (NHP) was tested to identify modifications protecting against enzymatic destruction without loss of immunogenicity. MART-1(27–35) peptide (AAGIGILTV) (SEQ ID NO: 530) and modified forms were incubated in plasma for varied time intervals and evaluated for their ability to reconstitute the epitope for MART-1(27–35)-reactive CTL. Loss of CTL reactivity signaled loss of immunoreactive peptide. When 1 microM MART-1(27–35) peptide was incubated in plasma prior to pulsing on target cells, CTL reactivity was lost within 3 hr, and the calculated half-life of this peptide was 22 sec. This degradation was mediated by peptidases. The stability of MART-1(27–35) was markedly prolonged by C-terminal amidation and/or N-terminal acetylation (peptide capping), or by polyethylene-glycol modification (PEGylation) of the C-terminus. These modified peptides were recognized by CTL.

Romero and colleagues demonstrated that CpG is an efficient adjuvant for specific CTL induction against tumor antigen-derived peptide (Miconnet I. J. Immunol. 2002 168:1212–8). Mice transgenic for a chimeric MHC class I molecule were immunized with a peptide analog of MART-1/Melan-A(26–35) in the presence of CpG oligonucleotides alone or emulsified in IFA. The CTL response was monitored ex vivo by tetramer staining of lymphocytes. In blood, spleen, and lymph nodes, peptide mixed with CpG ODN alone was able to elicit a stronger systemic CTL response as compared with peptide emulsified in IFA. Moreover, CpG ODN in combination with IFA further enhanced the CTL response in terms of the frequency of tetramer+CD8+ T cells ex vivo. The CTL induced in vivo against peptide analog in the presence of CpG ODN are functional, as they were able to recognize and kill melanoma cells in vitro.

Mitchell and colleagues demonstrated synthetic insertion of signal sequences enhance MHC Class I presentation of a peptide from the melanoma antigen MART-1 (Minev B R. Eur J. Immunol. 2000 30:2115–24). Addition of synthetic signal sequences at the N terminus, but not at the C terminus, of an epitope from the human melanoma antigen MART-1 enhanced its presentation in both TAP-deficient and TAP-expressing cells. A peptide construct, composed of the epitope replacing the hydrophobic part of a natural signal sequence, was also very effective. Interestingly, an artificial signal sequence containing the same epitope was the most efficient construct for enhancing its presentation. These peptide constructs facilitated epitope presentation when loaded into the cytosol of TAP-deficient T2 cells, TAP-expressing melanoma cells and human dendritic cells.

Zajac and colleagues demonstrated immunogenicity of nonreplicating recombinant vaccinia expressing HLA-A201 targeted or complete MART-1/Melan-A antigen (Schutz A. Cancer Gene Ther. 2001 8:655–61). The first recombinant virus expressed a minigene encoding a fusion product between an endoplasmic reticulum (ER)-targeting signal and the HLA-A201 binding MART-1/Melan-A 27–35 peptide. The second viral construct encoded the complete MART-1/Melan-A protein. The capacity of HLA-A201 cells infected with either viral construct to generate and to stimulate MART-1/Melan-A 27–35 specific cytotoxic T-lymphocytes (CTL), was comparatively characterized. The results obtained confirmed the capacity of vaccinia virus-encoded ER-minigene to generate a very strong antigenic signal. In cytotoxicity assays, recognition of target cells infected with high amounts of both recombinant viruses with activated specific C-TL clones, resulted in similar lytic activity. With regard to calcium mobilization, TCR down-regulation, IFN-gamma release, and T cell proliferation assays, the targeted epitope elicited 10- to 1000-fold stronger responses. Remarkably, the immunogenic difference between the two formulations, in their respective capacity to generate CTL from naive HLA-A2 peripheral blood mononuclear cells in vitro as measured by tetramer detection, was lower (2- to 3-fold). Recombinant vectors expressing complete antigens have demonstrated their capacity to generate specific responses and such vaccines might take advantage of a broader potential of presentation. However, as demonstrated for the HLA-A201-restricted MART-1/Melan-A immunodominant epitope, nonreplicative vaccinia virus expressing ER-targeted minigenes appear to represent a significantly more immunogenic epitope vaccine formulation. Enhanced further with Ii-RGC.

Falo and colleagues demonstrated direct transfection and activation of human cutaneous dendritic cells (Larregina A T. Gene Ther. 2001 8:608–17). A gene gun was used to transfect human skin organ cultures with a particular goal of expressing transgenic antigens in resident cutaneous dendritic cells. Gold particles delivered to human skin are observed primarily in the epidermis, even when high helium delivery pressures are used. Langerhans cells resident in the basal epidermis can be transfected, and gene gun delivery is sufficient to stimulate the activation and migration of skin dendritic cells. RT-PCR analysis of dendritic cells, which have migrated from transfected skin, demonstrates transgenic mRNA, indicating direct transfection of cutaneous dendritic cells. Transfected epidermal Langerhans cells can efficiently present a peptide derived from the transgenic melanoma antigen MART-1 to a MART-1-specific CTL.

Mule and colleagues demonstrated that administration of tumor lysate-pulsed DCs is nontoxic and capable of inducing immunological response to tumor antigen (Chang A E. Clin Cancer Res. 2002 8:1021–32). Fourteen patients with stage IV solid malignancies were treated in cohorts that received $10^6$, $10^7$, and $10^8$ dendtiric cells i.d. every 2 weeks for three vaccines. Each vaccine was composed of a mixture of half DCs pulsed with autologous tumor lysate and the other half with keyhole limpet hemocyanin (KLH). Local accumulation of CD4+ and CD8+ T cells were found at the vaccination sites. There was a significant proliferative response of PBMCs to KLH induced by the vaccine. In 5 of 6 patients, the vaccine resulted in increased IFN-gamma production by PBMCs to KLH in an ELISPOT assay. Using the same assay, 3 of 7 patients' PBMCs displayed increased IFN-gamma production in response to autologous tumor lysate. One patient with melanoma also was observed to have an increased frequency of MART-1- and gp100-reactive CD8(+) T cells after vaccination. By delayed-type hypersensitivity testing, 8 of 9 and 4 of 10 patients demonstrated reactivity to KLH and autologous tumor, respectively. Ii-Key/antigenic epitope hybrids will improve the efficiency of this immunopriming technology.

Kourilsky and colleagues demonstrated cross-presentation by dendritic cells of tumor antigen expressed in apoptotic recombinant canarypox virus-infected dendritic cells (Motta I. J. Immunol. 2001 167:1795–802). Recombinant canarypox virus (ALVAC) encoding the melanoma-associated Ag, Melan-A/MART-1 (MART-1), was tested in cancer immunotherapy, using a dendritic cell (DC)-based approach. ALVAC MART-1-infected DC express, and process and present, the antigen encoded by the viral vector. One consistent feature of infection by ALVAC was induction of apoptosis, and cross-presentation of Ag when uninfected DC are cocultured with ALVAC MART-1-infected DC. Uptake of apoptotic virally infected DC by uninfected DC and subsequent expression of tumor antigen in the latter were verified by flow cytometry analysis, image cytometry, and confocal microscopy. Functional activity was monitored in vitro by the stimulation of a MART-1-specific cytotoxic T cell clone. Heightened efficiency in Ag presentation was indicated by 2- to 3-fold increase in IFN-gamma production by the T cell clone, as compared with the ALVAC-infected DC alone. Cocultures of ALVAC MART-1-infected and uninfected DC are able to induce MART-1-specific T cell immune responses, as assessed by HLA class I/peptide tetramer binding, IFN-gamma ELISPOT assays, and cytotoxicity tests.

The amino acid sequence of melanoma antigen MART-1 as given in GenBank as 1082589|pir||A55253 melanoma antigen MART-1-human is presented in Table 15.1. Predicted MHC Class II-presented epitopes of MART-1/Melan-A are listed in Table 15.2. Experimentally defined MHC Class II-presented epitopes of MART-1/Melan-A are listed in Table 15.3. Designed Ii-Key/MART-1/Melan-1 hybrids containing some of the MHC Class II-presented epitopes of Tables 15.2 and 15.3 are listed in Table 15.4. Predicted MHC Class I-presented epitopes of MART-1/Melan-A are listed in Table 15.5. Experimentally defined MHC Class I-presented epitopes of MART-1/Melan-A are listed in Table 15.6. Designed Ii-Key/MART-1 hybrids containing some of the MHC Class I— and Class II-presented epitopes of Tables 15.2, 15.3, 15.5, and 15.6 are listed in Table 15.7.

TABLE 15.1

Deduced amino acid sequence of melanoma antigen MART-1. (SEQ ID NO:531)

| | |
|---|---|
| 1 | mpredahfiy gypkkghghs yttaeeaagi giltvilgvl lligcwycrr |
| 51 | rngyralmdk slhvgtqcal trrcpqegfd hrdskvslqe kncepvvpna |
| 101 | ppayeklsae qspppysp |

TABLE 15.2

Predicted MHC Class II-presented epitopes of MART-1/Melan-A.

| PEPTIDE | Pos. | Sequence | Score | Ii-Key | SEQ ID NO: |
|---|---|---|---|---|---|
| 15.2.1 | 33 | LTVILGVLL | 5.00 | — | 532 |

TABLE 15.2-continued

Predicted MHC Class II-presented epitopes of MART-1/Melan-A.

| PEPTIDE | Pos. | Sequence | Score | Ii-Key | SEQ ID NO: |
|---|---|---|---|---|---|
| 15.2.2 | 35 | VILGVLLLI | 4.70 | — | 533 |
| 15.2.3 | 96 | VVPNAPPAY | 4.10 | 6 | 534 |
| 15.2.4 | 30 | IGILTVILG | 4.28 | — | 535 |
| 15.2.5 | 9 | IYGYPKKGH | 4.10— | — | 536 |
| | | | 5.10 | | |

Pos. is the residue position in the primary sequence of the first amino acid in the antigenic epitope. Sequence is the amino acid sequence of the predicted MHC Class II-presented epitope. Score is the score reported by the ProPred program, for the relative likelihood of being presented by many common HLA-DR alleles. Ii-Key is the number of residue positions intervening between an Ii-Key motif and the first residue of the antigenic epitope.

TABLE 15.3

Experimentally defined MHC Class II-presented epitopes of MART-1/Melan-A.

| PEPTIDE | Pos. | Sequence | Ii-Key | SEQ ID NO: |
|---|---|---|---|---|
| 15.3.1 | 51 | RNGYRALMDKSLHVGTQ CALTRR | — | 537 |

Pos. is the residue position in the primary sequence of the first amino acid in the antigenic epitope. Sequence is the amino acid sequence of the predicted MHC Class II-presented epitope. Ii-Key is the number of residue positions intervening between an Ii-Key motif and the first residue of the antigenic epitope. Peptide 15.3.1 is presented by HLA-DR4 (Zarour H. Proc Natl Acad Sci USA. 2000 97:400–5).

TABLE 15.4

Designed Ii-Key/MART-1/Melan-1 hybrids containing some of the MHC Class II-presented epitopes of Table 1.

| PEPTIDE | Pos. | Sequence | SEQ ID NO: |
|---|---|---|---|
| | | A. Non-overlapping | |
| 15.4.1 | 95 | Ac-LRMK-ava-VVPNAPPAY-$NH_2$ | 538 |
| 15.4.2 | 8 | Ac-LRMK-ava-IYGYPKKGH-$NH_2$ | 539 |
| 15.4.3 | 51 | Ac-LRMK-ava-RNGYPALMDKSLHVGTQCALTRR-$NH_2$ | 540 |
| | | B. Overlapping | |
| 15.4.4 | 32 | Ac-LRMK-ava-LTVILGVLL-$NH_2$ | 541 |
| 15.4.5 | 34 | Ac-LRMK-ava-VILGVLLLI-$NH_2$ | 542 |
| 15.4.6 | 29 | Ac-LRMK-ava-IGILTVILG-$NH_2$ | 543 |

TABLE 15.4-continued

Designed Ii-Key/MART-1/Melan-1 hybrids containing some of the MHC Class II-presented epitopes of Table 1.

| PEPTIDE | Pos. | Sequence | SEQ ID NO: |
|---|---|---|---|
| 15.4.7 | 29/32/34 | Ac-LRMK-ava-IGILTVILGVLLLI-$NH_2$ | 544 |

Pos. is the residue position in the primary sequence of the first amino acid in the antigenic epitope. Sequence is the amino acid sequence of a hybrid peptide containing a MHC Class II epitope of Table 15.2.

TABLE 15.5

Predicted MHC Class I-presented epitopes of MART-1/Melan-A.

| PEPTIDE | Pos. | Sequence | Score | SEQ ID NO: |
|---|---|---|---|---|
| 15.5.1 | 40 | LLLIGCWYC | 1289.01 | 545 |
| 15.5.2 | 56 | ALMDKSLHV | 1055.10 | 546 |
| 15.5.3 | 25 | EEAAGIGIL | 40.0 | 547 |
| 15.5.4 | 109 | AEQSPPPYS | 12.0 | 548 |

Pos. is the residue position in the primary sequence of the first amino acid in the antigenic epitope. Sequence is the amino acid sequence of a hybrid peptide containing a MHC Class II epitope of Table 1.2. The MHC Class I-presented epitopes of Table 9.4 were predicted with the use of the online program at (http://bimas.dcrt.nih.gov/molbio/hla_b-ind/). Score is the $T_{1/2}$ of disassociation of a peptide containing this subsequence (Tsang K Y. J Natl Cancer Inst. 1995 87:982–90). Peptide 15.5.1 is presented by HLA-A*0201, HLA-A3, and HLA-A31. Peptide 15.5.2 is presented by HLA-A*0201. Peptides 15.5.3 and 15.5.4 are presented by HLA-B40.

TABLE 15.6

Experimentally defined MHC Class I-presented epitopes of MART-1/Melan-A.

| PEPTIDE | Pos. | Sequence | SEQ ID NO: |
|---|---|---|---|
| 15.6.1 | 27 | AAGIGILTV | 549 |
| 15.6.2 | 32 | ILTVILGVL | 550 |
| 15.6.3 | 24 | AEEAAGIGILT | 551 |

Pos. is the residue position in the primary sequence of the first amino acid in the antigenic epitope. Sequence is the amino acid sequence of the experimentally defined MHC Class II-presented epitope. Peptide 15.6.1 is presented by HLA-A*0201 (Kawakami, Y. J Exp Med. 1994 180:347–52). Peptide 15.6.2 is presented by HLA-A*0201 (Castelli C. J Exp Med. 1995 181:63–8). Peptide 15.6.3 is presented by HLA-B*4501 (Schneider J. Intl J Cancer. 1998 75:451–8).

TABLE 15.7

Designed Ii-Key/MART-1 hybrids containing some of the MHC Class I- and Class II-presented epitopes of 15.2, 15.3, 15.5, and 15.6).

| SEQ ID NO: | Pos. | Sequence | SEQ ID NO: |
|---|---|---|---|
| 15.7.1 | 27 and 51 | Ac-LRMK-ava-AAGIGTLTV-RNGYRALMDKSLHVGTQCALTRR-$NH_2$ | 552 |

Pos. is the residue position in the primary sequence of the first amino acid in the antigenic epitope. Sequence is the amino acid sequence of a hybrid peptide containing a MHC Class II-presented epitope of Table 15.2 and a MHC Class I-presented epitope of Table 15.6.

Example 16

Ii-Key/Her-2 Neu Antigenic Epitope Hybrids

Immunotherapy directed against the epidermal growth factor receptor which is overexpressed on some cancer cells can control the growth of those tumors. HER-2/neu is over-expressed on tumors in up to 30% of patients with invasive breast cancer and that over-expression is associated with poor clinical outcome. Carr et al. demonstrated in a retrospective consecutive series from 1995 to 1999 that the HER-2/neu gene was amplified in invasive breast carcinomas of 40 of 90 patients (43%) (Carr J A. Arch Surg. 2000 135:1469–7420). Following initial therapy, patients with HER-2/neu amplification had a shorter median disease-free interval (22 months) than did patients with breast cancers not amplifying that gene (40 months; p=0.003). Disease recurred in seventy-two (72%) patients, with 18 (25%) recurring locally. HER-2/neu gene amplification is an independent prognostic indicator for a subset of breast cancer patients who are at high risk for early recurrence regardless of tumor grade, estrogen/progesterone receptor status, and lymph node status. In both early stage, lymph node-negative and node-positive disease, as well as in women with metastatic disease, HER-2/neu overexpression is associated with worse survival. Women with tumors that overexpress HER-2/neu have a less favorable outcome despite adjuvant treatment with either hormonal therapy or chemotherapy. Among HER-2/neu-negative, early stage patients in the Naples GUN trial, tamoxifen benefited overall survival. However, among patients with HER-2/neu-gene amplification, tamoxifen did not improve survival (De Placido S. Br J Cancer. 1990 62:643–6). HER-2/neu over-expression is an independent predictor for tamoxifen failure. Over-expression of HER-2/neu is selective for tumor cells and is observed early in the course of malignant transformation. More importantly, the cytological characteristics of HER-2/neu over-expression (32%) in primary and metastatic lesions is nearly identical (Masood S. Ann Clin Lab Sci. 2000 30:259–65). Inasmuch as micrometastases are the primary source of relapse following primary therapy and HER-2/neu is over-expressed in metastases, HER-2/neu is an excellent target for immunotherapy of patients with early disease, both to consolidate the anti-tumor response locally and to eradicate micrometastases. Likewise, HER-2/neu should be targeted in conjunction with other major treatment regimens in patients who have relapsed following initial therapy.

Of many approaches to targeting HER-2/neu, the clinically most advanced approach is passive immunotherapy with trastuzumab (Herceptin®), an FDA-approved humanized monoclonal antibody that binds to the extracellular domain of the HER-2/neu receptor for epidermal growth factor (EGF). This monoclonal antibody is indicated both as a single agent and in combination with classical chemotherapies. Slamon et al. evaluated Herceptin® in combination with doxorubicin and cyclophosphamide (AC), or paclitaxel in 496 women with metastatic breast carcinomas that over expressed HER-2/neu (Vogel C L. J Clin Oncol. 2002 20:719–26; Slamon D J. N Engl J. Med. 2001 344:783–92). Patients receiving Herceptin®, as compared to patients randomized to chemotherapy alone (either paclitaxel or AC), had a significantly longer time to disease progression (7.4 mo vs. 4.6 mo; p<0.0001), a higher rate of objective response (50% vs. 32%; p<0.001), a longer duration of response (median 9.1 vs. 6.1; p<0.001), a higher 1 year survival rate (78% vs. 67%; p=0.008), longer survival (median survival 25.1 mo vs. 20.3 mo; p=0.046), and a 20% reduction in the risk of death.

While clinical trials might proceed to alternate trastuzumab dosing regimens and combination therapies, one can suggest that the mechanism of action of trastuzumab will not lead to significantly increased efficacy. Specifically, Trastuzumab blocks the HER-2/neu EGF receptor and induces antibody dependent cellular cytotoxicity (Sliwkowski M X. Semin Oncol. 1999 4 Suppl 12:60–70). ADCC does not lead to antigen-specific memory of T- or B-lymphocytes, nor does it induce proliferation of antigen-specific cytotoxic T-lymphocytes.

HER-2/neu is also the target for several vaccine trials to induce an active specific immune response. In the NCI PDQ, three current clinical trials use HER-2/neu protein, antigen-pulsed dendritic cells, liposome-encapsulated HER-2/neu MHC peptide epitopes, and a DNA vaccine (http://www-.cancer.gov/cancer_information/doc.aspx?viewid=F2 AFAEA4-64BD-4E44-B421-56026E252389. The rationale, of course, is to enhance therapeutic efficacy and clinical ease of administration by inducing: (1) antigen-specific $CD8^+$ and $CD4^+$ lymphocytes; (2) autoantibodies against HER-2/neu with memory B-cells; and (3) memory helper T cells.

Compared to cell-based vaccines, DNA vaccines, and gene therapy approaches, peptide vaccination is preferred for several reasons. Specifically, peptide vaccines are: (1) easily constructed and manufactured; (2) chemically stable; (3) free of adventitious agents and other pathogens; and, (4) devoid of oncogenic potential. Until recently, most groups have focused on the use of MHC Class I peptide vaccines, which have triggered low-intensity CD8+ cytotoxic T cell responses. Shiku and colleagues have identified a novel human Her-2/neu2-derived peptide which is homologous to a mouse H-$2K^d$-restricted tumor antigen induces HLA-A24-restricted cytotoxic T lymphocytes in ovarian cancer patients and healthy individuals (Okugawa T. Eur J. Immunol. 2000 30:3338–46; Ikuta Y. Int J Cancer. 2000 87: 553–8; Nagata Y. J. Immunol. 1997 159:1336–43). In addition they have demonstrated presentation of a MHC Class I-binding peptide by monocyte-derived dendritic cells incorporating a hydrophobized polysaccharide-truncated Her-2/neu protein complex (Ikuta Y. Blood. 2002 99:3717–24; Araki H. Br J Haematol. 2001 114:681–9).

Peptide vaccines do enhance responses by CTL cells recognizing MHC Class I-presented peptides, but can be augmented by also immunizing T helper cells with MHC Class II-presented peptides. HER-2/neu-derived, MHC Class II-presented peptides are expressed by human breast, colorectal and pancreatic adenocarcinomas and are recognized by in vitro-induced, specific $CD4^+$ T cell clones (Perez S. Cancer Immunol Immunother. 2002 50:615–24; Sotiriadou R. Br J Cancer. 2001 85:1527–34). Murray et al. showed that the Her-2/neu(777–789) peptide induced peripheral blood mononuclear cells from patients with metastatic breast cancer to secrete IFN-γ (Murray J L. Semin Oncol. 2000 27 Suppl:71–5). This group also showed that Her-2/neu(369–377) induced strong CTL response in peripheral blood mononuclear cells from healthy donors (Anderson B W. Clin Cancer Res. 2000 6:4192–200; Anderson B W. Cancer Immunol Immunother. 2000 49:459–68), as well as the secretion of CXC chemokine IP-10 from peripheral blood mononuclear cells from breast cancer patients and healthy donors (Lee T V. J Interferon Cytokine Res. 2000 20:391–401). However, in a clinical trial with that MHC Class I peptide only 3/9 patients had lymphocyte proliferative responses that were above baseline following vaccination (Murray J L. Semin Oncol. 2000 27 Suppl: 71–5). Increased CTL proliferation and IFN-ã levels were seen in stimulated cultures of peripheral blood mononuclear cells of only one vaccinated patient. In 3 of 5 patients, IFN-ã and CTL activity were increased significantly by IL-12 addition, indicating that weak antigen presentation leads to weak CTL induction, which is reversed partially in vitro with pro-inflammatory cytokines. However, MHC Class I peptide immunization does not induce helper $CD4^+$ T cell responses. For this reason, peptide vaccines are sought with either only a MHC Class II presented, $CD4^+$ T-helper cell stimulating epitope or with a peptide in which a MHC Class II-presented, CD4+ T-helper cell stimulating epitope overlays a MHC Class I-presented, $CD8^+$ T-cytotoxic cell stimulating epitope.

Peripheral blood mononuclear cells from healthy donors and ovarian cancer patients do respond to Her-2/neu peptides (Fisk B. Anticancer Res. 1997 17:45–53). Peptide sequences from Her-2/neu containing anchors for major human MHC-class II molecules induced proliferative and cytokine responses at a higher frequency in healthy donors than in ovarian cancer patients. Four Her-2/neu peptides of sequences: 396–406, 474–487, 777–789, and 884–899 stimulated proliferation of a larger number of healthy donors than three other distinct HER-2 peptides 449–464, 975–987 and 1086–1098. The pattern of responses of twenty-five ovarian cancer patients was different from that of healthy donors. T cell lines were developed by stimulation with peptides of peripheral blood mononuclear cells of an ovarian cancer patient who showed a stable response to all four Her-2/neu peptides over six months. Each T cell line differed in secretion of IFN-gamma and IL-10. These results demonstrate (a) that Her-2/neu peptides can stimulate expansion of T cells in both healthy donors and ovarian cancer patients, and (b) different peptides induce different cytokine secretion patterns. (J Interferon Cytokine Res. 2002 May; 22(5): 583–92)

Ioannides and colleagues demonstrated axillary lymph nodes from patients with breast carcinoma respond to HER-2/neu peptides (Kuerer H M. J Interferon Cytokine Res. 2002 22:583–92). Freshly isolated lymphocytes from lymph nodes of 7 women undergoing surgery for invasive breast cancer were stimulated with HER-2/neu peptides at 50 μgm/ml and with control antigens. IFN-γ, IL-4, and IL-10 levels were determined at priming and at restimulation with HER-2/neu peptides. Lymphocytes isolated from the axillary lymph nodes of the patients responded to HER-2/neu peptides, proliferating and specific cytokine production. Proliferative responses to HER-2/neu peptides were seen in lymphocytes of patients with and without overexpression of HER-2/neu in the primary tumor. In some patients, the proliferative response to HER-2/neu peptides in lymphocytes from lymph nodes with metastases was absent or decreased compared to response in lymphocytes from lymph nodes without metastases from the same patient ($p<0.05$). HER-2/neu peptides induced a predominantly T helper type 1 (Th1) pattern of cytokine response in nodal lymphocytes isolated from breast cancer patients. A Th1-specific cytokine production pattern was maintained at priming and restimulation with HER-2/neu peptides and was amplified with IL-12 costimulation. These results indicate that HER-2/neu peptides can activate T cells in draining lymph nodes from women with invasive breast cancer.

Patients immunized with an HLA-A2-presented, Her-2/neu peptide developed only a low level and short-lived CTL response, in the absence of concurrent vaccination with a MHC Class II-presented epitope (Ward R L. Hum Immunol. 1999 60:510–5). Six HLA-A2 patients with Her-2/neu-overexpressing cancers received 6 monthly vaccinations with a vaccine preparation consisting of 500 μg of Her-2/neu(369–377) peptide, admixed with 100 μg of GM-CSF. The patients had either stage III or IV breast or ovarian cancer. Immune responses to the Her-2/neu(369–377) peptide were examined using an IFN-γ enzyme-linked immunosorbent spot assay. Although HER-2/neu MHC class I epitopes induced HER-2/neu peptide-specific IFN-γ-producing CD8+ T cells, the magnitudes of the responses were low, as well as short-lived, indicating that CD4+ T-cell help is required for robust and lasting immunity to this epitope.

Disis and colleagues immunized with breast cancer patients a HER-2/neu helper peptide vaccine generating HER-2/neu CD8 T-cell immunity (Knutson K L. J Clin Invest. 2001 107:477–84). Nineteen HLA-A2 patients with HER-2/neu-overexpressing cancers received a vaccine preparation consisting of Her-2/neu(369–384), Her-2/neu (688–703), and Her-2/neu(971–984). Contained within these sequences are HLA-A2-binding motifs Her-2/neu (369–377), Her-2/neu(689–697), and Her-2/neu(971–979). After vaccination, the mean peptide-specific T-cell precursor frequency to the HLA-A2 peptides increased in the majority of patients. In addition, the peptide-specific T cells were able to lyse tumors. The responses were long-lived and detected for more than 1 year after the final vaccination in some patients. These results demonstrate that Her-2/neu MHC class II epitopes containing overlaying MHC Class I epitopes induce long-lasting Her-2/neu-specific IFN-γ-producing CD8 T cells.

Disis and colleagues immunized sixty-four patients with HER-2/neu-overexpressing breast, ovarian, or non-small-cell lung cancers with vaccines composed of peptides derived from potential T-helper epitopes of the HER-2/neu protein mixed with granulocyte-macrophage colony-stimulating factor and administered intradermally (Disis M L. J Clin Oncol. 2002 20:2624–32). Nine different epitopes were used: 3 derived from the intracellular domain of her-2/neu (p776–790, p927–941, and p1166–1180), 3 derived from the extracellular domain of her-2/neu (p42–56, p98–114, and p328–345), and 3 with helper epitopes that encompass in their natural sequence HLA-A2 binding motifs (p369–384, p688–703, and p971–984). Ninety-two percent of patients developed T-cell immunity to HER-2/neu peptides and 68% to a HER-2/neu protein domain. Epitope spreading was observed in 84% of patients and correlated with the generation of a HER-2/neu protein-specific T-cell immunity ($P=0.03$). At 1-year follow-up, immunity to the HER-2/neu protein persisted in 38% of patients. No patient developed any detected autoimmune toxicity, particularly in organs known to express basal levels of her-2/neu protein including the liver, digestive tract, and skin. The incorporation of MHC Class II epitopes used in this study in Ii-Key hybrid molecules might lead to more rapid anti-her-2/neu immune responses with lower and fewer doses, greater epitope spreading, induction of higher affinity T-cells against tumor, more prolonged immune responses against epitopes and her-2/neu protein, and greater clinical efficacy.

Finding tumor-reactive CTLs in tumor infiltrates and in the peripheral blood of cancer patients, raises the question that any anti-tumor immune response does not control disease spread (Anderson B W. Clin Cancer Res. 2000 6:4192–200). One might then question whether amplification of this response by peptide vaccines is useful during disease progression. Induction of tumor-reactive CTLs in healthy donors at risk, as well as in patients free of disease, has been proposed on the hypothesis that CTLs that recognize tumors early are more effective in containing their progression than CTLs that expand only when the disease progresses. Priming of cytolytic T cell activity in 10 healthy donors was tested with Her-2/neu(369–377) peptide as an immunogen and autologous peripheral blood mononuclear cell-derived dendritic cells as antigen presenting cells. Of those two responded at priming with Her-2/neu(369–377) peptide presented on autologous dendritic cells by induction of Her-2/neu(369–377) peptide-specific CTL activity. Three other responders were identified after two additional restimulations. Induction of cytolytic activity at priming was enhanced in responders by tumor necrosis factor-alpha and IL-12 but not in the non-responders.

Determinant spreading and Th1 responses were induced by in vitro stimulation with Her-2/neu peptides (Anderson B W. Cancer Immunol Immunother 2000 49:459–68). The induction of a response to Her-2/neu(776–789) induced reactivity to other Her-2/neu peptides. Her-2/neu(776–789) expanded a response to Her-2/neu (884–899) in both an ovarian cancer patient with progressive disease and a healthy donor who shared HLA-DR11. This response was characterized mainly by increased IFN-γ secretion, and proliferation, but did riot occur with another donor who shared only HLA-DR14 and HLA-DQ5 with the patient. Epitope spreading can also be enhanced by the coordinated use of Ii-Key/antigenic epitope hybrids immunizations with Ii reverse gene construct, Her-2/neu gene immunizations.

Hess and colleagues found that a chimeric construct of an MHC class II binding peptide from Her-2/neu and the N-terminal flanking region of CLIP elicited potent antitumor activity against a Her-2/neu-positive tumor in a rat model system (Hess A D. Clin Immunol 2001 101:67–76). Induction of effective antitumor immunity required presentation of the chimeric peptide on irradiated tumor cells or in concert with a Her-2/neu MHC class I-restricted peptide from Her-2/neu. Adoptive transfer studies showed the need for CD4 T helper cells for protective antitumor immunity. Immunization with the epitope-only peptide caused a weak immune response to the unmodified peptide in vitro of both type 1 (IL-2, IFN-γ) and type 2 (IL-4, IL-10) cytokine-producing cells analyzed by RT-PCR (qualitative and quantitative) and by limiting dilution assay. Comparatively, immunization with the chimeric construct elicited a potent immune response to the parent epitope with predominantly type 1 cytokine-producing cells.

Accelerated Her-2/neu degradation enhanced ovarian tumor recognition by CTL (Castilleja A. Mol Cell Biochem. 2001 217:21–33). In those studies, Her-2/neu degradation was enhanced in the ovarian tumor line, SKOV3.A2, that constitutively overexpressed Her-2/neu by the addition of geldanamycin, which down-modulated Her-2/neu from the cell surface and promoted its polyubiquitinylation and degradation. Presentation of the immunodominant cytotoxic T lymphocyte (CTL) epitope, Her-2/neu(369–377) from SKOV.A2 was inhibited by proteosome inhibitors, such as LLnL. Additional experiments indicated that the newly synthesized Her-2/neu in the presence of GA was the main source of epitopes recognized by CTL. Twenty-hour GA-treated SKOV3.A2 cells were better inducers of CTL activity directed to a number of Her-2/neu CTL epitopes, in peripheral blood mononuclear cells compared with control untreated SKOV3.A2 cells thereby promoting immunogenecity. Similarly geldanamycin and other compounds acting by a similar mechanism, are expected to enhance binding of MHC Class II epitopes in the ER in the absence of Ii protein.

Ward and colleagues used phage-displayed ErbB-2 gene fragment libraries and synthetic peptides to epitope-map a panel of anti-Her-2/neu monoclonal antibodies (Yip Y L. Cancer Immunol Immunother. 2002 50:569–87; Yip Y L. J. Immunol. 2001 166:5271–8). The epitopes of three monoclonal antibodies, N12, N28, and L87, were successfully located to Her-2/neu(C531–A586), Her-2/neu(T216–C235), and Her-2/neu(C220–C235) of Her-2/neu, respectively. It was found that while N12 inhibited tumor cell proliferation, N28 stimulated the proliferation of a subset of breast cancer cell lines over-expressing Her-2/neu. The peptide region recognized by N12, Her-2/neu(C531–A586), was used as an immunogen to selectively induce an inhibitory immune response in mice. Mice immunized with the GST fusion peptide, GST-Her-2/neu(C531–A586), recognized native Her-2/neu, the peptide Her-2/neu(531–586), three 15-amino acid peptides of Her-2/neu(533–548), Her-2/neu (545–5560), and Her-2/neu(571–586). More importantly, immunoglobulins purified from mouse sera were able to inhibit up to 85% of tumor cell proliferation. This study supports the use of some of the potential antibody recognized determinants in the construction of Ii-Key/Her-2/neu MHC Class II-presented antigenic epitope/antibody-recognized determinant hybrids. The antibody recognized determinants are presented in Table 16.8 and hybrids containing those epitopes are presented in Table 16.9. Such hybrids containing antibody-recognized determinants might be preferred can be used for the development of both passive and active immunotherapies of Her-2/neu over-expressing tumors.

Given the experimentally identified MHC Class II-presented epitopes (above) such epitope can be synthesized within Ii-Key/Her-2/neu antigenic epitope hybrids for stimulation of a diagnostic or therapeutic immune response.

The amino acid sequence of human Her-2/neu protein [*Homo sapiens*](gi|19575768|) was obtained from GenBank (Table 16.1). An important consideration in the selection of peptides for cancer immunotherapy is the high degree of sequence homology between Her-2/neu and another member of the subclass I family of growth factor receptor (EGF-r) (Lustgarten J. Hum Immunol. 1997 52:109–18). Unlike Her-2/neu, the EGF-r is widely expressed in the body. Peptide sequences identical between Her-2/neu and the mouse or human EGF-r were not selected for two reasons. First, it is likely that T-cell tolerance to such sequences would have eliminated from the repertoire high affinity T cells with specificity for such epitopes. Second, it would be undesirable to target CTL against normal cell expressing EGF-r peptides. Predicted MHC Class II-presented epitopes of Her-2/neu protein are presented in Table 16.2. Experimentally determined MHC Class II-restricted epitope of human Her-2/neu protein are listed in Table 16.3. Designed Ii-Key/Her-2/neu hybrids using some of the MHC Class II-presented epitopes of Tables 2 and 3 are listed in Table 16.4. Predicted MHC Class I-presented epitopes of Her-2/neu protein are listed in Table 16.5. Experimentally determined MHC Class I-presented epitopes of Her-2/neu protein are listed in Table 16.6. Designed Ii-key/MHC Class II epitope/MHC Class I epitope hybrids are listed in Table 16.7. Antibody-recognized determinants on Her-2/neu are listed in Table 16.8 Designed Ii-Key/Her-2/neu hybrids using some of the antibody-recognized determinants of Table 16.8 and MHC Class II-presented epitopes of Tables 2 and 3 are presented in Table 16.9.

TABLE 16.1

(SEQ ID NO:553)
Deduced amino acid sequence of Her-2/neu.

| | | | | | |
|---|---|---|---|---|---|
| 1 | melaalcrwg | lllallppga | astqvctgtd | mklrlpaspe | thldmlrhly |
| 51 | qgcqvvqgnl | eltylptnas | lsflqdiqev | qgyvliahnq | vrqvplqrlr |
| 101 | ivrgtqlfed | nyalavldng | dplnnttpvt | gaspgglrel | qlrslteilk |
| 151 | ggvliqrnpq | lcyqdtilwk | difhknnqla | ltlidtnrsr | achpcspmck |
| 201 | gsrcwgesse | dcqsltrtvc | aggcarckgp | lptdccheqc | aagctgpkhs |
| 251 | dclaclhfnh | sgicelhcpa | lvtyntdtfe | smpnpegryt | fqascvtacp |
| 301 | ynylstdvgs | ctlvcplhnq | evtaedgtqr | cekcskpcar | vcyglgmehl |
| 351 | revravtsan | iqetagckki | fgslaflpes | fdgdpasnta | plqpeqlqvf |
| 401 | etleeitgyl | yisawpdslp | dlsvfqnlqv | irgrilhnga | ysltlqglgi |
| 451 | swlglrslre | lgsglalihh | nthlcfvhtv | pwdqlfrnph | qallhtanrp |
| 501 | edecvgegla | chqlcarghc | wgpgptqcvn | csqflrgqec | veecrvlqgl |
| 551 | preyvnarhc | lpchpecqpq | ngsvtcfgpe | adqcvacahy | kdppfcvarc |
| 601 | psgvkpdlsy | mpiwkfpdee | gacqpcpinc | thscvdlddk | gcpaeqrasp |
| 651 | ltsiisavvg | illvvvlgvv | fgilikrrqq | kirkytmrrl | lqetelvepl |
| 701 | tpsgampnqa | qmrilketel | rkvkvlgsga | fgtvykgiwi | pdgenvkipv |
| 751 | aikvlrents | pkankeilde | ayvmagvgsp | yvsrllgicl | tstvqlvtql |
| 801 | mpygclldhv | renrgrlgsq | dllnwcmqia | kgmsyledvr | lvhrdlaarn |
| 851 | vlvkspnhvk | itdfglarll | dideteyhad | ggkvpikwma | lesilrrrft |
| 901 | hqsdvwsygv | tvwelmtfga | kpydgipare | ipdllekger | lpqppictid |
| 951 | vymimvkcwm | idsecrprfr | elvsefsrma | rdpqrfvviq | nedlgpaspl |
| 1001 | dstfyrslle | dddmgdlvda | eeylvpqqgf | fcpdpapgag | gmvhhrhrss |
| 1051 | strsgggdlt | lglepseeea | prsplapseg | agsdvfdgdl | gmgaakglqs |
| 1101 | lpthdpsplq | rysedptvpl | psetdgyvap | ltcspqpeyv | nqpdvrpqpp |
| 1151 | spregplpaa | rpagatlerp | ktlspgkngv | vkdvfafgga | venpeyltpq |
| 1201 | ggaapqphpp | pafspafdnl | yywdqdpper | gappstfkgt | ptaenpeylg |
| 1251 | ldvpv | | | | |

TABLE 16.2

Predicted MHC Class II-presented epitopes of Her-2/neu protein.

| PEPTIDE | Pos. | Sequence | Score | Ii-Key | SEQ. ID. NO. |
|---|---|---|---|---|---|
| 16.2.1 | 985 | FVVIQNEDL | 7.40 | 6 | 554 |
| 16.2.2 | 98 | LRIVRGTQL | 7.30 | 4 | 555 |

TABLE 16.2-continued

Predicted MHC Class II-presented epitopes of Her-2/neu protein.

| PEPTIDE | Pos. | Sequence | Score | Ii-Key | SEQ. ID. NO. |
|---|---|---|---|---|---|
| 16.2.3 | 952 | MIMVKCWMI | 7.20 | — | 556 |

TABLE 16.2-continued

Predicted MHC Class II-presented epitopes of Her-2/neu protein.

| PEPTIDE | Pos. | Sequence | Score | Ii-Key | SEQ. ID. NO. |
|---|---|---|---|---|---|
| 16.2.4 | 894 | LRRRFTHQS | 7.00 | 6 | 557 |
| 16.2.5 | 684 | YTMRRLLQE | 6.70 | 6 | 558 |
| 16.2.6 | 664 | VVLGVVFGI | 5.90 | — | 559 |
| 16.2.7 | 1041 | MVHHRHRSS | 5.60 | — | 560 |
| 16.2.8 | 421 | LSVFQNLQV | 5.50 | — | 561 |
| 16.2.9 | 180 | LTLIDTNRS | 5.40 | 4 | 562 |
| 16.2.10 | 670 | FGILIKRRQ | 5.40 | — | 563 |
| 16.2.11 | 396 | LQVFETLEE | 5.20 | — | 564 |
| 16.2.12 | 61 | LTYLPTNAS | 5.10 | 11 | 565 |
| 16.2.13 | 951 | YMIMVKCWM | 5.00 | — | 566 |
| 16.2.14 | 719 | LRKVKVLGS | 5.00 | 4 | 567 |
| 16.2.15 | 424 | FQNLQVIRG | 5.20 | — | 568 |

Pos. is the residue position in the primary sequence of the first amino acid in the antigenic epitope. Sequence is the amino acid sequence of the predicted MHC Class II-presented epitope. Score is the score reported by the ProPred program, for high scoring selections with multiple common HLA-DR alleles. Ii-Key is the number of residue positions intervening between an Ii-Key motif and the first residue of the antigenic epitope.

TABLE 16.3

Experimentally determined MHC Class II-restricted epitope of human Her-2/neu protein.

| PEPTIDE | Pos. | Sequence | SEQ. ID. NO. |
|---|---|---|---|
| 16.3.1 | 884 | VPIKWMALESILRRR | 569 |
| 16.3.2 | 776 | GSPYVSRLLGICL | 570 |
| 16.3.3 | 396 | QLQVFETLEEI | 571 |
| 16.3.4 | 474 | LCFVHTVPWDQLF | 572 |
| 16.3.5 | 450 | GISWLGLRSLRE | 573 |
| 16.3.6 | 975 | EFSRMARDPQRF | 574 |
| 16.3.7 | 1086 | FDGDLGMAAKGL | 575 |
| 16.3.8 | 42 | HLDMLRHLYQGCQVV | 576 |
| 16.3.9 | 98 | LRIVRGTQLFEDNYAL | 577 |
| 16.3.10 | 328 | TQRCEKCSKPCARVCYGL | 578 |
| 16.3.11 | 776 | LGSGAFGTVYKGIWI | 579 |
| 16.3.12 | 927 | PAREIPDLLEKGERL | 580 |
| 16.3.13 | 1166 | TLERPKTLSPGKNGV | 581 |
| 16.3.14 | 369 | KKIFGSLLAFLPESFDGD | 582 |

TABLE 16.3-continued

Experimentally determined MHC Class II-restricted epitope of human Her-2/neu protein.

| PEPTIDE | Pos. | Sequence | SEQ. ID. NO. |
|---|---|---|---|
| 16.3.15 | 688 | RQQKIRKYTMRRLLQE | 583 |
| 16.3.16 | 971 | ELVSEFSRMARDPQ | 584 |

Pos. is the residue position in the primary sequence of the first amino acid in the peptide. Sequence is the amino acid sequence of the experimentally determined MHC Class II-presented epitope. Ii-Key is the number of residue positions intervening between an Ii-Key motif and the first residue of the antigenic epitope. Peptide 16.3.1 was reported by Perez S. et al. (Cancer Immunol Immunother. 2002 50:615–24). Peptide 16.3.2 was reported by Sotiriadou R. et al. (Br J Cancer. 2001 85:1527–34). Peptide 16.3.3 was reported by Fisk B. et al. (Anticancer Res. 1997 17:45–53). Peptides 16.3.8–16.3.16 are those reported in a Phase I clinical trial by Disis and colleagues (Disis M L. J Clin Oncol 2002 20:2624–32). Peptide 16.3.9 contains a predicted HLA-DRB1-0101-presented motif LRIVRTGTQL (SEQ ID NO: 585) and PEPTIDE 16.3.16 contains a DRB1-0101-presented motif LVSEFSRMA (SEQ ID NO: 586); both stimulated lymphocytes from an immunized patients. Additional peptides in the series studied by Disis et al. might be found to containing MHC Class II-presented motifs when tested for additional HLA-DB alleles and to lower indices for scoring. Such epitopes are subject to being incorporated in Ii-Key/Her-2 antigenic epitope hybrids.

TABLE 16.4

Designed Ii-Key/Her-2/neu hybrids using some of the MHC Class II-presented epitopes of Tables 2 and 3.

| PEPTIDE | Pos. | Sequence | SEQ. ID. NO. |
|---|---|---|---|
| | | A. Non-overlapping | |
| 16.4.1 | 776 | Ac-LRMK-ava-GSPYVSRLLGICL-$NH_2$ | 587 |
| 16.4.2 | 396 | Ac-LRMK-ava-QLQVFETLEEI-$NH_2$ | 588 |
| 16.4.3 | 985 | Ac-LRMK-ava-FVVIQNEDL-$NH_2$ | 589 |
| 16.4.4 | 98 | Ac-LRMK-ava-LRIVRGTQL-$NH_2$ | 590 |
| 16.4.5 | 894 | Ac-LRMK-ava-LRRRFTHQS-$NH_2$ | 591 |
| 16.4.6 | 684 | Ac-LRMK-ava-YTMRRLLQE-$NH_2$ | 592 |
| 16.4.7 | 1041 | Ac-LRMK-ava-MVHHRHRSS-$NH_2$ | 593 |
| 16.4.8 | 972 | Ac-LRMK-ava-LVSEFSRMA-$NH_2$ | 594 |
| | | B. Overlapping | |
| 16.4.8 | 884, 894 | Ac-LRMK-ava-VPIKWMALESILRRRFT HQS-$NH_2$ | 595 |
| 16.4.9 | 664, 670 | Ac-LRMK-ava-VVLGVVFGILIKRRQ-$NH_2$ | 596 |
| 16.4.10 | 951, 952 | Ac-LRMK-ava-YMIMVKCWMI-$NH_2$ | 597 |

TABLE 16.4-continued

Designed Ii-Key/Her-2/neu hybrids using some of the MHC Class II-presented epitopes of Tables 2 and 3.

| PEPTIDE | Pos. | Sequence | SEQ. ID. NO. |
|---|---|---|---|
| 16.4.11 | 421, 424 | Ac-LRMK-ava-LSVFQNLQVIRG-$NH_2$ | 598 |

Pos. is the residue position in the primary sequence of the first amino acid in the antigenic epitope. Sequence is the amino acid sequence of a hybrid peptide containing a MHC Class II epitope of Table 16.2 and 16.3.

TABLE 16.5

Predicted MHC Class I-presented epitopes of Her-2/neu protein.

| PEPTIDE | Pos. | Sequence | Score | SEQ. ID. NO. |
|---|---|---|---|---|
| 16.5.1 | 661 | ILLVVVLGV | 1006.2 | 599 |
| 16.5.1 | 369 | KIFGSLAFL | 481.2 | 600 |
| 16.5.1 | 167 | ILWKDIFHK | 450.0 | 601 |
| 16.5.1 | 63 | TYLPTNASL | 360.0 | 602 |
| 16.5.2 | 106 | QLFEDNYAL | 324.1 | 603 |
| 16.5.3 | 553 | EYVNARHCL | 300.0 | 604 |
| 16.5.4 | 440 | AYSLTLQGL | 240.0 | 605 |
| 16.5.5 | 907 | SYGVTVWEL | 220.0 | 606 |
| 16.5.6 | 1022 | EYLVPQQGF | 180.0 | 607 |
| 16.5.7 | 689 | RLIQETELV | 126.1 | 608 |
| 16.5.8 | 714 | ILKETELRK | 60.0 | 609 |
| 16.5.9 | 754 | VLRENTSPK | 30.0 | 610 |
| 16.5.10 | 673 | ILIKRRQQK | 30.0 | 611 |

Pos. is the residue position in the primary sequence of the first amino acid in the antigenic epitope. Sequence is the amino acid sequence of the predicted MHC Class I-presented epitope. The MHC Class I-presented epitopes were predicted with the use of the online program at (http://bimas.dcrt.nih.gov/molbio/hla_bind/). Score is the $T_{1/2}$ of disassociation of a peptide containing this subsequence (Tsang K Y. J Natl Cancer Inst. 1995 87:982–90).

TABLE 16.6

Experimentally determined MHC Class I-presented epitopes of Her-2/neu protein.

| PEPTIDE | Pos. | Sequence | SEQ. ID. NO. |
|---|---|---|---|
| 16.6.1 | 106 | QLFEDNYAL | 612 |
| 16.6.2 | 369 | KIFGSLAFL | 613 |

TABLE 16.6-continued

Experimentally determined MHC Class I-presented epitopes of Her-2/neu protein.

| PEPTIDE | Pos. | Sequence | SEQ. ID. NO. |
|---|---|---|---|
| 16.6.3 | 689 | RLLQETELV | 614 |
| 16.6.4 | 435 | ILHNGAYSL | 615 |
| 16.6.5 | 665 | VVLGVVFGI | 616 |
| 16.6.6 | 952 | YMIMVKCWM | 617 |
| 16.6.7 | 654 | IISAVVGIL | 618 |
| 16.6.8 | 654 | FLSAVVGILV | 619 |
| 16.6.9 | 773 | VMAGVGSPYV | 620 |
| 16.6.10 | 754 | VLRENTSPK | 621 |

Pos. is the residue position in the primary sequence of the first amino acid in the antigenic epitope. Sequence is the amino acid sequence of the experimentally defined MHC Class I-presented epitope. Peptide 16.6.1 is presented by HLA-A2.1 (Kono K. Int J Cancer. 1998 78:202–8). Peptide 16.6.2 is presented by HLA-A2.1 (Kono K. Int J Cancer. 1998 78:202–8), as confirmed by Rongcun Y., et al. (J. Immunol. 1999 163:1037–44). It was also shown to be immunogenic in double transgenic mice expressing HLA-A2.1 and human CD8 (Lustgarten J. Hum Immunol. 1997 52:109–18). Peptide 16.6.3 is presented by HLA-A2.1 (Kono, K. Int J Cancer. 1998 78:202–8; Rongcun Y. J. Immunol. 1999 163:1037–44). It was nonimmunogenic in the study of Lustgarten J. et al. (Hum Immunol. 1997 52:109–18). Peptides 16.6.4, 16.6.5 and 16.6.6 are presented by HLA-A2.1 (Rongcun Y. J. Immunol. 1999 163:1037–44). Peptide 16.6.7 is presented by HLA-A2 (Peoples G. Proc Natl Acad Sci USA. 1995 92:432–6) and is nonimmnogenic in the study of Lustgarten, J. et al. (Hum Immunol. 1997 52:109–18). Peptide 16.6.8 is presented by HLA-A2 (Tanaka Y. Int J Cancer. 2001 94:540–4). Peptide 16.6.9 is presented by HLA-A2.1 (Lustgarten J. Hum Immunol. 52:109–18). Peptide 16.6.10 is presented by HLA-A3 (Kawashima I. Cancer Res. 1999 59:431–5).

TABLE 16.7

Designed Ii-key/MHC Class II epitope/MHC Class I epitope hybrids.

| PEPTIDE | Pos. | Sequence | SEQ. ID. NO. |
|---|---|---|---|
| 16.7.1 | II:76, I:73 | Ac-LRMK-*ava*-VMAGVGSPYVSRLLGICL-$NH_2$ | 622 |
| 16.7.2 | II:396, I:369 | Ac-LRMK-*ava*- QLQVFETLEEI KIFGSLAFL-$NH_2$ | 623 |
| 16.7.3 | II:670, I:673 | Ac-LRMK-*ava*-FGILIKRRQQK-$NH_2$ | 624 |

Pos. is the residue position in the primary sequence of the first amino acid in the antigenic epitope, with MHC Class II indicated as I: and MHC Class II indicated as II:. Sequence is the amino acid sequence of a hybrid peptide containing a MHC class II epitope of Table 1.2.

TABLE 16.8

| Antibody-recognized determinants on Her-2/neu. | | | |
|---|---|---|---|
| Peptide | Pos. | Sequence | SEQ ID NO: |
| 16.8.1 | 216 | TRTVCAGGCARCKGP | 625 |
| 16.8.2 | 220 | CAGGCARCKGPLPTD | 626 |
| 16.8.3 | 533 | QFLRQECVEECRVLQ | 627 |
| 16.8.4 | 545 | VLQGLPREYVNARHC | 628 |
| 16.8.5 | 571 | NGSVTCFGPEADQCV | 629 |

These peptides are reported to react with serums of mice which were immunized with a GST fusion protein containing the Her-2/neu(C220–C235) sequence (Yip Y L. Cancer Immunol Immunother. 2002 50:569–87; Yip Y L. J. Immunol. 2001 166:5271–8).

TABLE 16.9

| Designed Ii-Key/Her-2/neu hybrids using some of the antibody-recognized determinants of Table 16.8 and MHC Class II-presented epitopes of Tables 2 and 3. | | | |
|---|---|---|---|
| PEPTIDE | Pos. | Sequence | SEQ. ID. NO. |
| A. Non-overlapping (MHC Class II and antibody-recognized epitopes) | | | |
| 16.9.1 | 776; 216,220 | Ac-LRMK-*ava*-GSPYVSRLLGICL-TRTVCAGGCARCKGPLPTD-NH | 630 |
| 16.9.2 | 396;571 | AC-LRMK-*ava*-QLQVFETLEEI-NGSVTCFGPEADQCV-$NH_2$ | 631 |
| B. Overlapping | | | |
| 16.9.3 | 534;533 | Ac-LRMK-*ava*-SQFLRGQECVEECRVLQ-$NH_2$ | 632 |
| 16.9.4 | 555;556 | Ac-LRMK-*ava*-RVLQGLPREYVNARHC-$NH_2$ | 633 |

Pos. is the residue position in the primary sequence of the first amino acid in the MHC Class II-presented epitope and after the semicolon is the first residue in the peptide reported to contain an antibody-recognized epitope. Sequence is the amino acid sequence of a hybrid peptide.

Example 17

Ii-Key/Anthrax MHC Class II Antigenic Epitope Hybrids

Ii-Key/antigenic epitope hybrids can be applied as vaccines against anthrax and other bioterrorism agents. In order to understand well the applications of Ii-Key/antigenic epitope hybrids as stand-alone vaccines or as components of a multivaccine protocol against anthrax, a review of the biology and pathogenesis of *bacillus anthracis* is useful. Likewise, the currently available vaccines against anthrax are considered in light of improvements offered by the products and methods of this disclosure. Specifically, the Ii-Key/antigenic epitope hybrid technology provides for enhanced antigen-specific T-helper cell responses, which enable existing vaccines and independently offer a significant degree of protection against anthrax infection. The Ii-Key/anthrax epitope peptide vaccine offers safety and effectiveness for use by both military and civilian populations.

Anthrax is an infectious disease caused by the spores of the bacterium, *Bacillus anthracis*, a large gram-positive, non-motile, bacterial rod. Human anthrax disease has three major forms: cutaneous, inhalational, and gastrointestinal. If untreated, anthrax in all forms can lead to septicemia and death. Early treatment of cutaneous anthrax is usually curative. Patients with gastrointestinal anthrax have reported case fatalities of 25% to 75%. Case fatality rates for inhalation anthrax are 90% to 100%. Early treatment of all forms of anthrax with antibiotics is essential because antibiotics are ineffective once the bacteria grow densely enough to secrete anthrax toxin (Leppla S H. Nature Medicine. 2001 7:659–660). Inhalational anthrax has two phases. During the first phase, which occurs within one to five days following exposure, the patient has flu-like symptoms (cough, malaise, fatigue and mild fever). The following phase includes sudden onset of severe respiratory distress, chest pain, and fever. Within a day, septic shock and death will likely occur. In the case of inhalational anthrax, antibiotic therapy is of limited benefit except when given immediately following exposure.

Anthrax toxin, the major virulence factor produced by *B. anthracis*, consists of three proteins. PA binds to human cells and forms a channel through which LF, the dominant virulence factor, enters the cytosol (Leppla S H. Nature Medicine. 2001 7:659–660). LF is a metalloproteinase that cleaves mitogen-activated protein kinases (MEKs), resulting in cell death and a clinical picture resembling septic shock. It is the binding of LF to PA63 (an area on PA that is made available following cellular binding and furin catalysis of PA) that triggers LF-PA63 binding, oligomerization, heptamer formation, and cytosolic transport of LN (Leppla S H. Bacterial protein toxins (eds. Fehrenbach F. et al.) 111–112 Gustav Fischer, New York, 1988).

Anthrax lethal toxin comprises two proteins: protective antigen (PA; MW 83 kDa) and lethal factor (LF; MW 87 kDa). The crystal structure of PA was determined in monomeric and heptameric forms (Liddington R. J Appl Microbiol. 1999 87:282–290). It bears no resemblance to other bacterial toxins of known three-dimensional structure, and defines a new structural class, which includes homologous toxins from other Gram-positive bacteria. Membrane insertion involves the water-soluble heptamer undergoing a substantial pH-induced conformational change thereby creating a 14-stranded beta-barrel. Recent work by Collier's group lends support to this model of membrane insertion (Benson E L. Biochemistry. 1998 37:3941–8). Lethal factor is the catalytic component of anthrax lethal toxin. It binds to the surface of the cell-bound PA heptamer and, following endocytosis and acidification of the endosome, translocates to the cytosol.

Liddington and colleagues determined the crystal structure of the anthrax lethal factor (Pannifer A D. Nature 2001 414:229–33). Lethal factor (LF) is highly specific protease that cleaves members of the mitogen-activated protein kinase kinase (MAPKK) family near their amino termini, leading to the inhibition of one or more signaling pathways. The crystal structure of LF and its complex with the N terminus of MAPKK-2 was determined. LF comprises four domains: domain I binds the membrane-translocating component of anthrax toxin, the protective antigen (PA); domains II, III and IV together create a long deep groove that holds the 16-residue N-terminal tail of MAPKK-2 before cleavage. Domain II resembles the ADP-ribosylating toxin from *Bacillus cereus*, but the active site has been mutated and recruited to augment substrate recognition. Domain III is inserted into domain II, and seems to have arisen from a repeated duplication of a structural element of domain II. Domain IV is distantly related to the zinc metalloprotease family, and contains the catalytic center; it also resembles domain I. The structure thus reveals a protein that has evolved through a process of gene duplication, mutation and fusion, into an enzyme with high and unusual specificity.

Proteasome activity is required for anthrax lethal toxin to kill macrophages (Tang G. Infect Immun. 1999 67:3055–60). Anthrax lethal toxin (LeTx), consisting of protective antigen (PA) and lethal factor (LF), rapidly kills primary mouse macrophages and macrophage-like cell lines. LF is translocated by PA into the cytosol of target cells, where it cleaves mitogen-activated protein kinase kinase 1 (MEK1) and possibly other proteins. Proteasome inhibitors such as acetyl-Leu-Leu-norleucinal, MG132, and lactacystin efficiently block LeTx cytotoxicity, whereas other protease inhibitors do not. Various data indicate that the proteasome mediates a toxic process initiated by LF in the cell cytosol. This process probably involves degradation of unidentified molecules that are essential for macrophage homeostasis. Moreover, this proteasome-dependent process is an early step in LeTx intoxication, but it is downstream of the cleavage by LF of MEK1 or other putative substrates.

Leppla and colleagues found oligomerization of anthrax toxin protective antigen and binding of lethal factor during endocytic uptake into mammalian cells (Singh Y. Infect Immun. 1999 67:1853–9). The protective antigen (PA) protein of anthrax toxin binds to a cellular receptor and is cleaved by cell surface furin to produce a 63-kDa fragment (PA63). The receptor-bound PA63 oligomerizes to a heptamer and acts to translocate the catalytic moieties of the toxin, lethal factor (LF) and edema factor (EF), from endosomes to the cytosol. The essential role of PA oligomerization in LF translocation was shown with PA protein cleaved at residues 313–314. The structure of the toxin proteins and the kinetics of proteolytic activation, LF binding, and internalization are balanced in a way that allows each PA63 subunit to internalize an LF molecule.

Leppla and colleagues identified three advances which point to possible therapies by inhibiting the toxin (Chaudry G J. Trends Microbiol. 2002 10:58–62). Identification of the cell surface toxin receptor could lead to the design of binding competitors and receptor decoys. Determination of the crystal structure of the lethal factor protease will facilitate ongoing efforts to develop protease inhibitors as therapies. Finally, the susceptibility of certain inbred mice to anthrax lethal toxin was associated with mutations in the kinesin-like protein Kif1C, a discovery that could help to explain how anthrax toxin kills animals.

Various vaccine strategies have been developed to protect humans against the pathological effects of PA and LF, which are released by *Bacillus anthracis*. In order to appreciate the usefulness of Ii-Key (MHC Class II and Ii-Key/MHC Class II epitope/ARD hybrids in augmenting those vaccines, it is useful to review the current state of vaccination against and treatment of anthrax infections.

During the bioterrorism attacks of late 2001 in which thousands of people were potentially exposed to anthrax spores contained in letters to elected officials and employees of media outlets, more than 30,000 individuals received prophylactic antibiotic therapy (principally ciprofloxacin and doxycycline) for 60 days. Because anthrax spores can persist in the lungs of animals for more than 60 days, these potentially exposed individuals were then offered another 40-day course of antibiotics and therapeutic vaccination with the Anthrax Vaccine Adsorbed upon completion of the initial antibiotic regimen. However, since there is only a narrow time-window for effective antibiotic therapy following exposure to anthrax spores, using antibiotics on a mass scale is not a realistic option. Prophylactic and therapeutic vaccination against anthrax and anthrax toxin is thus the most promising form of mass intervention in case of an anthrax-bioterrorism event.

Prior to its emergence as a potentially preferred bioterrorism weapon, anthrax infection was limited to animals and humans with occupations involving direct and extensive handling of animals or animal products. Approval of the current anthrax vaccine, Anthrax Vaccine Adsorbed was based on a clinical trial conducted by Philip S. Brachman in the 1950's involving U.S. mill workers who processed animal hides. Prior to the availability of this vaccine, the yearly average number of human anthrax cases was 1.2 per 100 employees in these mills. The Brachman study provided evidence for the efficacy of anthrax vaccination: (a) 26 patients developed anthrax during the study—5 inhalation and 21 cutaneous; (b) of the 5 inhalation anthrax cases, 2 patients received placebo and 3 were in the observation group; (c) four of the 5 patients with inhalation anthrax died; (d) of the 21 cases of cutaneous anthrax, 15 individuals received placebo, three were in the observation group, and two individuals were partially immunized, and one individual was fully immunized; (e) the authors calculated vaccine efficacy level of 92.5% for fully vaccinated individuals (Brachman P S. American Journal of Public Health. 1962 52:432–440).

In 1966 the CDC initiated a clinical study of a vaccine that was a modification of the vaccine used in the Brachman trial. Although both vaccines were based on immunity induced by protective antigen (PA), their methods of preparation differed. The IND trial used three lots of material produced by the Michigan Department of Public Health (MDPH). The data submitted to the Division of Biologics Standards described the CDC's experience with 16,000 doses of the anthrax vaccine administered to 7,000 study participants. Mild local reactions ranged between 3 to 36%, moderate reactions between 1 to 3%, and severe local reactions in less than 1%. Systemic reactions were reported in 4 cases over the 5-year period; these reactions included transient fever, chills, nausea, and general body aches. The vaccine was approved in 1970 for individuals who might contact animal products that might be contaminated with *B. anthracis* spores, individuals at high risk (including veterinarians), and those engaged in diagnostic or investigational activities that might bring them in contact with the spores.

In 1985 an Advisory Panel Review under the Public Health Service Act designated the anthrax vaccine produced by MDPH as a Category I product, that is safe, effective and not misbranded (Federal Register 1985 50:51002). The efficacy data from the Brachman study and the safety data from the CDC study were the basis for these findings. In May 1988, the Department of Defense (DOD) approved the prophylactic vaccination of US military personnel. In December 2001, therapeutic vaccination was also initiated in individuals previously exposed to anthrax spores (as a result of acts of bioterrorism in Florida, New York, and Washington, D.C.), and who were receiving prophylactic antibiotic therapy.

The current AVA vaccine produced by BioPort (the successor to MDPH in anthrax vaccine manufacturing) is derived from a strain of *B. anthracis* that does not cause anthrax disease. It is a cell-free filtrate containing no whole bacteria. The vaccination protocol includes an initial dose of 0.5 ml s.c., followed by 0.5 ml s.c. booster doses at 2 and 4 weeks, and 6, 12 and 18 months, with yearly boosters thereafter. The manufacturing process is difficult, costly, time consuming, limited in scale, and laden with many biologics controls. Development of a nontoxinogenic and nonencapsulated recombinant *B. anthracis* spore vaccine and lethal factor DNA vaccine have been initiated recently (Cohen S. Infect Immun. 2000 68:4549–58; Price B M. Infect Immun. 2002 69:4509–15). Also three new anthrax vaccines based on the PA protein are being studied (Friedlander A M. JAMA 1999 282:2104–6; Thomas L J. 4$^{th}$ International Conference on Anthrax. Abstracts Book. Jun. 10–13, 2001, Annapolis, Md., USA; Turnbull P C B. Curr Opin Infect Dis. 2001 13:11). Being products of biologic manufacturing, the process and controls are much more involved and wrought with regulatory issues than for simple peptides.

The Anthrax Vaccine Expert Committee (AVEC) reviewed adverse events reported to the Vaccine Adverse Event Reporting System (VAERS) (Sever J L. Pharmacoepidemiol Drug Saf. 2002 11:189–202; Geier D A. Clin Exp Rheumatol. 2002 20:217–20). Nearly half the reports noted a local injection-site adverse effect, with more than one-third of these involving a moderate to large degree of inflammation. Six events qualified as serious adverse effects, and all were judged to be certain consequences of vaccination. Three-quarters of the reports cited a systemic adverse effect (most common: flu-like symptoms, malaise, rash, arthralgia, headache), but only six individual medically important events were judged possibly or probably due to vaccine (aggravation of spondyloarthropathy (2), anaphylactoid reaction, arthritis (2), bronchiolitis obliterans organizing pneumonia). They concluded, since some cases of local inflammation involved distal paresthesia, AVEC recommends giving subcutaneous injections of AVA over the inferior deltoid instead of the triceps to avoid compression injury to the ulnar nerve.

Ii-Key/LF(MHC Class II epitope) hybrids will induce strong Th1 immune responses that will in turn augment CTL activity, macrophage-mediated bacteria lysis, and B cell-mediated antibody production. The resulting immune responses will mediate destruction of the bacteria via enhanced macrophage activation. In addition, the hybrid will provide for augmented B cell activation, which, in the setting of concomitant or subsequent exposure to LF, will hasten and enhance the production of antibodies that block binding of LF to PA, thereby preventing internalization of anthrax toxin.

Prophylactic vaccination with the Ii-Key/LF(MHC II epitope) hybrid peptide vaccine will induce memory T-helper cells that, upon subsequent exposure to *B. anthracis*, will activate macrophages more potently and more rapidly, thereby resulting in efficient lysis and clearance of bacteria. Priming with the Ii-Key/LF(MHC II epitope) hybrid peptide vaccine will lead to an expanded population of specific T-helper cells that will more quickly and efficiently activate B cells for antibody production upon vaccination with LF vaccine or exposure to *B. anthracis*. Boosting with the Ii-Key/LF(MHC Class II epitope) hybrid peptide vaccine in patients previously vaccinated or previously exposed to the disease will create a robust and rapid anamnestic response involving efficient activation of macrophages and B cells. Prior vaccination with the Ii-Key/LF (MHC II epitope) hybrid will result in more rapid stimulation of T-helper cells and activation of B-cells providing for augmented and more rapid antibody production, which is critical in the neutralization of anthrax toxin, upon exposure to a classical anthrax vaccine or the infection itself.

In another aspect Ii-Key/anthrax MHCC lass II epitope/anthrax ARD hybrids can be used to create an effective blocking antibody eliciting vaccine. Compound peptide constructs consisting of ARDS from PA binding sites on LF, are designed with covalently linkage to the Ii-Key/antigenic epitope hybrids. In some instances the sequences of the MHC Class II epitope and an ARD overlap. These double hybrid constructs [Ii-Key/LF(MHC II epitope)/LF1–255 (ARD)] trigger robust production of antibodies to LF1–255 via concomitant antigen-specific activation of T-helper cells and B-cells. The double hybrid construct focus and magnify the immune response on the most critical area, the PA63 binding site for LF. The antibodies produced following vaccination disrupt LF binding to PA63 and anthrax toxin internalization, thereby obviating the virulence of the disease. Methods of the process of developing immunization procedures with these Ii-Key/antigenic epitope hybrids for protection against anthrax and anthrax toxins include the following. 1. The most effective double hybrid(s) (in terms of inducing the most potent CD4+ T cell immunity and blocking the binding of LF1–255 to PA63 and entry of LF1–255 into cells) are tested in vivo in animal infection models to evaluate inhibition of bacteria growth and the virulence of the lethal toxin. 2. Immunization formulations (different doses with or without adjuvants), roots of immunization (s.c. or i.v.), and immunization schedules (with or without boosts) are evaluated in animal models. Toward application in a human trial, dose, dosage schedule, formulation, cytokine adjuvant, and basic local and systemic toxicities are evaluated in a murine protective model. 3. Activation of Th memory cells is tested in groups of immunized mice at 3, 6, 9 and 12 months for potency of CD4+ cell responses on a secondary challenge with the peptide, recombinant protein, or cDNA LF vaccine. 4. The most potent human HLA-DR restricted LF epitopes are determined for human clinical application. The most potent epitope for certain HLA-DR alleles are predicted using the Rammensee program. In as much as LF MHC Class II epitope aa576–591 might be presented by both HLA-DR1 and HLA-DR4, efforts to identify other pan-DR allele binding epitopes are made. The predicted Ii-Key/LF(HLA-DR epitope) constructs are tested for activity in ex vivo human PBMC stimulation and re-stimulation studies. Th1 and Th2 responses (double staining for CD4 and IFN-7 or CD4 and IL-4) are evaluated. 5. Double hybrids of the structure Ii-Key/LF(HLA-DR)/LF1–255(ARD) are synthesized using the most active Ii-Key/LF(HLA-DR epitope) and the most active antibody determinant (ARD). These are tested in animal toxicology and pharmacokinetics studies. 6. Clinical in vivo immunization and ex vivo PBMC re-stimulation studies in volunteers are performed with double hybrids to evaluate Th1 and Th2 responses. The several most promising double hybrids are evaluated in a subsequent clinical trial in which the induction of CD4+ T cell activation (double staining of PBMC for CD4 and IFN-γ or IL-4) and blocking antibodies are evaluated. ex vivo studies of the induced antibodies are performed to evaluate inhibition of the binding of LF1–255 to PA63 and LF1–255 entry into cells. The optimal hybrid(s) are further developed as an anthrax vaccine in clinical trials involving greater numbers of individuals. Appropriate efficacy endpoints and immunological surrogates are selected based on extensive discussion with appropriate regulatory agencies.

Ii-Key hybrid anthrax vaccines have significant advantages. (1) Safety. Since the Ii-Key hybrid vaccines are small peptides, as opposed to the full-length LF or PA protein, there is less risk of inducing unwanted immune responses against extraneous regions of the protein(s) which may be cross-reactive with normal host molecules, thereby resulting in autoimmune mediated toxicity. Peptide vaccine does not have reverse affect and thus can be safely used for large military and civilian populations; (2) Efficacy. To date, vaccines based on MHC Class II epitopes have not induced robust antigen specific immune responses primarily due to low binding efficiency. The Ii-Key hybrid technology enhances the charging efficiency of MHC Class II epitopes such that strong antigen-specific immune responses that are usually seen only in the context of concomitant IL-12 administration are observed. (3) Precise-targeting. Although current vaccines may induce high titers of polyclonal antibodies. However, these antibodies are not always against critical target, the LF binding site for PA. The Ii-Key double hybrid, Ii-Key/LF(MHC II epitope/LF1–255(ARD), will result in the production of antibodies specifically and precisely targeted to the LF binding sites for PA, thereby making efficient use of the resources brought to bear by the immune system. (4) Dual-action—the Ii-Key double hybrid will induce T-helper memory cells that will activate macrophages to effect cell-mediated bacterial lysis and clearing, as well as strong antibodies to the PA63 binding sites that will obviate the virulence of the anthrax toxin. Even in the setting of dense bacterial growth, the antibodies to PA binding sites on LF will protect from the virulent effects of the anthrax toxin. (5) Platform technology—once shown to be effective in the anthrax system, this approach is readily adaptable for use in other Category A (i.e., botulism, plague and smallpox), Category B, and Category C bioterrorism threats.

Ii-Key/LF(MHC II epitope) hybrids are designed to induce of LF-specific CD4+ T cell activation, which forms a major defense line to inhibit the growth of *B. anthracis*. Then the most potent Ii-Key/LF(MHC II epitope) hybrid are linked to putative ARDs of the PA63 binding site on LF to form double hybrids of the structure Ii-Key/LF(MHC II epitope)LF1–255(ARD). The ARDs are chosen from the published mapping of the sites on LF for binding to PA by mutation/binding assay (Lacy D B. J Biol. Chem. 2002 277:3005–10). The linkage of Ii-Key/LF(MHC Class II epitope) hybrid to ARDs will offer strong CD4+ T cell help for the induction of antibodies to the covalently linked ARDs (Golvano J. Eur J. Immunol. 1990 20:2363–6. These antibodies will bind to the surface of the PA binding sites on LF and block the binding of LF to PA63. The induction of high-titered antibodies against precisely targeted binding sites creates another line of defense, which abrogates the toxicity of *B. anthracis* LF, although the bacterial infection can be ongoing. MHC Class II-presented LF epitopes predicted with the SYFPEITHI program identifies three epitopes match perfectly the consensus sequence of the H-2$E^k$ motif: LF(91–106; HISLEALSDKKKIK) (SEQ ID NO: 634) LF(249–264; EQEINLSLEELKDQR) (SEQ ID NO: 635); LF(305–320; DDIIHSLSQEEKELL) (SEQ ID NO: 636). The activity of all hybrids in T cell activation studies will be compared with epitopes unlinked to Ii-Key. T cell activation is measured by two-color staining (anti-CD4 plus anti-IFN-γ for Th1 and anti-CD4 plus anti-IL-4 for Th2). AKR or C3H mice (H-$2K^k$) are immunized (3 mice/group) with varying doses (0.8, 4, and 20 nmol) of the Ii-Key/LF(MHC II epitope) hybrids. The concentration of 20 nmol, used by Berzofsky and colleagues (Berzofsky, J. A. J Clin Invest. 1991 88: 876–84), induced optimal T cell proliferation. A much lower concentration of hybrids will induce the same or higher levels of T cell response. In the first experiment, the adjuvant emulsion consists of equal volumes of CFA containing 1 mg/ml of *Mycobacterium tuberculosis* and hybrid peptides dissolved in PBS. Mice are immunized s.c. on the left side at the base of the tail. The same amount of hybrid peptides in incomplete Freund's adjuvant (IFA) are injected into the right side at the base of the tail 9 days later. Hybrids are injected in saline intravenously according to the same schedule to test the requirement for CFA in the efficacy of hybrids. It should be noted that Ii-Key hybrids will interact directly with MHC Class II molecules on the cell surface of APCs, thereby bypassing classical MHC Class II epitope processing and rendering the adjuvant superfluous. Four days following the second injection, the activation of lymphocytes from spleen, popliteal, inguinal, and para-aortic nodes of immunized mice are determined by established two color staining for CD4 and either IFN-γ or IL-4 (Varga S M. J. Immunol. 2001 166: 1554–61).

Ii-Key/LF(MHC II epitope)/LF1–255(ARD) double hybrids will produce antibodies which inhibit binding of LF to PA. The binding of LF to PA and subsequent entry of LF into cells are essential for the principal toxicity of *B. anthracis* infections. Blocking the binding of LF to PA is thus an effective way to control the virulence of *B. anthracis*. Lacy et al. have identified the PA binding sites on the surface of LF 1–255 by mutation/binding assays. Nine overlapping ARDs from these sites are synthesized in Ii-Key/MHC Class II antigenic epitope/ARD hybrids. Coupling to either a carrier or a MHC Class II epitope is required in order to induce antibodies against these short peptides (Golvano J. Eur J. Immunol. 1990 20:2363–6). LF has been crystallized and its functional domains have been defined (Pannifer A D. Nature 2001 414:229–33; Lacy D B. J Biol. Chem. 2002 277:3005–10). By LF mutation and PA/LF binding experiments, Lacy et al. have mapped the PA63 binding sites on LF. Mutations clustered at two locations greatly abolish the binding of LF to PA63: aa182–188 and aa223–236. Because these two clusters are located on the surface of LF, at that exposed binding site (Lacy D B. J Biol. Chem. 2002 277:3005–10), they are logically good targets for developing antibodies to block the binding of LF to PA63.

In another aspect this disclosure relates to augmenting the immune response to DNA vaccines for PA or LF. The Ii-Key/anthrax antigenic epitope hybrids of this disclosure can be applied as a prevaccine given in advance of a DNA vaccine for an anthrax-coded protein. Several examples of such vaccines follow.

Galloway and colleagues developed protection against anthrax lethal toxin challenge by immunization with plasmids encoding LF(10–254) or PA(175–764) or both (Price B M. Infect Immun. 2001 69:4509–15). Gold particles coated with either or both plasmids were gene-gun injected into mice three times at 2-week intervals. Antibody titers both PA and LF were five times greater than titers from mice immunized with either gene alone. All mice immunized with either or both plasmids survived an i.v. challenge with a lethal dose of PA+LF.

Gu and colleagues also studied comparable PA DNA vaccines (GU M L. Vaccine 1999 17:340–4). A 1:100 dilution of serum from mice immunized with PA DNA protected cells in vitro against cytotoxic concentrations of PA. 7 of 8 mice immunized three times with the PA DNA vaccine were protected against lethal challenge with a combination of anthrax protective antigen plus lethal factor. The augmentation of such immunizations with DNA vaccines for PA might be further augmented by a later boost with recombinant protective antigen. Such protein antigens will further enhance antibody production to PA because although Ii-Key hybrids augment the MHC-Class II restricted response to antigen expressed from a DNA vaccine, there is presumably not enough PA protein available extracellularly to bind to B cells for internalization and processing of MHC Class Ii epitopes to activate those B cells to progress to plasma cells and soluble immunoglobulin production.

The efficacy of Ii-Key/anthrax antigenic epitope hybrids in potentiating DNA and protein vaccines can be tested in guinea pigs, rabbits, and rhesus macaques against spore challenge by *Bacillus anthracis* isolates of diverse geographical origin (Fellows P F. Vaccine 2001 19:3241–7).

In another aspect the Ii-Key/anthrax MHC Class II epitope/anthrax ARD hybrids can be used to elicit antibodies which block the interaction of LF with PA required for the internalization of LF into cells. Examples of the creation and use of antibodies with such protective blocking effects follow.

Georgiou and colleagues found protection against anthrax toxin by recombinant antibody fragments correlates with antigen affinity (Maynard J A. Nat Biotechnol. 2002 20:597–601). The tripartite toxin produced by *Bacillus anthracis* is the key determinant in the etiology of anthrax. They engineered a panel of toxin-neutralizing antibodies, including single-chain variable fragments (scFvs) and scFvs fused to a human constant kappa domain (scAbs), that bind to the protective antigen subunit of the toxin with equilibrium dissociation constants (K(d)) between 63 nM and 0.25 nM. The entire antibody panel showed high serum, thermal, and denaturant stability. in vitro, post-challenge protection of macrophages from the action of the holotoxin correlated with the $K^d$ of the scFv variants. Strong correlations among antibody construct affinity, serum half-life, and protection were also observed in a rat model of toxin challenge. High-affinity toxin-neutralizing antibodies can be of therapeutic value for alleviating the symptoms of anthrax toxin in infected individuals and for medium-term prophylaxis to infection.

In another aspect, this disclosure relates to Ii-Key/anthrax MHC Class II epitope/ARD hybrids to generate protective antibodies to a segment of PA binding LF for internalization into cells. Varughese and colleagues identified two such potential sites in solvent-exposed loops of domain 4 of PA (aa 679 to 693 and 704 to 723) by mutagenesis and testing of the purified proteins for toxicity in the presence of LF (Varughese M. Infect Immun. 1999 67:1860–5). Mutations were designed in these loops and were introduced by errors occurring during PCR. Substitutions within the large loop (aa 704 to 723) had no effect on PA activity. Comparisons among 28 mutant proteins showed that the large loop (aa 704 to 722) is not involved in receptor binding, whereas residues in and near the small loop (aa 679 to 693) are relevant to receptor interaction. Peptides through that small loop are good candidates for incorporation in Ii-Key/LF MHC Class II epitope/LF ARD hybrids.

Anthrax lethal factor can be used either to draw other proteins into a cell or for its toxic activity to inactivate MAP-kinase-kinase (Duesbery N S. Science 1998 280: 734–7; Liu S. Cancer Res. 2000 60:6061–7; Liu S, J Biol. Chem. 2001 276:17976–84).

The hybrids of this disclosure will enhance responses to subsequently administered anthrax toxoid vaccine adsorbed to alum (Pittman P R. Vaccine 2002 20:1412–20). The IM route of administering this is safe and has comparable peak anti-PA IgG antibody levels when two doses are administered 4 weeks apart compared to the licensed initial dose schedule of three doses administered 2 weeks apart.

The Ii-Key/antigenic epitope hybrids of this disclosure can be assayed in a rabbit model of inhalational anthrax (Pitt M L. Vaccine 2001 19:4768–73). A serological correlate of vaccine-induced immunity was identified in the rabbit model of inhalational anthrax. Animals are inoculated intramuscularly at 0 and 4 weeks with varying doses of Anthrax Vaccine Adsorbed ranging from a human dose to a 1:256 dilution in phosphate-buffered saline. At 6 and 10 weeks, both the quantitative anti-PA IgG ELISA and the toxin-neutralizing antibody assays were used to measure antibody levels to PA. Rabbits were aerosol-challenged at weeks with a lethal dose of *Bacillus anthracis* spores. All the rabbits that received the undiluted and 1:4 dilution of vaccine survived, whereas those receiving the higher dilutions of vaccine (1:16, 1:64 and 1:256) had deaths in their groups. Results showed that antibody levels to PA at both 6 and 10 weeks were significant ($P<0.0001$) predictors of survival. In addition non-invasive nasal immunization can be used to vaccinate against anthrax (Gaur R. Vaccine 2002 20:2836–9). Mice were inoculated intranasally, subcutaneously or through the skin on days 0, 15 and 28 with purified PA. Intranasal and subcutaneous immunization with PA resulted in high IgG ELISA titers. High titers of IgA were observed only in intranasally immunized mice. In a cytotoxicity assay these sera protected J774A.1 cells from lethal toxin challenge.

Table 17.1 presents the deduced amino acid sequence of anthrax toxin lethal factor (GenBank gi|16974824; Pannifer A D. Nature 2001 414:229–233. (2001)). Table 17.2 presents predicted MHC Class II-presented epitopes of anthrax toxin lethal factor. Table 17.3 presents predicted MHC Class I-presented epitopes of anthrax toxin lethal factor. Designed Ii-Key/MHC Class II epitope hybrids for anthrax lethal factor are presented in Table 17.4. Table 17.5 presents designed Ii-Key/MHC Class II epitope/ARD hybrids for anthrax lethal factor. Table 17.6 presents the deduced amino acid sequence of anthrax protective antigen (GenBank gi:9280533; Cohen, S. Infect Immun. 2000 68:4549–4558). Table 17.7 presents predicted MHC Class II-presented epitopes of anthrax protective antigen. Table 17.8 presents predicted MHC Class I-presented epitopes of anthrax protective antigen. Designed Ii-Key/MHC Class II epitope hybrids for anthrax protective antigen are presented in Table 17.9. Table 17.10 presents designed Ii-Key/anthrax protective antigen MHC Class II epitope/anthrax protective antigen ARD hybrids.

TABLE 17.1

| Deduced amino acid sequence of anthrax toxin lethal factor (SEQ ID NO: 637) |
|---|
| 1 agghgdvgmh vkekeknkde nkrkdeernk tqeehlkeim khivkievkg |
| 51 eeavkkeaae kllekvpsdv lemykaiggk iyivdgditk hislealsed |
| 101 kkkikdiygk dallhehyvy akegyepvlv iqssedyven tekalnvyye |
| 151 igkilsrdil skinqpyqkf ldvlntikna sdsdgqdllf tnqlkehptd |
| 201 fsvefleqns nevqevfaka fayyiepqhr dvlqlyapea fnymdkfneq |
| 251 einlsleelk dqrmlsryek wekikqhyqh wsdslseegr gllkklqipi |
| 301 epkkddiihs lsqeekellk riqidssdfl steekeflkk lqidirdsls |
| 351 eeekellnri qvdssnplse kekeflkklk ldiqpydinq rlqdtgglid |
| 401 spsinldvrk qykrdiqnid allhqsigst lynkiylyen mninnltatl |
| 451 gadlvdstdn tkinrgifne fkknfkysis snymivdine rpaldnerlk |
| 501 wriqlspdtr agylengkli lqrnigleik dvqiikqsek eyiridakvv |
| 551 pkskidtkiq eaqlninqew nkalglpkyt klitfnvhnr yasnivesay |
| 601 lilnewknni qsdlikkvtn ylvdgngrfv ftditlpnia eqythqdeiy |
| 651 eqvhskglyv pesrsillhg pskgvelrnd segfihefgh avddyagyll |
| 701 dknqsdlvtn skkfidifke egsnltsygr tneaeffaea frlmhstdha |
| 751 erlkvqknap ktfqfindqi kfiins |

TABLE 17.2

Predicted MHC Class II-presented epitopes of anthrax toxin lethal factor.

| Peptide | Pos. | Sequence | Score | Allele | Ii-Key | SEQ. ID. NO: |
|---|---|---|---|---|---|---|
| 17.2.1 | 501 | WRIQLSPDT | 3.1 | 1, 4 | 0 | 638 |
| 17.2.2 | 542 | YIRIDAKVV | 2.4 | 1 | 4 | 639 |
| 17.2.3 | 741 | FRLMHSTDH | 2.4 | 1, 3, 4 | 0 | 640 |
| 17.2.4 | 521 | LQRNIGLEI | 1.6 | 1, 8(519), 15,15 (518) | 0 | 641 |
| 17.2.5 | 341 | LQIDIRDSL | 5.4 | 3 | 0 | 642 |
| 17.2.6 | 404 | INLDVRKQY | 4.5 | 3, 13(407) | 0 | 643 |
| 17.2.7 | 677 | LRNDSEGFI | 4.3 | 3 | 7 | 644 |
| 17.2.8 | 129 | LVIQSSEDY | 3.6 | 4, 11(124) | 0 | 645 |
| 17.2.9 | 698 | YLLDKNQSD | 3.0 | 4 | 8 | 646 |
| 17.2.10 | 477 | YSISSNYMI | 7.2 | 7 | 4 | 647 |
| 17.2.11 | 398 | LIDSPSINL | 6.7 | 7 | 5 | 648 |
| 17.2.12 | 595 | IVESAYLIL | 6.0 | 7 | 9 | 649 |
| 17.2.13 | 475 | FKYSISSNY | 5.5 | 7 | 2 | 650 |
| 17.2.14 | 241 | FNYMDKFNE | 4.7 | 8 | 6 | 651 |
| 17.2.15 | 375 | FLKKLKLDI | 4.2 | 8, 11 | 0 | 652 |
| 17.2.16 | 549 | VVPKSKIDT | 3.9 | 8 | 3 | 653 |
| 17.2.17 | 148 | YYEIGKILS | 3.4 | 11 | 0 | 654 |
| 17.2.18 | 416 | IQNIDALLH | 3.2 | 11 | 5 | 655 |
| 17.2.19 | 707 | LVTNSKKFI | 4.1 | 13 | 4 | 656 |
| 17.2.20 | 582 | LITFNVHNR | 3.9 | 13 | 5 | 657 |
| 17.2.21 | 527 | LEIKDVQII | 3.8 | 13 | 4 | 658 |
| 17.2.22 | 435 | IYLYENMNI | 7.5 | 15 | 7 | 659 |
| 17.2.23 | 71 | LEMYKAIGG | 4.7 | 15 | 3 | 660 |

Pos. is the first amino acid of the predicted MHC Class II-presented epitope of the specified sequence. Score is the score calculated by the ProPred program for the first of the given HLA-DRB*_01 alleles which were examined. The second listed allele is for exactly the same epitope or for an overlapping epitope for which the first amino acid position is given in parentheses.

TABLE 17.3

| Predicted MHC Class I-presented epitopes of anthrax toxin lethal factor. | | | | |
|---|---|---|---|---|
| PEPTIDE | Pos. | Sequence | Score | SEQ. ID. NO: |
| 17.3.1 | 684 | FIHEFGHAV | 685.4 | 661 |
| 17.3.2 | 765 | FINDQIKFI | 342.2 | 662 |
| 17.3.3 | 147 | VYYEIGKIL | 336.0 | 663 |
| 17.3.4 | 277 | HYQHWSDSL | 300.0 | 664 |
| 17.3.5 | 113 | LLHEHYVYA | 285.7 | 665 |
| 17.3.6 | 331 | STEEKEFLK | 225.0 | 666 |
| 17.3.7 | 295 | KLQIPIEPK | 135.0 | 667 |
| 17.3.8 | 659 | YVPESRSIL | 126.0 | 668 |

Pos. is the first amino acid of the epitope of the listed sequence. The score is calculated with the SPEYETHEI program for HLA-A2.

TABLE 17.4

| Designed Ii-Key/MHC Class II epitope hybrids for anthrax lethal factor. | | | |
|---|---|---|---|
| PEPTIDE | Pos. | Sequence | SEQ. ID. NO: |
| 17.4.1 | 501 | Ac-LRMK-WRIQLSPDT-$NH_2$ | 669 |
| 17.4.2 | 542 | Ac-LRMK-YIRIDAKVV-$NH_2$ | 670 |
| 17.4.3 | 741 | Ac-LRMK-FRLMHSTDH-$NH_2$ | 671 |
| 17.4.4 | 519 | Ac-LRMK-LIQRNIGLEI-$NH_2$ | 672 |
| 17.4.5 | 341 | Ac-LRMK-LQIDIRDSL-$NH_2$ | 673 |
| 17.4.6 | 404 | Ac-LRMK-INLDVRKQYKRDI-$NH_2$ | 674 |
| 17.4.7 | 677 | Ac-LRMK-LRNDSEGFI-$NH_2$ | 675 |
| 17.4.8 | 125 | Ac-LRMK-YEPVQSSEDY-$NH_2$ | 676 |

These hybrids incorporate some for the predicted MHC Class II epitopes of Table 17.3.

TABLE 17.5

| Designed Ii-Key/ anthrax lethal factor MHC Class II epitope/ARD hybrids. | | | |
|---|---|---|---|
| PEPTIDE | Pos. | Sequence | SEQ ID NO: |
| 17.5.1 | 166-184 II:170 | Ac-LRMK-PYQKFLDVLNTIKNASDSD-$NH_2$ | 677 |
| 17.5.2 | 190-213 II:191;203 | Ac-LRMK-TNQLKEHPTDFSVEFLEQNSNEVQ-$NH_2$ | 678 |
| 17.5.3 | 200-224 II:203,215 | Ac-LRMK-DFSVEFLEQNSNEVQEVFAKAFAYYI-$NH_2$ | 679 |
| 17.5.4 | 228-243 II:230 | Ac-LRMK-QHRDVLQLYAPEAFN-$NH_2$ | 680 |

Pos. is the first and last amino acids of the LF sequence, which is incorporated into the hybrid. The first amino acid of the predicted MHC Class II epitopes are listed after II:. The MHC Class II alleles predicted with high scores to present individual epitopes are the following: 170: HLA-DRB*1301. 191: HLA-DRB*0401. 203: HLA-DRB*0401. 215: HLA-DRB*0101. 230: HLA-DRB*0101. 239:HLA-DRB*0801. Only the __01 alleles were scored with the ProPred predicting program. These peptides were chose from the segment of LF(182–236) containing interaction sites for binding to PA as indicated by loss of activity upon alanine substitutions at D182, D187, Y223, H229, L235 and Y236 (Lacy D B. J Biol. Chem. 2002 277:3005–10). In these hybrids the intervening sequence is supplied by the natural sequence of LF, potentially contributing to the ARD structure. Upon identification of biological activity with any of these hybrids, additional hybrids would be tested with systematic deletions/extensions of the epitope-containing peptide sequence.

TABLE 17.6

| Deduced amino acid sequence of anthrax protective antigen. (SEQ ID NO: 681) | | | | | |
|---|---|---|---|---|---|
| 1 | mkkrkvlipl | malstilvss | tgnleviqae | vkqenrllne | sesssqgllg |
| 51 | yyfsdlnfqa | pmvvtssttg | dlsipssele | nipsenqyfq | saiwsgfikv |
| 101 | kksdeytfat | sadnhvtmwv | ddqevinkas | nsnkirlekg | rlyqikiqyq |
| 151 | renptekgld | fklywtdsqn | kkevissdnl | qlpelkqkss | nsrkkrstsa |
| 201 | gptvpdrdnd | gipdsleveg | ytvdvknkrt | flspwisnih | ekkgltkyks |
| 251 | spekwstasd | pysdfekvtg | ridknvspea | rhplvaaypi | vhvdmeniil |
| 301 | sknedqstqn | tdsqtrtisk | ntstsrthts | evhgnaevha | sffdiggsvs |
| 351 | agfsnsnsst | vaidhslsla | gertwaetmg | lntadtarln | aniryvntgt |

TABLE 17.6-continued

| Deduced amino acid sequence of anthrax protective antigen. (SEQ ID NO: 681) |
|---|
| 401 apiynvlptt slvlgknqtl atikakenql sqilapnnyy psknlapial |
| 351 naqddfsstp itmnynqfle lektkqlrld tdgvygniat ynfengrvrv |
| 501 dtgsnwsevl pqiqettari ifngkdlnlv erriaavnps dplettkpdm |
| 551 tlkealkiaf gfnepngnlq yqgkditefd fnfdqqtsqn iknqlaelnv |
| 601 tniytvldki klnakmnili rdkrfhydrn niavgadesv vkeahrevin |
| 651 ssteglllni dkdirkilsg yiveiedteg lkevindryd mlnisslrqd |
| 701 gktfidfkky ndklplyisn pnykvnvyav tkentiinps engdtstngi |
| 751 kkilifskkg yeig |

TABLE 17.7

Predicted MHC Class II-presented epitopes of anthrax protective antigen.

| PEPTIDE | Pos. | SEQUENCE | Allele | Score | SEQ ID NO |
|---|---|---|---|---|---|
| 17.7.1 | 404 | YNVLPTTSL | B1, B7 (405) | 1.6 | 682 |
| 17.7.2 | 7 | LIPLMALST | B1 | 1.4 | 683 |
| 17.7.3 | 395 | YVNTGTAPI | B1, B3 (392), B4, B7, B13 (392) | 1.1, 3.9, 4.9, 7.3, 2.8, | 684 |
| 17.7.4 | 717 | YISNPNYKV | B1 | 1.0 | 685 |
| 17.7.5 | 697 | LRQDGKTFI | B3, B13 (690) | 6.3, 2.8 686 | |
| 17.7.6 | 619 | LIRDKRFHY | B3, B8 (617) B13 (617) | 5.9, 5.8, 4.7 | 687 |
| 17.7.7 | 610 | IKLNAKMNT | B3, B11 (603), B13 | 5.3, 2.7, 4.1 | 688 |
| 17.7.8 | 625 | FHYDRNNIA | B4 | 4.9 | 689 |
| 17.7.9 | 298 | IILSKNEDQ | B4 | 3.9 | 690 |
| 17.7.10 | 174 | VISSDNLQL | B7, B15 | 6.8, 4.1 | 691 |
| 17.7.11 | 648 | VINSSTEGL | B7 | 6.8 | 692 |
| 17.7.12 | 161 | FKLYWTDSQ | B8 | 4.0 | 693 |
| 17.7.13 | 225 | VKNKRTFLS | B8, B13 | 3.5 | 694 |
| 17.7.14 | 96 | FIKVKKSDE | B8 | 2.7 | 695 |
| 17.7.15 | 752 | ILIFSKKGY | B13 | 4.9 | 696 |
| 17.7.16 | 47 | LLGYYFSDL | B15 | 4.2 | 697 |
| 17.7.17 | 663 | IRKILSGYI | B15 | 4.1 | 698 |
| 17.7.18 | 360 | VAIDHSLSL | B15 | 4.1 | 699 |

Pos. is the first amino acid of the predicted epitope. Allele is the HLA-DRB*__01 allele with a high score for presentation of the epitope. When a second allele is listed it predicts either exactly the same sequence or an overlaying sequence, the first amino acid residue position of which is given in parentheses. The score is the prediction score in the ProPred program for the given epitope and allele.

TABLE 17.8

Predicted MHC Class I epitopes of anthrax protective antigen.

| PEPTIDE | Pos. | Sequence | SEQ ID NO |
|---|---|---|---|
| 17.8.1 | 607 | ILSGYIVEI | 700 |
| 17.8.2 | 32 | AIWSGFIKV | 701 |
| 17.8.3 | 171 | FLSPWISNI | 702 |
| 17.8.4 | 328 | RLNANIRYV | 703 |
| 17.8.5 | 530 | NIKNQLAEL | 704 |
| 17.8.6 | 155 | SLEVEGYTV | 705 |
| 17.8.7 | 551 | KLNARMNIL | 706 |
| 17.8.8 | 657 | YISNPNYKV | 707 |
| 17.8.9 | 225 | VAAYPIVHV | 708 |
| 17.8.10 | 352 | LVLGKNQTL | 709 |

Pos. is the first amino acid of the epitope of the listed sequence. The score is calculated with the SYFPEITHI program for HLA-A2.

TABLE 17.9

Designed Ii-Key/anthrax protective antigen MHC Class II epitope hybrids.

| PEPTIDE | Pos. | Sequence | SEQ. ID. NO: |
|---|---|---|---|
| 17.9.1 | 404 | Ac-LRMK-NVLPTTSL-$NH_2$ | 710 |
| 17.9.2 | 7 | Ac-LRMK-LIPLMALST-$NH_2$ | 711 |
| 17.9.3 | 395 | Ac-LRMK-VNTGTAPI-$NH_2$ | 712 |
| 17.9.4 | 717 | Ac-LRMK-YISNPNYKV-$NH_2$ | 713 |
| 17.9.5 | 697 | Ac-LRMK-LRQDGKTFI-$NH_2$ | 714 |
| 17.9.6 | 619 | Ac-LRMK-LIRDKRFHY-$NH_2$ | 715 |
| 17.9.7 | 610 | Ac-LRMK-IKLNAKMNI-$NH_2$ | 716 |
| 17.9.8 | 625 | Ac-LRMK-FHYDRNNIA-$NH_2$ | 717 |
| 17.9.9 | 298 | Ac-LRMK-IILSKNEDQ-$NH_2$ | 718 |
| 17.9.10 | 174 | Ac-LRMK-VISSDNLQL-$NH_2$ | 719 |

TABLE 17.10

Designed Ii-Key/anthrax protective antigen MHC Class II epitope/anthrax protective antigen ARD hybrids.

| PEPTIDE | Pos. | Sequence | SEQ. ID. NO: |
|---|---|---|---|
| 17.10.1 | 173-200 II:173 | Ac-LRMK-ava-VISSDNLQLPELKQKSSNSRKKRSTSAG-$NH_2$ | 720 |
| 17.10.2 | 212-232 II:221, 223, 225 | Ac-LRMK-PDSLEVEGYTVDVKNKRTFLS-$NH_2$ | 721 |
| 17.10.3 | 203-232 II:221, 223, 225 | Ac-LRMK-VPDRDNDGIPDSLEVEGYTVDVKNKRTFLS-$NH_2$ | 722 |
| 17.10.4 | 664-684 II:664, 667, 672 | Ac-LRML-ava-IRKILSGYIVEIEDTEGLKEV-$NH_2$ | 723 |
| 17.10.5 | 685-705 II:690, 696 | Ac-LRMK-INDRYDMLNISSLRQDGKTFI-$NH_2$ | 724 |

Pos. is the first and last amino acids of the PA sequence, which is incorporated into the hybrid. The first amino acid of the predicted MHC Class II epitopes are listed after II. The MHC Lass II alleles predicted with high scores to present individual epitopes are the following: 173: HLA-DRB0401, 0701, 1501. 221 HLA-DRB0301. 223: HLA-DRB1101. 225: HLA-DRB0301, 801, 1101, 1301. 664: HLA-DRB0101, 0301. 690:HLA-DRB0401, 1101. 696: HLA-DRB0301. Only the **01 alleles were scored with the ProPred predicting program. In hybrids 17.10.2 (SEQ ID NO: 721), 0.3 (SEQ ID NO: 722), and 0.5 (SEQ ID NO: 724) the intervening sequence is supplied by the natural sequence of PA, potentially contributing to the ARD structure. Upon identification of biological activity with any of these hybrids, additional hybrids would be tested with systematic deletions/extensions of the epitope-containing peptide sequence. Peptides 17.10.1 (SEQ ID NO: 720) and 17.10.2 (SEQ ID NO: 721) were chosen from the region PA(197–222) shown by Collier and colleagues to be sensitive to LF binding with alanine substitutions at K197, R200, P205, 1207, 1210 and K214 (Cunningham K. Proc Natl Acad Sci USA 2002 99:7049–53). Peptides 17.10.4 (SEQ ID NO: 723) and 17.10.5 (SEQ ID NO: 724) were chosen from the smaller loop of PA(679–693) shown by Leppla and colleagues to contain interaction sites for binding to PA (Varughese M. Infect Immun. 1999 67:1860–5). Upon identification of biological activity with any of these hybrids, additional hybrids would be tested with systematic deletions/extensions of the epitope-containing peptide sequence. Additional Ii-Key/PA MHC Class II epitope/ARD hybrids can be constructed with the peptides derived by phage display analyses to bind with PA-neutralizing antibodies. In these peptides the MHC Class II epitopes would be chosen from the best experimentally determined MHC class II-presented epitopes. Examples are presented in Table 17.11 for such constructs, using only a single MHC Class II-presented epitope.

TABLE 17.11

Designed Ii-Key/anthrax protective antigen MHC Class II epitope/anthrax protective antigen ARD hybrids.

| PEPTIDE | Pos. | Sequence | SEQ. ID. NO: |
|---|---|---|---|
| 17.11.1 | 11:163 | Ac-LRMK-YVNTGTAPI-$NH_2$ | 725 |
| 17.11.2 | 209-230 II:222 | Ac -LRMK-YVNTGTAPI-$NH_2$ | 726 |
| 17.11.3 | 655-675 II:655, 664, 667 | Ac-LRMK-ava-YVNTGTAPI-$NH_2$ | 727 |
| 17.11.4 | 655-680 II:664, 667 | Ac-LRMK-ava-YVNTGTAPI-$NH_2$ | 728 |
| 17.11.5 | 666-680 II:667 | Ac-LRMK-ava-YVNTGTAPI-$NH_2$ | 729 |
| 17.11.6 | 693-706 II:693 | Ac-LRMK-ava-YVNTGTAPI-$NH_2$ | 730 |
| 17.11.7 | 688-706 II:693 | Ac-LRMK-YVNTGTAPI-$NH_2$ | 731 |
| 17.11.8 | 686-706 II:693 | Ac-LRMK-NGIKKILTFSKKGYEIG-$NH_2$ | 732 |

Pos. is the first amino acid of the MHC Class II-presented epitope, for which only one example is given. The best epitopes determined experimentally are favored. The sequences following that epitope are the ARD sequences discovered by Collier and colleagues by selection and sequencing of phages which interact with PA binding antibodies. Some of those antibodies inhibit internalization of LF.

Example 18

Ii-Key/Variola B5R Protein Antigenic Epitope Hybrids

Ii-Key/smallpox antigenic epitope vaccines offer robust and relatively safe protection against smallpox, when used either alone or in combination with other vaccination methods. The potency and safety of certain other vaccines such as vaccinia virus are enhanced substantially, when preceded by one or more immunizations with an Ii-Key/smallpox antigenic epitope vaccine. Protection of a large population can be achieved with solely the use of the Ii-Key/smallpox antigenic epitope hybrid vaccine or preferably with such a vaccine in which the MHC Class II epitope is joined or overlapped in sequence with a MHC Class I-presented (cytotoxic T lymphocyte inducing) epitope and/or an antibody-recognized (virus neutralizing) epitope. Immunization with Ii-Key/smallpox antigenic epitope vaccines also improves clinical outlook for individuals infected with smallpox virus without prior vaccinia immunizations. The Ii-Key/antigenic epitope hybrid vaccines will enhance the protective responses of persons receiving a preventative vaccine with either vaccinia virus or a DNA for a smallpox or vaccinia viral protein. The efficacy of vaccinia virus vaccines given to individuals immediately upon exposure or potentially exposure to smallpox ("ring vaccination"), will be accelerated in terms of the speed and potency of the protective response. The biology and clinical course of smallpox infections is reviewed in order to understand the substantial benefits brought to the prevention of smallpox by the products and methods of this Disclosure.

Variola major, the smallpox virus, belongs to the family Poxyiridae, subfamily Chordopoxyirinae, and genus *orthopoxvirus*, which includes vaccinia (the smallpox vaccine), monkey poxvirus, and several others animal poxviruses that cross-react serologically (Breman J G. N Engl J. Med. 2002 346:1300–8; Moss B. in Fields B N. Fields Virology. 1996: 2637–71; Fenner F. in Fields B N. Virology. 1996: 2673–83). The poxviruses are among the largest viruses known, containing one linear, double-stranded DNA molecule of 130 to 375 kb and replicating inn the cytoplasm.

There are five patterns of smallpox infections. Variola major (ordinary smallpox) was responsible for 90% of cases in the pre-eradication era and is associated with an overall case-fatality rate of 30% (15% to 45%) in unvaccinated patients. Flat-type or malignant smallpox and hemorrhagic smallpox typically occur in patients with a defective immune system, and case fatality rates are 97% and 96% respectively. Smallpox in children is generally similar to smallpox in adults except the case fatality rate in infants is over 40%. Variola minor is the mildest form that predominated in outbreaks in the U.S. and Great Britain, with case fatality rates <1% (Fenner F. Bull WHO. 1988 1–68, 121–208; Henderson D A. JAMA. 1999 281:2127–39).

The smallpox virus enters through the respiratory tract, passing rapidly to lymph nodes to multiply in the reticuloendothelial system over 14 days. Mucous membranes in the oropharynx become infected, as well as the capillary epithelium of the dermis leading to skin lesions. Oropharyngx and skin lesions contain abundant viral particles; virus is also present in the urine and conjunctival secretions. Cytotoxic T-cells and B-cells arise to limit the infection; neutralizing antibodies appear in the first week of infection but are delayed if infection is severe (Fenner F. in Fields B N. Virology. 1996: 2673–831996; Roberts J A. Br J Exp Pathol. 1962 43:451–61; Bedson H S. J Pathol Bacteriol. 1963 85:1–20; Buller R M. Microbiol Rev. 1991 55:80–122; Zaucha G M. Lab Invest. 2001 81:1581–600; Sarkar J K. Bull World Health Organ. 1973 48:517–22). The incubation period is 7 to 17 days (mean 10 to 12). The prodromal phase, which lasts for two to three days, is characterized by severe headache, backache, and fever, all beginning abruptly (Dixon C W. Smallpox. London, 1962). Enanthema of the tongue, mouth, and oropharynx precede the rash by a day. The rash begins as small, reddish macules, which become papules with a diameter of 2 to 3 mm. The papules become vesicles with a diameter of 2 to 5 mm. Pustules of 4 to 6 mm diameter develop four to seven days after the rash. Smallpox lesions with a peripheral distribution, generally are all at the same stage of development (in contrast to chicken pox lesions). Lesions on the palms and soles persist the longest. Death from smallpox is ascribed to toxemia, associated with immune complexes, and hypotension secondary to fluid and protein loss.

Variola is transmitted predominantly from person to person by droplet inhalation, most commonly among those with close face-to-face contact (Fenner F. Bull WHO. 1988 1–68, 121–208). Airborne and fomite (laundry, bedding) transmission occurs (Dixon C W. Smallpox. London, 1962). Patients are infectious from the time of fever onset, immediately prior to rash development. Secondary attack rates range from 37% to >70% (Rao A R. Indian J Med Res. 1968 56:1826–54; Arnt N. Am J Epidemiol. 1972 94:363–70; Heiner G G. Am J Epidemiol. 1971 94:316–26), with a primary case infecting 3.6 to 6 others (Gani R. Nature. 2001 414:748–51). In the 1970s outbreaks in Yugoslavia and Germany, there were 11 to 38 infected contacts per index case (Fenner F. Bull WHO. 1988 1–68, 121 –208). Thus in populations with low herd immunity, transmission rapidly creates outbreak cases before control measures take hold. Infectivity lasts until all lesions have scabbed over and the scabs have fallen off.

Patients with smallpox are treated supportively—adequate fluid intake (which is difficult due to oropharyngeal enanthema), alleviation of pain and fever, keeping skin lesions clean to prevent bacterial superinfection. Although no antivirals are approved for smallpox by the U.S. FDA, many compounds have been screened for therapeutic activity. Cidofivir (Vistide®, approved for CMV retinitis) shows activity against orthopoxviruses, including variola (CIDRAP/IDSA. 2002).

Smallpox vaccination began in China in 1000 AD with "variolation", administration of infectious material from an infected patient to uninfected individuals. Edward Jenner discovered in the late 1700s that cowpox protected against smallpox. Vaccinia virus, genetically distinct from cowpox, has replaced cowpox as a vaccine (CIDRAP/IDSA. 2002). Protection is afforded for 5–10 years after primary vaccination; neutralizing antibodies are detected up to 10 years in 75% of individuals receiving 2 doses of vaccine, and up to 30 years in those vaccinated with 3 doses (Henderson D A. JAMA. 1999:281:2127–39). After an intensive worldwide campaign initiated in earnest in 1967, smallpox eradication was declared in 1980. With no natural reservoirs, variola has since existed only in laboratories. The WHO has sanctioned two depositories—The Center for Disease Control and Prevention (Atlanta, Ga.) and the State Research Center of Virology and Biotechnology (the Vektor Institute) in Novosibirsk, Russia. Inappropriately available variola virus could be a weapon of terrorists. Since less than 20% of 157 million individuals vaccinated before the early 1970s (when routine vaccination was discontinued in the US) are protected today and 119 million Americans have never been vaccinated, the need and problems of vaccinating against smallpox are being considered most carefully.

The Working Group on Civilian Biodefense has identified a number of widely known organisms that could cause disease and deaths in sufficient numbers to cripple a city or region. Smallpox used as a biological weapon, is perhaps the most serious threat to civilian populations due to its ease of transmission, case-fatality rate of 30% or more among unvaccinated persons, and the absence of a specific therapy. Although smallpox has long been feared as the most terrible of all infectious diseases, its potential for devastation today is much greater than at any previous time. Routine vaccination throughout the US ceased 25 years ago. In a now highly susceptible, mobile population, smallpox would spread widely and rapidly throughout this country and the world (Henderson D A JAMA. 1999 281:2127–39; Fenner F. Bull WHO. 1988 1–68, 121 –208).

The U.S. vaccinia vaccine since the 1970s, Dryvax, is a lyophilized live vaccinia virus preparation manufactured by Wyeth. The vaccine is administered on a bifurcated needle containing a droplet of the reconstituted product; the skin of the upper arm is poked approximately 15 times creating a wound producing a drop of blood. To elicit a protective response, a "Jennerian pustule" must be induced. In an effort to expand current supplies in light of bioterrorism threats, recent clinical trials have tested the protective effects of Dryvax at dilutions of 1:1, 1:5, 1:10, and 1:100 (Frey S E. N Engl J. Med. 2002 346:1265–75; Frey S E. N Engl J. Med. 2002 346:1275–80). A major response was observed in 95% with undiluted product, 70% with 1:10 diluted vaccine, and 15% with 1:100 diluted vaccine. One month after vaccination, 34 of the 36 subjects with major reactions developed antibody responses compared to 1 of 24 patients who did not develop Jennerian pustules (Frey S E. N Engl J. Med. 2002 346:1275–80). Vigorous cytotoxic T-cell and IFN-ã responses occurred in 94% of subjects with major reactions and only 1 of 24 patients who did not develop Jennerian pustules.

Routine vaccination was discontinued in 1979 because the risk of complications from the vaccine outweighed the threat of endemic smallpox (Fenner F. Bull WHO. 1988 1–68, 121–208). A 10 state study indicated that there were 1254 complications per 1 million primary vaccinations including encephalitis, progressive vaccinia, eczema vaccinatum, generalized vaccinia, and erythema multiforme (Lane J M. J Infect Dis. 1970 122:303–9). A nationwide survey showed that the case fatality rate was 1 per 1 million primary vaccinations (Lane J M. N Engl J. Med. 1969 281:1201–8). Certain groups of individuals are contraindicated to be vaccinated—those with conditions causing immunodeficiency (i.e., HIV infection, leukemia, lymphoma, generalized malignancy, agammaglobulinemia, organ transplant recipients, or therapy with alkylating agents, antimetabolites, radiation, or large doses of corticosteroids), persons with eczema, persons with household contacts who are immunodeficient or who have a history of eczema, and pregnant women.

Based on the observed morbidity and mortality associated with vaccinia vaccination in the US from 1967 to 1979, a mass smallpox preventative vaccination campaign in the U.S. general public aged 1 to 65 could result in as many as 4,600 serious adverse events and 285 deaths (excluding high-risk persons and their immediate contacts) (Kemper A R. Eff Clin Pract. 2002 5:84–6). Indeed, dictating that everyone receives the Dryvax vaccine would sentence as many as 400 people to death and many others to seriously debilitating side effects (Grand Rapids Press Apr. 10, 2002).

Therefore, the CDC has recommended a "ring vaccination" or containment strategy. In this approach, the following individuals receive the vaccine following actual or potential release of variola virus: persons directly exposed to the release; persons with face-to-face or household contact with an infected patient or in close proximity (within 2 m); personnel directly involved in the evaluation, care, or transport of infected patients; laboratory personnel involved in processing specimens; and others likely to have contact with infectious materials (CDC Interim Smallpox Response Plan CDC November 2001; Vaccinia ACIP Morb Mortal Wkly Rep. 2001 50:1–25).

Compared to mass vaccination, ring vaccination is clearly not optimal the following reasons. (1) Pre-emptive voluntary vaccination eliminates the value of smallpox as a weapon, serving as an effective deterrent. (2) Ring vaccination is effective only for the eradication of small, localized outbreaks in a population with widespread immunity. In a largely non-immune mobile population, epidemic control after multiple simultaneous exposures is a vastly different challenge. (3) Ring vaccination requires prompt identification and vaccination of infected individuals within the 3-day post exposure period when the vaccination might be effective. A person might be infective for several days before smallpox is clinically obvious, therefore, identification of cases of exposure to an infected terrorist, for example, within a four-day period is logistically impossible. (4) The CDC is assuming that each infected person will infect only 2 to 3 others, however, as many as 38 secondary infections have been observed. (5) The logistical complexity of administering millions of vaccine doses in an acute emergency is daunting and likely to induce panic and collapse of the medical and public health service as was observed in the Dark Winter simulation exercise conducted by Johns Hopkins University in June 2001 (Bicknell W J. N Engl J. Med. 2002 346: 1323–25; Henderson D A. JAMA. 1999 281: 2127–39; Millar J D. Public Health Policy Advisory Board. 2000; Fenner F. Bull WHO. 1988:1–68, 121–208; O'Toole T. Johns Hopkins Center for Civilian Biodefense Strategies. 2001). In contrast, pre-exposure vaccination does not pose the logistical difficulties of vaccination during an outbreak and is less expensive. In addition, pre-exposure vaccination reduces the risk of infection among immunocompromised persons (Rosenthal S R. Emerg Infect Dis. 2001 7:920–6).

Improved vaccines capable of safely and rapidly eliciting long-lasting immunity against smallpox in all persons are clearly needed. Whether used in mass or ring vaccination strategies, greater safety and efficacy relative to Dryvax is required. The Ii-Key/antigenic epitope hybrid used alone or in combination with DNA vaccines will have the following preferred characteristics relative to Dryvax: (1) significantly reduced complication rate including death and debilitating side effects, (2) more rapid induction of protective antibodies and viral-specific cytotoxic T-cells (3) simpler vaccination method, (4) greater period of protection following primary vaccination, and (5) broader target population including use in immunocompromised individuals and in pregnancy.

One preferred approach to protecting large populations is administration of one or more immunizations with an Ii-Key/smallpox antigenic epitope hybrid of this Disclosure, followed according to the ring immunization concept by vaccinia or similar viral vaccines in the population subset of exposed or potentially exposed individuals. However, in addition, when individuals who were not in the immunized ring, contract smallpox, significant protection is afforded by prior expansion and memory of $CD4^+$ T helper cell clones, CD8+ cytotoxic T lymphocyte clones, and B cell immunoglobulin producing clones as the case might be. Such responses create a more rapid time frame for development of clinically protective responses frame to presentation of those same and other epitopes by the smallpox virus, than would be the case in individuals not immunized with the hybrids. The process of inducing responses to viral epitopes other than that in the immunizing Ii-Key/smallpox antigenic epitope hybrid, is referred to as epitope spreading.

Although vaccination is generally regarded to be the best defense against smallpox virus, the approved vaccines and some in development are not optimally safe or potent. The Ii-Key/smallpox MHC Class II epitope hybrid vaccines can be used either alone or together with other approaches, including whole virus preparations, DNA and RNA vaccines, inactivated whole virus, and virus-like particles. The Ii-Key/antigenic epitope hybrid vaccines revealed in this Disclosure can be used in conjunction with diluted whole virus preparations, e.g., Dryvax, in order to improve the major reaction rate typically observed with diluted preparations and allow for decreased rates of complications (Frey S E. N Engl J Med 2002 346:1265–75; Frey S E. N Engl J Med 2002 346:1275–80). In addition, Ii-Key/smallpox MHC Class II epitope hybrid vaccines can be used with attenuated virus strains that have been developed (Ankara MVA and Japanese strain LC16 m8) in order to augment their efficacy (Rosenthal S R. Emerg Infect Dis 2001 7:920–6; Henderson D A JAMA. 1999:281:2127–39). Ii-Key/smallpox MHC Class II epitope hybrid vaccines can be used with DNA or RNA vaccines targeting gene products that are critical for viral pathogenicity and infectivity, for example, B5R and others (Phillpotts R J. Acta Virol 2000 44:151–6; Mathew E C. J Gen Virol 2001 82:1199–213).

Ii-Key/smallpox antigenic epitope hybrids offer potent and safe vaccines against smallpox. One favored example uses Ii-Key/antigenic epitope hybrids containing the Ii-Key LRMK (SEQ ID NO: 3) motif and an MHC Class II epitope of the smallpox B5R gene product gp42. Such a construct can be further enhanced with a linked or overlapping MHC Class I epitope(s) and/or antibody-determined epitope(s). By boosting the Th response >200 times to the MHC Class II epitope, Th1 cells are recruited to elicit potent CTL and humoral responses with immunological memory. Addition of a MHC Class I epitope to the hybrid affords antigenic epitope-specific enhancement of the cytotoxic T lymphocyte response. Addition of an antibody-recognized epitope to the hybrid affords antigenic epitope-specific enhancement of the antibody-determined response.

Smallpox gp42 is selected for several reasons. (1) Gene B5R encodes a 42 kD glycoprotein that is expressed throughout the course of infection and forms part of the envelope of the extracellular virus. (2) gp42 is required for the envelopment and egress of extracellular virus and virus virulence. (3) gp42-specific IgG neutralizing antibodies are correlated with protection against *orthopox* infection in humans (Phillpotts R J. Acta Virol 2000 44:151–6; Englestad M. Virology. 194:627–37; Mathew E C. J Gen Virol 2001 82:1199–213). In the course of routine experimentation to identify the biologically function and vaccine potential of additional proteins coded for or induced by the smallpox virus, additional candidates for the design, synthesis and use of Ii-Key/smallpox antigenic epitope hybrids will be targeted. The methods of this Disclosure can be applied without undue experimentation toward the development of additional Ii-Key/smallpox antigenic epitope hybrid vaccines. Other extracellular envelope proteins such as A33R, A34R; A36R, and A56R, can be used to produce Ii-Key/antigenic epitope hybrids.

In addition to the above vaccine methods, the Ii-Key/smallpox antigenic epitope hybrids can be used to enhance responses to DNA vaccines encoding B5R gp42. Such DNA vaccines can also be enhanced further by incorporating the Ii reverse gene construct in the same plasmid or delivery construct. Suppression of Ii protein expression allows for the presentation of endogenous gp42 epitopes. In the context of B5R DNA vaccination, targeted Ii-suppressed antigen presenting cells will present an increased repertoire of novel, perhaps cryptic, B5R epitopes.

This invention relates in part to the design of Ii-Key/Variola B5R protein antigenic epitope hybrids. The genes of the variola virus have been identified and sequenced principally by investigators in Russia (Shchelkunov S N. FEBS Lett. 1993 319:80–83; Shchelkunov S N. Virus Res. 1994 34:207–236; Shchelkunov S N. Virus Genes 1995: 9:231–245; Shchelkunov S N. Virus Res. 1996 40:169–183). The sequence of Variola virus B5R protein (g510228) is presented in Table 18.1. Predicted MHC Class II-presented epitopes of the B5R protein are presented in Table 18.2. Table 18.3 lists Ii-Key/variola B5R protein epitope hybrids containing some of the MHC Class II-presented epitopes of Table 18.2. Predicted MHC Class I-presented epitopes of variola B5R protein are presented in Table 18.4. Table 18.5 lists Ii-Key/MHC Class II-presented/MHC Class I-presented B5R hybrids.

TABLE 18.1

Deduced amino acid sequence of the B5R protein of the variola virus. (SEQ ID NO: 731)

| | | | | |
|---|---|---|---|---|
| 1 | mktisvvtll | cvlpavvyst | ctvptmnnak | ltstetsfnd | kqkvtftcds |
| 51 | gyysldpnav | cetdkwkyen | pckkmctvsd | yvselynkpl | yevnaiitli |
| 101 | ckdetkyfrc | eekngntswn | dtvtcpnaec | qslqldhgsc | qpvkekysfg |
| 151 | ehitincdvg | yevigasyit | ctanswnvip | scqqkcdips | lsnglisgst |
| 201 | fsiggvihls | cksgfiltgs | psstcidgkw | npvlpicirs | neefdpvedg |
| 251 | pddetdlskl | skdvvqyeqe | iesleatyhi | iivaltimgv | iflisvivlv |
| 301 | cscnknndqy | kfhklll | | | |

TABLE 18.2

Predicted MHC Class II-presented epitopes of the B5R protein.

| PEPTIDE | Pos. | Sequence | Ii-Key | Score | Allele | SEQ ID NO: |
|---|---|---|---|---|---|---|
| 18.2.1 | 289 | VIFLISVIV | 6 | 2.2 | 01 | 734 |
| 18.2.2 | 290 | IFLISVIVL | 7 | 3.8 | 03, 07, 15 | 735 |
| 18.2.3 | 291 | FLISVIVLV | 8 | 6.3 | 07 | 736 |
| 18.2.4 | 51 | YYSLDPNAV | 4 | 2.2 | 01 | 737 |
| 18.2.5 | 229 | WNPVLPICI | 13 | 2.1 | 01, 07 | 738 |
| 18.2.6 | 206 | IHLSCKSGF | 4 | 4.8 | 03 | 739 |
| 18.2.7 | 281 | IVALTIMGV | 0 | 4.2 | 03, 11, 13, 15 | 740 |
| 18.2.8 | 279 | IIIVALTTM | 0 | 3.8 | 03 | 741 |
| 18.2.9 | 214 | FILTGSPSS | 0 | 3.8 | 04 | 742 |
| 18.2.10 | 175 | WNVIPSCQQ | 0 | 3.6 | 04 | 743 |
| 18.2.11 | 52 | YSLDPNAVC | 5 | 3.4 | 04, 08, 11 | 744 |
| 18.2.12 | 277 | YHIIIVALT | 11 | 3.5 | 08, 11 | 745 |
| 18.2.13 | 284 | LTIMGVIFL | 0 | 2.3 | 08, 07, 13, 15 | 746 |
| 18.2.14 | 6 | VTLLCVLPA | 0 | 3.8 | 06, 01, 13 | 747 |
| 18.2.15 | 84 | LYNKPLYEV | 6 | 2.5 | 14 | 748 |
| 18.2.16 | 289 | VIFLISVIV | 6 | 3.6 | 15 | 749 |

Pos. is the residue position in the primary sequence of the first amino acid in the antigenic epitope. Sequence is the amino acid sequence of the predicted MHC Class II-presented epitope. When a given sequence is predicted to be presented by multiple HLA-DR alleles, the first residue position of each sequence is indicated. Score is the score reported by the ProPred program, for the relative likelihood of being presented by the first HLA-DR allele listed. The respective alleles are in each case the HLA-DRB*___01 allele. Ii-Key is the number of residue positions intervening between an Ii-Key motif and the first residue of the antigenic epitope.

TABLE 18.3

Ii-Key/variola B5R epitope hybrids containing some of the MHC Class II-presented epitopes of Table 18.2.

| PEPTIDE | Pos. | Sequence | SEQ ID NO: |
|---|---|---|---|
| 18.3.1 | 289, 290, 291 | Ac-LRMK-ava-VIFLISVTVLV-$NH_2$ | 750 |
| 18.3.2 | 16 | Ac-LRMK-ava-YYSLDPNAV-$NH_2$ | 751 |
| 18.3.3 | 229 | Ac-LRMK-ava-WNPVLPICI-$NH_2$ | 752 |
| 18.3.4 | 206 | Ac-LRMK-ava-IHLISCKSGF-$NH_2$ | 753 |
| 18.3.5 | 279, 281 | Ac-LRMK-ava-IIIVALTIMGV-$NH_2$ | 754 |

TABLE 18.3-continued

Ii-Key/variola B5R epitope hybrids containing some of the MHC Class II-presented epitopes of Table 18.2.

| PEPTIDE | Pos. | Sequence | SEQ ID NO: |
|---|---|---|---|
| 18.3.6 | 214 | Ac-LRMK-ava-FILTGSPSS-$NH_2$ | 755 |
| 18.3.7 | 175 | Ac-LRMK-ava-WNVIPSCQQ-$NH_2$ | 756 |
| 18.3.8 | 52 | Ac-LRMK-ava-YHIIIVALT-$NH_2$ | 757 |
| 18.3.9 | 277 | Ac-LRMK-ava-YHIIIVALT-$NH_2$ | 758 |
| 18.3.10 | 284 | Ac-LRMK-ava-LTIMGVIFL-$NH_2$ | 759 |
| 18.3.11 | 6 | Ac-LRMK-ava-VTLLCVLPA-$NH_2$ | 760 |
| 18.3.12 | 84 | Ac-LRMK-ava-LYNKPLYEV-$NH_2$ | 761 |
| 18.3.13 | 289 | Ac-LRMK-ava-VIFLISVIV-$NH_2$ | 762 |

Pos. is the residue position in the primary sequence of the first amino acid in the antigenic epitope. In cases of closely overlapping predictions, the first residue position is given for each predicted epitope. Sequence is the amino acid sequence of a hybrid peptide containing a MHC Class II epitope of Table 18.2.

TABLE 18.4

Predicted MHC Class I-presented epitopes of variola B5R protein.

| PEPTIDE | Pos. | Sequence | Score | SEQ ID NO: |
|---|---|---|---|---|
| 18.4.1 | 292 | FLISVIVLV | 736 | 763 |
| 18.4.2 | 8 | TLICVLPAV | 592 | 764 |
| 18.4.3 | 74 | KMCTVSKYV | 474 | 765 |
| 18.4.4 | 286 | TIMGVIFLI | 71 | 766 |
| 18.4.5 | 9 | LLVCLPAVV | 48 | 767 |
| 18.4.6 | 12 | VLPAVVYST | 29 | 768 |
| 18.4.7 | 290 | VIFLISVIV | 25 | 769 |
| 18.4.8 | 282 | IVALTIMGV | 24 | 770 |
| 18.4.9 | 77 | TVSKYVSEL | 18 | 771 |
| 18.4.10 | 195 | LISGSTFSI | 14 | 772 |

Pos. is the residue position in the primary sequence of the first amino acid in the antigenic epitope predicted for HLA-A201 (Parker K C. J. Immunol. 152:163–175). Sequence is the amino acid sequence of the predicted MHC Class I-presented epitope. Score is the $T_{1/2}$ of disassociation of a peptide containing this subsequence (Tsang K Y. J Natl Cancer Inst. 1995 87:982–90). The MHC Class I-presented epitopes of this Table were predicted with the use of the online program at (http://bimas.dcrt.nih.gov/molbio/hla_b-ind/).

TABLE 18.5

Ii-Key/MHC Class II-presented/MHC Class I-presented B5R hybrids.

| PEPTIDE | Pos. | Sequence | SEQ ID NO: |
|---|---|---|---|
| 18.5.1 | II:289, 290, 291 I:290, 292 | Ac-LRMK-ava-VIFLISVIVLV-$NH_2$ | 773 |
| 18.5.2 | II:286, 289, 290, 291 I:290, 292 | Ac-LRMK-ava-TIMGVIFLISVIVLV-$NH_2$ | 774 |
| 18.5.3 | II:277, 279, 284 I:286 | Ac-LRMK-ava-YHIIIVALTIMGVIFLI-$NH_2$ | 775 |
| 18.5.4 | II:6 I:8,9 | Ac-LRMK-ava-VTLLCVLPAVV-$NH_2$ | 776 |

Pos. is the residue position in the primary sequence of the first amino acid in either the MHC class II-presented antigenic epitope (II:) or the MHC class I-presented antigenic epitope (I:). Sequence is the amino acid sequence of a hybrid peptide containing a MHC Class II-presented epitope of Table 18.2 and a MHC Class I-presented epitope of Table 18.5.

Example 19

Ii-Key/Ebola Virus Antigenic Epitope Hybrids

Being among the most virulent infectious agents known, the Filoviruses, which include the Marburg and Ebola viruses, are classified at biosafety level 4 due to the extreme pathogenicity of certain strains and the absence of a protective vaccine or effective antiviral drug (Wilson J A. Cell Mol Life Sci. 2001 58:1826–41). Ebola virus causes a hemorrhagic fever, a severe, mostly fatal disease in humans and nonhuman primates, recognized in sporadic clusters since 1976. The natural reservoir for Ebola virus is an animal native to Africa (Peters C J. *J Infect Dis.* 1999 179 (Suppl 1): ix–xvi). The strain Ebola-Reston was isolated in the U.S. from imported cynomologous monkeys. Public concern over Ebola virus in non-African countries is derived from potential for spread of the viruses by international commerce; jet travel, and bioterrorism.

Clusters of Ebola virus infections in humans appear to depend upon the first patient contacting an infected animal. After an index case-patient is infected, transmission occurs among humans by direct contact with (1) blood and/or secretions of an infected person and (2) objects, such as needles and syringes, that have been contaminated with infected secretions. All Ebola viruses can be transmitted in aerosols under research conditions.

Within a few days of becoming infected with Ebola virus, most patients have high fever, headache, myalgia, abdominal pain, fatigue and diarrhea. Some patients have sore throat, hiccups, rash, red eyes, and bloody emesis and diarrhea. Within a week of becoming infected with Ebola virus, most patients have chest pain, shock, and death, while some experience blindness and bleeding (Gear H S. Reviews of Infectious Diseases. 1989 11 (suppl 4):5777–5782). Why some patients recover from Ebola hemorrhagic fever is not understood, although those who do develop a significant immune response to the virus.

Treatment of patients with Ebola hemorrhagic fever is supportive, consisting primarily in balancing the patient's fluids and electrolytes, maintaining oxygenation and blood pressure, and treating accompanying infections (CDC. Management of patients with suspected viral hemorrhagic fever. Morbidity and Mortality Weekly Report. 1988 37 (suppl 3):1–16).

Ebola virus has caused a series of devastating hemorrhagic fever outbreaks, the first being reported in 1976 in Yambuku, Zaire where 318 people contracted Ebola hemorrhagic fever, with 88% dying. Disease spread by close personal contact and contaminated needles and syringes in hospitals and clinics. Also in 1976, in the Sudan (Nzara and Maridi), 284 people contracted Ebola hemorrhagic fever, with 53% dying and the disease being spread mainly through close personal contacts in hospitals (Bowen E T W. Lancet 1977 1:571–3). In 1979, there was a recurrent outbreak in the Sudan, with 34 patients and 65% dying (Baron R C. Bull WHO 1983 62:997–1003). In 1994, 44 people in Gabon (Minkebe, Makokou, and gold-mining camps deep within the rain forest) developed Ebola hemorrhagic fever, with 63% dying. This outbreak was thought initially to be yellow fever, however in 1995 it was identified to be Ebola hemorrhagic fever (Georges A J. J Infect Dis. 1999 179 Suppl 1:S65–75). In 1995, 315 people in Kikwit, Democratic Republic of the Congo (formerly Zaire) contracted Ebola hemorrhagic fever, with 81% dying (Le Geuenno B. Lancet. 1995 345:1271–4). This outbreak was traced to an index case-patient who worked in a forest adjoining the city; the outbreak spread through families and hospitals. In 1996 in Mayibout, Gabon, 37 people developed Ebola hemorrhagic fever, with 57% dying. A dead, infected chimpanzee, eaten by 19 people in the forest, initiated this outbreak. In the same year in Boue, Gabon, 60 patients were infected with Ebola-Zaire, with 75% dying. The index case-patient was a hunter who lived in a forest camp; a dead, infected chimpanzee was found nearby. Finally, in 2000 and 2001 in Uganda (Gulu, Masindi, and Mbarara) 425 people contracted Ebola hemorrhagic fever, with 53% dying. The three most important risk factors associated with infection were: attending funerals of Ebola hemorrhagic fever case-patients, contacting case-patients in one's family, and providing medical care to Ebola case-patients without using adequate personal protective measures and practices (CDC: SPB: Disease Information Fact Sheets: Ebola: Case Table 2001).

Because the natural reservoir for Ebola virus is undetermined and human-to-human spread is documented, vaccines appear to be the best method to limit infectious spread (Nabel G L. Trans Am Clin Climatol Assoc. 2001 112: 79–84). Antibodies isolated from serums of patients recovered from the 1995 Ebola infection Kikwit, Democratic Republic of the Congo, using recombinant phage display adsorption techniques, neutralized Ebola infectivity (Maruyama T. J. Virol. 1999 73:6024–30). This finding coupled with the fact that dying patients do not mount an immunologically potent response offers hope that preventative vaccines will be effective. While no such vaccines are available, several vaccine approaches are under development including DNA and RNA replicon vaccines encoding Ebola viral proteins NP (major nucleocapsid protein), VP35 (phosphoprotein), VP40 (membrane-associated matrix protein), GP (transmembrane glycoprotein), sGP (secreted glycoprotein), VP30 (ribonucleoprotein associated—minor), and VP24 (membrane-associated protein—minor) (WO 99/32147; WO 00/00617; Wilson J A. Virology. 2001 286:

384–90; Pushko P. Vaccine. 2000 19:142–53; and Vanderzanden L. Virology. 1998 246:134–44).

The NIAID plans to initiate clinical trials with an adenoviral vaccine encoding genes for Ebola glycoprotein and nucleoprotein within 2 years. This vaccine induces protective immunity in non-human primate studies (Sullivan N J, Nature 2000 408:605–9; Cheary M, Dutch Firm to Develop Ebola Vaccine with US, Reuters May 16, 2002). Another vaccine is being developed with Ebola-like particles which are nonreplicating due to the absence of Ebola genetic materials, but possessing proteins contained on the inner and outer membranes (UASAMRIID, Bavari S, *J Exp Med.* 2002 195:1–11). A variety of vaccine strategies that protected mice and guinea pigs from lethal challenges with Ebola virus have been tested in non-human primates including: RNA replicon particles derived from attenuated strain of VEE expressing Ebola glycoprotein and nucleoprotein, recombinant Vaccinia virus expressing Ebola glycoprotein, liposomes containing lipid A and inactivated Ebola virus, and a concentrated inactivated whole Ebola virion preparation (Geisbert T W. Emerg Infect Dis. 2002 8:503–7; Pushko P. J. Virol. 2001 75:11677–85; and Pushko P. Vaccine. 2000 19:142–53). Unfortunately, none of these approaches were successful in protecting non-human primates from lethal Ebola virus challenge.

Vaccinating nice with Venezuelan equine encephalitis (VEE) virus replicons encoding Ebola virus nucleoprotein induced both antibodies and MHC Class I-restricted cytotoxic T-cells to an 11 amino-acid, Ebola virus NP(43–53). Passive transfer of polyclonal antibodies did not protect mice from a lethal challenge with Ebola virus; however, adoptive transfer of Ebola virus NP-specific CTLs did protect mice from an Ebola virus lethal challenge (Wilson J A. J. Virol. 2001 75:2660–4). Protective recombinant antibodies have been identified to 5 unique epitopes of Ebola glycoprotein, with one of the epitopes being conserved among all strains known to be pathogenic for humans (Wilson J A. Science. 2000 287:1664–6). Some of those monoclonal antibodies were also therapeutically effective upon administration to mice 2 days following a lethal challenge with Ebola virus. These data support view that both antibody and cell-mediated responses are important for protection against Ebola virus and therefore vaccine strategies designed to promote both antibody and CTL responses are preferred.

Although vaccines are generally regarded to be the best defense against Ebola virus, vaccines in development have not been demonstrated to be optimally protective. In the case of DNA vaccines, whether presented in plasmids, in viral particles, or in another formulation, some of these developmental issues include: 1) delivery vector of formulation (cDNA as naked DNA, or in plasmid or bacterial vectors, or with lipid or other transfecting carrier, or on gold particles or in PLG particles), 2) route of administration (skin, mucosal (GI or respiratory tracts), or muscle) 3) choice or one or multiple EBOLA genes and promoters for those genes, 4) genetic or protein adjuvants for cytokines or the products of this Disclosure, 5) dose, dosage schedule and other pharmacokinetic and pharmacodynamic considerations.

This example presents the design of a potent and relatively safe vaccine against Ebola virus VP24. The deduced amino acid sequence of Ebola VP24 is from GenBank g16751326 (Leroy E M. J Gen Virol 2002 83: 67–73). The strain of this protein was the one present in deceased, surviving and asymptomatically infected individuals during the 1996 outbreak in Gabon. Sequences of GP, NP, VP24 and VP40 genes were obtained with comparative studies and phylogenetic characterization.

Although experimentally determined MHC Class II epitopes are a more expeditious route to the construction of Ii-Key/antigenic epitope hybrids, such can be made with epitopes predicted with algorithms. Such epitopes predicted to be presented by multiple HLA-DR alleles are presented in Table 2. Ii-Key/Ebola MHC Class II antigenic epitope hybrids containing the Ii-Key LRMK (SEQ ID NO: 3) motif and single or significantly overlapping MHC Class II epitopes of VP24 are presented in Table 3. Such hybrids can be constructed with the fusion of MHC Class I-presented epitopes. Again in the absence of experimentally determined MHC Class I-presented epitopes, algorithm-predicted epitopes have been identified (Table 4). Such epitopes can be fused into Ii-Key/MHC Class II antigenic epitope hybrids, preferably when the highest degree in overlap of the MHC Class II and MHC Class I sequences are obtained. Examples of such products are presented in Table 5. When experimentally determined, antibody-recognized determinants have been identified experimentally or by prediction, additional hybrids composed of Ii-Key/MHC Class II-presented antigenic epitopes and such antibody-recognized epitopes can be designed by the methods presented herein without undue experimentation. Furthermore, the methods applied to the design and testing of Ii-Key/antigenic epitope hybrids composed of epitopes form VP24 can also be applied to similar vaccine hybrids with epitopes form other Ebola virus proteins, such as GP, NP, sGP, VP24, VP30, VP35 and VP40. The experimental validation of these hybrids can be accomplished in vaccination studies of mice by routine methods (Wilson J A. Virology. 2001 286:384–90). Among additional objective in such murine studies is the testing of the concept that presentation of a MHC Class II-presented epitope in and Ii-Key/antigenic epitope hybrid will lead to presentation by a low responder allele, functionally converting the presentation to a promiscuous epitope, as discussed in the Background of the Invention. In the study of Wilson J A and colleagues, although immunization with VP24 was capable of stimulating a potent immune response in a BALB/c model, VP24 induced no protective effects in the C57BL/6 strain (Wilson J A. J. Virol. 2001 75:2660–4). Thus, immunization of both BALB/c and C57BL/6 strains of mice with a MHC Class II-presented VP24 epitope will yield comparable immune responses as measure by antibody titers to the epitope in ELISAs, by induction of CD4+/IFNγ+ cells in the two-color FACS analysis, and by induction of CD4+/IFNγ+ cells in ELISPOT assays. Furthermore C57BL/6 mice will be protected against a lethal challenge against VEE.

The sequence of Ebola virus membrane associated protein VP24 (GenBank # g16751326; Leroy E M. J Gen Virol 2002 83: 67–73) is presented in Table 1. Predicted MHC Class II-presented epitopes are presented in Table 2. Ii-Key/Ebola virus VP24 MHC class II epitope hybrids are presented in Table 3. Predicted Ebola virus VP24 MHC Class I-presented epitopes are presented in Table 4. Ii-Key/Ebola VP 24 MHC Class II-predicted epitope/Ebola VP 24 MHC Class I-predicted epitope hybrids are presented in Table 5.

TABLE 19.1

| Sequence of Ebola virus membrane associated protein VP24 (SEQ ID NO: 777) |
|---|
| 1 makatgrynl ispkkdlekg vvlsdlcnfl vsqtiqgwkv ywagiefdvt |
| 51 hkgmallhrl ktndfapaws mtrnlfphlf qnpnstiesp lwalrvilaa |
| 101 giqdqlidqs lieplagalg lisdwllttn tnhfnmrtqr vkeqlslkml |
| 151 slirsnilkf inkldalhvv nyngllssie igtqnhtiii trtnmgflve |
| 201 lqepdksamn rkkpgpakfs llhestlkaf tqgsstrmqs lilefnssla i |

TABLE 19.2

Predicted MHC Class II-presented epitopes.

| PEPTIDE | POS. | Sequence | Score | DR | Ii-Key | SEQ ID NO: |
|---|---|---|---|---|---|---|
| 19.2.1 | 93 | LRVILAAGI | 2.90 | 0101 | 11 | 778 |
| 19.2.2 | 20 | VVLSDLCNF | 4.90 | 0301 | 3 | 779 |
| 19.2.3 | 151 | LIRSNILKF | 4.30 | 0301 | 5 | 780 |
| 19.2.4 | 146 | LKMLSLIRS | 4.20 | 0301 | 7 | 781 |
| 19.2.5 | 157 | LKFINKLDA | 3.90 | 0301 | 5 | 782 |
| 19.2.6 | 135 | MTRQRVKEQ | 3.60 | 0306 | 0 | 783 |
| 19.2.7 | 169 | VNYNGLLSS | 3.40 | 0306 | 5 | 784 |
| 19.2.8 | 220 | LLHESTLKA | 4.30 | 0401 | 0 | 785 |
| 19.2.9 | 124 | WLLTTNTNH | 3.98 | 0401 | 0 | 786 |
| 19.2.10 | 187 | IIITRTNMG | 3.80 | 0401 | 0 | 787 |
| 19.2.11 | 28 | FLVSQTIQG | 3.28 | 0401 | 4 | 788 |
| 19.2.12 | 34 | IQGWKVYWA | 4.80 | 0402 | 11 | 789 |

The epitopes of this Table were chosen by the following procedure. The sequence of EBOLA VP24 (GenBank g16751326) was subjected to HLA-DR epitope screening with the ProPred program. The 4 highest scoring epitopes of each allele was identified. Among that set, the first 14 unique epitopes were reported here, with the HLA-DR allele of their first occurrence. Many epitopes that are reported here, were in fact scored by the sequence algorithms of several alleles. Pos. is the amino acid residue position of the first amino acid of the epitope. Score is the score calculated by the ProPred program. Ii-Key is the number of amino acid residues intervening between the first amino acid of the epitope and N-terminally, a 5-amino acid-motif containing at least two amino acids of the group LIVFM (SEQ ID NO: 790) and at least one amino acid of the group HKR.

TABLE 19.3

Ii-Key/Ebola virus VP24 MHC class II epitope hybrids.

| PEPTIDE | POS. | Sequence | SEQ ID NO: |
|---|---|---|---|
| 19.3.1 | 20 | Ac-LRMK-VVLSDLCNF-$NH_2$ | 791 |
| 19.3.2 | 28 | Ac-LRMK-FLVSQTIQG-$NH_2$ | 792 |
| 19.3.3 | 34 | Ac-LRMK-IQGWKVYWA-$NH_2$ | 793 |
| 19.3.4 | 28; 34 | Ac-LRMK-FLVSQTIQGWKVYWA-$NH_2$ | 794 |
| 19.3.5 | 146 | Ac-LRMK-LKMLSLIRS-$NH_2$ | 795 |
| 19.3.6 | 151 | Ac-LRMK-LIRSNILKF-$NH_2$ | 796 |
| 19.3.7 | 157 | Ac-LRMK-LKFINKLDA-$NH_2$ | 797 |
| 19.3.8 | 146; 151 | Ac-LRMK-LKMLSLIRSNILKF-$NH_2$ | 798 |
| 19.3.9 | 169 | Ac-LRMK-VNYNGLLSS-$NH_2$ | 799 |
| 19.3.10 | 220 | Ac-LRMK-LLHESTLKA-$NH_2$ | 800 |
| 19.3.11 | | Ac-LRMK-$NH_2$ | 801 |

TABLE 19.4

Predicted Ebola virus VP24 MHC Class I-presented epitopes.

| PEPTIDE | POS. | Sequence | Score | SEQ ID NO: |
|---|---|---|---|---|
| 19.4.1 | 22 | VLSDLCNFL | 819 | 802 |
| 19.4.2 | 241 | LILEFNSSL | 288 | 803 |
| 19.4.3 | 156 | NILKFINKL | 95 | 804 |
| 19.4.4 | 118 | ALGLISDWL | 58 | 805 |
| 19.4.5 | 32 | SQTIQGWKV | 53 | 806 |
| 19.4.6 | 144 | QLSLKMLSL | 49 | 807 |
| 19.4.7 | 110 | SLIEPLAGA | 47 | 808 |
| 19.4.8 | 221 | LLHESTLKA | 35 | 809 |
| 19.4.9 | 9 | NLISPKKDL | 21 | 810 |
| 19.4.10 | 149 | MLSLIRSNI | 18 | 811 |
| 19.4.11 | 121 | LISDWLLTT | 16 | 812 |
| 19.4.12 | 120 | GLISDWLLT | 13 | 813 |

These HLA*A201 epitopes were scored with a computer-assisted algorithm (Parker K C. J. Immunol. 152:163–175).

TABLE 19.5

Ii-Key/Ebola VP 24 MHC Class II-predicted epitope/Ebola VP 24 MHC Class I-predicted epitope hybrids.

| PEPTIDE | POS. | Sequence | SEQ ID NO: |
|---|---|---|---|
| 19.5.1 | II:20; I:22 | Ac-LRMK-VVLSDLCNPL-$NH_2$ | 814 |
| 19.5.2 | II:28; I:22 | Ac-LRMK-VLSDLCNFLVSQTIQG-$NH_2$ | 815 |
| 19.5.3 | II:124; I:120, 121 | Ac-LMRK-GLISDWLLTTNTNH-$NH_2$ | 816 |
| 19.5.4 | II:146; I:144 | Ac-LRMK-QLSLKMLSIRS-$NH_2$ | 817 |
| 19.5.5 | II:146; I:146, 149 | Ac-LRMK-QLSLKMLSLIRSN-I $NH_2$ | 818 |
| 19.5.6 | II:157; I:156 | Ac-LRMK-NILKFINKLDA-$NH_2$ | 819 |
| 19.5.7 | II:151, 157; I:149, 156 | Ac-LRMK-LIRSNILKFINKLDA-$NH_2$ | 820 |
| 19.5.8 | II:220; I:221 | Ac-LRMK-LLHESTLKA-$NH_2$ | 821 |

Example 20

Ii-Key/Myelin Basic Protein MHC Class II-Presented Epitope Hybrids

In another aspect, induction of suppressor T-immunoregulatory cells specific for autoantigens, such as myelin basic protein in multiple sclerosis and collagen in arthritis, is a well-investigated and promising strategy for the control of these human autoimmune diseases. Administering peptide from myelin basic protein or collagen by oral or respiratory routes decreases antibodies to these proteins, suppresses cellular immune responses, and delays or inhibits development of experimental allergic encephalitis or collagen arthritis in animal models. In addition, certain hMBP peptides, which bind to and neutralize anti-MBP antibodies, have been tested in the clinic. MBP75–85 peptide administered intrathecally neutralized anti-myelin basic protein antibodies; intravenous administration of this peptide resulted in decreased titers of free and bound anti-myelin basic protein levels through an active immunotolerance-inducing mechanism. Various peptides ranging from 10 amino acids to 25 amino acids within the MBP sequence of 61 to 106 demonstrated this activity. Such peptides and methods of their use, which can be adapted for novel therapies with Ii-Key/antigenic epitope hybrids, have been described in U.S. Pat. No. 5,858,364: H L Weiner and D A Hafler, Jan. 12, 1999—Pharmaceutical dosage form for treatment of multiple sclerosis; and U.S. Pat. No. 5,571,499: D A Hafler and H L Weiner, Nov. 5, 1996—Treatment of autoimmune disease by aerosol administration of autoantigens and U.S. Pat. No. 6,258,781: K G Warren and I Catz, Jul. 10, 2001—Peptide specificity of anti-myelin basic protein and the administration of myelin basic protein peptides to multiple sclerosis patients, the disclosures of which are incorporated herein by reference. These results have been considered in detail below with respect to the incorporation of such epitopes in to Ii-Key/antigenic epitope hybrids to increase the potency, safety, memory and Th subset preference of such therapeutic effects.

Multiple sclerosis (MS), a demyelinating apparently autoimmune disease of the central nervous system associated with inflammation and gliosis, demonstrates T lymphocytes and autoantibodies directed to myelin proteins. Immunosuppressive therapies of multiple sclerosis can be developed with peptide epitopes from several myelin proteins. Such epitopes incorporated into Ii-Key/antigenic epitope hybrids can be tested in experimental allergic encephalitis, the animal model of multiple sclerosis. These proteins include myelin basic protein (MBP), proteolipid protein (PLP), myelin oligodendrocyte glycoprotein (MOG), and myelin-associated oligodendrocyte basic protein (MOBP) (Zamvill S S. *Nature.* 1986 324:258–60; Kono D H. *J Exp Med.* 1988 168:213–27; Madsen L S. *Nat Genet.* 1999 23:343–7; Tuohy V K. *J. Immunol.* 1989 142:1523–7; Greer J M. *J Immunol.* 1992 149:783–8; Mendel I. *Eur J. Immunol.* 1995 25:1951–9). The MHC Class II-presented epitopes of particular therapeutic interest are summarized here and then the experimental data supporting their use in Ii-Key/antigenic epitope hybrids are reviewed in detail in part to consider methods for their use in both preclinical animal models and in the development and use of clinical therapies based on such studies. MBP85–99 is immunodominant in humans, and several epitopes in this region induce EAE in mice (MBP87–98, MBP91–104, and MBP84–102). PLP139–151 and PLP178–191 are encephalitogenic epitopes in mice; when whole protein is used to immunize mice, lymph node cells respond to both of these epitopes indicating they are co-dominant. The encephalitogenic potential of several predicted T-cell epitopes from MOG (1–21, 35–55, 67–87, 104–117, and 202–218) were tested in mice; only MOG35–55 induced specific T-cell responses and EAE. This epitope stimulates specific T cell responses to MOG40–55 and T cell lines reactive to MOG40–55 were encephalitogenic upon transfer to syngeneic mice. MOBP37–60 is encephalitogenic in mice. Peripheral blood lymphocytes from a patient with MS mount a proliferative response to MOBP, especially MOBP21–39. The use of a DNA plasmid encoding multiple encephalitogenic epitopes derived from MBP (7–50, 83–106, and 142–168), MOG (1–25, 32–58, and 63–97), and PLP (30–60, 84–116, and 139–155) was shown to protect mice from developing EAE induced by PLP139–151.

Ii-Key/antigenic epitope hybrids comprising MHC Class II-presented epitopes derived from autoantigenic peptides from MBP, PLP, MOG, and MOBP, as described above, will have many preferred characteristics as immunopharmacological therapeutics. The useful effects of such Ii-Key/antigenic epitope hybrids in the treatment of MS, whether used as peptides or DNA vaccines include the following: (1) more rapid and potent immunosuppressive responses, (2) longer-duration of immunosuppressive responses and memory for later challenges, (3) decreased incidence of neo-reactivities as a result of intra- or intermolecular spread of autoimmunity, (4) greater breadth of response as a result of more potent presentation of epitopes on otherwise low-responding alleles, and (5) greater protection against the development, or slowing or reversal of, clinical manifestations of disease.

Warren, Catz and colleagues have demonstrated that human myelin basic protein (hMBP) peptide-based tolerance induction might be an effective antigen-specific immunotherapy for MS (Warren K G. J Neurol Sci. 1995 133:

85–94; Warren K G. Neurol Sci. 1997 148:67–78; Warren K G. J Neurol Sci. 1997 152:31–8). Tolerance to myelin basic protein (MBP) was examined in a Phase I clinical trial in MS patients with chronic progressive disease using hMPB peptide P85VVHFFKNIVTP96 (SEQ ID NO: 822) that is immunodominant for MBP-specific T cells and B cells. Tolerance induction was monitored by titers of MBP-specific autoantibodies in the CSF. Intravenous but not intrathecal or subcutaneous injection induced tolerance to MBP. Four kinetic patterns of response were observed in 41 patients (Warren K G. Mult Scler. 2000 6:300–11): Group A (15 patients) illustrated prolonged anti-BMP suppression into the normal range; Group B (10 patients) illustrated significant anti-MBP suppression into the normal range for shorter durations; Group C (eight patients) showed significant CSF anti-MBP suppression after the initial injection but lost the ability to suppress the autoantibody titer following subsequent injections; and Group D (eight patients) failed to show significant CSF anti-MBP suppression. In the control group, anti-MBP antibodies remained persistently elevated over the 2-year period. Tolerance duration depended on MHC Class II haplotypes of patients; tolerance was long-lived in all patients with disease-associated HLA-DR2. No neurological or systemic side effects were observed, regardless of the route of peptide administration.

Lees and colleagues identified several encephalitogenic determinants of myelin proteolipid protein active in SJL mice (Tuohy V K. J. Immunol. 1989 142:1523–7; Greer J M. J. Immunol. 1992 149:783–8). Immunization with PLP, the major protein constituent of central nervous system myelin, induces an acute form of EAE SJL/J (H-2s) mice. Immunization with PL139–154(HCLGKWLGHPDKFVGI) (SEQ ID NO: 823) induced severe clinical and histological EAE in 3 of 20 mice. In addition, PLP(178–191) also induced EAE in these mice Two CD4+, peptide-specific, I-A(s)-restricted T cell lines, selected by stimulation of lymph node cells with either PLP 178–191 or 139–151, were each encephalitogenic in naive syngeneic mice.

Ben-Nun and colleagues tested several peptides from pMOG, finding that a myelin oligodendrocyte glycoprotein peptide induces typical chronic experimental autoimmune encephalomyelitis in H-2b mice (Mendel I. Eur J. Immunol. 1995 25:1951–9; Kaye J F. J Neuroimmunol. 2000 102: 189–98). This group also tested the hypothesis that multiple potentially pathogenic antimyelin T cell reactivities could be inhibited by tolerogenic administration of an artificial “multiantigen/multiepitope” protein (Zhong M C. J Clin Invest. 2002 110:81–90). A synthetic gene was constructed to encode selected disease-relevant epitopes of myelin basic protein (MBP), proteolipid protein (PLP), and myelin oligodendrocyte glycoprotein (MOG). Systemic administration of hmTAP not only suppressed and treated experimental autoimmune encephalomyelitis (EAE) initiated by autoreactivity to a PLP epitope, but also abrogated complex EAE transferred by multispecific line T cells reactive against encephalitogenic epitopes of MBP, PLP, and MOG. In addition Oldstone and colleagues identified the MOBP37–60 epitope, which induced experimental allergic encephalomyelitis in mice with a severe clinical course (Holz A. J. Immunol. 2000 164:1103–9). Also PBL from patients with relapsing/remitting multiple sclerosis mount a proliferative response to human MOBP, especially at amino acids 21–39.

Anti-myelin antibodies can be found in some patients without MS (Warren K G. Eur Neurol. 1999 42:95–104). Wucherpfenning, Catz, Warren and colleagues affinity-purified MBP autoantibodies from central nervous system lesions of 11 postmortem cases (Wucherpfennig K W. J Clin Invest. 1997 100:1114–22). The MBP (83–97) peptide was immunodominant in all cases since it inhibited autoantibody binding to MBP>95%. Residues contributing to autoantibody binding were located in a 10-amino acid segment (V86–T95) that also contained the MHC/T cell receptor contact residues of the T cell epitope. In the epitope center, the same residues were important for antibody binding and T cell recognition.

Ii-Key Hybrids comprising MBP82–98 epitopes will increase the duration of anti-MBP suppressive responses, increase the proportion of patients developing sustained anti-MBP suppressive responses, increase the magnitude of the anti-MBP suppressive response, and decrease the number and frequency of doses needed to induce clinically effective anti-MBP suppressive responses. Because epitope charging with Ii-Key Hybrids is much greater than epitope alone, Ii-Key/MBP (85–96) Hybrids will facilitate binding to a greater repertoire of HLA DR alleles, thereby increasing the proportion of patients responding to treatment. Ii-Key/MBP (MBP85–96) Hybrids will also trigger a cell-mediated suppressive immune response to the MBP85–96 epitope. Ii-Key Hybrids comprising this and/or other MHC Class II epitopes either alone, or in combination with MHC Class I or B-cell antibody recognized determinants (arranged linearly in tandem to—or imbedded within—the MHC Class II epitope) will also induce enhanced immunosuppressive responses the MBP that provide for clinically significant therapeutics for patients with multiple sclerosis.

Selected preclinical studies reveal mechanisms and specific structural (chemical) data that are useful in determining optimal epitope structure and methods of use of Ii-Key/antigenic epitope hybrids in the treatment of MS. Krogsgaard M, Wucherpfennig K W, Fugger L and colleagues used phage display technology to select HLA-DR2-peptide-specific antibodies from HLA-DR2-transgenic mice immunized with HLA-DR2 molecules complexed with MBP 85–99 (Krogsgaard M. J Exp Med. 2000 191:1395–412). The MK16-selected antibodies recognized only complexes of DR2 and MBP and recognized intra- and extracellular HLA-DR2-MBP peptide complexes when antigen-presenting cells (APCs) had been pulsed with recombinant MBP. MK16 antibodies inhibited interleukin 2 secretion by two transfectants that expressed human MBP-specific T cell receptors. Analysis of the structural requirement for MK16 binding demonstrated that the two major HLA-DR2 anchor residues of MBP 85–99 and the COOH-terminal part of the peptide, in particular residues Val-96, Pro-98, and Arg-99, were important for binding. Based on these results, the antibody was used to determine if the HLA-DR2-MBP peptide complex was presented in MS lesions. The antibody stained APCs in MS lesions, in particular microglia/macrophages but also in some cases hypertrophic astrocytes. Staining of APCs was only observed in MS cases with the HLA-DR2 haplotype but not in cases with other haplotypes. These results demonstrated that HLA-DR2 molecules in MS lesions present a myelin-derived self-peptide and indicate that microglia/macrophages rather than astrocytes are the predominant APCs in these lesions.

Fugger and colleagues expressed in transgenic mice three human components involved in T-cell recognition of an MS-relevant autoantigen presented by the HLA-DR2 molecule: DRA*0101/DRB1*1501 (HLA-DR2), an MHC class II candidate MS susceptibility genes found in individuals of European descent; a T-cell receptor (TCR) from an MS-patient-derived T-cell clone specific for the HLA-DR2 bound immunodominant myelin basic protein (MBP) 4102 peptide; and the human CD4 co-receptor (Madsen L S. Nat Genet. 1999 23:258–9). The amino acid sequence of the MBP 84–102 peptide is the same in both human and mouse MBP. Following administration of the MBP peptide, together with adjuvant and pertussis toxin, transgenic mice developed focal CNS inflammation and demyelination that led to clinical manifestations and disease courses resembling those seen in MS. Spontaneous disease was observed in 4% of mice. When DR2 and TCR double-transgenic mice were backcrossed twice to Rag2 (for recombination-activating gene 2)-deficient mice, the incidence of spontaneous disease increased, demonstrating that T cells specific for the HLA-DR2 bound MBP peptide are sufficient and necessary for development of disease. This study provided evidence that HLA-DR2 can mediate both induced and spontaneous disease resembling MS by presenting an MBP self-peptide to T cells.

Susceptibility to multiple sclerosis is associated with the human histocompatibility leukocyte antigen (HLA)-DR2 (DRB1*1501) haplotype. Wiley and colleagues determined the structure of HLA-DR2 was determined with a bound peptide from human myelin basic protein (MBP) that was immunodominant for human MBP-specific T cells (Smith K J. J Exp Med. 1998 188:1511–20; Gauthier L. Proc Natl Acad Sci U S A. 1998 95:11828–33). Residues of MBP peptide that are important for T cell receptor recognition are prominent, solvent exposed residues in the crystal structure. A distinguishing feature of the HLA-DR2 peptide binding site is a large, primarily hydrophobic P4 pocket that accommodates a phenylalanine of the MBP peptide. The necessary space for this aromatic side chain is created by an alanine at the polymorphic DRbeta 71 position. These features make the P4 pocket of HLA-DR2 distinct from DR molecules associated with other autoimmune diseases.

The binding site orientation of Ii-Key/antigenic epitope hybrids can be proposed from analysis of the binding of TCR with hMBP/DR2 complexes. The structural basis for the specificity of ternary complex formation by the TCR and MHC/peptide complexes was examined for myelin basic protein (MBP)-specific T-cell clones restricted by different DR2 subtypes (Wucherpfennig K W. Proc Natl Acad Sci USA. 1995 92:8896–900). Conserved features of this system allowed a model for positioning of the TCR on DR2/peptide complexes to be developed: (i) The DR2 subtypes that presented the immunodominant MBP peptide differed only at a few polymorphic positions of the DR beta chain. (ii) TCR recognition of a polymorphic residue on the helical portion of the DR beta chain (position DR beta 67) was important in determining the MHC restriction. (iii) The TCR variable region (V) alpha 3.1 gene segment was used by all of the T-cell clones. TCR V beta usage was more diverse but correlated with the MHC restriction, i.e., with the polymorphic DR beta chains. (iv) Two clones with conserved TCR alpha chains but different TCR beta chains had a different MHC restriction but similar peptide specificity. The difference in MHC restriction between these T-cell clones appeared due to recognition of a cluster of polymorphic DR beta-chain residues (DR beta 67–71). MBP(85–99)-specific TCRs, therefore, appeared to be positioned on the DR2/peptide complex such that the TCR beta chain contacted the polymorphic DR beta-chain helix while the conserved TCR alpha chain contacted the nonpolymorphic DR alpha chain.

Table 20.1 presents the deduced amino acid sequence of human myelin basic protein (GenBank gi:17378805). Table 20.2 presents MHC Class II-presented epitopes of human myelin basic protein predicted with the SYFPEITHI program. Table 20.3 presents sequences identified experimentally to contain hMBP MHC Class II-presented epitopes (Pette M. Proc Natl Acad Sci USA. 1998 87:7968). Table 20.4 presents hybrids incorporating epitopes of Table 20.2. Table 20.5 presents Ii-Key/antigenic epitope hybrids incorporating epitopes from peptides of Table 20.3. Table 20.6 presents the deduced amino acids sequence of human proteolipid protein 1 (GenBank gi 19923104). Table 20.7 presents MHC Class II-presented epitopes of proteolipid protein 1 predicted with the SYFPEITHI program. Table 20.8 presents sequences identified experimentally to contain proteolipid protein 1 MHC Class II-presented epitopes. Table 20.9 presents hybrids incorporating epitopes of Table 20.7. Table 20.10 presents Ii-Key/antigenic epitope hybrids incorporating epitopes within peptides of Table 20.8. Table 20.11 presents the deduced amino acids sequence of human myelin-oligodendrocyte glycoprotein precursor (GenBank gi: 2497312). Table 20.12 presents MHC Class II-presented epitopes of oligodendrocyte glycoprotein precursor predicted with the SYFPEITHI program. Table 20.13 presents sequences identified experimentally to contain oligodendrocyte glycoprotein precursor MHC Class II-presented epitopes. Table 20.14 presents hybrids incorporating epitopes of Table 20.12. Table 20.15 presents Ii-Key/antigenic epitope hybrids incorporating epitopes within peptides of Table 20.13.

TABLE 20.1

Deduced amino acids sequence of human myelin basic protein. (SEq ID NO: 824)

| | | | | | |
|---|---|---|---|---|---|
| 1 | mgnhagkrel | naekastnse | tnrgesekkr | nlgelsrtts | ednevfgead |
| 51 | anqnngtssq | dtavtdskrt | adpknawqda | hpadpgsrph | lirlfsrdap |
| 101 | gredntfkdr | psesdelqti | qedsaatses | ldvmasqkrp | sqrhgskyla |
| 151 | tastmdharh | gflprhrdtg | ildsigrffg | gdrgapkrgs | gkdshhpart |
| 201 | ahygslpqks | hgrtqdenpv | vhffknivtp | rtpppsqgkg | rglslsrfsw |
| 251 | gaegqrpgfg | yggrasdyks | ahkgfkgvda | qgtlskifkl | ggrdsrsgsp |
| 301 | marr | | | | |

TABLE 20.2

Predicted MHC Class II-presented epitopes of human myelin basic protein.

| PEPTIDE | Pos. | Sequence | Allele | Ii-Key | SEQ ID NO: |
|---|---|---|---|---|---|
| 20.2.1 | 284 | LSKIFKLGG | 01, 11(281) | 4 | 825 |
| 20.2.2 | 88 | RPHLIRLFS | 01,03(89), 04(88) | 0 | 826 |
| 20.2.3 | 4 | HAGKRELNA | 01 | 0 | 827 |
| 20.2.4 | 272 | HKGFKGVDA | 01, 02(273) | 0 | 828 |
| 20.2.5 | 117 | LQTIQEDSA | 03 | 0 | 829 |
| 20.2.6 | 167 | RDTGILDSI | 03, 11(169) | 3 | 830 |
| 20.2.7 | 66 | DSKRTADPK | 03 | 0 | 831 |
| 20.2.8 | 221 | VHFFKNIVT | 04 | 0 | 832 |
| 20.2.9 | 152 | ASTMDHARH | 04 | 0 | 833 |
| 20.2.10 | 29 | KRNLGELSR | 01, 04, 11 | 0 | 834 |
| 20.2.11 | 176 | GRFFGGDRG | 04, 11(175) | 9 | 835 |

Pos. is the first amino acid of the predicted MHC Class II-presented epitope of the specified sequence. Score is the score calculated by the SYFPEITHI program for the first of the given HLA-DRB*_01 alleles which were examined. The second listed allele is for exactly the same epitope or for an overlapping epitope for which the first amino acid position is given in parentheses.

TABLE 20.3

Experimentally determined MHC Class II-presented epitopes of human myelin basic protein.

| Peptide | Pos. | Presenting MHC II | Sequence | Predicted epitope | SEQ ID NO |
|---|---|---|---|---|---|
| 20.3.1 | 1–44 | DR2a | MGNHAGKREL NAEKASTNSE TNRGESEKKR NLGELSRTTS EDNE | | 836 |
| 20.3.2 | 76–91 | DR2a | AWQDA HPADPGSRPH LIRLFSRDAP GREDNTFKDR P | 837 | |
| 20.3.3 | 131–145 | DR2a | LDVMASQKRP SQRHG | 132 | 838 |
| 20.3.4 | 139–153 | DR2a; DR1 | P SQRHGSKYLA TASTM | 148 | 839 |
| 20.3.5 | 80–99 | DR2b | A HPADPGSRPH LIRLFSRDA | 91, 92 | 840 |
| 20.3.6 | 148–162 | DR2b | LA TASTMDHARH GF | 148 | 841 |

Pos. is the first and last amino acids of the segments of hMBP reported to contain MHC Class II-presented epitopes. Sequence is a peptide identified by Pette and colleagues to contain hMBP MHC Class II-presented epitopes (Pette M. Proc Natl. Acad Sci USA. 1998 87:7968). The peptides MBP85–99, MBP85–96 and MBP83–97 have also been characterized by others (Krogsgaard M. J Experi Med. 2000 191:1395–412; Gauthier L. Proc. Natl. Acad Sci USA. 1998 95:11828–33). Presenting allele includes MHC Class II alleles which are reported to present epitopes in the respective segments. Seq. is the sequence of the segment. Predicted epitope is the first amino acid of the epitopes predicted to be presented by respective MHC Class II alleles, using the ProPred algorithm. HMBP(91–98; FIRLFSRDA) (SEQ ID NO: 842) presented by HLA-DRB*0101, 1101, and 1301. hMBP(92–99; IRLFSRDAP) (SEQ ID NO: 843) presented by HLA-DRB*1301 and 1501. hMBP(120–128; IQWDSAATA) (SEQ ID NO: 844) presented by HLA-DRB*03. hMBP(133–141; VMASQKRPS) (SEQ ID NO: 845) presented by HLA-DRB*0101, and 1301. hMPB(148–157; LATASTMDH) (SEQ ID NO: 846) presented by HLA-DRB*0401 and 1101. hMBP(162–170) presented by HLA-DRB*0801.

TABLE 20.4

Ii-Key/human MBP antigenic epitope hybrids with MHC Class II-Presented epitopes of TABLE 20.2.

| PEPTIDE | Pos. | Sequence | SEQ ID NO |
|---|---|---|---|
| 20.4.1 | 284 | Ac-LRMK-LSKIFKLGG-$NH_2$ | 847 |
| 20.4.2 | 88 | Ac-LRMK-RPHLIRLFS-$NH_2$ | 848 |
| 20.4.3 | 4 | Ac-LRMK-HAGKRELNA-$NH_2$ | 849 |
| 20.4.4 | 272 | Ac-LRMK-HKGFKGVDA-$NH_2$ | 850 |
| 20.4.5 | 117 | Ac-LRMK-HKGFKGVDA-$NH_2$ | 851 |

TABLE 20.5

Ii-Key/human MBP antigenic epitope hybrids with MHC Class II-Presented epitopes of TABLE 20.3.

| PEPTIDE | Pos. | Sequence | SEQ ID NO |
|---|---|---|---|
| 20.5.1 | 91 | Ac-LRMK-FIRLFSRDA-NH2 | 852 |
| 20.5.2 | 92 | Ac-LRMK-IRLFSRDAP-NH2 | 853 |
| 20.5.3 | 133 | Ac-LRMK-VMASQKRPS-NH2 | 854 |
| 20.5.4 | 148 | Ac-LRMK-LATASTMDH-NH2 | 855 |

Another major component of CNS myelin, the proteolipid protein (PLP), induces an acute form of EAE in SJL/J mice (Tuohy V K. J. Immunol. 1989 142:1523–7; Greer J M. J. Immunol. 1992 149:783–8). A principal MHC Class II-presented epitope was found in 139–154 HCLGKWLGHP-DKFVGI (SEQ ID NO: 856); and in certain serine-substituted homologs. The sequence of the homologous human sequences are presented in Table 20.2. A second peptide murine 178–191 of PLP (Human homolog sequence: FNT 181 WTTCDSIAFP S) (SEQ ID NO: 857) was also identified to be encephalitogenic in SJL/J (h-2s) mice (Greer J M. J. Immunol. 192 149:783–8).

TABLE 20.6

Deduced amino acids sequence of human proteolipid protein. (SEQ ID NO: 858)

```
  1 mglleccarc lvgapfaslv atglcffgva lfcgcgheal tgtekliety
 51 fsknyqdyey linvihafqy viygtasfff lygalllaeg fyttgavrqi
101 fgdyktticg kglsatvtgg qkgrgsrgqh qahslervch clgkwlghpd
151 kfvgityalt vvwllvfacs avpvyiyfnt wttcdsiafp sktsasigsl
201 cadarmygvl pwiafpgkvc gsnllsickt aefqmtfhlf iaafvgaaat
251 lvslltfmia atynfavlkl mgrgtkf
```

TABLE 20.7

Predicted MHC Class II-presented epitopes of human myelin proteolipid protein.

| PEPTIDE | POS. | Sequence | Allele | Ii-Key | SEQ ID NO: |
|---|---|---|---|---|---|
| 20.6.1 | 77 | FFFLYGALL | 01, 07(78), 08(78), 15(78) | 8 | 859 |
| 20.6.2 | 243 | FVGAAATLV | 01, 04(244), 11(244) | 4 | 860 |
| 20.6.3 | 236 | FHLFIAAFV | 01, 07(232), 11(232) | 7 | 861 |

TABLE 20.7-continued

Predicted MHC Class II-presented epitopes of human myelin proteolipid protein.

| PEPTIDE | POS. | Sequence | Allele | Ii-Key | SEQ ID NO: |
|---|---|---|---|---|---|
| 20.6.4 | 250 | LVSLLTFMI | 01, 03, 04, 13, 15 | 8 | 862 |
| 20.6.5 | 162 | WLLVFACSA | 01, 03(160), 07(156), 08, 11(160) | 7 | 863 |
| 20.6.6 | 99 | IFGDYKTTI | 03 | 0 | 864 |
| 20.6.7 | 199 | LCADARMYG | 03 | 0 | 865 |
| 20.6.8 | 70 | VIYGTASFF | 03, 04(69), 08(69), 11(69), 13(69) | 3 | 866 |
| 20.6.10 | 57 | YEYLINVIH | 04 | 8 | 867 |
| 20.6.11 | 152 | VGITYALTV | 08 | 6 | 868 |

Pos. is the first amino acid of the predicted MHC Class II-presented epitope of the specified sequence. Score is the score calculated by the ProPred program for the first of the given HLA-DRB*_01 alleles which were examined. The second listed allele is for exactly the same epitope or for an overlapping epitope for which the first amino acid position is given in parentheses).

TABLE 20.8

Experimentally determined MHC Class II-presented epitopes of human myelin proteolipid protein.

| PEPTIDE | Pos. | Sequence | Ii-Key | SEQ ID NO: |
|---|---|---|---|---|
| 20.7.1 | M139-151 139-154 | HCLGKWLGHPDKFVGI | 5 | 869 |

A series of 4 or more overlapping sequences from position 152 (FVGITYALTVVWLLVFAC) (SEQ ID NO: 870) are presented by alleles HLA-DRB 01, 03, 04, 07, 08, 11, 13, 15. The Ii-Key motif LGKWL (SEQ ID NO: 871) is separated by 5 amino acids from F152.

TABLE 20.9

| Ii-Key/PLP epitope hybrids containing MHC Class II-presented epitopes of Table 20.7. | | | |
|---|---|---|---|
| PEPTIDE | Pos. | Sequence | SEQ ID NO |
| 20.8.1 | 77 | Ac-LRMK-FFFLYGALL-$NH_2$ | 872 |
| 20.8.2 | 243 | Ac-LRMK-FVGAAATLV-$NH_2$ | 873 |
| 20.8.3 | 236 | Ac-LRMK-FHLFIAAFV-$NH_2$ | 874 |
| 20.8.4 | 250 | Ac-LRMK-LVSLLTFMI-$NH_2$ | 875 |

TABLE 20.10

| Ii-Key/PLP epitope hybrids containing MHC Class II-presented epitopes of Table 20.8. | | | |
|---|---|---|---|
| PEPTIDE | Pos. | Sequence | SEQ ID NO |
| 20.9.1 | 152 | Ac-LRMK-FVGITYALTVVWLLVFAC-$NH_2$ | 876 |

A third protein of myelin, human myelin-oligodendrocyte glycoprotein (MOG) has also been shown to be encephalitogenic in mice (Mendel I. Eur J. Immunol. 1995 25:1951–9; Kaye J F. J Neuroimmunol. 2000 102:189–98).

TABLE 20.11

| Deduced amino acid sequence of myelin-oligodendrocyte glycoprotein precursor. (SEQ ID NO: 877) | | | | | |
|---|---|---|---|---|---|
| 1 | maslsrpslp | sclcsfllll | llqvsssyag | qfrvigprhp | iralvgdeve |
| 51 | lpcrispgkn | atgmevgwyr | ppfsrvvhly | rngkdqdgdq | apeyrgrtel |
| 101 | lkdaigegkv | tlrirnvrfs | deggftcffr | dhsyqeeaam | elkvedpfyw |
| 151 | vspgvlvlla | vlpvlllqit | vglvflclqy | rlrgklraei | enlhrtfdph |
| 201 | flrvpcwkit | lfvivpvlgp | lvaliicynw | lhrrlagqfl | eelrnpf |

TABLE 20.12

| Predicted MHC Class II-presented epitopes of human myelin myelin-oligodendrocyte glycoprotein precursor. | | | | | |
|---|---|---|---|---|---|
| PEPTIDE | Pos. | Sequence | Allele | Ii-Key | SEQ ID NO: |
| 20.11.1 | 155 | LVLLAVLPV | 01, 03, 04 | 5 | 878 |
| 20.11.2 | 200 | FLRVPCWKI | 01, 07 | 3 | 879 |
| 20.11.3 | 31 | FRVIGPRHP | 01 | 0 | 880 |
| 20.11.4 | 217 | LGPLVALII | 01 | 5 | 881 |
| 20.11.5 | 211 | FVIVPVLGP | 01, 04, 11 | 6 | 882 |
| 20.11.6 | 15 | FLLLLLLQV | 01, 03(18), 04(18), 15(12) | 0 | 883 |
| 20.11.7 | 43 | LVGDEVELP | 03 | 5 | 884 |
| 20.11.8 | 99 | LLKDAIGEG | 03 | 0 | 885 |

TABLE 20.12-continued

| Predicted MHC Class II-presented epitopes of human myelin myelin-oligodendrocyte glycoprotein precursor. | | | | | |
|---|---|---|---|---|---|
| PEPTIDE | Pos. | Sequence | Allele | Ii-Key | SEQ ID NO: |
| 20.11.9 | 111 | LRIRNVRFS | 03, 08 | 6 | 886 |
| 20.11.10 | 164 | LLLQITVGL | 04, 07(166) | 0 | 887 |
| 20.11.11 | 149 | WVSPGVLVL | 07 | 5 | 888 |
| 20.11.12 | 179 | YRLRGKLRA | 08 | 0 | 889 |
| 20.11.13 | 229 | WLHRRLAGQ | 08 | 0 | 890 |

Pos. is the first amino acid of the predicted MHC Class II-presented epitope of the specified sequence. Score is the score calculated by the ProPred program for the first of the given HLA-DRB*__01 alleles which were examined. The second listed allele is for exactly the same epitope or for an overlapping epitope for which the first amino acid position is given in parentheses).

TABLE 20.13

| Experimentally determined MHC Class II-presented epitopes of myelin-oligodendrocyte glycoprotein precursor. | | | |
|---|---|---|---|
| PEPTIDE | Pos. | Sequence | SEQ ID NO: |
| 20.12.1 | h21-39 | LLQVSSSYAG QFRVIGPRH | 891 |

TABLE 20.14

| Ii-Key/MOG epitope hybrids containing MHC Class II-presented epitopes of Table 20.12. | | | |
|---|---|---|---|
| PEPTIDE | Pos. | Sequence | SEQ ID NO: |
| 20.13.1 | 155 | Ac-LRMK-LVLLAVLPV-$NH_2$ | 892 |
| 20.13.2 | 200 | Ac-LRMK-FLRVPCWKI-$NH_2$ | 893 |
| 20.13.3 | 31 | Ac-LRMK-FRVIGPRHP-$NH_2$ | 894 |
| 20.13.4 | 211 | Ac-LRMK-FVIVPVLGP-$NH_2$ | 895 |

TABLE 20.15

| Ii-Key/MOG epitope hybrids containing MHC Class II-presented epitopes of Table 20.13. | | | |
|---|---|---|---|
| PEPTIDE | Pos. | Sequence | SEQ ID NO |
| 20.14.1 | 16–27 | Ac-LRMK-FLLLLLLQVSSSY-$NH_2$ | 896 |
| 20.14.2 | 13–23 | Ac-LRMK-FRVIGPRHPIRA-$NH_2$ | 897 |

Peptide 20.14.1 contains three overlapping MHC Class II-presented epitopes presented by alleles HLA-DRB 01, 03, 04, 07, 11, 13, and 15. Peptide 20.14.2 contains two overlapping MHC Class II-presented epitopes presented by alleles HLA_DRB 01, 08 and 11.

Example 21

Identification and Use of Peptide Sequences Containing Ii-Key Motifs Appropriately Placed from the N-Terminal End of MHC Class II Antigenic Epitopes In another aspect this invention relates to methods to select a preferred set of biologically active MHC Class II-presented epitopes in antigenic proteins. Specifically, this disclosure provides methods to identify in the amino acid sequence of a protein the presence or absence of a Ii-Key immunoregulatory motif of 5 amino acids preceding an experimentally determined or algorithm-predicted, MHC Class II-presented, antigenic epitope. This immunoregulatory Ii-Key motif enhances charging of the linked antigenic epitope into the antigenic peptide binding site of MHC Class II molecules. Given predictions of antigenic epitopes within a protein, identifying the subset of those epitopes preceded by an Ii-Key motif improves greatly the efficiency of vaccine peptide selection. Also, by modifying the sequence of a protein, either to introduce or to eliminate an Ii-Key motif before selected MHC Class II-presented epitopes, the immunological response to that protein can be altered.

This disclosure presents a method to identify an Ii-Key immunoregulatory motif. Specifically, in the sequence of a protein, the immunoregulatory, Ii-Key motif is a segment of 5 contiguous amino acids containing at least two amino acids of the group comprising Leu, Ile, Val, Phe, and Met, and at least one of the group comprising His, Lys, and Arg, where that contiguous 5 amino acid segment is separated by 5 to 11 amino acids from the N-terminal residue of the MHC Class II-presented epitope. The subset of such antigenic epitopes with the presence of an appropriately spaced Ii-Key motif are more potent than epitopes not preceded by such an Ii-Key motif in enhancing the potency of the CD4+ T cell immune response. Such epitopes are also more likely to be dominant or biologically active. Peptides with such epitopes are favored as vaccines to protect against infectious diseases and cancer, and as immunosuppressive vaccines for allergy, autoimmune disease, and graft rejection.

In another aspect, this invention relates to therapeutic proteins with sequences which are modified in a manner to alter immune responses to the therapeutic proteins. Such proteins include therapeutic proteins, such as hormones, cytokines, or other molecules interacting with cell surface receptors, and enzymes. Modifications of an Ii-Key motif can be made to eliminate its function, or such an Ii-Key motif can be introduced before a putative antigenic epitope when such a motif is lacking. Such modifications can suppress a disadvantageous immune response to the therapeutic protein. Such products include the therapeutic protein, and fragments thereof, and genetic constructs leading to their expression.

This invention is based in the discovery that a naturally occurring Ii-Key motif appropriately spaced before a potential antigenic epitope, selects for biological activity in a subset of MHC Class II binding motifs. The binding of radiolabeled, photo-crosslinking, antigenic peptides to MHC Class II molecules is more efficient during the cleavage and release of the Ii protein from MHC Class II alpha and beta chains in the presence of cathepsin B but not cathepsin D (Daibata M. Mol Immunol. 1994 31:255–260). Mutants of putative cleavage sites in the Ii protein confirmed the role of residues in the R78–K86 region in the final cleavage and release of the avidin-labeled Ii fragments that are still immunoprecipitated with MHC Class II alpha and beta chains (Xu M. Mol Immunol. 1994 31:723–731). The biochemical mechanism of this "final cleavage" region was tested with synthetic Ii-L87-K, which contains six residues with cationic side chains, no anionic side chains and four spaced prolines. This Ii-Key peptide promoted binding or release of antigenic peptides in vitro (Adams S. Eur J. Immunol. 1995 25:1693–1702). Structure-activity relationships were characterized with 160 homologs, in antigenic peptide presentation to murine T hybridomas (Adams S. Arzneimittel-Forschung. 1997 47:1069–1077), and with purified HLA-DR1 in a peptide binding/release assay (Xu M. Arzneimittel-Forschung. 1999 49:791–9). The Ii-Key segment hIi(77–92) of the Ii protein promotes the binding of synthetic peptides to MHC Class II molecules by acting at an allosteric site adjacent to one end of the antigenic peptide-binding trough. Furthermore, by coupling this Ii-Key segment through a simple polymethylene linker to an antigenic peptide, the potency of presentation of the epitope to a T hybridoma was enhanced 500 times, relative to only the antigenic epitope (Humphreys R E. Vaccine. 2000 18:2693–7). Thus, comparable, naturally occurring, appropriately spaced Ii-Key motifs can be expected to promote the selection of the subset of antigenic epitopes before which they occur at an appropriately spaced interval. Since synthetic hybrids containing linkers of either the natural sequence of Ii-protein extending from the LRMK SEQ ID NO: 3) motif, or 5-amino-pentanoic acid, were comparably active, no specific side chain interactions were required between the linker and the alpha helices of the antigen-binding site. Thus, the specific amino acids forming a spacer region appear not to be relevant. The hypothesis that naturally occurring Ii-Key-spacer motifs regulate selection of potential MHC Class II epitopes in vivo was tested for presence and spacing of a generic Ii-Key motif from both the N-terminus (active hypothesis) or the C-terminus (indifferent hypothesis) of defined MHC Class II-presented epitopes.

Ii-key motifs in antigenic proteins serve to catalyze insertion of closely following, MHC Class II-presented, antigenic epitopes into peptide binding sites of MHC Class II molecules. It is the Ii-Key motif appropriately spaced before a potential MHC Class II binding peptide, which makes that epitope immunogenic. From this discovery, comes a novel method to select a subset of epitopes identified by consensus motifs for their dominant role in antigen presentation. Such epitopes can be exploited in preventative and therapeutic vaccines. Therapeutic proteins can also be modified to either enhance or suppress immunogenicity.

The following method to identify Ii-Key motifs within the amino acid sequence of antigenic proteins was designed prior to examination of the data set, and tested without alteration. An Ii-Key box was defined to be 5 contiguous residue positions containing at least two residues of the group L, I, V, F, and M and at least one residue of the group H, K, and R. This was the simplest model based on two concepts.

The first critical concept in the design of the method of this invention was the discovery of the motif defining the Ii-Key "core segment". In the natural sequence of the human Ii protein, the core motif was defined to be $L^{77}$ RMK (SEQ ID NO: 3) on the basis of previous experimental studies showing retention by this peptide of at least half-maximal activity of the best Ii-Key peptide in a systematic series of hybrids (Adams S. Arzneimittel-Forschung. 1997 47:1069–77; Humphreys R E. Vaccine 2000 18:2693–7). The core motif of four amino acids is contained within a previously defined segment of 7 amino acids (LRMKLPK) (SEQ ID NO: 4) studied through analysis of 84 homologs with 12 amino acid substitutions at each residue position (Adams S. Arzneimittel-Forschung. 1997 47:1069–77; Xu M. Arzneimittel-Forschung. 1999 49:791–9). In those studies, biological activity was discovered not to require precisely alternating hydrophobic/cationic side chains, provided that at least two hydrophobic and one cationic residue were present within a segment of 4 or 5 residues. For this reason, in defining the structure of an Ii-Key motif in the present invention, the presence of two hydrophobic side chains and at least one cationic side chain in any sequence within a stretch of 5 amino acids was considered to be sufficient for the function of Ii-Key in charging antigenic epitopes into MHC Class II molecules.

The second critical concept in the design of the method of this invention was the discovery of the functional equivalence of L, I, V, F, and M in one set, and H, K, and R in another respective set, in governing the structure of locally folded segments of proteins. This equivalency was discovered in a systematic survey of groups of amino acids in certain patterns either throughout proteins (Vazquez S. Proc Natl Acad Sci USA. 1993 90:9100–4) or in geometrically defined positions around alpha helices (Torgerson S. J Biol. Chem. 1991 266:5521–24; Vazquez S. J Biol. Chem. 1992 267:7406–10; Rennell D. J Biol. Chem. 1992 267:17748–52).

The above method of identifying naturally occurring Ii-Key motifs appropriately spaced from the N-terminus of MHC Class II-presented epitopes was validated though the following analysis. All 36 of the antigenic epitopes reported by Rammensee and colleagues (Rammensee H G. Immunogenetics. 1995 41:178–228) in their analysis of motifs predicting MHC Class II-presented peptides were analyzed, excluding homologous epitopes (for example from difference MHC Class II alleles). The sequences for each of these reported proteins upstream and downstream with respect to the antigenic epitope were obtained from GenBank (http://www.ncbi.nlm.nih.gov/entrez/query.fcgi?db=Protein). Given the definition of an Ii-Key box to contain 5 contiguous residue positions containing at least two residues of the group L, I, V, F, and M and at least one residue of the group H, K, and R, then the distance of such boxes from the N-terminus or C-terminus of known MHC Class II-presented epitopes within antigenic proteins were determined. A significant minimal spacing of such Ii-Key boxes from the N-terminus but not the C-terminus of such epitopes was anticipated because the biological effect was anticipated to be at the N-terminus and not the C-terminus. The predicted lack of biological effect of such boxes at the C-terminus (and thus the spacing form the C-terminus) was a useful null hypothesis for statistical analysis. Segments of 5 contiguous residues extending progressively in an N-terminal direction from a Rammensee-reported antigenic epitope were tested for the occurrence of an Ii-Key box. The box with the least number of intervening residue positions between the Ii-Key box and the Rammensee-reported antigenic epitope was scored in terms of the number of intervening residue positions (Table 1). A similar analysis, in the mirror image manner was scored distally from the C-terminus of the Rammensee-reported antigenic epitope. The least intervening residue positions to the first Ii-Key box were scored from the C-terminus of the antigenic epitope (Table 21.1).

The response of T cells to a MHC Class II-restricted antigenic epitope is enhanced greatly when that epitope is presented to T cells in a synthetic hybrid peptide linking an Ii-Key sequence (such as Acetyl-Leu-Arg-Met-Lys (SEQ ID NO: 3) [Ac-LRMK-] (SEQ ID NO: 3)) thorough a spacer 5-amino-pentanoic acid to the N-terminus of the MHC Class II-presented epitope. In order to test whether homologous, naturally occurring, Ii-Key/spacer/epitope motifs select for antigenic epitopes during processing of antigenic proteins, the frequency of one prototypic pattern was tested in a series of proteins with respect to placement about their experimentally determined MHC Class II epitopes. A non-empirical, N-terminal distribution ($p<0.025$) was found for a prototypic Ii-Key/spacer pattern (a 5 amino acid segment containing at least two residues of the group Leu, Ile, Val, Phe, and Met [LIVFM] (SEQ ID NO: 790) and at least one of the group Arg, His, and Lys [RHK]), and spacer length of 4 to 8 residues. This placement was significant in comparison to the empirical placement of the motif from the C-terminus (the indifferent hypothesis). This observation helps to explain the biological activity of only some epitopes among sets of predicted "MHC Class II consensus motifs" in antigenic proteins. It also leads to methods to modulate the immune response to certain antigens.

TABLE 21.1

Spacer length (residue positions) between Ii-Key boxes and terminus of the antigenic epitope.

| Spacer length | N-terminus | C-terminus |
|---|---|---|
| 0 | 2 | 9 |
| 1 | 1 | 2 |
| 2 | 1 | 3 |
| 3 | 0 | 0 |
| 4 | 0 | 0 |
| 5 | 2 | 3 |
| 6 | 5 | 1 |
| 7 | 0 | 2 |
| 8 | 1 | 2 |
| 9 | 4 | 1 |
| 10 | 4 | 1 |
| 11 | 2 | 2 |
| 12 | 0 | 1 |
| 13 | 2 | 0 |
| 14 | 2 | 0 |
| No box | 9 | 7 |
| Sum | 29 | 29 |

By inspection, the pattern for occurrence and placement of the Ii-Key box from the N-terminus of the epitope is very different from that on the C-terminal side, and the pattern of the C-terminal side is not different from that expected to be generated by the Monte Carlo model (random assignment of residue types at the frequency of occurrence in the data set). These observations were subjected to quantitative statistical analysis. The probabilities that the observed difference might have occurred as a random event for various groupings of spacer lengths are given in Table 21.2.

TABLE 21.2

| Analysis of distributions of Ii-Key motifs of certain spacer lengths. | | | | |
|---|---|---|---|---|
| Spacer length | N (obs) | C (obs) | Chi square Vs 0–4 | p ≦ |
| 0 to 4 | 4 | 14 | | |
| 5 to 8 | 8 | 6 | 4.097 | 0.05 |
| 5 to 11 | 18 | 12 | 6.467 | 0.025 |
| 5 to 14 | 22 | 13 | 7.854 | 0.01 |

Variations on the definition of a positive Ii-Key box and length and character of a spacer can be proposed. However, the testing of such alternatives must be performed on a new data set, to avoid a type I statistical error. Such an error did not occur in our present study since the scored motif was precisely and completely defined prior to examination of the current data set. We refrain from the suggestion of alternative Ii-Key box and spacer patterns, which might fit this data set better.

The fact that Ii-Key motif are found appropriately spaced to the N-terminal side of antigenically active MHC Class II-epitopes supports the view that such Ii-Key motifs are active in the selection of peptides to become bound to MHC Class II molecules in post-Golgi antigen charging compartment of antigen presenting cells. Likewise, the fact that Ii-Key/MHC Class II antigenic epitope hybrid peptides are well presented after immunization in Freund's incomplete adjuvant indicates that the Ii-Key motif on such peptides is active in selection of the epitopes of those peptides for charging in the post-Golgi antigenic peptide charging compartment.

Alteration can be introduced in therapeutic proteins to enhance a favorable characteristic. Use of many therapeutic proteins is limited because an immune response, as evidenced by neutralizing antibodies, developed against the protein, as has been observed with insulin, erythropoietin, and beta-interferon. Given a therapeutic protein to which an immunological response in some patients limits therapeutic use, the current invention may be used to prevent the immune response or mute the response in patients who have developed such response. The process includes the following steps. Examine the primary amino acid sequence. Define within the primary amino acid sequence motifs of MHC Class II-restricted epitopes. Choose epitope which are suitable to be altered at a few amino acids, in a manner to create an Ii-Key box-spacer motif N-terminal to the first residue of the antigenic motif. Synthesize the protein by recombinant molecular genetic methods or by peptide synthesis method. Test the synthetic variant for the induction of a suppressing immune response to the protein, for example by reduction of antibodies upon challenge with the parental therapeutic protein.

Ii-Key motifs upstream to selected MHC Class II-presented epitopes in clinically relevant antigens might lead to novel therapeutic vaccines. Perhaps engineering an Ii-Key spacer motif can alter the immunogenicity of an antigenic epitope within a protein. Particularly for the most N-terminal antigenic epitopes, introduction of one or a few altered residues may be tolerated (Rennell D. J Biol. Chem. 1992 267:17748–52). Such manipulations could generate forms of therapeutic proteins amenable to induction of tolerance.

This method of analysis can be extended to additional antigenic or therapeutic proteins of interest to which in vivo immunosuppressive responses are damaging to the host. For example, an examination of antigenic epitopes in HIV reverse transcriptase shows that antigenic epitopes there may have such upstream Ii-Key like segments, perhaps governing biological potency to establish dominance in establishing tolerance. A conserved universal Th epitope in HIV-1 reverse transcriptase is preceded by an Ii-key-spacer motif. An HIV-1 reverse transcriptase epitope, which was highly conserved among various HIV-1 isolates and was presented by at least four HLA-DR molecules, was discovered by Van der Burg and colleagues in a systematic survey of 20 amino acid peptides through the sequence of that enzyme (van der Burg. J. Immunol. 1999 162:152–160). This peptide and the upstream 15 amino acids are the following:

```
                           271–290
NDIQK LVGKL NWASQI         YPGIKVRQLCKLLRGTKALT
(SEQ ID NO:898)            (SEQ ID NO:899)
```

Possible MHC Class II-presented epitopes are single underlined and the putative Ii-Key motifs is double underlined. This example illustrates how the presence of an Ii-Key motif appropriately spaced before a MHC Class II-presented epitope can enhance the presentation of that epitope. Further, the presence of the Ii-Key motif may be responsible for the development of a highly efficient immunosuppressive response.

Example 22

Enhancement of Antibody, T Helper Cell, and CTL Responses to MHC Class I Epitopes by Immunizations with Ii-Key/MHC Class II Epitope Hybrids Substantially greater immune responses were found in mice immunized with epitopes presented in Ii-Key antigenic epitope hybrids, than in antigenic epitope peptides alone. The immune responses were measured by titers of antibodies to individual antigenic epitopes, epitope-specific-CD4+/IFN-γ+ cells, and epitope-specific IFN-γ release in the ELISPOT assay.

Two different antigenic epitopes, from pigeon cytochrome C and from HIV gp160, were used in these comparative studies. The PGCC(95–104) epitope was presented in an Ii-Key/antigenic epitope hybrid peptide (Ac-LRMK-ava-IAYLKQATAK-$NH_2$; "Ii-Key/PGCC"; SEQ ID NO: 900) or in an antigenic epitope peptide (Ac-IAYLKQATAK-$NH_2$; ("PGCC"); SEQ ID NO: 901). The HIV gp160(843–855) epitope was presented in: 1) an Ii-Key/antigenic epitope hybrid peptide with two ava residues (Ac-LRMK-ava-ava-AYRAIRHIPR-$NH_2$; "Ii-Key/two-ava/gp160(843–855)"; SEQ ID NO: 902); 2) an Ii-Key/antigenic epitope hybrid peptide with one ava residue (Ac-LRMK-ava-AYRAIRHIPR-$NH_2$; "Ii-Key/one-ava/gp160(843–855)"; SEQ ID NO: 903); 3) an Ii-Key/antigenic epitope hybrid peptide with one ava residue (Ac-LRMK-ava-YRAIRHIPR-$NH_2$; alanine-843 is deleted for more precise measurement of space between epitope and Ii-Key; "Ii-Key/one-ava/gp160 (844–855)"; SEQ ID NO: 904); 4) an Ii-Key/antigenic epitope peptide with no "ava" (Ac-LRMK-AYRAIRHIPR-$NH_2$; "gp160(843–855)"); SEQ ID NO: 905). "ava" is delta-aminovaleric acid, which is 5-aminopentanoic acid. Its maximal linear extent approximates the length of the backbone atoms of 2.5 amino acids in a peptidyl sequence. Thus, the two-ava linker bridges the Ii-Key motif from the antigenic epitope by about 5 amino acids. Five amino acids is the number of amino acids of an extended antigenic peptide occupying the antigenic peptide binding trough from the residue that lies in the P1 site to the N-terminally exposed end of a peptide that lies in that trough.

An ELISA assay for antibody responses following immunization with the experimental peptides indicated above was performed as follows. Fifty microliters (μl) of a solution of the coating peptide at 2 μg/well in 0.1 M carbonate buffer, pH 9.5 was added to each well of a 96-well Nunc-immunoplate (#442404) for an overnight incubation at 4° C. After aspiration, 250 μl of phosphate-buffer saline solution containing 3% fetal bovine serum (assay diluent) was added to each well for 2 hr at RT. After washing three times with assay diluent, 50 μl of 20-times diluted mouse serum in 1:3 serial dilution in assay diluent was added to each well for 2 hr at RT. After washing three times with assay diluent, 50 μl of 1 μg/ml biotinylated goat anti-mouse IgG1 or IgG2a was added to each well and incubated for 1 hr at RT. After washing three times with assay diluent, 50 μl of streptavidin-horse radish peroxidase conjugate (1:1000) was added to each well and incubated for 30 min at RT. After washing three times with assay diluent, 100 μl of tetramethylbenzidine/$H_2O_2$ solution (Pharmingen 264 KK) was added to each well for 15 min in the dark at room temperature. The reaction was stopped with 100 μl 1N $H_2SO_4$ in each well and the absorbance was read immediately at 450 nm.

Significantly greater antibody titers against PGCC epitope were induced by immunizing with Ii-Key/PGCC(95–104) than with PGCC(95–104) peptide alone, either in CFA (Table 22.1) or in IFA (Table 22.2). C3H/HeJ mice (H-$2^k$) were immunized with 10 nmole of peptides (50 μl) emulsified with an equal volume of complete Freund's adjuvant (CFA), subcutaneously at the base of the tail. On day 14 the mice were boosted subcutaneously at the base of the tail with 10 nmole of peptides (50 μl) emulsified with an equal volume of incomplete Freund's adjuvant (IFA). On day 28 the mice were boosted intravenously with 40 nmole peptides dissolved in Hank's balanced salts solution (HBSS). On day 33 the mice were sacrificed and serum samples were assayed for antibody titers against the PGCC(95–104) epitope peptide.

TABLE 22.1

Antibody induction after immunizations with PGCC(95–104) epitope with complete Freund's adjuvant.

| | Dilution$^{-1}$ | | | |
|---|---|---|---|---|
| Immunogen | 20 | 60 | 180 | 540 |
| Ii-Key/PGCC | 1.409 | 1.489 | 0.252 | 0.53 |
| PGCC | 0.128 | 0.057 | 0.016 | 0.004 |
| None | 0.105 | 0.72 | 0.049 | 0.036 |

To vaccinate with IFA, C3H/HeJ mice (H-$2^k$) were immunized with 10 nmole of peptides (50 μl) emulsified with equal amount of IFA, subcutaneously at the base of the tail. On day 14 the mice were boosted with 10 nmole of peptides (50 μl) emulsified with an equal volume of IFA, again subcutaneously at the base of the tail. On day 28 the mice were boosted intravenously with 40 nmole peptides dissolved in Hank's balanced salts solution (HBSS). On day 33 the mice were sacrificed and serum samples were assayed for antibody titers against the PGCC(95–104) epitope peptide.

TABLE 22.2

Antibody induction after immunizations with PGCC(95–104) epitope with incomplete Freund's adjuvant.

| | Dilution $^{-1}$ | | | | | |
|---|---|---|---|---|---|---|
| Immunogen | 20 | 60 | 180 | 540 | 1620 | 4860 |
| Ii-Key/PGCC | 3.503 | 2.995 | 0.782 | 0.205 | 0.071 | 0.024 |
| PGCC | 0.102 | 0.186 | 0.019 | 0.005 | −0.003 | 0.003 |
| None | 0.042 | 0.004 | −0.003 | 0.007 | 0.006 | 0.005 |

Significantly greater antibody titers against the HIV gp160(843–855) epitope resulted from immunization with Ii-Key/HIV gp160(843–855) hybrid than with HIV gp160 (843–855) peptide, both being administered in saline solution (Table 3). B10.A (5R) mice (H-2) were immunized with 20 nmole of peptides in 50 μl phosphate-buffered saline solution, intramuscularly in right and left rear legs on days 1 and 2, respectively. On day 14 the mice were boosted intramuscularly with 40 nmole of peptides in 200 μl Hank's balanced salts solution intramuscularly in a rear leg. On day 30 the mice were boosted intravenously with 40 nmole peptides dissolved in Hank's balanced salts solution (HBSS). On day 35 the mice were sacrificed and serum samples were assayed for antibody titers against the HIV gp160(843–855) peptide.

TABLE 22.3

Antibody induction after immunizations with HIV gp160 (843–855) epitope peptide in saline solution.

| | Dilution$^{-1}$ | | | |
|---|---|---|---|---|
| Immunogen | 20 | 60 | 180 | 540 |
| Ii-Key/one-ava/ gp160 (843–855) | 0.600 | 0.157 | 0.073 | 0.024 |
| Ii-Key/two-ava/ gp160 (843–855) | 0.131 | 0.039 | 0.027 | 0.003 |
| Gp160 (843–855) | 0.052 | 0.023 | 0.000 | −0.005 |
| None | 0.084 | 0.045 | 0.004 | −0.003 |

The above results demonstrate that presentation of the antigenic epitope in an Ii-Key/antigenic epitope hybrid greatly enhances induction of an antibody response regardless whether CFA or IFA is the vehicle for the first immunization. IFA is composed of bayol oil, and CFA is composed of IFA to which has been added heat-killed *mycobacterium tuberculosis*. In the experiments of Tables 1 and 2, IFA was the vehicle for the second immunization, a subcutaneous booster injection, and HBSS was the vehicle for the third immunization, an intravenous booster injection. Because CFA and IFA mediate phagocytosis of the peptides by professional antigen presenting cells, their use leads to charging of the epitope peptide in the post-Golgi, antigen charging compartment. Therefore, Ii-Key/antigenic epitope hybrids have benefit from two mechanisms for charging to MHC Class II molecules: at cell surface MHC Class II molecules, for example on paraformaldehyde-fixed cells (Adams S. Eur J. Immunol 1995 25:1693–1702), and in the post-Golgi antigen charging compartment, after internalization.

The frequency of CD4/IFN-γ Th-1 helper T cells were greatly increased after immunization with Ii-Key/gp160

(843–855) hybrid, as compared to immunization with gp160 (843–855) peptide (Table 4). To test the mechanism for the much greater immunogenecity of Ii-Key/epitope hybrids epitope peptides, B10(A) 5R mice were immunized with 10 nmole of either gp160(843–855) peptide or Ii-Key/gp160 (843–855) in CFA subcutaneously at the right side of the base of the tail. On day 10 the mice were boosted with 40 nmole of hybrid peptide or epitope peptide in saline by intravenous injection. On day 26 mice were sacrificed and splenic cells were obtained. $1\times10^6$ splenic mononuclear cells were stimulated overnight in the presence of 10 units of recombinant IL-2 and indicated peptides (10 μg/ml). During the last 3 hours of incubation, 2 μM monensin (Golgi-stop, Pharmingen) was added to the cultures, and cells were then stained for both cellular surface markers and intracellular IFN-γ. The FACS assay to quantify antigen specific Th1 helper cell responses was performed as follows. The cells were incubated with 1 μg fluorescein blocking reagent (FC/block, Pharmingen) per $10^6$ cells in 100 μl of staining buffer (Dulbecco's phosphate-buffered saline solution without magnesium or calcium). Those cells were stained at $10^6$ cells/100 μl with either rat-anti-mouse CD3 or CD4 monoclonal antibodies for 30 min at 4° C. After washing, the cells were re-suspended, fixed with 4% formaldehyde, and permeablized with 0.5% saponin for 20 min at 4° C. The cells were suspended in staining buffer with 0.5% saponin, and stained with the appropriate anti-cytokine or isotype control antibody (IFN-γ, XMG1.2, Pharmingen or IFN-γ isotype control, R3–34, Pharmingen). The cells were incubated for 30 min at 4° C. in the dark, washed and fixed for 10 min with 0.3% formaldehyde in 0.5% saponins in staining buffer for flow cytometric analysis. Flow cytometric analysis was performed as follows. First, $CD3^+$ cells were gated using dual color dot plot of side scatter versus CD3 FITC as the T-gate population. The $CD3^+$ cells were then analyzed for CD4 expression to target the $CD3^+/CD4^+$ T-helper cell population. Within this specific cell population, dual color dot plots were used to analyze intracellular interferon-γ cytokine stained by phycoerthyrin (PE)-labeled antibody versus $CD3^+/CD4^+$ cells stained with fluorescein-labeled antibody.

The increase in $CD4^+$/IFN-$\gamma^+$ cells is consistent with stimulation and expansion of antigen-specific Th-1 helper T cells. The Th-1 helper T cell subpopulation is characterized by predominant production of IFN-γ while the Th-2 subpopulation of helper T cells is characterized by preferential production of IL-4 and IL-10. Anti-CD3 antibody, which reacts with T cell receptors, measures all T cells, both resting and $CD4^+$ and $CD8^+$ subpopulations. The increase from about 1.0% to about 2.0% in the CD4+/IFNγ $^+$ antigen-specific subpopulation (as compared with naïve mice) is consistent with studies of others on mice immunization with various antigens (Caraher E M. J Immunol Methods 2000 244:29; O'Hagan D. J Virol 2001 75:9037; Karulin A Y. J. Immunol. 2002 168:545–53; Targoni O S. J. Immunol. 2001 166:4757–64; Hesse M D. J. Immunol. 2001 167:1353–61; Heeger P S. J. Immunol. 2000 165:1278–84; Helms T. J. Immunol. 2000 164:3723–32; Yip H C. J. Immunol. 1999 162:3942–9).

TABLE 22.4

Double color FACS analysis of murine splenic T cells after vaccination with Ii-Key/HIV gp160 (843–855) hybrid or epitope peptides.

| | Percentage of cells | | |
|---|---|---|---|
| Immunogen | $CD4^+$ | $CD4^+$/IFN-$\gamma^+$ | $CD3^+$/IFN-$\gamma^+$ |
| Naïve | 32.40 | 1.06 | 2.47 |
| gp160 (843–855) | 31.03 | 0.94 | 2.05 |
| Ii-Key/gp160 (843–855) | 31.70 | 1.83 | 4.03 |

An ELISPOT assay for IFN-γ cytokine responses was performed in order to titer more exactly splenic T lymphocyte subset responses to immunization with Ii-Key-ava-gp160(843–855) or gp160(843–855). The assay was performed as follows. A solution of the cytokine-specific capture antibody (100 μl at 6 μg/ml in phosphate-buffered saline solution, pH 7.2) was added to each well of a 96-well Immunospot plate (M200) for an overnight incubation at 4° C. After aspiration, phosphate-buffer saline solution 200 μl containing 10% fetal bovine serum and 1% penicillin-streptomycin-glutamine (mouse medium) was added to each well for 2 hr at RT. After washing four times with 1% Tween-20 in phosphate-buffered saline solution (wash buffer I), 100 μl of single cell suspensions from the spleens of immunized mice at $10^6$ cells/well were re-stimulated with 100 μl of peptide-epitope at 5 μg/well in mouse medium and incubated for 20–40 hr at 37° C., 5% $CO_2$. After washing twice with phosphate-buffered saline solution (wash buffer II) and four times with wash buffer 1,100 μl of 2 μg/ml biotinylated anti-mouse IFN-γ in 1× phosphate buffer saline with 10% fetal bovine serum (dilution buffer) was added to each well for 2 hr at RT. After washing five times with wash buffer 1,100 μl of streptavidin-horse radish peroxidase conjugate (1:500) in dilution buffer was added to each well for 1 hr at RT. After washing four times with wash buffer I and two times with wash buffer II, 100 μl of the 3-amino-9-ethylcarbazole/$H_2O_2$ substrate (Pharmingen 551951) was added and incubated for 30–60 min in the dark at RT. The reaction was stopped by washing three times with 200 μl of deionized water. ELISPOT data analysis was performed by using the Immunospot 1.7e software (Cellular Limited Technology). Digitized images of quadruplicate wells were analyzed for the presence of spots in which color density exceeds background based on comparison of control cells (naive splenocytes) and experimental cells (splenocytes of immunized mice) cells. Additional counting parameters for spot size and circularity were applied to gate out speckles caused by non-specific antibody binding. Each spot represents a single cell secreting IFN-γ.

IFN-γ/Th-1 responses were elicited to the HIV gp160 (843–855) epitope from immunization with Ii-key/HIV gp160(844–855) hybrid and HIV gp160(843–855) peptide, both being administered in saline solution (Table 5). C3H/HeJ(H-$2^k$) mice were immunized with 40 nmole of peptides (50 μl) emulsified with equal volume of incomplete Freund's adjuvant (IFA), subcutaneously at the base of the tail. On day 13 the mice were boosted subcutaneously at the base of the tail with 40 nmole of peptides (50 μl) emulsified with equal amount of incomplete Freund's adjuvant (IFA). On day 31, the mice were boosted intravenously with 40 nmole peptides dissolved in 100 μl Hank's balanced salts solution (HBSS). On day 35, the mice were sacrificed and single cell suspensions from spleens were assayed for IFN-γ responses to HIV gp160(843–855) peptide.

TABLE 22.5

ELISPOT analysis of murine splenic T cells after vaccination with Ii-Key/HIV gp160 (843–855) hybrid or epitope peptides.

| Immunogen | Number | Size |
|---|---|---|
| Ii-Key/gp160 (844–855) | 59 (+/−5) | 0.028 (+/−0.006) |
| gp160 (843–855) | 5 (+/−3.6) | 0.019 (+/−0.01) |
| None | 0 | 0 |

Number is the mean number of spots (and standard deviation) in triplicate wells and Size is the mean spot size in $mm^2$ (and standard deviation). Ii-Key/gp160(844–855) has one ava spacer (Ii-key-ava-gp160(844–855)).

The data of Tables 22.4 and 22.5 supports the view derived from the data of Tables 1–3 that Ii-Key/antigenic epitope hybrids are significantly more potent immunogens than the comparable antigenic peptides. Furthermore, antigenic epitopes in Ii-Key/antigenic epitope hybrids are well presented after subcutaneous immunization in PBS, without an adjuvant. This fact points to effective use of these peptides as vaccines in humans, for whom various other adjuvants, e.g., CFA or even IFA, are either contraindicated or not preferred.

A cDNA sequence for an Ii-Key/antigenic epitope hybrid peptide can be constructed for delivery as a minigene DNA vaccine. Such a construct is either a minigene composed of one or several repeated gene constructs each encoding the Ii-Key/antigenic epitope, or as such one or more inserts into a DNA vaccine coding for expression of a protein from which the antigenic epitope of the minigene construct was derived. Standard molecular biology techniques are used to generate such minigene constructs (Leifert J A. Hum Gene Ther. 2001 12:1881–92; Liu W J. Virology. 2000 273: 374–82).

The DNA structure coding for such a minigene contains the codons for 1) a biologically active Ii-Key peptide such as LRMK or a biologically active homolog of the Ii-Key peptide as taught in U.S. Pat. No. 5,919,639, 2) a spacer composed of ala—ala—ala or other biologically accepted functional equivalent of ava or ala—ala—ala, and 3) the antigenic epitope.

This disclosure reveals that a spacer composed of one delta-aminovaleric acid, which is 5-aminopentanoic acid, is preferred to a spacer composed of two such residues or no spacer at all. Since the linear extent of one delta-aminovaleric acid residue in an Ii-Key/antigenic epitope peptide approximates the linear extent along the backbone of about 2.5 amino acids, the length of the spacer-equivalent in the DNA construct of the minigene is preferably 2, 3 or 4 amino acids, but the length of that spacer can extend from one to 11 amino acids. The codons in the spacer-equivalent segment of the minigene can encode functionally accepted amino acids, but preferable are drawn from the group including small side chain amino acids such as alanine, glycine and serine.

As with other examples presented in this disclosure, the amino acids of the antigenic epitope segment of the Ii-Key/antigenic epitope hybrid may be composed of amino acid sequences coding for one MHC Class II-presented antigenic epitope only, or for such an epitope with attached or overlapping sequence(s) coding for one or more of the following a) a second MHC Class II-presented epitope, b) a MHC Class I-presented epitope, and c) an antibody-recognized epitope.

Immunization with Ii-Key/Class II epitope hybrids enhances CTL responses to MHC Class I epitopes activity by augmenting antigen-specific T helper cell responses. Improved potency of MHC Class II epitope presentation potentiates responses to activity of MHC class I epitopes. Mice were immunized with mixtures of Ii-Key/MHC Class II hybrid with CTL epitope, or MHC Class II epitope+CTL epitope, or CTL epitope alone. The ELISPOT assay showed that immunizing mice with Ii-Key/MHC Class II hybrid with CTL epitope produced enhanced CTL activity (Table 22.6). C3D2F1/J mice were immunized subcutaneously at the base of the tail with a mixture of either: 1) 40 nmole of Ii-key/HIV helper T epitope GP120(91–100)] & 20 nmole of HIV CTL epitope (p18) in IFA, 2) 40 nmole of HIV helper T epitope GP120(91–100) and 20 nmole HIV CTL epitope (p18) in IFA, 3) 20 nmole of HIV CTL epitope (p18) in IFA, or 4) No immunogen. On day 14, the mice were boosted with the same immunogens, as described above, at the base of the tail. On day 32, the mice were boosted one more time subcutaneously. Single cell suspensions from individual mouse spleens were challenged ex vivo five days following the last boost in cultures ($10^6$ cells/well) containing CTL epitope p18 (5 ìg/well), a non-specific epitope (5 ìg/well) and medium alone. Table 22.6 represents the mean spot values and SD calculated from data averaged from three mice per group in six to nine wells.

TABLE 22.6

ELISPOT analysis of CTL spots after immunization of mice with mixture of Ii-Key/gp120 (91–100) with CTL epitope p18 or mixture of gp120 (91–100) with p18, or p18 alone.

| Immunogen | CTL reaction | Non-specific peptide reaction | Medium |
|---|---|---|---|
| Ii-Key/gp120 (91–100) + p18 | 27 | 6 | 0 |
| Gp120 + p18 | 11 | 5 | 0 |
| P18 | 7 | 0 | 0 |
| naïve | 5 | 2 | 0 |

Thus, mice immunized with Ii-Key/MHC Class II helper epitopes+CTL epitope exhibited a much greater antigen specific CTL response than mice immunized with CTL epitope alone or MHC Class II epitope+CTL epitope. Covalent coupling of Ii-Key/MHC Class II hybrids and CTL epitopes, or MHC Class II sequences within which CTL epitopes are resident, will also provide enhanced CTL responses. In addition, minigenes and DNA vaccines composed of Ii-Key/MHC Class II hybrids CTL sequences will also induce enhanced CTL reactions.

The invention claimed is:

1. An isolated nucleic acid molecule comprising:

a) a first expressible nucleic acid sequence encoding a protein of interest or polypeptide of interest which contains a first MHC Class II-presented epitope; and b) a second expressible nucleic acid sequence encoding an antigen presentation enhancing hybrid polypeptide comprising:

i) an N-terminal element consisting essentially of the residues LRMK (amino acids 1–4) of SEQ ID NO.: 1 and 0–12 additional sequential residues of SEQ ID NO.: 1, and modifications of SEQ ID No: 1 that retain antigen presentation enhancing activity;

ii) a C-terminal element comprising a second an MHC Class II-presented epitope, said second MHC Class II-presented epitope being in the form of a polypeptide or peptidomimetic structure which binds to the antigenic peptide binding site of an MHC class II molecule, the second MHC Class II-presented epitope being from the same protein or polypeptide of interest encoded by the nucleic acid sequence a); and iii) an intervening peptidyl structure linking the N-terminal and C-terminal elements of the hybrid, the peptidyl structure having a length of about 20 amino acids or less.

2. The isolated nucleic acid of claim 1 wherein the modifications of element b) i) are selected from the group consisting of:

a) deletion of amino acids from the C-terminus of SEQ ID No: 1;

b) N-terminal extensions of SEQ ID No: 1;

c) amino acid substitutions of SEQ ID No: 1 excluding said residues LRMK.

3. The isolated nucleic acid of claim 1 wherein the C-terminal element further comprises an MHC Class I-presented epitope, or a portion thereof, the amino acid residues comprising the MHC Class I-presented epitope or portion thereof being constituent residues of the MHC Class II-presented epitope.

4. The isolated nucleic acid of claim 1 wherein the C-terminal element further comprises an antibody-recognized determinant, or a portion thereof, the amino acid residues comprising the antibody-recognized determinant or a portion thereof being constituent residues of the MHC Class II-presented epitope.

5. The isolated nucleic acid sequence of claim 1 wherein the protein or polypeptide of interest corresponds to a protein or polypeptide encoded by of an infectious pathogen.

6. The isolated nucleic acid sequence of claim 5 wherein the infectious pathogen is selected from the group consisting of anthrax, EBOLA, HIV and influenza.

7. The isolated nucleic acid sequence of claim 5 wherein the infectious pathogen is vaccinia virus.

8. The isolated nucleic acid sequence of claim 1 wherein the protein of interest is gp42.

* * * * *